US008729066B2

(12) United States Patent
Yuan et al.

(10) Patent No.: US 8,729,066 B2
(45) Date of Patent: May 20, 2014

(54) 1,2- BIS-SULFONAMIDE DERIVATIVES AS CHEMOKINE RECEPTOR MODULATORS

(71) Applicant: Allergan, Inc., Irvine, CA (US)

(72) Inventors: Haiqing Yuan, Irvine, CA (US); Richard L. Beard, Newport Beach, CA (US); Michael E. Garst, Newport Beach, CA (US); Xiaoxia Liu, Irvine, CA (US); John E. Donello, Dana Point, CA (US); Veena Viswanath, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/034,945

(22) Filed: Sep. 24, 2013

(65) Prior Publication Data

US 2014/0051682 A1 Feb. 20, 2014

Related U.S. Application Data

(62) Division of application No. 13/316,762, filed on Dec. 12, 2011, now Pat. No. 8,580,779.

(60) Provisional application No. 61/423,941, filed on Dec. 16, 2010.

(51) Int. Cl.
*A61K 31/55* (2006.01)

(52) U.S. Cl.
USPC .................................... 514/212.07; 424/400

(58) Field of Classification Search
USPC .................................... 514/212.07; 424/400
See application file for complete search history.

(56) References Cited

U.S. PATENT DOCUMENTS

| | | | |
|---|---|---|---|
| 6,423,343 B1 | 7/2002 | Lee et al. | |
| 7,622,583 B2 | 11/2009 | Ungashe | |
| 2007/0037794 A1 | 2/2007 | Ungashe | |
| 2008/0293720 A1 | 11/2008 | Cleary | |

FOREIGN PATENT DOCUMENTS

| | | | |
|---|---|---|---|
| WO | 01-28537 | | 4/2001 |
| WO | 03-099773 | | 4/2003 |
| WO | 2005-004810 | | 1/2005 |
| WO | 2006-047302 | | 5/2006 |
| WO | WO-2006047302 | * | 5/2006 |
| WO | 2007-067875 | | 6/2007 |
| WO | 2008-008374 | | 1/2008 |

OTHER PUBLICATIONS

Ambati, Jayakrishna et al, 2003, An Animal Model of Age-Related Macular Degeneration in Senescent Ccl-2- or Ccr-2Deficient Mice, Nature Medicine, 9, 1390-1397.

Beech, John et al, 2001, Neuroprotection in Ischemia—Reperfusion Injury: An Antiinflammatory Approach Using a Novel Broad-Spectrum Chemokine Inhibitor, Journal of Cerebral Blood Flow and Metabolism, 21, 683-689.

Cross, L.C. et al, 1976, Rules for the Nomenclature of Organic Chemistry, Section E: Stereochemistry, Pure & Appl. Chem., 45, 11-30.

Fang, I-Mo et al, 2004, Expression of chemokine and receptors in Lewis rats with experimental autoimmune anterior uveitis, Experimental Eye Research, 78, 1043-1055.

Feria, Manuel et al, 2006, The CCR2 Receptor as a Therapeutic Target, Expert Opin. Ther Patents, 16, 49-57.

Gerard, Craig et al, 2001, Chemokines and Disease, nature immunology, Chemokine Reviews, 2, 108-115, Nature Publishing Group.

Grainger, David et al, 2003, Broad-Spectrum Chemokine Inhibitors (BSCIs) and Their Anti-Inflammatory Effects in Vivo, Biochemical Pharmacology, 65, 1027-1034.

Heinrich Stahl, 2002, Handbook of Pharmaceutical Salts, Verlag Helvetica Chimica Acta—Zurich, 329-345.

Keino, Kiroshi et al, 2003, Chemokine and Chemokine Receptor Expression During Experimental Autoimmune Uveoretinitis in Mice, Graefe's Arch Clin Exp Ophthalmol, 241, 111-115.

Klitgaard, Torben et al, 2004, Chemokine Receptors and Early Activation Markers in Acute Anterior Uveitis, Acta Ophthalmol. Scand., 82, 179-183.

Meleth, Annal et al, Nov. 2005, Serum Inflammatory Makers in Diabetic Retinopathy, Investigative Ophthalmology & Visual Science, 46, 4295-4301.

Reckless, Jill et al, 1999, Identification of Oligopeptide Sequences Which Inhibit Migration Induced by a Wide Range of Chemokines, Biochem. J., 340, 803-811.

Takeuchi, Aya et al, Oct. 2005, CCR5-Deficient Mice Develop Experimental Autoimmune Uveoretinitis in the Context of a Deviant Effector Response, Investigative Ophthalmology & Visual Science, 46, 3753-3760.

Tokuyama, Hirotake et al, 2005, The Simultaneous Blockage of Chemokine Receptors CCR2, CCR5 and CXCR3 by a Non-Peptide Chemokine Receptor Antagonist Protects Mice From Dextran Sodium Sulfate-Mediated Colitis, International Immunology, 17, 1023-1034.

Tuaillon, Nadine et al, May 2002, MCP-1 Expression in Endotoxin-Induced Uveitis, Investigative Ophthalmology & Visual Science, 43, 1493-1498.

Wallace, Graham et al, 2004, The Role of Chemokines and Their Receptors in Ocular Disease, Progress in Retinal and Eye Research, 23, 435-448.

Weisberg, Stuart et al, Jan. 2006, CCR2 Modulates Inflammatory and Metabolic Effects of High-Fat Feeding, The Journal of Clinical Investigation, 116, 115-124.

Wells, Timothy et al, Jan. 2006, Chemokine blockers—therapeutics in the making?, Trends in Pharmacological Sciences, 27, 41-47.

Yamagami, Satoru et al, Apr. 2005, CCR5 Chemokine Receptor Mediates Recruitment of MHC Class II-Positive Langerhans Cells in the Mouse Corneal Epithelium, Investigative Ophthalmology & Visual Science, 46, 1201-1207.

(Continued)

*Primary Examiner* — Ernst Arnold
*Assistant Examiner* — Jianfeng Song
(74) *Attorney, Agent, or Firm* — Doina G. Ene

(57) ABSTRACT

The present invention relates to novel bis-sulfonamide derivatives, processes for preparing them, pharmaceutical compositions containing them and their use as pharmaceuticals as modulators of chemokine receptors.

11 Claims, No Drawings

(56) References Cited

OTHER PUBLICATIONS

Yang, Chang-Hao et al, 2005, Effects of the NF-B Inhibitor Pyrrolidine Dithiocarbamate on Experimentally Induced Autoimmune Anterior Uveitis, Investigative Ophthalmology & Visual Science, 46, 1339-1347.

Vippagunta, et al., "Crystalline Solids," Advanced Drug Delivery Reviews, 2001.

Muller, Inorganic Chemistry, pp. 14-15, 1993.

International Search Report for PCT/US2011/06441, Mar. 27, 2012.

* cited by examiner

1,2- BIS-SULFONAMIDE DERIVATIVES AS CHEMOKINE RECEPTOR MODULATORS

RELATED APPLICATION

This application is a divisional application of U.S. Non-Provisional patent application Ser. No. 13/316,762, filed Dec. 12, 2011, which claims the benefit of U.S. Provisional Application Ser. No. 61/423,941, filed Dec. 16, 2010, all of which are incorporated here by reference in their entirety.

FIELD OF THE INVENTION

The present invention relates to novel 1,2-bis-sulfonamide derivatives, processes for preparing them, pharmaceutical compositions containing them and their use as pharmaceutical modulators of chemokine receptors. The invention relates specifically to the use of these compounds and their pharmaceutical compositions to treat disorders associated with chemokine receptor (CCR) modulation.

BACKGROUND OF THE INVENTION

Chemokines are a group of 7- to 14-kd peptides that play an important role in orchestrating leukocyte recruitment and migration during inflammation, and therefore represent an important target for anti-inflammatory therapies (Wells et al., 2006). They act by binding to seven-transmembrane, G protein-coupled receptors, the chemokine receptors. The chemokine system is complex, with about ~50 chemokines and 20 chemokine receptors identified in humans, often acting with redundancy, making selection of specific antagonists difficult (Gerard and Rollins, 2001). Genetic knockout strategies have confirmed the importance of chemokines as regulators of immune function, but the deletion of specific chemokines has led to only specific and relatively mild defects in the inflammatory response further emphasizing the complex redundancy of the system. Selectivity is crucial for use of chemokine receptor antagonists in systemic diseases where a single chemokine-receptor system is implicated such as atheroscelorsis where the macrophage/monocyte system is the major player in order to allow a subtle and specific control over immune function (Weisberg et al., 2006; Feria and Diaz Gonzalez et al., 2006).

Many ocular conditions are characterized by inappropriate migration and infiltration of cells such as leukocytes and endothelial cells into the eye with deleterious effects to ocular structures (Wallace et al., 2004). Chemokines have been identified in such diseases and misregulation of the chemokine system is apparent in corneal graft rejection, diabetic retinopathy, age-related macular degeneration (ARMD), chronic inflammatory diseases such as uveitis, dry eye etc. Mice lacking CCR2 or MCP-1 develop features of ARMD with age, including drusen deposits, choroidal neovascularization and photoreceptor atrophy indicating a crucial role for this chemokine and its receptor signaling (Amabati et al., 2003). Thus CCR2 receptor-specific inhibitor might have potential therapeutic benefit in ocular diseases like ARMD. In contrast, various human and animal studies have identified several chemokines in different forms of uveitis, produced both by resident and infiltrating cells, that strongly suggests a prominent role for these molecules in its pathogenesis. Studies in rat and mice models of uveitis have demonstrated up-regulation of monocyte chemoattractant protein-1 (MCP-1), macrophage inflammatory protein-1 (MIP-1), RANTES, stromal derived factor-1 (SDF-1) which are powerful chemoattractants for monocytes and T-cells (Fang et al., 2004; Keino et al., 2003). Similar findings have been reported in peripheral blood mononuclear cells in patients with acute anterior uveitis (AAU), the most common form of human uveitis (Klitgaard et al., 2004). MCP-1 knockout mice and CCR5 knockout mice show reduced endotoxin-induced uveitis, which is the animal model for AAU (Takeuchi et al., 2005; Tuallion et al., 2002). It has also been demonstrated that blocking the chemokine system upstream with the use of NF-κB blockers significantly attenuates experimental AAU in rats (Yang et al., 2005). Blockage of NF-κB results in transcriptional inhibition of multiple chemokines. Given the complexity of pathogenesis in uveitis it is unlikely that a selective inhibition of a chemokine receptor in monotherapy will offer therapeutic benefit. A similar role of multiple chemokines have been shown to be correlated with clinical stage of disease in diabetic retinopathy and dry eye (Meleth et al., 2005; Yamagami et al., 2005). In these ocular diseases the use of broad spectrum chemokine receptor inhibitor which inhibits the function of a wide range of chemokines maybe beneficial.

The first broad spectrum chemokine inhibitor (BSCI) to be reported was termed Peptide 3, which was derived from the sequence of human chemokine MCP-1 and was shown to block the migration of monocytes in response to MCP-1, MIP-1, RANTES and SDF-1 (Reckless and Grainger. 1999). A cyclic retro inverse analogue of Peptide 3, constructed of D-amino acids in the reverse sequence, called NR58-3.14.3 was observed to be a more potent chemokine inhibitor (Beech et al., 2001). NR58-3.14.3 has been used to test for anti-inflammatory activities in animal models of atherosclerosis, lung inflammation, irritable bowel syndrome etc (Beech et al., 2001; Grainger and Reckless. 2003; Tokuyama et al., 2005). However there are several disadvantages to using these BSCI as a long-term therapeutic strategy. The known BSCIs which are peptides which have relatively low potency, poor pharmacokinetics, and are unstable in vivo. In addition, systemic use of broad spectrum chemokine receptor inhibitors could potentially lead to deleterious side effects due to their systemic anti-inflammatory activity. However in ocular diseases, a local or topical application would prevent the broad spectrum inhibitor to be taken up systemically. Identification of a small molecule inhibitor of several chemokine receptors could be very useful for treatment of inflammatory ocular diseases. Given the evidence for the role of multiple chemokines in several ocular diseases and these results, we propose that the use of small and large molecule broad spectrum chemokine receptor inhibitors will have utility in the local treatment of ocular inflammatory diseases including, but not limited to, uveitis, dry eye, diabetic retinopathy, allergic eye disease and proliferative retinopathies. Manipulation of multiple chemokines therefore represents a novel therapeutic approach in treating ocular diseases.

WO 2001028537 discloses preparation of bissulfonamide derivatives as inhibitors of dehydroquinate synthetase and type II dehydroquinase enzymes. Compounds N,N'-(4-chloro-1,2-phenylene)bis-2-thiophenesulfonamide (CAS 335336-21-5) and N,N'-(4-chloro-5-methyl-1,2-phenylene) bis-)2-thiophenesulfonamide (CAS 335335-03-0) are disclosed in WO 2001028537.

WO 2006047302 discloses bis-sulfonamide compounds as agonists of GalR1, their preparation, pharmaceutical compositions, and use in therapy. Compounds N,N'-(1,2-phenylenebis-)-2-benzofuransulfonamide (CAS 885052-53-9) and N-[2-[[(4-chlorophenyl)sulfonyl]phenyl]-2-benzofuransulfonamide (CAS 885052-31-3) are disclosed in WO 2006047302.

U.S. Pat. No. 7,622,583 discloses heteroaryl sulfonamides as antagonists of the CCR2 receptor.

US 2008/0293720 discloses pyridinyl sulfonamide modulators of chemokine receptors.

WO2005004810 discloses arylsulfonamides derivatives as bradykinin B1 antagonists or inverse agonists.

WO03/099773 discloses CCR9 inhibitors and methods of use thereof. WO2008008374 discloses CCR2 inhibitors and methods of use thereof.

SUMMARY OF THE INVENTION

A group of novel 1,2-bis-sulfonamide derivatives which are potent and selective chemokine receptor modulators has been discovered. As such, the compounds described herein are useful in treating a wide variety of disorders associated with modulation of chemokine receptors. The term "modulator" as used herein, includes but is not limited to: receptor agonist, antagonist, inverse agonist, inverse antagonist, partial agonist, partial antagonist.

This invention describes compounds of Formula I, which have chemokine receptor biological activity. The compounds in accordance with the present invention are thus of use in medicine, for example in the treatment of humans with diseases and conditions that are alleviated by CCR modulation.

In one aspect, the invention provides a compound having Formula I or a pharmaceutically acceptable salt thereof or stereoisomeric forms thereof, or the individual geometrical isomers, enantiomers, diastereoisomers, tautomers, zwitterions and pharmaceutically acceptable salts thereof:

Formula I

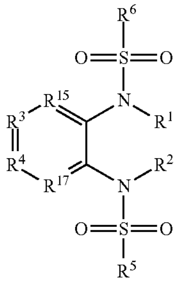

wherein:

$R^1$ is H or substituted or unsubstituted $C_{1-6}$ alkyl;

$R^2$ is H or substituted or unsubstituted $C_{1-6}$ alkyl;

$R^3$ is N or C—$R^7$;

$R^4$ is N or C—$R^8$;

$R^5$ is substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl or is substituted or unsubstituted $C_{6-10}$ aryl;

$R^6$ is 2-benzofuran, 2-thienyl, 5-chloro-2-thienyl, 4,5-dichloro-2-thienyl, 4-chloro-3-methylphenyl, or 4-chloro-3-trifluoromethylphenyl;

$R^{15}$ is N or C—$R^{16}$;

$R^{17}$ is N or C—$R^{18}$;

$R^7$ is H, substituted or unsubstituted $C_{1-6}$ alkyl, halogen, —$OC_{1-6}$ alkyl, CN, $C_{2-6}$ alkenyl, $C_{2-6}$ alkynyl, C(O)$R^9$, $NR^{10}R^{11}$ or hydroxyl;

$R^8$ is H, substituted or unsubstituted $C_{1-6}$ alkyl, halogen, —$OC_{1-6}$ alkyl, CN, $C_{2-6}$ alkenyl, $C_{2-6}$ alkynyl, C(O)$R^{12}$, $NR^{13}R^{14}$ or hydroxyl;

$R^{16}$ is H, substituted or unsubstituted $C_{1-6}$ alkyl, halogen, —$OC_{1-6}$ alkyl, CN, $C_{2-6}$ alkenyl, $C_{2-6}$ alkynyl, C(O)$R^{19}$, $NR^{20}R^{21}$ or hydroxyl;

$R^{18}$ is H, substituted or unsubstituted $C_{1-6}$ alkyl, halogen, —$OC_{1-6}$ alkyl, CN, $C_{2-6}$ alkenyl, $C_{2-6}$ alkynyl, C(O)$R^{22}$, $NR^{23}R^{24}$ or hydroxyl;

$R^9$ is H or substituted or unsubstituted $C_{1-6}$ alkyl;

$R^{10}$ is H or substituted or unsubstituted $C_{1-6}$ alkyl;

$R^{11}$ is H or substituted or unsubstituted $C_{1-6}$ alkyl;

$R^{12}$ is H or substituted or unsubstituted $C_{1-6}$ alkyl;

$R^{13}$ is H or substituted or unsubstituted $C_{1-6}$ alkyl;

$R^{14}$ is H or substituted or unsubstituted $C_{1-6}$ alkyl;

$R^{19}$ is H or substituted or unsubstituted $C_{1-6}$ alkyl;

$R^{20}$ is H or substituted or unsubstituted $C_{1-6}$ alkyl;

$R^{21}$ is H or substituted or unsubstituted $C_{1-6}$ alkyl;

$R^{22}$ is H or substituted or unsubstituted $C_{1-6}$ alkyl $R^{23}$ is H or substituted or unsubstituted $C_{1-6}$ alkyl;

$R^{24}$ is H or substituted or unsubstituted $C_{1-6}$ alkyl; and including compounds:

N-[3-({[4-chloro-3-(trifluoromethyl)phenyl]sulfonyl}amino)pyridin-2-yl]thiophene-2-sulfonamide;

N-[2-({[4-chloro-3-(trifluoromethyl)phenyl]sulfonyl}amino)phenyl]thiophene-2-sulfonamide; and N-{4,5-dichloro-2-[(3-thienylsulfonyl)amino]phenyl}thiophene-2-sulfonamide;

and with the provisos:

a) $R^6$ is not the same as $R^5$;

b) when $R^5$ is a substituted heterocycle then it is not

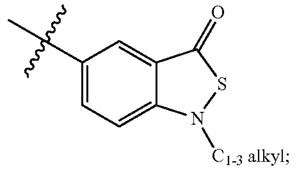

c). when $R^6$ is 2-thienyl then $R^7$, $R^8$, $R^{16}$ and $R^{18}$ are not all hydrogenatoms in same time atoms;

d). the compound is not of the following structures:

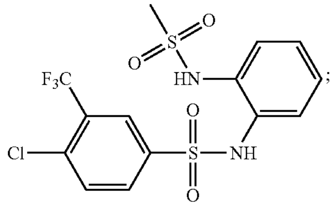
;

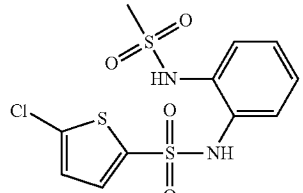
;

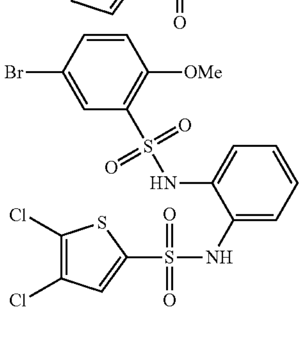
or

-continued

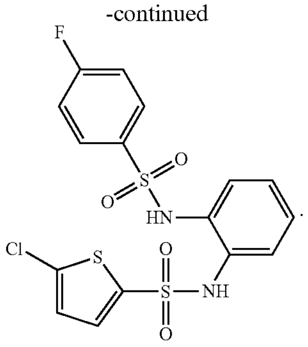

In another aspect, the invention provides a compound having Formula I wherein:

$R^1$ is H or substituted or unsubstituted $C_{1-6}$ alkyl;

$R^2$ is H or substituted or unsubstituted $C_{1-6}$ alkyl;

$R^3$ is C—$R^7$;

$R^4$ is C—$R^8$;

$R^5$ is substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl or is substituted or unsubstituted $C_{6-10}$ aryl;

$R^6$ is 2-benzofuran, 2-thienyl, 5-chloro-2-thienyl, 4,5-dichloro-2-thienyl, 4-chloro-3-methylphenyl, or 4-chloro-3-trifluoromethylphenyl;

$R^{15}$ is C—$R^{16}$;

$R^{17}$ is C—$R^{18}$;

$R^7$ is H, substituted or unsubstituted $C_{1-6}$ alkyl, halogen, —$OC_{1-3}$ alkyl, CN, $C_{2-6}$ alkenyl, $C_{2-6}$ alkynyl, $C(O)R^9$, $NR^{10}R^{11}$ or hydroxyl;

$R^8$ is H, substituted or unsubstituted $C_{1-6}$ alkyl, halogen, —$OC_{1-3}$ alkyl, CN, $C_{2-6}$ alkenyl, $C_{2-6}$ alkynyl, $C(O)R^{12}$, $NR^{13}R^{14}$ or hydroxyl;

$R^{16}$ is H, substituted or unsubstituted $C_{1-6}$ alkyl, halogen, —$OC_{1-3}$ alkyl, CN, $C_{2-6}$ alkenyl, $C_{2-6}$ alkynyl, $C(O)R^{19}$, $NR^{20}R^{21}$ or hydroxyl;

$R^{18}$ is H, substituted or unsubstituted $C_{1-6}$ alkyl, halogen, —$OC_{1-3}$ alkyl, CN, $C_{2-6}$ alkenyl, $C_{2-6}$ alkynyl, $C(O)R^{22}$, $NR^{23}R^{24}$ or hydroxyl;

$R^9$ is H or substituted or unsubstituted $C_{1-6}$ alkyl;

$R^{10}$ is H or substituted or unsubstituted $C_{1-6}$ alkyl;

$R^{11}$ is H or substituted or unsubstituted $C_{1-6}$ alkyl;

$R^{12}$ is H or substituted or unsubstituted $C_{1-6}$ alkyl;

$R^{13}$ is H or substituted or unsubstituted $C_{1-6}$ alkyl;

$R^{14}$ is H or substituted or unsubstituted $C_{1-6}$ alkyl;

$R^{19}$ is H or substituted or unsubstituted $C_{1-6}$ alkyl;

$R^{20}$ is H or substituted or unsubstituted $C_{1-6}$ alkyl;

$R^{21}$ is H or substituted or unsubstituted $C_{1-6}$ alkyl;

$R^{22}$ is H or substituted or unsubstituted $C_{1-6}$ alkyl;

$R^{23}$ is H or substituted or unsubstituted $C_{1-6}$ alkyl;

$R^{24}$ is H or substituted or unsubstituted $C_{1-6}$ alkyl;

including compounds:

N-[3-({[4-chloro-3-(trifluoromethyl)phenyl]sulfonyl}amino)pyridin-2-yl]thiophene-2-sulfonamide;

N-[2-({[4-chloro-3-(trifluoromethyl)phenyl]sulfonyl}amino)phenyl]thiophene-2-sulfonamide; and N-{4,5-dichloro-2-[(3-thienylsulfonyl)amino]phenyl}thiophene-2-sulfonamide; and with the provisos:

a) $R^6$ is not the same as $R^5$;

b) when $R^5$ is a substituted heterocycle then it is not

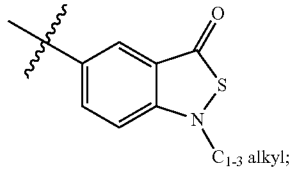

c). when $R^6$ is 2-thienyl then $R^7$, $R^8$, $R^{16}$ and $R^{18}$ are not all hydrogen in same time.

d). the compound is not of the following structures:

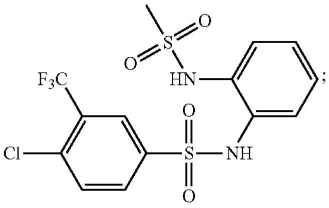

;

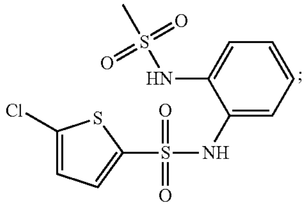

;

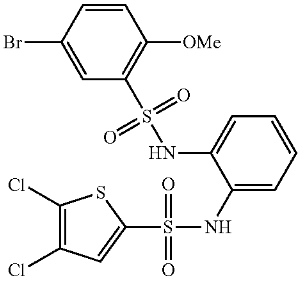

or

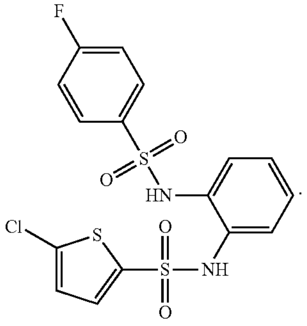

.

In another aspect, the invention provides a compound having Formula I wherein:

$R^1$ is H or substituted or unsubstituted $C_{1-6}$ alkyl;

$R^2$ is H or substituted or unsubstituted $C_{1-6}$ alkyl;

$R^3$ is N or C—$R^7$;

$R^4$ is N or C—$R^8$;

$R^5$ is substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl or is substituted or unsubstituted $C_{6-10}$ aryl;

$R^6$ is 2-benzofuran, 2-thienyl, 5-chloro-2-thienyl, 4,5-dichloro-2-thienyl, 4-chloro-3-methylphenyl, or 4-chloro-3-trifluoromethylphenyl;

$R^{15}$ is N or C—$R^{16}$;

$R^{17}$ is N;

$R^7$ is H, substituted or unsubstituted $C_{1-6}$ alkyl, halogen, —$OC_{1-3}$ alkyl, CN, $C_{2-6}$ alkenyl, $C_{2-6}$ alkynyl, C(O)$R^9$, $NR^{10}R^{11}$ or hydroxyl;

$R^8$ is H, substituted or unsubstituted $C_{1-6}$ alkyl, halogen, —$OC_{1-3}$ alkyl, CN, $C_{2-6}$ alkenyl, $C_{2-6}$ alkynyl, C(O)$R^{12}$, $NR^{13}R^{14}$ or hydroxyl;

$R^{16}$ is H, substituted or unsubstituted $C_{1-6}$ alkyl, halogen, —$OC_{1-3}$ alkyl, CN, $C_{2-6}$ alkenyl, $C_{2-6}$ alkynyl, C(O)$R^{19}$, $NR^{20}R^{21}$ or hydroxyl;

$R^{18}$ is H, substituted or unsubstituted $C_{1-6}$ alkyl, halogen, —$OC_{1-3}$ alkyl, CN, $C_{2-6}$ alkenyl, $C_{2-6}$ alkynyl, C(O)$R^{22}$, $NR^{23}R^{24}$ or hydroxyl;

$R^9$ is H or substituted or unsubstituted $C_{1-6}$ alkyl;

$R^{10}$ is H or substituted or unsubstituted $C_{1-6}$ alkyl;

$R^{11}$ is H or substituted or unsubstituted $C_{1-6}$ alkyl;

$R^{12}$ is H or substituted or unsubstituted $C_{1-6}$ alkyl;

$R^{13}$ is H or substituted or unsubstituted $C_{1-6}$ alkyl;

$R^{14}$ is H or substituted or unsubstituted $C_{1-6}$ alkyl;

$R^{19}$ is H or substituted or unsubstituted $C_{1-6}$ alkyl;

$R^{20}$ is H or substituted or unsubstituted $C_{1-6}$ alkyl;

$R^{21}$ is H or substituted or unsubstituted $C_{1-6}$ alkyl;

$R^{22}$ is H or substituted or unsubstituted $C_{1-6}$ alkyl;

$R^{23}$ is H or substituted or unsubstituted $C_{1-6}$ alkyl;

$R^{24}$ is H or substituted or unsubstituted $C_{1-6}$ alkyl;

and including compounds:

N-[3-({[4-chloro-3-(trifluoromethyl)phenyl] sulfonyl}amino)pyridin-2-yl]thiophene-2-sulfonamide;

N-[2-({[4-chloro-3-(trifluoromethyl)phenyl] sulfonyl}amino)phenyl]thiophene-2-sulfonamide N-{4,5-dichloro-2-[(3-thienylsulfonyl)amino] phenyl}thiophene-2-sulfonamide; and with the provisos:

a) $R^6$ is not the same as $R^5$;

b) $R^5$ is not

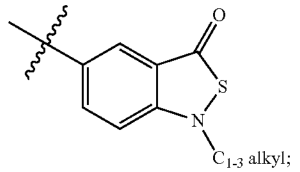

c). when $R^6$ is 2-thienyl then $R^7$, $R^8$, $R^{16}$ and $R^{18}$ are not all hydrogen in same time;

d). the compound is not of the following structures:

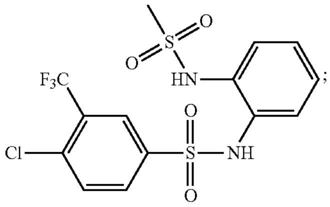

;

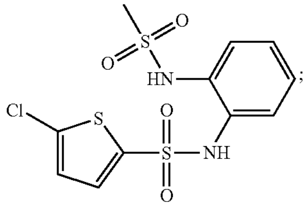

;

-continued

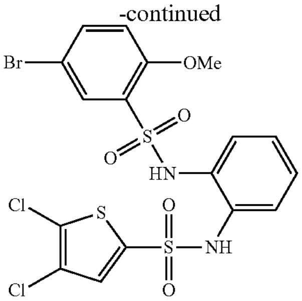

or

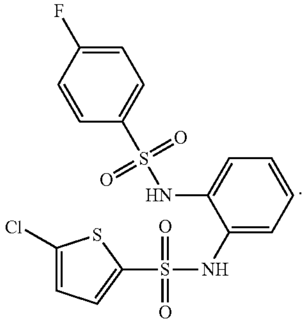

.

In another aspect, the invention provides a compound having Formula I wherein:

$R^1$ is H or substituted or unsubstituted $C_{1-6}$ alkyl;

$R^2$ is H or substituted or unsubstituted $C_{1-6}$ alkyl;

$R^3$ is C—$R^7$;

$R^4$ is C—$R^8$;

$R^5$ is substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl or is substituted or unsubstituted phenyl;

$R^6$ is 2-benzofuran, 2-thienyl, 5-chloro-2-thienyl, 4,5-dichloro-2-thienyl, 4-chloro-3-methylphenyl, or 4-chloro-3-trifluoromethylphenyl;

$R^{15}$ is C—$R^{16}$;

$R^{17}$ is C—$R^{18}$;

$R^7$ is H, substituted or unsubstituted $C_{1-6}$ alkyl, halogen, —$OC_{1-3}$ alkyl, CN, $C_{2-6}$ alkenyl, $C_{2-6}$ alkynyl, C(O)$R^9$, $NR^{10}R^{11}$ or hydroxyl;

$R^8$ is H, substituted or unsubstituted $C_{1-6}$ alkyl, halogen, —$OC_{1-3}$ alkyl, CN, $C_{2-6}$ alkenyl, $C_{2-6}$ alkynyl, C(O)$R^{12}$, $NR^{13}R^{14}$ or hydroxyl;

$R^{16}$ is H;

$R^{18}$ is H;

$R^9$ is H or substituted or unsubstituted $C_{1-6}$ alkyl;

$R^{10}$ is H or substituted or unsubstituted $C_{1-6}$ alkyl;

$R^{11}$ is H or substituted or unsubstituted $C_{1-6}$ alkyl;

$R^{12}$ is H or substituted or unsubstituted $C_{1-6}$ alkyl;

$R^{13}$ is H or substituted or unsubstituted $C_{1-6}$ alkyl;

$R^{14}$ is H or substituted or unsubstituted $C_{1-6}$ alkyl;

$R^{19}$ is H or substituted or unsubstituted $C_{1-6}$ alkyl;

$R^{20}$ is H or substituted or unsubstituted $C_{1-6}$ alkyl;

$R^{21}$ is H or substituted or unsubstituted $C_{1-6}$ alkyl;

$R^{22}$ is H or substituted or unsubstituted $C_{1-6}$ alkyl;

$R^{23}$ is H or substituted or unsubstituted $C_{1-6}$ alkyl;

$R^{24}$ is H or substituted or unsubstituted $C_{1-6}$ alkyl;

and including compounds:

N-[3-({[4-chloro-3-(trifluoromethyl)phenyl] sulfonyl}amino)pyridin-2-yl]thiophene-2-sulfonamide;

N-[2-({[4-chloro-3-(trifluoromethyl)phenyl] sulfonyl}amino)phenyl]thiophene-2-sulfonamide N-{4,5-dichloro-2-[(3-thienylsulfonyl)amino]phenyl}thiophene-2-sulfonamide;

and with the provisos:

a) $R^6$ is not the same as $R^5$;

b) when $R^5$ is a substituted heterocycle then it is not

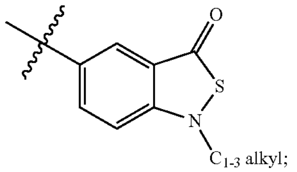

c). when $R^6$ is 2-thienyl then $R^7$, $R^8$, $R^{16}$ and $R^{18}$ are not all hydrogen in same time;

d). the compound is not of the following structures:

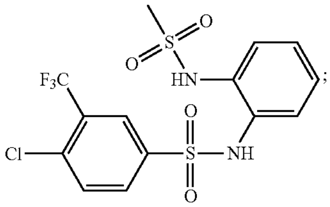

;

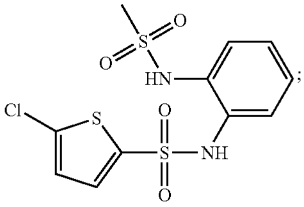

;

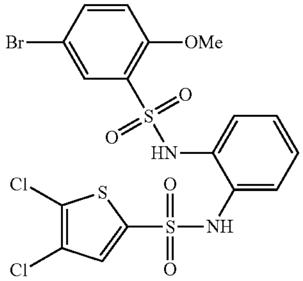

or

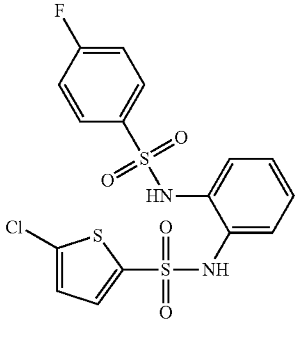

.

In another aspect, the invention provides a compound having Formula I wherein:

$R^1$ is H or substituted or unsubstituted $C_{1-6}$ alkyl;

$R^2$ is H or substituted or unsubstituted $C_{1-6}$ alkyl;

$R^3$ is C—$R^7$;

$R^4$ is C—$R^8$;

$R^5$ is substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl or is substituted or unsubstituted phenyl;

$R^6$ is 2-benzofuran;

$R^{15}$ is C—$R^{16}$;

$R^{17}$ is C—$R^{18}$;

$R^7$ is H, substituted or unsubstituted $C_{1-6}$ alkyl, halogen, —$OC_{1-3}$ alkyl, CN, $C_{2-6}$ alkenyl, $C_{2-6}$ alkynyl, C(O)$R^9$, $NR^{10}R^{11}$ or hydroxyl;

$R^8$ is H, substituted or unsubstituted $C_{1-6}$ alkyl, halogen, —$OC_{1-3}$ alkyl, CN, $C_{2-6}$ alkenyl, $C_{2-6}$ alkynyl, C(O)$R^{12}$, $NR^{13}R^{14}$ or hydroxyl;

$R^{16}$ is H;

$R^{18}$ is H;

$R^9$ is H or substituted or unsubstituted $C_{1-6}$ alkyl;

$R^{10}$ is H or substituted or unsubstituted $C_{1-6}$ alkyl;

$R^{11}$ is H or substituted or unsubstituted $C_{1-6}$ alkyl;

$R^{12}$ is H or substituted or unsubstituted $C_{1-6}$ alkyl;

$R^{13}$ is H or substituted or unsubstituted $C_{1-6}$ alkyl;

$R^{14}$ is H or substituted or unsubstituted $C_{1-6}$ alkyl;

$R^{19}$ is H or substituted or unsubstituted $C_{1-6}$ alkyl;

$R^{20}$ is H or substituted or unsubstituted $C_{1-6}$ alkyl;

$R^{21}$ is H or substituted or unsubstituted $C_{1-6}$ alkyl;

$R^{22}$ is H or substituted or unsubstituted $C_{1-6}$ alkyl;

$R^{23}$ is H or substituted or unsubstituted $C_{1-6}$ alkyl;

$R^{24}$ is H or substituted or unsubstituted $C_{1-6}$ alkyl;

and including compounds:

N-[3-({[4-chloro-3-(trifluoromethyl)phenyl]sulfonyl}amino)pyridin-2-yl]thiophene-2-sulfonamide;

N-[2-({[4-chloro-3-(trifluoromethyl)phenyl]sulfonyl}amino)phenyl]thiophene-2-sulfonamide N-{4,5-dichloro-2-[(3-thienylsulfonyl)amino]phenyl}thiophene-2-sulfonamide;

and with the provisos:

a) $R^6$ is not the same as $R^5$;

b) when $R^5$ is a substituted heterocycle then it is not

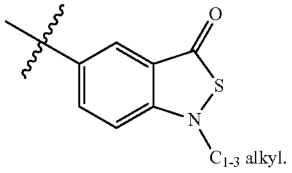

In another aspect, the invention provides a compound having Formula I wherein:

$R^1$ is H or substituted or unsubstituted $C_{1-6}$ alkyl;

$R^2$ is H or substituted or unsubstituted $C_{1-6}$ alkyl;

$R^3$ is C—$R^7$;

$R^4$ is C—$R^8$;

$R^5$ is substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl or is substituted or unsubstituted $C_{6-10}$ aryl;

$R^6$ is 2-thienyl;

$R^{15}$ is C—$R^{16}$;

$R^{17}$ is C—$R^{18}$;

$R^7$ is H, substituted or unsubstituted $C_{1-6}$ alkyl, halogen, —$OC_{1-3}$ alkyl, CN, $C_{2-6}$ alkenyl, $C_{2-6}$ alkynyl, C(O)$R^9$, $NR^{10}R^{11}$ or hydroxyl;

$R^8$ is H, substituted or unsubstituted $C_{1-6}$ alkyl, halogen, —$OC_{1-3}$ alkyl, CN, $C_{2-6}$ alkenyl, $C_{2-6}$ alkynyl, C(O)$R^{12}$, $NR^{13}R^{14}$ or hydroxyl;

$R^{16}$ is H;

$R^{18}$ is H;

$R^9$ is H or substituted or unsubstituted $C_{1-6}$ alkyl;

$R^{10}$ is H or substituted or unsubstituted $C_{1-6}$ alkyl;
$R^{11}$ is H or substituted or unsubstituted $C_{1-6}$ alkyl;
$R^{12}$ is H or substituted or unsubstituted $C_{1-6}$ alkyl;
$R^{13}$ is H or substituted or unsubstituted $C_{1-6}$ alkyl;
$R^{14}$ is H or substituted or unsubstituted $C_{1-6}$ alkyl;
$R^{19}$ is H or substituted or unsubstituted $C_{1-6}$ alkyl;
$R^{20}$ is H or substituted or unsubstituted $C_{1-6}$ alkyl;
$R^{21}$ is H or substituted or unsubstituted $C_{1-6}$ alkyl;
$R^{22}$ is H or substituted or unsubstituted $C_{1-6}$ alkyl;
$R^{23}$ is H or substituted or unsubstituted $C_{1-6}$ alkyl;
$R^{24}$ is H or substituted or unsubstituted $C_{1-6}$ alkyl;
and including compounds:
N-[3-({[4-chloro-3-(trifluoromethyl)phenyl]sulfonyl}amino)pyridin-2-yl]thiophene-2-sulfonamide;
N-[2-({[4-chloro-3-(trifluoromethyl)phenyl]sulfonyl}amino)phenyl]thiophene-2-sulfonamide
N-{4,5-dichloro-2-[(3-thienylsulfonyl)amino]phenyl}thiophene-2-sulfonamide; and with the provisos:
a) $R^6$ is not the same as $R^5$;
b) when $R^5$ is a substituted heterocycle then it is not

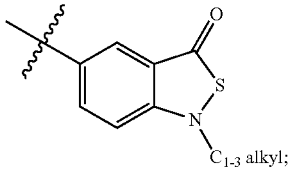

c). when $R^6$ is 2-thienyl then $R^7$, $R^8$, $R^{16}$ and $R^{18}$ are not all hydrogen in same time.

In another aspect, the invention provides a compound having Formula I wherein:
$R^1$ is H or substituted or unsubstituted $C_{1-6}$ alkyl;
$R^2$ is H or substituted or unsubstituted $C_{1-6}$ alkyl;
$R^3$ is C—$R^7$;
$R^4$ is C—$R^8$;
$R^5$ is substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl or is substituted or unsubstituted $C_{6-10}$ aryl;
$R^6$ is 4-chloro-3-trifluoromethylphenyl;
$R^{15}$ is C—$R^{16}$;
$R^{17}$ is C—$R^{16}$;
$R^7$ is H, substituted or unsubstituted $C_{1-6}$ alkyl, halogen, —$OC_{1-3}$ alkyl, CN, $C_{2-6}$ alkenyl, $C_{2-6}$ alkynyl, $C(O)R^9$, $NR^{10}R^{11}$ or hydroxyl;
$R^8$ is H, substituted or unsubstituted $C_{1-6}$ alkyl, halogen, —$OC_{1-3}$ alkyl, CN, $C_{2-6}$ alkenyl, $C_{2-6}$ alkynyl, $C(O)R^{12}$, $NR^{13}R^{14}$ or hydroxyl;
$R^{16}$ is H;
$R^{18}$ is H;
$R^9$ is H or substituted or unsubstituted $C_{1-6}$ alkyl;
$R^{10}$ is H or substituted or unsubstituted $C_{1-6}$ alkyl;
$R^{11}$ is H or substituted or unsubstituted $C_{1-6}$ alkyl;
$R^{12}$ is H or substituted or unsubstituted $C_{1-6}$ alkyl;
$R^{13}$ is H or substituted or unsubstituted $C_{1-6}$ alkyl;
$R^{14}$ is H or substituted or unsubstituted $C_{1-6}$ alkyl;
$R^{19}$ is H or substituted or unsubstituted $C_{1-6}$ alkyl;
$R^{20}$ is H or substituted or unsubstituted $C_{1-6}$ alkyl;
$R^{21}$ is H or substituted or unsubstituted $C_{1-6}$ alkyl;
$R^{22}$ is H or substituted or unsubstituted $C_{1-6}$ alkyl;
$R^{23}$ is H or substituted or unsubstituted $C_{1-6}$ alkyl;
$R^{24}$ is H or substituted or unsubstituted $C_{1-6}$ alkyl;
and including compounds:
N-[3-({[4-chloro-3-(trifluoromethyl)phenyl]sulfonyl}amino)pyridin-2-yl]thiophene-2-sulfonamide;
N-[2-({[4-chloro-3-(trifluoromethyl)phenyl]sulfonyl}amino)phenyl]thiophene-2-sulfonamide
N-{4,5-dichloro-2-[(3-thienylsulfonyl)amino]phenyl}thiophene-2-sulfonamide; and with the provisos:
a) $R^6$ is not the same as $R^5$;
b) when $R^5$ is a substituted heterocycle then it is not

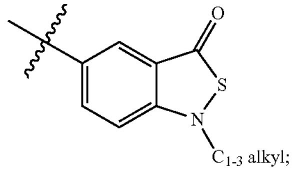

d). the compound is not of the following structure:

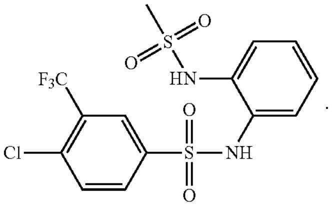 [SMILES: CS(=O)(=O)Nc1ccccc1NS(=O)(=O)c1ccc(Cl)c(C(F)(F)F)c1]

In another aspect, the invention provides a compound having Formula I wherein:
$R^1$ is H or substituted or unsubstituted $C_{1-6}$ alkyl;
$R^2$ is H or substituted or unsubstituted $C_{1-6}$ alkyl;
$R^3$ is C—$R^7$;
$R^4$ is C—$R^8$;
$R^5$ is substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl or is substituted or unsubstituted $C_{6-10}$ aryl;
$R^6$ is 5-chloro-2-thienyl, 4,5-dichloro-2-thienyl or 4-chloro-3-methylphenyl;
$R^{15}$ is C—$R^{16}$;
$R^{17}$ is C—$R^{18}$;
$R^7$ is H, substituted or unsubstituted $C_{1-8}$ alkyl, halogen, —$OC_{1-3}$ alkyl, CN, $C_{2-6}$ alkenyl, $C_{2-6}$ alkynyl, $C(O)R^9$, $NR^{10}R^{11}$ or hydroxyl;
$R^8$ is H, substituted or unsubstituted $C_{1-6}$ alkyl, halogen, —$OC_{1-3}$ alkyl, CN, $C_{2-6}$ alkenyl, $C_{2-6}$ alkynyl, $C(O)R^{12}$, $NR^{13}R^{14}$ or hydroxyl;
$R^{16}$ is H;
$R^{18}$ is H;
$R^9$ is H or substituted or unsubstituted $C_{1-6}$ alkyl;
$R^{10}$ is H or substituted or unsubstituted $C_{1-6}$ alkyl;
$R^{11}$ is H or substituted or unsubstituted $C_{1-6}$ alkyl;
$R^{12}$ is H or substituted or unsubstituted $C_{1-6}$ alkyl;
$R^{13}$ is H or substituted or unsubstituted $C_{1-6}$ alkyl;
$R^{14}$ is H or substituted or unsubstituted $C_{1-6}$ alkyl;
$R^{19}$ is H or substituted or unsubstituted $C_{1-6}$ alkyl;
$R^{20}$ is H or substituted or unsubstituted $C_{1-6}$ alkyl;
$R^{21}$ is H or substituted or unsubstituted $C_{1-6}$ alkyl;
$R^{22}$ is H or substituted or unsubstituted $C_{1-6}$ alkyl;
$R^{23}$ is H or substituted or unsubstituted $C_{1-6}$ alkyl;
$R^{24}$ is H or substituted or unsubstituted $C_{1-6}$ alkyl;
and including compounds:
N-[3-({[4-chloro-3-(trifluoromethyl)phenyl]sulfonyl}amino)pyridin-2-yl]thiophene-2-sulfonamide;

N-[2-({[4-chloro-3-(trifluoromethyl)phenyl]sulfonyl}amino)phenyl]thiophene-2-sulfonamide N-{4,5-dichloro-2-[(3-thienylsulfonyl)amino]phenyl}thiophene-2-sulfonamide;

and with the provisos:

a) $R^6$ is not the same as $R^5$;

b) when $R^5$ is a substituted heterocycle then it is not

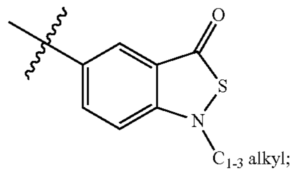

d). the compound is not of the following structures:

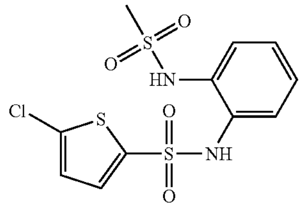

;

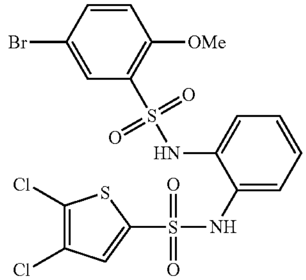

or

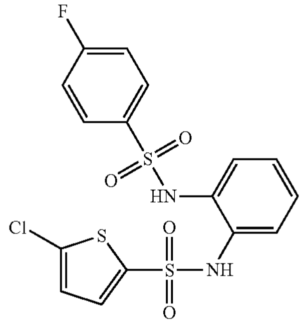

.

In another aspect, the invention provides a compound having Formula I wherein:

$R^1$ is H or substituted or unsubstituted $C_{1-6}$ alkyl;

$R^2$ is H or substituted or unsubstituted $C_{1-6}$ alkyl;

$R^3$ is C—$R^7$;

$R^4$ is C—$R^8$;

$R^5$ is substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl or is substituted or unsubstituted $C_{6-10}$ aryl;

$R^6$ is 2-benzofuran, 2-thienyl, 5-chloro-2-thienyl, 4,5-dichloro-2-thienyl, 4-chloro-3-methylphenyl, or 4-chloro-3-trifluoromethylphenyl;

$R^{15}$ is C—$R^{16}$;

$R^{17}$ is C—$R^{18}$;

$R^7$ is H, substituted or unsubstituted $C_{1-6}$ alkyl;

$R^8$ is H, substituted or unsubstituted $C_{1-6}$ alkyl;

$R^{16}$ is H;

$R^{18}$ is H;

and including compounds:

N-[3-({[4-chloro-3-(trifluoromethyl)phenyl]sulfonyl}amino)pyridin-2-yl]thiophene-2-sulfonamide;

N-[2-({[4-chloro-3-(trifluoromethyl)phenyl]sulfonyl}amino)phenyl]thiophene-2-sulfonamide N-{4,5-dichloro-2-[(3-thienylsulfonyl)amino]phenyl}thiophene-2-sulfonamide; and with the provisos:

a) $R^6$ is not the same as $R^5$;

b) when $R^5$ is a substituted heterocycle then it is not

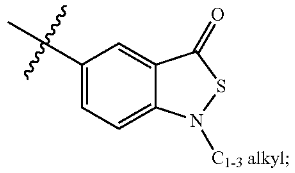

c). when $R^6$ is 2-thienyl then $R^7$, $R^8$, $R^{16}$ and $R^{18}$ are not all hydrogen in same time;

d). the compound is not of the following structures:

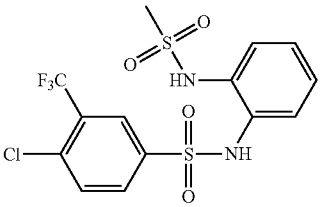

;

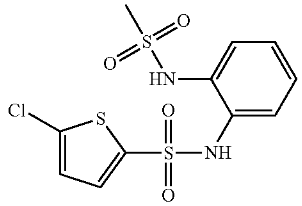

;

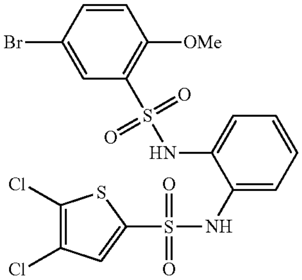

or

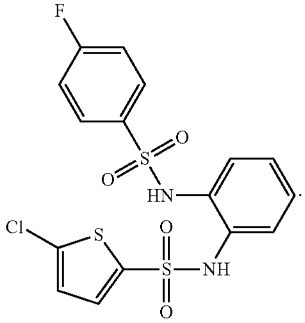

.

In another aspect, the invention provides a compound having Formula I wherein:

$R^1$ is H or substituted or unsubstituted $C_{1-6}$ alkyl;

$R^2$ is H or substituted or unsubstituted $C_{1-6}$ alkyl;

$R^3$ is C—$R^7$;

$R^4$ is C—$R^8$;

$R^5$ is substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl or is substituted or unsubstituted $C_{6-10}$ aryl;

$R^6$ is 2-benzofuran;

$R^{15}$ is C—$R^{16}$;

$R^{17}$ is C—$R^{18}$;

$R^7$ is H, substituted or unsubstituted $C_{1-6}$ alkyl;

$R^8$ is H, substituted or unsubstituted $C_{1-6}$ alkyl;

$R^{16}$ is H;

$R^{18}$ is H;

and including compounds:

N-[3-({[4-chloro-3-(trifluoromethyl)phenyl]sulfonyl}amino)pyridin-2-yl]thiophene-2-sulfonamide;

N-[2-({[4-chloro-3-(trifluoromethyl)phenyl]sulfonyl}amino)phenyl]thiophene-2-sulfonamide N-{4,5-dichloro-2-[(3-thienylsulfonyl)amino]phenyl}thiophene-2-sulfonamide;

and with the provisos:

a) $R^6$ is not the same as $R^5$;

b) when $R^5$ is a substituted heterocycle then it is not

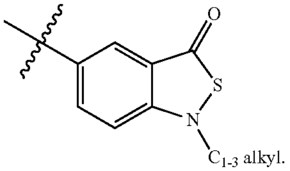

In another aspect, the invention provides a compound having Formula I wherein:

$R^1$ is H or substituted or unsubstituted $C_{1-6}$ alkyl;

$R^2$ is H or substituted or unsubstituted $C_{1-6}$ alkyl;

$R^3$ is C—$R^7$;

$R^4$ is C—$R^8$;

$R^5$ is substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl or is substituted or unsubstituted $C_{6-10}$ aryl;

$R^6$ is 2-thienyl;

$R^{15}$ is C—$R^{16}$;

$R^{17}$ is C—$R^{18}$;

$R^7$ is H, substituted or unsubstituted $C_{1-6}$ alkyl;

$R^8$ is H, substituted or unsubstituted $C_{1-6}$ alkyl;

$R^{16}$ is H;

$R^{18}$ is H;

and including compounds:

N-[3-({[4-chloro-3-(trifluoromethyl)phenyl]sulfonyl}amino)pyridin-2-yl]thiophene-2-sulfonamide;

N-[2-({[4-chloro-3-(trifluoromethyl)phenyl]sulfonyl}amino)phenyl]thiophene-2-sulfonamide N-{4,5-dichloro-2-[(3-thienylsulfonyl)amino]phenyl}thiophene-2-sulfonamide;

and with the provisos:

a) $R^6$ is not the same as $R^5$;

b) when $R^5$ is a substituted heterocycle then it is no

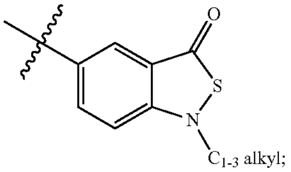

c). when $R^6$ is 2-thienyl then $R^7$, $R^8$, $R^{16}$ and $R^{18}$ are not all hydrogen in same time.

In another aspect, the invention provides a compound having Formula I wherein:

$R^1$ is H or substituted or unsubstituted $C_{1-6}$ alkyl;

$R^2$ is H or substituted or unsubstituted $C_{1-6}$ alkyl;

$R^3$ is C—$R^7$;

$R^4$ is C—$R^8$;

$R^5$ is substituted or unsubstituted $C_{1-6}$ alkyl, substituted or unsubstituted heterocycle, substituted or unsubstituted $C_{3-8}$ cycloalkyl, substituted or unsubstituted $C_{3-8}$ cycloalkenyl or is substituted or unsubstituted $C_{6-10}$ aryl;

$R^6$ is 4-chloro-3-trifluoromethylphenyl;

$R^{15}$ is C—$R^{16}$;

$R^{17}$ is C—$R^{18}$;

$R^7$ is H, substituted or unsubstituted $C_{1-6}$ alkyl;

$R^8$ is H, substituted or unsubstituted $C_{1-6}$ alkyl;

$R^{16}$ is H;

$R^{18}$ is H;

and including compounds:

N-[3-({[4-chloro-3-(trifluoromethyl)phenyl]sulfonyl}amino)pyridin-2-yl]thiophene-2-sulfonamide;

N-[2-({[4-chloro-3-(trifluoromethyl)phenyl]sulfonyl}amino)phenyl]thiophene-2-sulfonamide N-{4,5-dichloro-2-[(3-thienylsulfonyl)amino]phenyl}thiophene-2-sulfonamide;

and with the provisos:

a). $R^6$ is not the same as $R^5$;

a) when $R^5$ is a substituted heterocycle then it is not

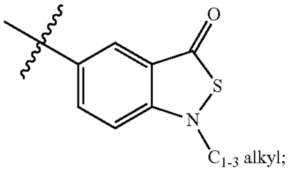

d). the compound is not of the following structures:

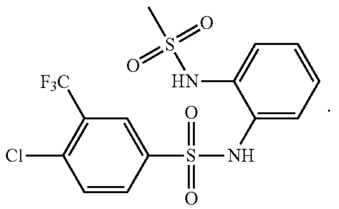 [SMILES: CS(=O)(=O)Nc1ccccc1NS(=O)(=O)c1ccc(Cl)c(C(F)(F)F)c1]

In another aspect, the invention provides a compound having Formula I wherein:

$R^1$ is H;

$R^2$ is H;

$R^3$ is C—$R^7$;

$R^4$ is C—$R^8$;

$R^5$ is 2-thienyl, phenyl, phenyl-4-acetamide, 4-chloro-3-trifluoromethylphenyl, -1-methyl-1H-imidazole, 3-pyridine, 2 aminophenyl, 1,3-dimethyl-1H-pyrazole, 1-methyl-1H-pyrazole, 1-methyl-1H-imidazole, 4-(1H-pyrazol-1-yl)phenyl, 1,3-thiazol-4-yl)phenyl, 4-(1,3-oxazol-5-yl)phenyl, 2-(methylamino)benzoate, 1-methyl-1H-indole, 2-oxoindoline, 1-methyl-2,3-dioxoindoline, 1-methyl-2-oxoindoline, 2-furan, 4-biphenyl, 3,5-difluorophenyl, 3,5-dichlorophenyl, -3,5-dimethylisoxazole, 4-chloro-2,5-difluorophenyl, 4-(2-methylphenoxy)phenyl, 5-isoxazol-3-ylthiophene, 2,6-dichlorophenyl, 4-(methylsulfonyl)phenyl, 3,4-difluorophenyl, 4-chloro-3-methylphenyl, 2-oxo-2,3-dihydro-1,3-benzoxazole, 4-benzoic acid, 2-methoxybenzoic acid, 3-cyanophenyl, 4-tert-butylphenyl, 1,3-benzothiazole, 1H-1,2,4-triazole, 2-chloro-1,3-benzothiazole, 2,4-dimethoxyphenyl, 2,5-dichloro-3-thienyl, 3-methoxyphenyl, 3-(methylsulfonyl)phenyl, 3-chloro-2-methylphenyl, 4-phenylpropanoic acid, 2-ethoxybenzoic acid, 2-methylphenyl}acetamide, 3,5-bis(trifluoromethyl)phenyl, 1H-pyrazole, 4-(trifluoromethoxy)phenyl, 4-(benzyloxy)phenyl, 2-chloro-4-fluorobenzoic acid, thiophene-2-carboxylate, 4-fluorobenzoic acid, 2-chloro-quinoline, 2,3-dihydro-1H-inden, 1-nathphtyl, 1,3-benzodioxole, 3,5-dichloro-2-hydroxyphenyl, 2-benzofuran, quinoline, 4-methylbenzoate, 2,4-dimethyl-1,3-thiazole, 4-methyl-1,3-thiazol-2-yl}acetamide, 5-chloro-8-quinoline, 2,4,5-trifluorophenyl, 3,4-dimethoxyphenyl, 3,5-dimethyl-1H-pyrazole, 1-(phenylsulfonyl)-1H-pyrrole, N-acetylindoline, 1,3,4-oxadiazol-2-yl-phenyl, 3-(1-methyl-1H-pyrazol-3-yl)phenyl, 2-thienylsulfonyl)amino]phenyl-4-methyl, 2-oxo-2H-chromene, 6-phenyl-3-pyridine, 2-chloro-4-(trifluoromethyl)phenyl, 6-phenoxypyridine, 5-phenylthiophene, 2,5-dimethyl-3-thienyl, 2-chlorophenyl-4-acetamide, (5-chloro-2,4-difluorophenyl, 4-(1-methyl-1H-pyrazol-3-yl)phenyl, 5-methyl-1-benzothiophene, 2,5-dimethylfuran, 4-(pyrrolidin-1-ylsulfonyl)phenyl, methyl-2-methyl-3-furoate, 3-oxo-3,4-dihydro-2H-1,4-benzoxazine, 2,4-dichloro-benzoic acid, 5-{[(dimethylamino)carbonyl]amino}-2-ethoxyphenyl, 2-methoxyphenyl}acetamide, 2-imidazo[2,1-b][1,3]thiazole, 6-morpholin-4-ylpyridine, 3-[(6-methylpyrazin-2-yl)oxy]phenyl, 5-pyridin-2-ylthiophene, 3-pyrimidin-2-ylphenyl, 4-dihydro-2H-pyrido[3,2-b][1,4]oxazine, 6-(dimethylamino)-2-naphthyl, 2-(methylsulfonyl)phenyl, 3-methyl-8-quinoline, 5-isoxazol-5-ylthiophene, 5-(dimethylamino)-1-naphthyl, 2-chloro-thienyl, methyl, ethyl, benzyl, isso-butyl, 2,2-dimethylchromane, 2-oxo-2,3,4,5-tetrahydro-1H-1-benzazepine, 4-methyl-3,4-dihydro-2H-1,4-benzoxazine, 4-acetyl-3,4-dihydro-2H-1,4-benzoxazine, 4-(benzyloxy)phenyl, 2,4-dimethyl-1,3-thiazole, 3,5-dimethylisoxazole, 5-chloro-3-methyl-1-benzothien-2-yl, 2-chloro-4-fluorobenzoic acid, 4-methyl-1,3-thiazol-2-yl}acetamide, 1H-1,2,4-triazole, phenyl}propanoic acid, 5-chlorothiophene-2-carboxylate, 3-phenylacetamide, 2-oxoindoline, 2-oxo-2,3-dihydro-1,3-benzoxazole, 5-isoxazol-3-yl-2-thienyl, 2-chloroquinoline, 1-(phenylsulfonyl)-1H-pyrrole, 2,5-dichloro-3-thienyl, 5-{[(dimethylamino)carbonyl]amino}-2-ethoxyphenyl, 6-morpholin-4-ylpyridine, 4-methoxythiophene, 3-furyl, 1-methyl-1H-pyrazole, 6-chloroimidazo[2,1-b][1,3]thiazole, 3-(5-methyl-1,2,4-oxadiazol-3-yl)phenyl, 3-pyrimidin-2-ylphenyl, 1-acetylindoline, isonicotinate, 3-(5-methyl-1,3,4-oxadiazol-2-yl)phenyl, 4-(3,5-dimethyl-1H-pyrazol-1-yl)phenyl, 3,5-dimethyl-1-phenyl-1H-pyrazole, 4-methyl-3,4-dihydro-2H-1,4-benzoxazine, 3,4-dihydro-2H-1,5-benzodioxepine, 2,2-dimethylchromane, 4-methyl-2-phenyl-1,3-thiazole, 5-pyridin-2-yl-2-thienyl, 4-methyl-3,4-dihydro-2H-pyrido[3,2-b][1,4]oxazine, 3-oxo-3,4-dihydro-2H-1,4-benzoxazine, 5,6-dichloro-3-pyridine, 2,3-dioxo-1,2,3,4-tetrahydroquinoxaline or 4-acetyl-3,4-dihydro-2H-1,4-benzoxazine;

$R^6$ is 2-benzofuran or 2-thienyl;

$R^{15}$ is C—$R^{16}$;

$R^{17}$ is N or C—$R^{18}$;

$R^7$ is H, methyl or chlorine;

$R^8$ is H or chlorine;

$R^{16}$ is H;

$R^{18}$ is H; and with the provisos:

a) $R^6$ is not the same as $R^5$;

b). when $R^6$ is 2-thienyl then $R^7$, $R^8$, $R^{16}$ and $R^{18}$ are not all hydrogen in same time.

The term "alkyl", as used herein, refers to saturated, monovalent or divalent hydrocarbon moieties having linear or branched moieties or combinations thereof and containing 1 to 6 carbon atoms. One methylene (—$CH_2$—) group, of the alkyl can be replaced by oxygen, sulfur, sulfoxide, nitrogen, carbonyl, carboxyl, sulfonyl, or by a divalent $C_{3-6}$ cycloalkyl. Hydrogen atoms on alkyl groups can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, ketones, sulfonamides groups, aryl, carboxylic acid and derivatives such as esters and amides, phosphonic acid groups, sulphonic acid groups, phosphoric acid.

The term "cycloalkyl", as used herein, refers to a monovalent or divalent group of 3 to 12 carbon atoms, derived from a saturated cyclic hydrocarbon. Cycloalkyl groups can be monocyclic or polycyclic. Cycloalkyl can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, sulfonamides groups, aryl, carboxylic acid and derivatives such as esters and amides, phosphonic acid groups, sulphonic acid groups, phosphoric acid.

The term "cycloalkenyl", as used herein, refers to a monovalent or divalent group of 3 to 12 carbon atoms, derived from a saturated cycloalkyl having one or more double bond. Cycloalkenyl groups can be monocyclic or polycyclic. Cycloalkenyl groups can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, sulfonamides groups, aryl, carboxylic acid and derivatives such as esters and amides, phosphonic acid groups, sulphonic acid groups, phosphoric acid.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, sulfonamides groups, aryl, carboxylic acid and derivatives such as esters and amides, phosphonic acid groups, sulphonic acid groups, phosphoric acid The term "alkynyl", as used herein, refers to a monovalent or divalent hydrocarbon radical having 2 to 6 carbon atoms, derived from a saturated alkyl, having at least one triple bond.

The term "heterocycle" as used herein, refers to a 3 to 12 membered ring, which can be aromatic or non-aromatic, saturated or non-saturated, containing at least one heteroatom selected from O or N or S or combinations of at least two thereof, interrupting the carbocyclic ring structure. The heterocyclic ring can be interrupted by a C═O; the S heteroatom can be oxidized. Heterocycles can be monocyclic or polycyclic. Heterocyclic ring moieties can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, ketones, sulfonamides groups, aryl, carboxylic acid and derivatives such as esters and amides, phosphonic acid groups, sulphonic acid groups, phosphoric acid.

Usually, in the present case, heterocyclic groups are pyridine, furan, azetidine, thiazol, thiophene, oxazol, pyrazol, benzofuran, isoxazole, 2-oxoindoline, 2-oxo-2,3-dihydro-1,3-benzoxazole, 2-oxo-2H-chromene, imidazole[2,1-b]thiazole1-H-pyrazole, indole, imidazole, quinoline.

The term "aryl" as used herein, refers to an organic moiety derived from an aromatic hydrocarbon consisting of a ring containing 6 to 10 carbon atoms. By removal of one hydrogen, aryl can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, ketones, sulfonamides groups, aryl, carboxylic acid and derivatives such as esters and amides, phosphonic acid groups, sulphonic acid groups, phosphoric acid. Aryl can be monocyclic or bicyclic.

The term "ketone" as used herein, represents a group of formula "—C(O)$R^x$" wherein $R^x$ is $C_{1-6}$ alkyl.

The term "hydroxyl" as used herein, represents a group of formula "—OH".

The term "amino" as used herein, represents a group of formula "—$NH_2$".

The term "carbonyl" as used herein, represents a group of formula "—C(O)".

The term "carboxyl" as used herein, represents a group of formula "—C(O)O—".

The term "sulfonyl" as used herein, represents a group of formula "—$SO_2$-".

The term "sulfate" as used herein, represents a group of formula "—O—S$(O)_2$—O—".

The term "carboxylic acid" as used herein, represents a group of formula "—C(O)OH".

The term "sulfoxide" as used herein, represents a group of formula "—S═O".

The term "phosphoric acid" as used herein, represents a group of formula "—P(O)$(OH)_2$".

The term "phosphoric acid" as used herein, represents a group of formula "—(O)P(O)$(OH)_2$".

The term "sulphonic acid" as used herein, represents a group of formula "—S$(O)_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

The term "amine" as used herein, represents a group of formula "—$NR^xR^y$", wherein $R^x$ and $R^y$ can be the same or independently H, alkyl, aryl, cycloalkyl, cycloalkenyl, heterocycle as defined above.

The term "amide" as used herein, represents a group of formula "—C(O)$NR^xR^y$," or "—C(O)N($R^x$)($R^y$)" or "$NR^x$C(O)$R^y$" wherein $R^x$ and $R^y$ can be the same or independently H, alkyl, aryl, cycloalkyl, cycloalkenyl, heterocycle as defined above.

The term "sulfonamide" as used herein, represents a group of formula "—S$(O)_2NR^xR^y$" or "$NR^xR^y$S$(O)_2$" or "—$NR^x$S$(O)_2R^y$" wherein $R^x$ and $R^y$ can be the same or independently H, alkyl, aryl, cycloalkyl, cycloalkenyl, heterocycle as defined above.

The term "ester" as used herein, represents a group of formula "—C(O)O($R^x$)", wherein $R^x$ is alkyl, aryl, cycloalkyl, cycloalkenyl, heterocycle as defined above.

The term "aldehyde" as used herein, represents a group of formula "—C(O)H".

Some compounds of the invention are:

N-[2-({[4-chloro-3-(trifluoromethyl)phenyl]sulfonyl}amino)phenyl]thiophene-2-sulfonamide;

N-{4,5-dichloro-2-[(phenylsulfonyl)amino]phenyl}thiophene-2-sulfonamide;

N-{4-[({4,5-dichloro-2-[(2-thienylsulfonyl)amino]phenyl}amino)sulfonyl]phenyl}acetamide;

N-[5-chloro-2-({[4-chloro-3-(trifluoromethyl)phenyl]sulfonyl}amino)-4-methylphenyl]thiophene-2-sulfonamide;

N-[2-({[4-chloro-3-(trifluoromethyl)phenyl]sulfonyl}amino)phenyl]-1-methyl-1H-imidazole-4-sulfonamide;

N-[5-chloro-2-({[4-chloro-3-(trifluoromethyl)phenyl]sulfonyl}amino)-4-methylphenyl]pyridine-3-sulfonamide;

N-(2-{[(4-aminophenyl)sulfonyl]amino}-5-chlorophenyl)-4-chloro-3-(trifluoromethyl)benzenesulfonamide;

5-chloro-N-[5-chloro-2-({[4-chloro-3-(trifluoromethyl)phenyl]sulfonyl}amino)-4-methylphenyl]-1,3-dimethyl-1H-pyrazole-4-sulfonamide;

N-[5-chloro-2-({[4-chloro-3-(trifluoromethyl)phenyl]sulfonyl}amino)-4-methylphenyl]-1,3,5-trimethyl-1H-pyrazole-4-sulfonamide;

N-[5-chloro-2-({[4-chloro-3-(trifluoromethyl)phenyl]sulfonyl}amino)-4-methylphenyl]-1-methyl-1H-pyrazole-4-sulfonamide;

N-[5-chloro-2-({[4-chloro-3-(trifluoromethyl)phenyl]sulfonyl}amino)-4-methylphenyl]-1-methyl-1H-imidazole-4-sulfonamide;

4-chloro-N-{4-chloro-5-methyl-2-[(phenylsulfonyl)amino]phenyl}-3-(trifluoromethyl)benzenesulfonamide;

4-chloro-N-{5-chloro-2-[(phenylsulfonyl)amino]phenyl}-3-(trifluoromethyl)benzenesulfonamide;

N-[4,5-dichloro-2-({[4-(1H-pyrazol-1-yl)phenyl]sulfonyl}amino)phenyl]thiophene-2-sulfonamide;

N-[4,5-dichloro-2-({[4-(1H-pyrazol-1-yl)phenyl]sulfonyl}amino)phenyl]thiophene-2-sulfonamide;

N-[4-chloro-2-({[4-chloro-3-(trifluoromethyl)phenyl]sulfonyl}amino)phenyl]thiophene-2-sulfonamide;

N-[4,5-dichloro-2-({[4-(2-methyl-1,3-thiazol-4-yl)phenyl]sulfonyl}amino)phenyl]thiophene-2-sulfonamide;

N-[4,5-dichloro-2-({[4-(2-methyl-1,3-thiazol-4-yl)phenyl]sulfonyl}amino)phenyl]thiophene-2-sulfonamide;

N-[4,5-dichloro-2-({[4-(1,3-oxazol-5-yl)phenyl]sulfonyl}amino)phenyl]thiophene-2-sulfonamide;

methyl 5-[({4,5-dichloro-2-[(2-thienylsulfonyl)amino]phenyl}amino)sulfonyl]-2-(methylamino)benzoate;

5-[({4,5-dichloro-2-[(2-thienylsulfonyl)amino]phenyl}amino)sulfonyl]-2-(methylamino)benzoic acid;

N-{4,5-dichloro-2-[(2-thienylsulfonyl)amino]phenyl}-1-methyl-1H-indole-5-sulfonamide;

N-{4,5-dichloro-2-[(2-thienylsulfonyl)amino]phenyl}-2-oxoindoline-5-sulfonamide;

N-{4,5-dichloro-2-[(2-thienylsulfonyl)amino]phenyl}-2-oxoindoline-5-sulfonamide;
N-{4,5-dichloro-2-[(2-thienylsulfonyl)amino]phenyl}-1-methyl-2,3-dioxoindoline-5-sulfonamide;
N-{4,5-dichloro-2-[(2-thienylsulfonyl)amino]phenyl}-1-methyl-2-oxoindoline-5-sulfonamide;
N-{4,5-dichloro-2-[(2-thienylsulfonyl)amino]phenyl}furan-2-sulfonamide;
N-{2-[(biphenyl-4-ylsulfonyl)amino]-4,5-dichlorophenyl}thiophene-2-sulfonamide;
N-(4,5-dichloro-2-{[(3,5-difluorophenyl)sulfonyl]amino}phenyl)thiophene-2-sulfonamide;
N-(4,5-dichloro-2-{[(3,5-dichlorophenyl)sulfonyl]amino}phenyl)thiophene-2-sulfonamide;
N-{4,5-dichloro-2-[(2-thienylsulfonyl)amino]phenyl}-3,5-dimethylisoxazole-4-sulfonamide;
N-(4,5-dichloro-2-{[(4-chloro-2,5-difluorophenyl)sulfonyl]amino}phenyl)thiophene-2-sulfonamide;
N-[4,5-dichloro-2-({[4-(2-methylphenoxy)phenyl]sulfonyl}amino)phenyl]thiophene-2-sulfonamide;
N-{4,5-dichloro-2-[(2-thienylsulfonyl)amino]phenyl}-5-isoxazol-3-ylthiophene-2-sulfonamide;
N-(4,5-dichloro-2-{[(2,4-dimethylphenyl)sulfonyl]amino}phenyl)thiophene-2-sulfonamide;
N-(4,5-dichloro-2-{[(2,6-dichlorophenyl)sulfonyl]amino}phenyl)thiophene-2-sulfonamide;
N-(4,5-dichloro-2-{[(3-fluorophenyl)sulfonyl]amino}phenyl)thiophene-2-sulfonamide;
N-[4,5-dichloro-2-({[4-(methylsulfonyl)phenyl]sulfonyl}amino)phenyl]thiophene-2-sulfonamide;
N-(4,5-dichloro-2-{[(3,4-difluorophenyl)sulfonyl]amino}phenyl)thiophene-2-sulfonamide;
N-(4,5-dichloro-2-{[(3-methylphenyl)sulfonyl]amino}phenyl)thiophene-2-sulfonamide;
5-chloro-N-{4,5-dichloro-2-[(2-thienylsulfonyl)amino]phenyl}-3-methyl-1-benzothiophene-2-sulfonamide;
N-(4,5-dichloro-2-{[(4-chloro-3-methylphenyl)sulfonyl]amino}phenyl)thiophene-2-sulfonamide;
N-{4,5-dichloro-2-[(2-thienylsulfonyl)amino]phenyl}-2-oxo-2,3-dihydro-1,3-benzoxazole-6-sulfonamide;
4-[({4,5-dichloro-2-[(2-thienylsulfonyl)amino]phenyl}amino)sulfonyl]benzoic acid;
5-[({4,5-dichloro-2-[(2-thienylsulfonyl)amino]phenyl}amino)sulfonyl]-2-methoxybenzoic acid;
N-(4,5-dichloro-2-{[(3-chloro-4-methylphenyl)sulfonyl]amino}phenyl)thiophene-2-sulfonamide;
N-(4,5-dichloro-2-{[(3-cyanophenyl)sulfonyl]amino}phenyl)thiophene-2-sulfonamide;
N-(4,5-dichloro-2-{[(4-methylphenyl)sulfonyl]amino}phenyl)thiophene-2-sulfonamide;
N-(2-{[(4-tert-butylphenyl)sulfonyl]amino}-4,5-dichlorophenyl)thiophene-2-sulfonamide;
N-{4,5-dichloro-2-[(2-thienylsulfonyl)amino]phenyl}-1,3-benzothiazole-6-sulfonamide;
N-(4,5-dichloro-2-{[(2-chloro-4-fluorophenyl)sulfonyl]amino}phenyl)thiophene-2-sulfonamide;
N-{4,5-dichloro-2-[(2-thienylsulfonyl)amino]phenyl}-1H-1,2,4-triazole-5-sulfonamide;
2-chloro-N-{4,5-dichloro-2-[(2-thienylsulfonyl)amino]phenyl}-1,3-benzothiazole-6-sulfonamide;
N-(4,5-dichloro-2-{[(3,4-dimethylphenyl)sulfonyl]amino}phenyl)thiophene-2-sulfonamide;
N-(4,5-dichloro-2-{[(2,4-dimethoxyphenyl)sulfonyl]amino}phenyl)thiophene-2-sulfonamide;
N-(4,5-dichloro-2-{[(2,5-dichloro-3-thienyl)sulfonyl]amino}phenyl)thiophene-2-sulfonamide;
N-(4,5-dichloro-2-{[(3-methoxyphenyl)sulfonyl]amino}phenyl)thiophene-2-sulfonamide;
N-[4,5-dichloro-2-({[4-(trifluoromethyl)phenyl]sulfonyl}amino)phenyl]thiophene-2-sulfonamide;
N-(4,5-dichloro-2-{[(3,4-dichlorophenyl)sulfonyl]amino}phenyl)thiophene-2-sulfonamide;
N-[4,5-dichloro-2-({[3-(methylsulfonyl)phenyl]sulfonyl}amino)phenyl]thiophene-2-sulfonamide;
N-(4,5-dichloro-2-{[(3-chloro-2-methylphenyl)sulfonyl]amino}phenyl)thiophene-2-sulfonamide;
3-{4-[({4,5-dichloro-2-[(2-thienylsulfonyl)amino]phenyl}amino)sulfonyl]phenyl}propanoic acid;
5-[({4,5-dichloro-2-[(2-thienylsulfonyl)amino]phenyl}amino)sulfonyl]-2-ethoxybenzoic acid;
N-{4-[({4,5-dichloro-2-[(2-thienylsulfonyl)amino]phenyl}amino)sulfonyl]-2-methylphenyl}acetamide;
N-[2-({[3,5-bis(trifluoromethyl)phenyl]sulfonyl}amino)-4,5-dichlorophenyl]thiophene-2-sulfonamide;
N-{4,5-dichloro-2-[(2-thienylsulfonyl)amino]phenyl}-1H-pyrazole-4-sulfonamide;
N-(4,5-dichloro-2-{[(3-chlorophenyl)sulfonyl]amino}phenyl)thiophene-2-sulfonamide;
N-[4,5-dichloro-2-({[4-(trifluoromethoxy)phenyl]sulfonyl}amino)phenyl]thiophene-2-sulfonamide;
N-[2-({[4-(benzyloxy)phenyl]sulfonyl}amino)-4,5-dichlorophenyl]thiophene-2-sulfonamide;
N-(4,5-dichloro-2-{[(2-fluorophenyl)sulfonyl]amino}phenyl)thiophene-2-sulfonamide;
2-chloro-5-[({4,5-dichloro-2-[(2-thienylsulfonyl)amino]phenyl}amino)sulfonyl]-4-fluorobenzoic acid;
methyl 5-chloro-3-[({4,5-dichloro-2-[(2-thienylsulfonyl)amino]phenyl}amino)sulfonyl]thiophene-2-carboxylate;
3-[({4,5-dichloro-2-[(2-thienylsulfonyl)amino]phenyl}amino)sulfonyl]-4-fluorobenzoic acid;
2-chloro-N-{4,5-dichloro-2-[(2-thienylsulfonyl)amino]phenyl}quinoline-6-sulfonamide;
N-(4,5-dichloro-2-{[(5-chloro-2-fluorophenyl)sulfonyl]amino}phenyl)thiophene-2-sulfonamide;
N-{4,5-dichloro-2-[(2,3-dihydro-1H-inden-5-ylsulfonyl)amino]phenyl}thiophene-2-sulfonamide;
N-(4,5-dichloro-2-{[(4-chlorophenyl)sulfonyl]amino}phenyl)thiophene-2-sulfonamide;
N-{4,5-dichloro-2-[(1-naphthylsulfonyl)amino]phenyl}thiophene-2-sulfonamide;
N-{4,5-dichloro-2-[(2-thienylsulfonyl)amino]phenyl}-1,3-benzodioxole-5-sulfonamide;
N-[4,5-dichloro-2-({[2-(trifluoromethoxy)phenyl]sulfonyl}amino)phenyl]thiophene-2-sulfonamide;
N-(4,5-dichloro-2-{[(3,5-dichloro-2-hydroxyphenyl)sulfonyl]amino}phenyl)thiophene-2-sulfonamide;
N-{4,5-dichloro-2-[(2-thienylsulfonyl)amino]phenyl}-1-benzofuran-5-sulfonamide;
N-(4,5-dichloro-2-{[(2,6-dimethylphenyl)sulfonyl]amino}phenyl)thiophene-2-sulfonamide;
N-{4,5-dichloro-2-[(2-thienylsulfonyl)amino]phenyl}quinoline-3-sulfonamide;
N-(4,5-dichloro-2-{[(2,3-dichlorophenyl)sulfonyl]amino}phenyl)thiophene-2-sulfonamide;
methyl 4-[({4,5-dichloro-2-[(2-thienylsulfonyl)amino]phenyl}amino)sulfonyl]benzoate;
N-{4,5-dichloro-2-[(2-thienylsulfonyl)amino]phenyl}quinoline-8-sulfonamide;
N-(4,5-dichloro-2-{[(2-chlorophenyl)sulfonyl]amino}phenyl)thiophene-2-sulfonamide;
N-{4,5-dichloro-2-[(2-thienylsulfonyl)amino]phenyl}-2,4-dimethyl-1,3-thiazole-5-sulfonamide;

N-(4,5-dichloro-2-{[(3-chloro-4-fluorophenyl)sulfonyl]amino}phenyl)thiophene-2-sulfonamide;

N-{5-[({4,5-dichloro-2-[(2-thienylsulfonyl)amino]phenyl}amino)sulfonyl]-4-methyl-1,3-thiazol-2-yl}acetamide;

N-{4,5-dichloro-2-[(2-thienylsulfonyl)amino]phenyl}isoquinoline-5-sulfonamide;

5-chloro-N-{4,5-dichloro-2-[(2-thienylsulfonyl)amino]phenyl}quinoline-8-sulfonamide;

N-(4,5-dichloro-2-{[(2,5-dichlorophenyl)sulfonyl]amino}phenyl)thiophene-2-sulfonamide;

N-(4,5-dichloro-2-{[(2,4,5-trifluorophenyl)sulfonyl]amino}phenyl)thiophene-2-sulfonamide;

N-(4,5-dichloro-2-{[(3,4-dimethoxyphenyl)sulfonyl]amino}phenyl)thiophene-2-sulfonamide;

N-(4,5-dichloro-2-{[(2-methoxyphenyl)sulfonyl]amino}phenyl)thiophene-2-sulfonamide;

N-[4,5-dichloro-2-({[3-(difluoromethoxy)phenyl]sulfonyl}amino)phenyl]thiophene-2-sulfonamide;

methyl 3-[({4,5-dichloro-2-[(2-thienylsulfonyl)amino]phenyl}amino)sulfonyl]thiophene-2-carboxylate;

N-(4,5-dichloro-2-{[(2,5-difluorophenyl)sulfonyl]amino}phenyl)thiophene-2-sulfonamide;

N-{4,5-dichloro-2-[(2-thienylsulfonyl)amino]phenyl}-3,5-dimethyl-1H-pyrazole-4-sulfonamide;

N-(4,5-dichloro-2-{[(2,4-difluorophenyl)sulfonyl]amino}phenyl)thiophene-2-sulfonamide;

N-{4,5-dichloro-2-[(2-thienylsulfonyl)amino]phenyl}quinoline-6-sulfonamide;

N-{4,5-dichloro-2-[(2-thienylsulfonyl)amino]phenyl}-1-(phenylsulfonyl)-1H-pyrrole-3-sulfonamide;

N-(4,5-dichloro-2-{[(3,5-dimethylphenyl)sulfonyl]amino}phenyl)thiophene-2-sulfonamide;

N-(4,5-dichloro-2-{[(4-methoxy-3-methylphenyl)sulfonyl]amino}phenyl)thiophene-2-sulfonamide;

N-(4,5-dichloro-2-{[(3-chloro-4-methoxyphenyl)sulfonyl]amino}phenyl)thiophene-2-sulfonamide;

N-{4,5-dichloro-2-[(2-thienylsulfonyl)amino]phenyl}-1-methyl-1H-pyrazole-5-sulfonamide;

1-acetyl-N-{4,5-dichloro-2-[(2-thienylsulfonyl)amino]phenyl}indoline-5-sulfonamide;

N-[4,5-dichloro-2-({[3-(5-methyl-1,3,4-oxadiazol-2-yl)phenyl]sulfonyl}amino)phenyl]thiophene-2-sulfonamide;

N-[4,5-dichloro-2-({[3-(1-methyl-1H-pyrazol-3-yl)phenyl]sulfonyl}amino)phenyl]thiophene-2-sulfonamide;

N-{4,5-dichloro-2-[(2-thienylsulfonyl)amino]phenyl}-4-methyl-2-phenyl-1,3-thiazole-5-sulfonamide;

N-{4,5-dichloro-2-[(2-thienylsulfonyl)amino]phenyl}-1-benzofuran-2-sulfonamide;

5-[({4,5-dichloro-2-[(2-thienylsulfonyl)amino]phenyl}amino)sulfonyl]-2-methylbenzoic acid;

N-{4,5-dichloro-2-[(2-thienylsulfonyl)amino]phenyl}-2-oxo-1,2,3,4-tetrahydroquinoline-6-sulfonamide;

N-{4,5-dichloro-2-[(2-thienylsulfonyl)amino]phenyl}-2-oxo-2H-chromene-6-sulfonamide;

N-{4,5-dichloro-2-[(2-thienylsulfonyl)amino]phenyl}-6-phenylpyridine-3-sulfonamide;

ethyl 3-[({4,5-dichloro-2-[(2-thienylsulfonyl)amino]phenyl}amino)sulfonyl]isonicotinate;

N-[4,5-dichloro-2-({[2-chloro-4-(trifluoromethyl)phenyl]sulfonyl}amino)phenyl]thiophene-2-sulfonamide;

N-{4,5-dichloro-2-[(2-thienylsulfonyl)amino]phenyl}-2,3-dihydro-1-benzofuran-5-sulfonamide;

N-{4,5-dichloro-2-[(2-thienylsulfonyl)amino]phenyl}-6-phenoxypyridine-3-sulfonamide;

N-{4,5-dichloro-2-[(2-thienylsulfonyl)amino]phenyl}-5-phenylthiophene-2-sulfonamide;

3-[({4,5-dichloro-2-[(2-thienylsulfonyl)amino]phenyl}amino)sulfonyl]-4-methylbenzoic acid;

N-(4,5-dichloro-2-{[(2,5-dimethyl-3-thienyl)sulfonyl]amino}phenyl)thiophene-2-sulfonamide;

N-{2-chloro-4-[({4,5-dichloro-2-[(2-thienylsulfonyl)amino]phenyl}amino)sulfonyl]phenyl}acetamide;

N-(4,5-dichloro-2-{[(5-chloro-2,4-difluorophenyl)sulfonyl]amino}phenyl)thiophene-2-sulfonamide;

N-[4,5-dichloro-2-({[4-(1-methyl-1H-pyrazol-3-yl)phenyl]sulfonyl}amino)phenyl]thiophene-2-sulfonamide;

N-{4,5-dichloro-2-[(2-thienylsulfonyl)amino]phenyl}-5-methyl-1-benzothiophene-2-sulfonamide;

N-{4,5-dichloro-2-[(2-thienylsulfonyl)amino]phenyl}-2,5-dimethylfuran-3-sulfonamide;

N-[4,5-dichloro-2-({[4-(pyrrolidin-1-ylsulfonyl)phenyl]sulfonyl}amino)phenyl]thiophene-2-sulfonamide;

methyl 5-[({4,5-dichloro-2-[(2-thienylsulfonyl)amino]phenyl}amino)sulfonyl]-2-methyl-3-furoate;

N-{4,5-dichloro-2-[(2-thienylsulfonyl)amino]phenyl}-3-oxo-3,4-dihydro-2H-1,4-benzoxazine-6-sulfonamide;

2,4-dichloro-5[({4,5-dichloro-2-[(2-thienylsulfonyl)amino]phenyl}amino)sulfonyl]benzoic acid;

N-[4,5-dichloro-2-({[4-(difluoromethoxy)phenyl]sulfonyl}amino)phenyl]thiophene-2-sulfonamide;

N-(4,5-dichloro-2-{[(5-{[(dimethylamino)carbonyl]amino}-2-ethoxyphenyl)sulfonyl]amino}phenyl)thiophene-2-sulfonamide;

N-{5[({4,5-dichloro-2-[(2-thienylsulfonyl)amino]phenyl}amino)sulfonyl]-2-methoxyphenyl}acetamide;

6-chloro-N-{4,5-dichloro-2-[(2-thienylsulfonyl)amino]phenyl}imidazo[2,1-b][1,3]thiazole-5-sulfonamide;

N-[4,5-dichloro-2-({[3-(1-methyl-1H-pyrazol-5-yl)phenyl]sulfonyl}amino)phenyl]thiophene-2-sulfonamide;

methyl 5-[({4,5-dichloro-2-[(2-thienylsulfonyl)amino]phenyl}amino)sulfonyl]-1-methyl-1H-pyrrole-2-carboxylate;

N-{4,5-dichloro-2-[(2-thienylsulfonyl)amino]phenyl}-5-methylfuran-2-sulfonamide;

N-[4,5-dichloro-2-({[4-(phenoxymethyl)phenyl]sulfonyl}amino)phenyl]thiophene-2-sulfonamide;

N-(4,5-dichloro-2-{[(4-phenoxyphenyl)sulfonyl]amino}phenyl)thiophene-2-sulfonamide;

5,6-dichloro-N-{4,5-dichloro-2-[(2-thienylsulfonyl)amino]phenyl}pyridine-3-sulfonamide;

N-(4,5-dichloro-2-{[(2-fluoro-4-methylphenyl)sulfonyl]amino}phenyl)thiophene-2-sulfonamide;

N-(4,5-dichloro-2-{[(2-ethoxy-5-{[(methylamino)carbonyl]amino}phenyl)sulfonyl]amino}phenyl)thiophene-2-sulfonamide;

N-{4,5-dichloro-2-[(2-thienylsulfonyl)amino]phenyl}-6-morpholin-4-ylpyridine-3-sulfonamide;

N-{4,5-dichloro-2-[({3-[(6-methylpyrazin-2-yl)oxy]phenyl}sulfonyl)amino]phenyl}thiophene-2-sulfonamide;

N-{4,5-dichloro-2-[(2-thienylsulfonyl)amino]phenyl}chromane-6-sulfonamide;

N-[4,5-dichloro-2-({[4-(3,5-dimethyl-1H-pyrazol-1-yl)phenyl]sulfonyl}amino)phenyl]thiophene-2-sulfonamide;

N-{4,5-dichloro-2-[(2-thienylsulfonyl)amino]phenyl}-5-methylthiophene-2-sulfonamide;

5-[({4,5-dichloro-2-[(2-thienylsulfonyl)amino]phenyl}amino)sulfonyl]-2-hydroxybenzoic acid;

N-{4,5-dichloro-2-[(2-thienylsulfonyl)amino]phenyl}-1-benzothiophene-2-sulfonamide;

N-(4,5-dichloro-2-{[(2,4-dichloro-5-methylphenyl)sulfonyl]amino}phenyl)thiophene-2-sulfonamide;

N-[4,5-dichloro-2-({[4-fluoro-3-(trifluoromethyl)phenyl]sulfonyl}amino)phenyl]thiophene-2-sulfonamide;
methyl 3-[({4,5-dichloro-2-[(2-thienylsulfonyl)amino]phenyl}amino)sulfonyl]benzoate;
methyl 5-[({4,5-dichloro-2-[(2-thienylsulfonyl)amino]phenyl}amino)sulfonyl]-4-methoxythiophene-3-carboxylate;
methyl 5-[({4,5-dichloro-2-[(2-thienylsulfonyl)amino]phenyl}amino)sulfonyl]-2-furoate;
N-(4,5-dichloro-2-{[(2-chloro-4-cyanophenyl)sulfonyl]amino}phenyl)thiophene-2-sulfonamide;
N-{4,5-dichloro-2-[(2-thienylsulfonyl)amino]phenyl}-1-methyl-1H-pyrazole-3-sulfonamide;
N-{4,5-dichloro-2-[(2-thienylsulfonyl)amino]phenyl}-1-methyl-1H-indole-7-sulfonamide;
N-{4,5-dichloro-2-[(2-thienylsulfonyl)amino]phenyl}-5-pyridin-2-ylthiophene-2-sulfonamide;
N-(4,5-dichloro-2-{[(4'-fluorobiphenyl-4-yl)sulfonyl]amino}phenyl)thiophene-2-sulfonamide;
N-(4,5-dichloro-2-{[(3-fluoro-4-methoxyphenyl)sulfonyl]amino}phenyl)thiophene-2-sulfonamide;
N-(4,5-dichloro-2-({[(3-chloro-2-fluorophenyl)sulfonyl]amino}phenyl)thiophene-2-sulfonamide;
N-{4,5-dichloro-2-[(2-thienylsulfonyl)amino]phenyl}-2-oxo-2,3-dihydro-1,3-benzothiazole-6-sulfonamide;
N-{4,5-dichloro-2-[(2-thienylsulfonyl)amino]phenyl}furan-3-sulfonamide;
N-[4,5-dichloro-2-({[3-(5-methyl-1,2,4-oxadiazol-3-yl)phenyl]sulfonyl}amino)phenyl]thiophene-2-sulfonamide;
ethyl 5-[({4,5-dichloro-2-[(2-thienylsulfonyl)amino]phenyl}amino)sulfonyl]-3-furoate;
N-{4,5-dichloro-2-[(2-thienylsulfonyl)amino]phenyl}-3,4-dihydro-2H-1,5-benzodioxepine-7-sulfonamide;
N-{4,5-dichloro-2-[(2-thienylsulfonyl)amino]phenyl}-2,3-dihydro-1-benzofuran-7-sulfonamide;
N-{4,5-dichloro-2-[(2-thienylsulfonyl)amino]phenyl}-2-methyl-1,3-benzothiazole-6-sulfonamide;
N-{4,5-dichloro-2-[(2-thienylsulfonyl)amino]phenyl}-1,3,5-trimethyl-1H-pyrazole-4-sulfonamide;
N-(4,5-dichloro-2-{[(4-chloro-2-fluorophenyl)sulfonyl]amino}phenyl)thiophene-2-sulfonamide;
N-(4,5-dichloro-2-{[(3-cyano-4-fluorophenyl)sulfonyl]amino}phenyl)thiophene-2-sulfonamide;
N-{5[({4,5-dichloro-2-[(2-thienylsulfonyl)amino]phenyl}amino)sulfonyl]-1,3-thiazol-2-yl}acetamide;
N-{4,5-dichloro-2-[({4-[(6-methylpyrazin-2-yl)oxy]phenyl}sulfonyl)amino]phenyl}thiophene-2-sulfonamide;
N-(4,5-dichloro-2-{[(3-pyrimidin-2-ylphenyl)sulfonyl]amino}phenyl)thiophene-2-sulfonamide;
methyl 3-[({4,5-dichloro-2-[(2-thienylsulfonyl)amino]phenyl}amino)sulfonyl]-4-methoxybenzoate;
N-{4,5-dichloro-2-[(2-thienylsulfonyl)amino]phenyl}-1-benzothiophene-3-sulfonamide;
N-{4,5-dichloro-2-[(2-thienylsulfonyl)amino]phenyl}-4-methyl-3,4-dihydro-2H-pyrido[3,2-b][1,4]oxazine-7-sulfonamide;
5-chloro-N-{4,5-dichloro-2-[(2-thienylsulfonyl)amino]phenyl}-1,3-dimethyl-1H-pyrazole-4-sulfonamide;
N-(4,5-dichloro-2-{[(5-chloro-2-naphthyl)sulfonyl]amino}phenyl)thiophene-2-sulfonamide;
N-{2-[(biphenyl-3-ylsulfonyl)amino]-4,5-dichlorophenyl}thiophene-2-sulfonamide;
N-(4,5-dichloro-2-{[(2-fluoro-5-methylphenyl)sulfonyl]amino}phenyl)thiophene-2-sulfonamide;
4-chloro-3-[({4,5-dichloro-2-[(2-thienylsulfonyl)amino]phenyl}amino)sulfonyl]benzoic acid;
3-[({4,5-dichloro-2-[(2-thienylsulfonyl)amino]phenyl}amino)sulfonyl]-4-methoxybenzoic acid;
N-[4,5-dichloro-2-({[4-(pyridin-2-yloxy)phenyl]sulfonyl}amino)phenyl]thiophene-2-sulfonamide;
N-{4,5-dichloro-2-[(2-naphthylsulfonyl)amino]phenyl}thiophene-2-sulfonamide;
3-[({4,5-dichloro-2-[(2-thienylsulfonyl)amino]phenyl}amino)sulfonyl]benzoic acid;
N-[4,5-dichloro-2-({[6-(dimethylamino)-2-naphthyl]sulfonyl}amino)phenyl]thiophene-2-sulfonamide;
N-{4,5-dichloro-2-[(2-thienylsulfonyl)amino]phenyl}pyridine-3-sulfonamide;
N-(4,5-dichloro-2-{[(4'-chlorobiphenyl-4-yl)sulfonyl]amino}phenyl)thiophene-2-sulfonamide;
N-(2-{[(3-acetylphenyl)sulfonyl]amino}-4,5-dichlorophenyl)thiophene-2-sulfonamide;
N-{4,5-dichloro-2-[(2-thienylsulfonyl)amino]phenyl}-2,3-dioxo-1,2,3,4-tetrahydroquinoxaline-6-sulfonamide;
N-{4[({4,5-dichloro-2-[(2-thienylsulfonyl)amino]phenyl}amino)sulfonyl]benzyl}acetamide;
N-[4,5-dichloro-2-({[3-(trifluoromethyl)phenyl]sulfonyl}amino)phenyl]thiophene-2-sulfonamide;
N-[4,5-dichloro-2-({[2-(methylsulfonyl)phenyl]sulfonyl}amino)phenyl]thiophene-2-sulfonamide;
N-{4,5-dichloro-2-[(2-thienylsulfonyl)amino]phenyl}-3-methylquinoline-8-sulfonamide;
N-{4,5-dichloro-2-[(2-thienylsulfonyl)amino]phenyl}-2,3-dihydro-1,4-benzodioxine-6-sulfonamide;
N-[4,5-dichloro-2-({[3-(2-methylpyrimidin-4-yl)phenyl]sulfonyl}amino)phenyl]thiophene-2-sulfonamide;
6-chloro-N-{4,5-dichloro-2-[(2-thienylsulfonyl)amino]phenyl}pyridine-3-sulfonamide;
N-{4,5-dichloro-2-[(2-thienylsulfonyl)amino]phenyl}-6-methoxypyridine-3-sulfonamide;
methyl 5-[({4,5-dichloro-2-[(2-thienylsulfonyl)amino]phenyl}amino)sulfonyl]-2-methylbenzoate;
N-(4,5-dichloro-2-{[(2,5-dimethoxyphenyl)sulfonyl]amino}phenyl)thiophene-2-sulfonamide;
N-(2-{[(4-acetylphenyl)sulfonyl]amino}-4,5-dichlorophenyl)thiophene-2-sulfonamide;
methyl 3-[({4,5-dichloro-2-[(2-thienylsulfonyl)amino]phenyl}amino)sulfonyl]-2-methylbenzoate;
N-{4,5-dichloro-2-[(2-thienylsulfonyl)amino]phenyl}-5-isoxazol-5-ylthiophene-2-sulfonamide;
N-{4,5-dichloro-2-[(2-thienylsulfonyl)amino]phenyl}-5-(1,3-oxazol-5-yl)thiophene-2-sulfonamide;
N-(4,5-dichloro-2-{[(5-chloro-2-methylphenyl)sulfonyl]amino}phenyl)thiophene-2-sulfonamide;
N-[4,5-dichloro-2-({[5-(dimethylamino)-1-naphthyl]sulfonyl}amino)phenyl]thiophene-2-sulfonamide;
methyl 2-[({4,5-dichloro-2-[(2-thienylsulfonyl)amino]phenyl}amino)sulfonyl]-4-methoxybenzoate;
5-chloro-N-{4,5-dichloro-2-[(2-thienylsulfonyl)amino]phenyl}thiophene-2-sulfonamide;
N-(4,5-dichloro-2-{[(4-pyrimidin-2-ylphenyl)sulfonyl]amino}phenyl)thiophene-2-sulfonamide;
N-{4,5-dichloro-2-[(methylsulfonyl)amino]phenyl}thiophene-2-sulfonamide;
N-(4,5-dichloro-2-{[(3,5-dichloro-4-hydroxyphenyl)sulfonyl]amino}phenyl)thiophene-2-sulfonamide;
N-[4,5-dichloro-2-({[4-chloro-3-(trifluoromethyl)phenyl]sulfonyl}amino)phenyl]thiophene-2-sulfonamide;
2-chloro-5-[({4,5-dichloro-2-[(2-thienylsulfonyl)amino]phenyl}amino)sulfonyl]benzoic acid;
N-[4,5-dichloro-2-({[4-(pyridin-3-yloxy)phenyl]sulfonyl}amino)phenyl]thiophene-2-sulfonamide;

N-{4,5-dichloro-2-[(2-thienylsulfonyl)amino]phenyl}-1-methyl-1H-imidazole-4-sulfonamide;
N-{4,5-dichloro-2-[(ethylsulfonyl)amino]phenyl}thiophene-2-sulfonamide;
N-(4,5-dichloro-2-{[(4-chloro-2-fluoro-5-methylphenyl)sulfonyl]amino}phenyl)thiophene-2-sulfonamide;
5-[({4,5-dichloro-2-[(2-thienylsulfonyl)amino]phenyl}amino)sulfonyl]-2-fluorobenzoic acid;
N-{2-[(biphenyl-2-ylsulfonyl)amino]-4,5-dichlorophenyl}thiophene-2-sulfonamide;
N-{3-[({4,5-dichloro-2-[(2-thienylsulfonyl)amino]phenyl}amino)sulfonyl]-4-methylphenyl}acetamide;
N-(2-{[(5-tert-butyl-2-methylphenyl)sulfonyl]amino}-4,5-dichlorophenyl)thiophene-2-sulfonamide;
N-{2-[(benzylsulfonyl)amino]-4,5-dichlorophenyl}thiophene-2-sulfonamide
N-{4,5-dichloro-2-[(isobutylsulfonyl)amino]phenyl}thiophene-2-sulfonamide
N-{4,5-dichloro-2-[(2-thienylsulfonyl)amino]phenyl}-2,2-dimethylchromane-6-sulfonamide;
N-{4,5-dichloro-2-[(2-thienylsulfonyl)amino]phenyl}-1,2-dimethyl-1H-imidazole-4-sulfonamide;
N-{4,5-dichloro-2-[(2-thienylsulfonyl)amino]phenyl}-2-oxo-2,3,4,5-tetrahydro-1H-1-benzazepine-7-sulfonamide;
N-(4,5-dichloro-2-{[(4-cyclohexylphenyl)sulfonyl]amino}phenyl)thiophene-2-sulfonamide;
4-chloro-N~1~-{4,5-dichloro-2-[(2-thienylsulfonyl)amino]phenyl}benzene-1,3-disulfonamide;
N-(4,5-dichloro-2-{[(4-fluorophenyl)sulfonyl]amino}phenyl)thiophene-2-sulfonamide;
N-{3-[({4,5-dichloro-2-[(2-thienylsulfonyl)amino]phenyl}amino)sulfonyl]phenyl}acetamide;
N-{4,5-dichloro-2-[(2-thienylsulfonyl)amino]phenyl}-1-methyl-1H-indole-4-sulfonamide;
N-(2-{[(4-bromo-3-methylphenyl)sulfonyl]amino}-4,5-dichlorophenyl)thiophene-2-sulfonamide;
N-(4,5-dichloro-2-{[(3-chloro-4-cyanophenyl)sulfonyl]amino}phenyl)thiophene-2-sulfonamide;
N-{4,5-dichloro-2-[(5,6,7,8-tetrahydronaphthalen-2-ylsulfonyl)amino]phenyl}thiophene-2-sulfonamide;
N-[4,5-dichloro-2-({[4-(2-chlorophenoxy)phenyl]sulfonyl}amino)phenyl]thiophene-2-sulfonamide;
N-(4,5-dichloro-2-{[(4-methoxyphenyl)sulfonyl]amino}phenyl)thiophene-2-sulfonamide;
N-(4,5-dichloro-2-{[(2-methylphenyl)sulfonyl]amino}phenyl)thiophene-2-sulfonamide;
2-{4-[({4,5-dichloro-2-[(2-thienylsulfonyl)amino]phenyl}amino)sulfonyl]phenoxy}acetamide;
N-(4,5-dichloro-2-{[(2,4-dichlorophenyl)sulfonyl]amino}phenyl)thiophene-2-sulfonamide;
N-{4,5-dichloro-2-[(2-thienylsulfonyl)amino]phenyl}-3,5-dimethyl-1-phenyl-1H-pyrazole-4-sulfonamide;
N-{4,5-dichloro-2-[(2-thienylsulfonyl)amino]phenyl}-4-methyl-3,4-dihydro-2H-1,4-benzoxazine-6-sulfonamide;
2-chloro-N-{4,5-dichloro-2-[(2-thienylsulfonyl)amino]phenyl}pyridine-3-sulfonamide;
4-acetyl-N-{4,5-dichloro-2-[(2-thienylsulfonyl)amino]phenyl}-3,4-dihydro-2H-1,4-benzoxazine-6-sulfonamide;
N-(4,5-dichloro-2-{[(2,6-difluorophenyl)sulfonyl]amino}phenyl)thiophene-2-sulfonamide;
N-{5-chloro-2-[(2-thienylsulfonyl)amino]phenyl}-1-benzofuran-2-sulfonamide;
N-{4-chloro-2-[(2-thienylsulfonyl)amino]phenyl}-1-benzofuran-2-sulfonamide;
N-{5-chloro-2-[(methylsulfonyl)amino]phenyl}-1-benzofuran-2-sulfonamide;
N-{2-[(1-benzofuran-2-ylsulfonyl)amino]-4-chlorophenyl}-1-methyl-1H-imidazole-4-sulfonamide;
N-{2-[(benzylsulfonyl)amino]-5-chlorophenyl}-1-benzofuran-2-sulfonamide;
N-(5-chloro-2-{[(3-fluorophenyl)sulfonyl]amino}phenyl)-1-benzofuran-2-sulfonamide;
N-(5-chloro-2-{[(4-fluorophenyl)sulfonyl]amino}phenyl)-1-benzofuran-2-sulfonamide;
N-(5-chloro-2-{[(3-cyanophenyl)sulfonyl]amino}phenyl)-1-benzofuran-2-sulfonamide;
N-(5-chloro-2-{[(4-methoxyphenyl)sulfonyl]amino}phenyl)-1-benzofuran-2-sulfonamide;
N-(5-chloro-2-{[(3-methoxyphenyl)sulfonyl]amino}phenyl)-1-benzofuran-2-sulfonamide;
N-(5-chloro-2-{[(3-chlorophenyl)sulfonyl]amino}phenyl)-1-benzofuran-2-sulfonamide;
N-(5-chloro-2-{[(4-chlorophenyl)sulfonyl]amino}phenyl)-1-benzofuran-2-sulfonamide;
N-{5-chloro-2-[(2-naphthylsulfonyl)amino]phenyl}-1-benzofuran-2-sulfonamide;
N-{2-[(1-benzofuran-2-ylsulfonyl)amino]-4-chlorophenyl}quinoline-8-sulfonamide;
N-(5-chloro-2-{[(3,4-dimethoxyphenyl)sulfonyl]amino}phenyl)-1-benzofuran-2-sulfonamide;
N-(5-chloro-2-{[(2,4-dichlorophenyl)sulfonyl]amino}phenyl)-1-benzofuran-2-sulfonamide;
N-{2-[(biphenyl-4-ylsulfonyl)amino]-5-chlorophenyl}-1-benzofuran-2-sulfonamide;
N-[5-chloro-2-({[4-(methylsulfonyl)phenyl]sulfonyl}amino)phenyl]-1-benzofuran-2-sulfonamide;
N-(5-chloro-2-{[(4-methylphenyl)sulfonyl]amino}phenyl)-1-benzofuran-2-sulfonamide;
N-[5-chloro-2-({[4-(trifluoromethyl)phenyl]sulfonyl}amino)phenyl]-1-benzofuran-2-sulfonamide;
N-[5-chloro-2-({[4-(trifluoromethoxy)phenyl]sulfonyl}amino)phenyl]-1-benzofuran-2-sulfonamide;
N-{5-chloro-2-[(1-naphthylsulfonyl)amino]phenyl}-1-benzofuran-2-sulfonamide;
N-(5-chloro-2-{[(2-chlorophenyl)sulfonyl]amino}phenyl)-1-benzofuran-2-sulfonamide;
N-[5-chloro-2-({[3-(trifluoromethyl)phenyl]sulfonyl}amino)phenyl]-1-benzofuran-2-sulfonamide;
N-(5-chloro-2-{[(2-methoxyphenyl)sulfonyl]amino}phenyl)-1-benzofuran-2-sulfonamide;
N-(5-chloro-2-{[(3,5-difluorophenyl)sulfonyl]amino}phenyl)-1-benzofuran-2-sulfonamide;
N-(5-chloro-2-{[(3,4-difluorophenyl)sulfonyl]amino}phenyl)-1-benzofuran-2-sulfonamide;
N-(2-{[(4-tert-butylphenyl)sulfonyl]amino}-5-chlorophenyl)-1-benzofuran-2-sulfonamide;
N-(5-chloro-2-{[(3,4-dichlorophenyl)sulfonyl]amino}phenyl)-1-benzofuran-2-sulfonamide;
N-[2-({[4-(benzyloxy)phenyl]sulfonyl}amino)-5-chlorophenyl]-1-benzofuran-2-sulfonamide;
N-{2-[(1-benzofuran-2-ylsulfonyl)amino]-4-chlorophenyl}-1,3-benzodioxole-5-sulfonamide;
N-{2-[(1-benzofuran-2-ylsulfonyl)amino]-4-chlorophenyl}-2,4-dimethyl-1,3-thiazole-5-sulfonamide;
N-[5-chloro-2-({[3-(difluoromethoxy)phenyl]sulfonyl}amino)phenyl]-1-benzofuran-2-sulfonamide;
N-(5-chloro-2-{[(3,5-dichlorophenyl)sulfonyl]amino}phenyl)-1-benzofuran-2-sulfonamide;
N-(5-chloro-2-{[(3-methylphenyl)sulfonyl]amino}phenyl)-1-benzofuran-2-sulfonamide;
N-{5-chloro-2-[(2-furylsulfonyl)amino]phenyl}-1-benzofuran-2-sulfonamide;

N-{2-[(1-benzothien-3-ylsulfonyl)amino]-5-chlorophenyl}-1-benzofuran-2-sulfonamide;
N-{2-[(1-benzofuran-2-ylsulfonyl)amino]-4-chlorophenyl}-1,3-benzothiazole-6-sulfonamide;
N-[5-chloro-2-({[3-(methylsulfonyl)phenyl]sulfonyl}amino)phenyl]-1-benzofuran-2-sulfonamide;
N-(5-chloro-2-{[(2-fluorophenyl)sulfonyl]amino}phenyl)-1-benzofuran-2-sulfonamide;
N-(5-chloro-2-{[(2,5-dimethoxyphenyl)sulfonyl]amino}phenyl)-1-benzofuran-2-sulfonamide;
N-[5-chloro-2-({[2-(trifluoromethoxy)phenyl]sulfonyl}amino)phenyl]-1-benzofuran-2-sulfonamide;
N-(5-chloro-2-{[(5-chloro-2-thienyl)sulfonyl]amino}phenyl)-1-benzofuran-2-sulfonamide;
N-(5-chloro-2-{[(3-chloro-4-fluorophenyl)sulfonyl]amino}phenyl)-1-benzofuran-2-sulfonamide;
methyl 3-[({2-[(1-benzofuran-2-ylsulfonyl)amino]-4-chlorophenyl}amino)sulfonyl]thiophene-2-carboxylate;
N-{5-chloro-2-[(ethylsulfonyl)amino]phenyl}-1-benzofuran-2-sulfonamide;
N-{2-[(1-benzofuran-2-ylsulfonyl)amino]-4-chlorophenyl}-3,5-dimethylisoxazole-4-sulfonamide;
N-(5-chloro-2-{[(5-chloro-3-methyl-1-benzothien-2-yl)sulfonyl]amino}phenyl)-1-benzofuran-2-sulfonamide;
N-(5-chloro-2-{[(2-chloro-4-fluorophenyl)sulfonyl]amino}phenyl)-1-benzofuran-2-sulfonamide;
N-(5-chloro-2-{[(3-chloro-2-methylphenyl)sulfonyl]amino}phenyl)-1-benzofuran-2-sulfonamide;
N-{5-chloro-2-[(isobutylsulfonyl)amino]phenyl}-1-benzofuran-2-sulfonamide;
5-[({2-[(1-benzofuran-2-ylsulfonyl)amino]-4-chlorophenyl}amino)sulfonyl]-2-chloro-4-fluorobenzoic acid;
N-{5-[({2-[(1-benzofuran-2-ylsulfonyl)amino]-4-chlorophenyl}amino)sulfonyl]-4-methyl-1,3-thiazol-2-yl}acetamide;
N-(5-chloro-2-{[(2,5-difluorophenyl)sulfonyl]amino}phenyl)-1-benzofuran-2-sulfonamide;
N-(5-chloro-2-{[(4-chloro-2,5-difluorophenyl)sulfonyl]amino}phenyl)-1-benzofuran-2-sulfonamide;
N-(5-chloro-2-{[(4-chloro-3-methylphenyl)sulfonyl]amino}phenyl)-1-benzofuran-2-sulfonamide;
N-{2-[(1-benzofuran-2-ylsulfonyl)amino]-4-chlorophenyl}-1H-1,2,4-triazole-5-sulfonamide;
3-{4-[({2-[(1-benzofuran-2-ylsulfonyl)amino]-4-chlorophenyl}amino)sulfonyl]phenyl}propanoic acid;
methyl 3-[({2-[(1-benzofuran-2-ylsulfonyl)amino]-4-chlorophenyl}amino)sulfonyl]-5-chlorothiophene-2-carboxylate;
N-{2-[(1-benzofuran-5-ylsulfonyl)amino]-5-chlorophenyl}-1-benzofuran-2-sulfonamide;
N-{3-[({2-[(1-benzofuran-2-ylsulfonyl)amino]-4-chlorophenyl}amino)sulfonyl]phenyl}acetamide;
N-{2-[(1-benzofuran-2-ylsulfonyl)amino]-4-chlorophenyl}-2-oxoindoline-5-sulfonamide;
N-{2-[(1-benzofuran-2-ylsulfonyl)amino]-4-chlorophenyl}-3,5-dimethyl-1H-pyrazole-4-sulfonamide;
N-[5-chloro-2-({[4-(2-methylphenoxy)phenyl]sulfonyl}amino)phenyl]-1-benzofuran-2-sulfonamide;
N-{2-[(1-benzofuran-2-ylsulfonyl)amino]-4-chlorophenyl}-2-oxo-2,3-dihydro-1,3-benzoxazole-6-sulfonamide;
N-{2-[(1-benzofuran-2-ylsulfonyl)amino]-4-chlorophenyl}-2-chloro-1,3-benzothiazole-6-sulfonamide;
5-[({2-[(1-benzofuran-2-ylsulfonyl)amino]-4-chlorophenyl}amino)sulfonyl]-2-ethoxybenzoic acid;
3-[({2-[(1-benzofuran-2-ylsulfonyl)amino]-4-chlorophenyl]amino)sulfonyl}-4-fluorobenzoic acid;
N-(5-chloro-2-{[(2,6-dimethylphenyl)sulfonyl]amino}phenyl)-1-benzofuran-2-sulfonamide;
N-{2-[(1-benzofuran-2-ylsulfonyl)amino]-4-chlorophenyl}isoquinoline-5-sulfonamide;
N-(5-chloro-2-{[(2-methylphenyl)sulfonyl]amino}phenyl)-1-benzofuran-2-sulfonamide;
N-(5-chloro-2-{[(2,4-difluorophenyl)sulfonyl]amino}phenyl)-1-benzofuran-2-sulfonamide;
N-(5-chloro-2-{[(5-isoxazol-3-yl-2-thienyl)sulfonyl]amino}phenyl)-1-benzofuran-2-sulfonamide;
4-[({2-[(1-benzofuran-2-ylsulfonyl)amino]-4-chlorophenyl}amino)sulfonyl]benzoic acid;
N-(5-chloro-2-{[(3,4-dimethylphenyl)sulfonyl]amino}phenyl)-1-benzofuran-2-sulfonamide;
3-[({2-[(1-benzofuran-2-ylsulfonyl)amino]-4-chlorophenyl}amino)sulfonyl]benzoic acid;
N-{4-[({2-[(1-benzofuran-2-ylsulfonyl)amino]-4-chlorophenyl}amino)sulfonyl]-2-methylphenyl}acetamide;
N-{2-[(1-benzofuran-2-ylsulfonyl)amino]-4-chlorophenyl}-2-chloroquinoline-6-sulfonamide;
N-{2-[(1-benzofuran-2-ylsulfonyl)amino]-4-chlorophenyl}quinoline-3-sulfonamide;
N-{2-[(1-benzofuran-2-ylsulfonyl)amino]-4-chlorophenyl}-5-chloroquinoline-8-sulfonamide;
N-{2-[(1-benzofuran-2-ylsulfonyl)amino]-4-chlorophenyl}quinoline-6-sulfonamide;
N-(5-chloro-2-{[(2,4-dimethylphenyl)sulfonyl]amino}phenyl)-1-benzofuran-2-sulfonamide;
5-[({2-[(1-benzofuran-2-ylsulfonyl)amino]-4-chlorophenyl}amino)sulfonyl]-2-methoxybenzoic acid;
N-(5-chloro-2-{[(2,4-dimethoxyphenyl)sulfonyl]amino}phenyl)-1-benzofuran-2-sulfonamide;
N-[2-({[3,5-bis(trifluoromethyl)phenyl]sulfonyl}amino)-5-chlorophenyl]-1-benzofuran-2-sulfonamide;
N-(5-chloro-2-{[(5-chloro-2-fluorophenyl)sulfonyl]amino}phenyl)-1-benzofuran-2-sulfonamide
N-(5-chloro-2-{[(2,3-dichlorophenyl)sulfonyl]amino}phenyl)-1-benzofuran-2-sulfonamide;
N-(5-chloro-2-{[(2,6-difluorophenyl)sulfonyl]amino}phenyl)-1-benzofuran-2-sulfonamide;
N-(5-chloro-2-{[(2,5-dichlorophenyl)sulfonyl]amino}phenyl)-1-benzofuran-2-sulfonamide;
N-{2-[(1-benzofuran-2-ylsulfonyl)amino]-4-chlorophenyl}-1-(phenylsulfonyl)-1H-pyrrole-3-sulfonamide;
N-(5-chloro-2-{[(2,6-dichlorophenyl)sulfonyl]amino}phenyl)-1-benzofuran-2-sulfonamide;
N-(5-chloro-2-{[(3-chloro-4-methylphenyl)sulfonyl]amino}phenyl)-1-benzofuran-2-sulfonamide;
N-[5-chloro-2-({[2-(methylsulfonyl)phenyl]sulfonyl}amino)phenyl]-1-benzofuran-2-sulfonamide;
N-(5-chloro-2-{[(2,5-dichloro-3-thienyl)sulfonyl]amino}phenyl)-1-benzofuran-2-sulfonamide;
N-[2-[(1-benzofuran-2-ylsulfonyl)amino]-4-chlorophenyl]-1H-pyrazole-4-sulfonamide;
N-{5-chloro-2-[(2,3-dihydro-1H-inden-5-ylsulfonyl)amino]phenyl}-1-benzofuran-2-sulfonamide;
methyl 4-[({2-[(1-benzofuran-2-ylsulfonyl)amino]-4-chlorophenyl}amino)sulfonyl]benzoate;
N-(5-chloro-2-{[(2,4,5-trifluorophenyl)sulfonyl]amino}phenyl)-1-benzofuran-2-sulfonamide;
N-(5-chloro-2-{[(3,5-dimethylphenyl)sulfonyl]amino}phenyl)-1-benzofuran-2-sulfonamide;
N-(5-chloro-2-{[(4-methoxy-3-methylphenyl)sulfonyl]amino}phenyl)-1-benzofuran-2-sulfonamide;
N-{2-[(1-benzofuran-2-ylsulfonyl)amino]-4-chlorophenyl}-2-oxo-1,2,3,4-tetrahydroquinoline-6-sulfonamide;

N-(5-chloro-2-{[(5-{[(dimethylamino)carbonyl]amino}-2-ethoxyphenyl)sulfonyl]amino}phenyl)-1-benzofuran-2-sulfonamide;
N-(5-chloro-2-{[(2-ethoxy-5-{[(methylamino)carbonyl]amino}phenyl)sulfonyl]amino}phenyl)-1-benzofuran-2-sulfonamide;
N-(2-{[(4-acetylphenyl)sulfonyl]amino}-5-chlorophenyl)-1-benzofuran-2-sulfonamide;
methyl 3-[({2-[(1-benzofuran-2-ylsulfonyl)amino]-4-chlorophenyl}amino)sulfonyl]benzoate;
N-{2-[(1-benzofuran-2-ylsulfonyl)amino]-4-chlorophenyl}-2-oxo-2,3-dihydro-1,3-benzothiazole-6-sulfonamide;
N-{5-[({2-[(1-benzofuran-2-ylsulfonyl)amino]-4-chlorophenyl]amino)sulfonyl}-1,3-thiazol-2-yl}acetamide;
N-(5-chloro-2-{[(3-chloro-4-methoxyphenyl)sulfonyl]amino}phenyl)-1-benzofuran-2-sulfonamide;
N-{2-[(1-benzofuran-2-ylsulfonyl)amino]-4-chlorophenyl}-2-oxo-2H-chromene-6-sulfonamide;
N-(5-chloro-2-{[(5-chloro-2,4-difluorophenyl)sulfonyl]amino}phenyl)-1-benzofuran-2-sulfonamide;
N-{5-[({2-[(1-benzofuran-2-ylsulfonyl)amino]-4-chlorophenyl}amino)sulfonyl]-2-methoxyphenyl}acetamide;
N-{2-[(1-benzofuran-2-ylsulfonyl)amino]-4-chlorophenyl}-6-morpholin-4-ylpyridine-3-sulfonamide;
methyl 5-[({2-[(1-benzofuran-2-ylsulfonyl)amino]-4-chlorophenyl}amino)sulfonyl]-4-methoxythiophene-3-carboxylate;
N-{5-chloro-2-[(3-furylsulfonyl)amino]phenyl}-1-benzofuran-2-sulfonamide;
N-{5-chloro-2-[({4-[(6-methylpyrazin-2-yl)oxy]phenyl}sulfonyl)amino]phenyl}-1-benzofuran-2-sulfonamide;
N-{2-[(1-benzofuran-2-ylsulfonyl)amino]-4-chlorophenyl}-methyl-1H-pyrazole-5-sulfonamide;
N-{2-[(1-benzofuran-2-ylsulfonyl)amino]-4-chlorophenyl}-6-phenylpyridine-3-sulfonamide;
N-[5-chloro-2-({[4-(1-methyl-1H-pyrazol-3-yl)phenyl]sulfonyl}amino)phenyl]-1-benzofuran-2-sulfonamide;
N-{2-[(1-benzofuran-2-ylsulfonyl)amino]-4-chlorophenyl}-6-chloroimidazo[2,1-b][1,3]thiazole-5-sulfonamide;
N-{5-chloro-2-[({3-[(6-methylpyrazin-2-yl)oxy]phenyl}sulfonyl)amino]phenyl}-1-benzofuran-2-sulfonamide;
methyl 5-[({2-[(1-benzofuran-2-ylsulfonyl)amino]-4-chlorophenyl}amino)sulfonyl]-2-furoate;
N-[5-chloro-2-({[3-(5-methyl-1,2,4-oxadiazol-3-yl)phenyl]sulfonyl}amino)phenyl]-1-benzofuran-2-sulfonamide;
N-(5-chloro-2-{[(3-pyrimidin-2-ylphenyl)sulfonyl]amino}phenyl)-1-benzofuran-2-sulfonamide;
1-acetyl-N-{2-[(1-benzofuran-2-ylsulfonyl)amino]-4-chlorophenyl}indoline-5-sulfonamide;
ethyl 3-[({2-[(1-benzofuran-2-ylsulfonyl)amino]-4-chlorophenyl}amino)sulfonyl]isonicotinate;
N-(5-chloro-2-{[(5-methyl-1-benzothien-2-yl)sulfonyl]amino}phenyl)-1-benzofuran-2-sulfonamide;
N-[5-chloro-2-({[3-(1-methyl-1H-pyrazol-5-yl)phenyl]sulfonyl}amino)phenyl]-1-benzofuran-2-sulfonamide;
N-{2-[(1-benzofuran-2-ylsulfonyl)amino]-4-chlorophenyl}chromane-6-sulfonamide;
N-(5-chloro-2-{[(2-chloro-4-cyanophenyl)sulfonyl]amino}phenyl)-1-benzofuran-2-sulfonamide;
ethyl 5-[({2-[(1-benzofuran-2-ylsulfonyl)amino]-4-chlorophenyl}amino)sulfonyl]-3-furoate;
methyl 3-[({2-[(1-benzofuran-2-ylsulfonyl)amino]-4-chlorophenyl}amino)sulfonyl]-4-methoxybenzoate;
N-(5-chloro-2-{[(4-pyrimidin-2-ylphenyl)sulfonyl]amino}phenyl)-1-benzofuran-2-sulfonamide;
N-[5-chloro-2-({[3-(5-methyl-1,3,4-oxadiazol-2-yl)phenyl]sulfonyl}amino)phenyl]-1-benzofuran-2-sulfonamide;
N-[5-chloro-2-({[2-chloro-4-(trifluoromethyl)phenyl]sulfonyl}amino)phenyl]-1-benzofuran-2-sulfonamide;
N-(5-chloro-2-{[(2,5-dimethyl-3-furyl)sulfonyl]amino}phenyl)-1-benzofuran-2-sulfonamide;
methyl 5-[({2-[(1-benzofuran-2-ylsulfonyl)amino]-4-chlorophenyl}amino)sulfonyl]-1-methyl-1H-pyrrole-2-carboxylate;
N-[5-chloro-2-({[4-(3,5-dimethyl-1H-pyrazol-1-yl)phenyl]sulfonyl}amino)phenyl]-1-benzofuran-2-sulfonamide;
N-(5-chloro-2-{[(4-chloro-2-fluoro-5-methylphenyl)sulfonyl]amino}phenyl)-1-benzofuran-2-sulfonamide;
N-{2-[(1-benzofuran-2-ylsulfonyl)amino]-4-chlorophenyl}-1-methyl-1H-pyrazole-3-sulfonamide;
N-{2-[(1-benzofuran-2-ylsulfonyl)amino]-4-chlorophenyl}-3,5-dimethyl-1-phenyl-1H-pyrazole-4-sulfonamide;
N-{2-[(1-benzofuran-2-ylsulfonyl)amino]-4-chlorophenyl}-4-methyl-3,4-dihydro-2H-1,4-benzoxazine-6-sulfonamide;
N-{2-[(1-benzofuran-2-ylsulfonyl)amino]-4-chlorophenyl}-3,4-dihydro-2H-1,5-benzodioxepine-7-sulfonamide;
N-[5-chloro-2-({[3-(1-methyl-1H-pyrazol-3-yl)phenyl]sulfonyl}amino)phenyl]-1-benzofuran-2-sulfonamide;
N-{5-chloro-2-[(2,3-dihydro-1-benzofuran-5-ylsulfonyl)amino]phenyl}-1-benzofuran-2-sulfonamide;
N-[5-chloro-2-({[4-(pyrrolidin-1-ylsulfonyl)phenyl]sulfonyl}amino)phenyl]-1-benzofuran-2-sulfonamide;
N-(5-chloro-2-{[(5-methyl-2-furyl)sulfonyl]amino}phenyl)-1-benzofuran-2-sulfonamide;
N-(5-chloro-2-{[(5-methyl-2-thienyl)sulfonyl]amino}phenyl)-1-benzofuran-2-sulfonamide;
N-{2-[(1-benzofuran-2-ylsulfonyl)amino]-4-chlorophenyl}-1-methyl-1H-indole-7-sulfonamide;
N-{5-chloro-2-[(2,3-dihydro-1-benzofuran-7-ylsulfonyl)amino]phenyl}-1-benzofuran-2-sulfonamide;
N-{2-[(1-benzofuran-2-ylsulfonyl)amino]-4-chlorophenyl}-2,2-dimethylchromane-6-sulfonamide;
N-[5-chloro-2-({[4-(2-methyl-1,3-thiazol-4-yl)phenyl]sulfonyl}amino)phenyl]-1-benzofuran-2-sulfonamide;
N-{2-[(1-benzofuran-2-ylsulfonyl)amino]-4-chlorophenyl}-4-methyl-2-phenyl-1,3-thiazole-5-sulfonamide;
N-{2-[(1-benzofuran-2-ylsulfonyl)amino]-4-chlorophenyl}-6-phenoxypyridine-3-sulfonamide;
methyl 5-[({2-[(1-benzofuran-2-ylsulfonyl)amino]-4-chlorophenyl}amino)sulfonyl]-2-methyl-3-furoate;
N-[5-chloro-2-({[4-(phenoxymethyl)phenyl]sulfonyl}amino)phenyl]-1-benzofuran-2-sulfonamide;
5-[({2-[(1-benzofuran-2-ylsulfonyl)amino]-4-chlorophenyl}amino)sulfonyl]-2-hydroxybenzoic acid;
N-(5-chloro-2-{[(5-pyridin-2-yl-2-thienyl)sulfonyl]amino}phenyl)-1-benzofuran-2-sulfonamide;
N-{2-[(1-benzofuran-2-ylsulfonyl)amino]-4-chlorophenyl}-2-methyl-1,3-benzothiazole-6-sulfonamide;
N-{2-[(1-benzofuran-2-ylsulfonyl)amino]-4-chlorophenyl}-4-methyl-3,4-dihydro-2H-pyrido[3,2-b][1,4]oxazine-7-sulfonamide;
N-{2-[(1-benzofuran-2-ylsulfonyl)amino]-4-chlorophenyl}-1-methyl-1H-indole-4-sulfonamide;
N-(5-chloro-2-{[(5-phenyl-2-thienyl)sulfonyl]amino}phenyl)-1-benzofuran-2-sulfonamide;
N-{2-[(1-benzofuran-2-ylsulfonyl)amino]-4-chlorophenyl}-3-oxo-3,4-dihydro-2H-1,4-benzoxazine-6-sulfonamide;
N-(5-chloro-2-{[(4-phenoxyphenyl)sulfonyl]amino}phenyl)-1-benzofuran-2-sulfonamide;

N-{2-[(1-benzothien-2-ylsulfonyl)amino]-5-chlorophenyl}-1-benzofuran-2-sulfonamide;

N-(5-chloro-2-{[(4'-fluorobiphenyl-4-yl)sulfonyl]amino}phenyl)-1-benzofuran-2-sulfonamide;

N-{2-[(1-benzofuran-2-ylsulfonyl)amino]-4-chlorophenyl}-1,3,5-trimethyl-1H-pyrazole-4-sulfonamide;

N-{2-[(1-benzofuran-2-ylsulfonyl)amino]-4-chlorophenyl}-5-chloro-1,3-dimethyl-1H-pyrazole-4-sulfonamide;

2-{4-[({2-[(1-benzofuran-2-ylsulfonyl)amino]-4-chlorophenyl}amino)sulfonyl]phenoxy}acetamide;

5-[({2-[(1-benzofuran-2-ylsulfonyl)amino]-4-chlorophenyl}amino)sulfonyl]-2-methylbenzoic acid;

3-[({2-[(1-benzofuran-2-ylsulfonyl)amino]-4-chlorophenyl}amino)sulfonyl]-4-methylbenzoic acid;

5-[({2-[(1-benzofuran-2-ylsulfonyl)amino]-4-chlorophenyl}amino)sulfonyl]-2,4-dichlorobenzoic acid;

N-{2-[(1-benzofuran-2-ylsulfonyl)amino]-4-chlorophenyl}-5,6-dichloropyridine-3-sulfonamide;

N-(5-chloro-2-{[(2,4-dichloro-5-methylphenyl)sulfonyl]amino}phenyl)-1-benzofuran-2-sulfonamide;

N-(5-chloro-2-{[(3-fluoro-4-methoxyphenyl)sulfonyl]amino}phenyl)-1-benzofuran-2-sulfonamide;

N-(5-chloro-2-{[(4-chloro-2-fluorophenyl)sulfonyl]amino}phenyl)-1-benzofuran-2-sulfonamide;

N-[5-chloro-2-({[4-(1H-pyrazol-1-yl)phenyl]sulfonyl}amino)phenyl]-1-benzofuran-2-sulfonamide;

N-(5-chloro-2-{[(2,5-dimethyl-3-thienyl)sulfonyl]amino}phenyl)-1-benzofuran-2-sulfonamide;

N-[5-chloro-2-({[4-(difluoromethoxy)phenyl]sulfonyl}amino)phenyl]-1-benzofuran-2-sulfonamide;

N-(5-chloro-2-{[(2-fluoro-4-methylphenyl)sulfonyl]amino}phenyl)-1-benzofuran-2-sulfonamide;

N-[5-chloro-2-({[4-fluoro-3-(trifluoromethyl)phenyl]sulfonyl}amino)phenyl]-1-benzofuran-2-sulfonamide;

N-(5-chloro-2-{[(3-chloro-2-fluorophenyl)sulfonyl]amino}phenyl)-1-benzofuran-2-sulfonamide;

N-(5-chloro-2-{[(3-cyano-4-fluorophenyl)sulfonyl]amino}phenyl)-1-benzofuran-2-sulfonamide;

N-(5-chloro-2-{[(5-chloro-2-naphthyl)sulfonyl]amino}phenyl)-1-benzofuran-2-sulfonamide;

N-{2-[(biphenyl-3-ylsulfonyl)amino]-5-chlorophenyl}-1-benzofuran-2-sulfonamide;

N-{2-[(1-benzofuran-2-ylsulfonyl)amino]-4-chlorophenyl}-2-chloropyridine-3-sulfonamide;

N-{2-[(1-benzofuran-2-ylsulfonyl)amino]-4-chlorophenyl}pyridine-3-sulfonamide;

N-{2-[(1-benzofuran-2-ylsulfonyl)amino]-4-chlorophenyl}-2,3-dihydro-1,4-benzodioxine-6-sulfonamide;

N-(5-chloro-2-{[(5-isoxazol-5-yl-2-thienyl)sulfonyl]amino}phenyl)-1-benzofuran-2-sulfonamide;

N-(5-chloro-2-{[(3,5-dichloro-4-hydroxyphenyl)sulfonyl]amino}phenyl)-1-benzofuran-2-sulfonamide;

5-[({2-[(1-benzofuran-2-ylsulfonyl)amino]-4-chlorophenyl}amino)sulfonyl]-2-fluorobenzoic acid;

N-{2-[(1-benzofuran-2-ylsulfonyl)amino]-4-chlorophenyl}-1,2-dimethyl-1H-imidazole-4-sulfonamide;

N-(2-{[(4-bromo-3-methylphenyl)sulfonyl]amino}-5-chlorophenyl)-1-benzofuran-2-sulfonamide;

N-(5-chloro-2-{[(2-fluoro-5-methylphenyl)sulfonyl]amino}phenyl)-1-benzofuran-2-sulfonamide;

N-(5-chloro-2-{[(4'-chlorobiphenyl-4-yl)sulfonyl]amino}phenyl)-1-benzofuran-2-sulfonamide;

N-[5-chloro-2-({[3-(2-methylpyrimidin-4-yl)phenyl]sulfonyl}amino)phenyl]-1-benzofuran-2-sulfonamide;

N-[5-chloro-2-({[5-(1,3-oxazol-5-yl)-2-thienyl]sulfonyl}amino)phenyl]-1-benzofuran-2-sulfonamide;

N-[5-chloro-2-({[4-chloro-3-(trifluoromethyl)phenyl]sulfonyl}amino)phenyl]-1-benzofuran-2-sulfonamide;

N-{2-[(biphenyl-2-ylsulfonyl)amino]-5-chlorophenyl}-1-benzofuran-2-sulfonamide;

N-{2-[(1-benzofuran-2-ylsulfonyl)amino]-4-chlorophenyl}-2-oxo-2,3,4,5-tetrahydro-1H-1-benzazepine-7-sulfonamide;

N-(5-chloro-2-{[(3-chloro-4-cyanophenyl)sulfonyl]amino}phenyl)-1-benzofuran-2-sulfonamide;

3-[({2-[(1-benzofuran-2-ylsulfonyl)amino]-4-chlorophenyl}amino)sulfonyl]-4-chlorobenzoic acid;

N-(2-{[(3-acetylphenyl)sulfonyl]amino}-5-chlorophenyl)-1-benzofuran-2-sulfonamide;

N-{2-[(1-benzofuran-2-ylsulfonyl)amino]-4-chlorophenyl}-6-chloropyridine-3-sulfonamide;

N-(5-chloro-2-{[(5-chloro-2-methylphenyl)sulfonyl]amino}phenyl)-1-benzofuran-2-sulfonamide;

5-[({2-[(1-benzofuran-2-ylsulfonyl)amino]-4-chlorophenyl}amino)sulfonyl]-2-chlorobenzoic acid;

N-{3-[({2-[(1-benzofuran-2-ylsulfonyl)amino]-4-chlorophenyl}amino)sulfonyl]-4-methylphenyl}acetamide;

N-(5-chloro-2-{[(4-cyclohexylphenyl)sulfonyl]amino}phenyl)-1-benzofuran-2-sulfonamide;

N-{5-chloro-2-[(5,6,7,8-tetrahydronaphthalen-2-ylsulfonyl)amino]phenyl}-1-benzofuran-2-sulfonamide;

3-[({2-[(1-benzofuran-2-ylsulfonyl)amino]-4-chlorophenyl}amino)sulfonyl]-4-methoxybenzoic acid;

N-{2-[(1-benzofuran-2-ylsulfonyl)amino]-4-chlorophenyl}-2,3-dioxo-1,2,3,4-tetrahydroquinoxaline-6-sulfonamide;

N-{2-[(1-benzofuran-2-ylsulfonyl)amino]-4-chlorophenyl}-6-methoxypyridine-3-sulfonamide;

4-acetyl-N-{2-[(1-benzofuran-2-ylsulfonyl)amino]-4-chlorophenyl}-3,4-dihydro-2H-1,4-benzoxazine-6-sulfonamide;

N-[5-chloro-2-({[5-(dimethylamino)-1-naphthyl]sulfonyl}amino)phenyl]-1-benzofuran-2-sulfonamide;

N-{4-[({2-[(1-benzofuran-2-ylsulfonyl)amino]-4-chlorophenyl}amino)sulfonyl]-2-chlorophenyl}acetamide;

N-[5-chloro-2-({[4-(pyridin-3-yloxy)phenyl]sulfonyl}amino)phenyl]-1-benzofuran-2-sulfonamide;

N-(2-{[(5-tert-butyl-2-methylphenyl)sulfonyl]amino}-5-chlorophenyl)-1-benzofuran-2-sulfonamide;

N~1~-{2-[(1-benzofuran-2-ylsulfonyl)amino]-4-chlorophenyl}-4-chlorobenzene-1,3-disulfonamide;

N-[5-chloro-2-({[4-(2-chlorophenoxy)phenyl]sulfonyl}amino)phenyl]-1-benzofuran-2-sulfonamide;

N-[5-chloro-2-({[4-(pyridin-2-yloxy)phenyl]sulfonyl}amino)phenyl]-1-benzofuran-2-sulfonamide;

N-{4-[({2-[(1-benzofuran-2-ylsulfonyl)amino]-4-chlorophenyl}amino)sulfonyl]benzyl}acetamide;

methyl 5-[({2-[(1-benzofuran-2-ylsulfonyl)amino]-4-chlorophenyl}amino)sulfonyl]-2-methylbenzoate;

methyl 2-[({2-[(1-benzofuran-2-ylsulfonyl)amino]-4-chlorophenyl}amino)sulfonyl]-4-methoxybenzoate;

methyl 3-[({2-[(1-benzofuran-2-ylsulfonyl)amino]-4-chlorophenyl}amino)sulfonyl]-2-methylbenzoate;

N-{2-[(1-benzofuran-2-ylsulfonyl)amino]-4-chlorophenyl}-3-methylquinoline-8-sulfonamide;

N-[5-chloro-2-({[6-(dimethylamino)-2-naphthyl]sulfonyl}amino)phenyl]-1-benzofuran-2-sulfonamide;

N-[3-({[4-chloro-3-(trifluoromethyl)phenyl]sulfonyl}amino)pyridin-2-yl]thiophene-2-sulfonamide;

N-[5-chloro-3-({[4-chloro-3-(trifluoromethyl)phenyl]sulfonyl}amino)pyridin-2-yl]thiophene-2-sulfonamide.

Preferred compounds of the invention are:

N-{2-[(1-benzofuran-2-ylsulfonyl)amino]-4-chlorophenyl}-1-methyl-1H-pyrazole-3-sulfonamide;
N-(5-chloro-2-{[(2,6-difluorophenyl)sulfonyl]amino}phenyl)-1-benzofuran-2-sulfonamide;
N-(5-chloro-2-{[(2-fluorophenyl)sulfonyl]amino}phenyl)-1-benzofuran-2-sulfonamide;
N-{2-[(1-benzofuran-2-ylsulfonyl)amino]-4-chlorophenyl}-6-chloroimidazo[2,1-b][1,3]thiazole-5-sulfonamide;
N-(4,5-dichloro-2-{[(2-fluoro-5-methylphenyl)sulfonyl]amino}phenyl)thiophene-2-sulfonamide;
N-(5-chloro-2-{[(2,6-dichlorophenyl)sulfonyl]amino}phenyl)-1-benzofuran-2-sulfonamide;
N-{2-[(1-benzofuran-2-ylsulfonyl)amino]-4-chlorophenyl}-5-chloro-1,3-dimethyl-1H-pyrazole-4-sulfonamide;
N-(5-chloro-2-{[(2-chlorophenyl)sulfonyl]amino}phenyl)-1-benzofuran-2-sulfonamide;
N-[5-chloro-2-({[3-(difluoromethoxy)phenyl]sulfonyl}amino)phenyl]-1-benzofuran-2-sulfonamide;
N-(5-chloro-2-{[(5-methyl-2-thienyl)sulfonyl]amino}phenyl)-1-benzofuran-2-sulfonamide;
N-(5-chloro-2-{[(5-chloro-2-thienyl)sulfonyl]amino}phenyl)-1-benzofuran-2-sulfonamide;
N-{5-chloro-2-[(2,3-dihydro-1-benzofuran-7-ylsulfonyl)amino]phenyl}-1-benzofuran-2-sulfonamide;
N-(5-chloro-2-{[(3-methoxyphenyl)sulfonyl]amino}phenyl)-1-benzofuran-2-sulfonamide;
N-{2-[(1-benzofuran-2-ylsulfonyl)amino]-4-chlorophenyl}-1-methyl-1H-indole-7-sulfonamide;
N-{5-chloro-2-[(methylsulfonyl)amino]phenyl}-1-benzofuran-2-sulfonamide;
N-(5-chloro-2-{[(3,4-dimethylphenyl)sulfonyl]amino}phenyl)-1-benzofuran-2-sulfonamide;
N-{2-[(biphenyl-2-ylsulfonyl)amino]-5-chlorophenyl}-1-benzofuran-2-sulfonamide;
N-{4,5-dichloro-2-[(2-thienylsulfonyl)amino]phenyl}-5-methylfuran-2-sulfonamide;
N-(4,5-dichloro-2-{[(2,4-difluorophenyl)sulfonyl]amino}phenyl)thiophene-2-sulfonamide;
N-(2-{[(4-bromo-3-methylphenyl)sulfonyl]amino}-4,5-dichlorophenyl)thiophene-2-sulfonamide;
N-{4,5-dichloro-2-[(phenylsulfonyl)amino]phenyl}thiophene-2-sulfonamide;
methyl 5-[({4,5-dichloro-2-[(2-thienylsulfonyl)amino]phenyl}amino)sulfonyl]-2-methylbenzoate;
N-{4,5-dichloro-2-[(5,6,7,8-tetrahydronaphthalen-2-ylsulfonyl)amino]phenyl}thiophene-2-sulfonamide;
N-(4,5-dichloro-2-{[(2-methylphenyl)sulfonyl]amino}phenyl)thiophene-2-sulfonamide;
N-{4,5-dichloro-2-[(2-thienylsulfonyl)amino]phenyl}-1-methyl-2,3-dioxoindoline-5-sulfonamide;
N-(5-chloro-2-{[(5-methyl-2-furyl)sulfonyl]amino}phenyl)-1-benzofuran-2-sulfonamide;
N-{4,5-dichloro-2-[(2-thienylsulfonyl)amino]phenyl}-1-benzofuran-2-sulfonamide;
N-(4,5-dichloro-2-{[(4-chloro-2-fluorophenyl)sulfonyl]amino}phenyl)thiophene-2-sulfonamide;
methyl 3-[({4,5-dichloro-2-[(2-thienylsulfonyl)amino]phenyl}amino)sulfonyl]thiophene-2-carboxylate;
N-(4,5-dichloro-2-{[(2,4,5-trifluorophenyl)sulfonyl]amino}phenyl)thiophene-2-sulfonamide;
N-{4,5-dichloro-2-[(2-thienylsulfonyl)amino]phenyl}furan-2-sulfonamide;
N-(5-chloro-2-{[(2-methylphenyl)sulfonyl]amino}phenyl)-1-benzofuran-2-sulfonamide;
5-chloro-N-{4,5-dichloro-2-[(2-thienylsulfonyl)amino]phenyl}thiophene-2-sulfonamide;
N-(5-chloro-2-{[(2,5-difluorophenyl)sulfonyl]amino}phenyl)-1-benzofuran-2-sulfonamide;
N-{5-chloro-2-[(2-furylsulfonyl)amino]phenyl}-1-benzofuran-2-sulfonamide;
N-(5-chloro-2-{[(2,3-dichlorophenyl)sulfonyl]amino}phenyl)-1-benzofuran-2-sulfonamide;
N-{4,5-dichloro-2-[(2-thienylsulfonyl)amino]phenyl}-1,3-benzothiazole-6-sulfonamide;
N-(4,5-dichloro-2-{[(4-chloro-2,5-difluorophenyl)sulfonyl]amino}phenyl)thiophene-2-sulfonamide;
methyl 3-[({4,5-dichloro-2-[(2-thienylsulfonyl)amino]phenyl}amino)sulfonyl]benzoate;
N-(4,5-dichloro-2-{[(2,6-difluorophenyl)sulfonyl]amino}phenyl)thiophene-2-sulfonamide;
methyl 5-[({4,5-dichloro-2-[(2-thienylsulfonyl)amino]phenyl}amino)sulfonyl]-1-methyl-1H-pyrrole-2-carboxylate;
N-(5-chloro-2-{[(2,4-difluorophenyl)sulfonyl]amino}phenyl)-1-benzofuran-2-sulfonamide;
N-{2-[(1-benzofuran-2-ylsulfonyl)amino]-4-chlorophenyl}-1,3-benzodioxole-5-sulfonamide;
N-{5-chloro-2-[(isobutylsulfonyl)amino]phenyl}-1-benzofuran-2-sulfonamide;
N-{4,5-dichloro-2-[(2-thienylsulfonyl)amino]phenyl}-1-benzothiophene-2-sulfonamide;
N-{2-[(1-benzofuran-2-ylsulfonyl)amino]-4-chlorophenyl}quinoline-8-sulfonamide;
N-(5-chloro-2-{[(3-methylphenyl)sulfonyl]amino}phenyl)-1-benzofuran-2-sulfonamide;
N-(4,5-dichloro-2-{[(3,4-dichlorophenyl)sulfonyl]amino}phenyl)thiophene-2-sulfonamide;
N-(4,5-dichloro-2-{[(2,4-dichlorophenyl)sulfonyl]amino}phenyl)thiophene-2-sulfonamide;
N-{4,5-dichloro-2-[(2-thienylsulfonyl)amino]phenyl}quinoline-6-sulfonamide;
N-[3-({[4-chloro-3-(trifluoromethyl)phenyl]sulfonyl}amino)pyridin-2-yl]thiophene-2-sulfonamide;
N-(4,5-dichloro-2-{[(3,5-dichloro-2-hydroxyphenyl)sulfonyl]amino}phenyl)thiophene-2-sulfonamide;
N-(5-chloro-2-{[(2-methoxyphenyl)sulfonyl]amino}phenyl)-1-benzofuran-2-sulfonamide;
5,6-dichloro-N-{4,5-dichloro-2-[(2-thienylsulfonyl)amino]phenyl}pyridine-3-sulfonamide;
N-(4,5-dichloro-2-{[(3-cyanophenyl)sulfonyl]amino}phenyl)thiophene-2-sulfonamide;
N-[5-chloro-2-({[4-chloro-3-(trifluoromethyl)phenyl]sulfonyl}amino)-4-methylphenyl]thiophene-2-sulfonamide;
N-{2-[(1-benzofuran-2-ylsulfonyl)amino]-4-chlorophenyl}-1-methyl-1H-imidazole-4-sulfonamide;
methyl 3-[({2-[(1-benzofuran-2-ylsulfonyl)amino]-4-chlorophenyl}amino)sulfonyl]thiophene-2-carboxylate;
N-(4,5-dichloro-2-{[(4-chloro-2-fluoro-5-methylphenyl)sulfonyl]amino}phenyl)thiophene-2-sulfonamide;
N-{2-[(1-benzofuran-2-ylsulfonyl)amino]-4-chlorophenyl}-3,5-dimethyl-1H-pyrazole-4-sulfonamide;
6-chloro-N-{4,5-dichloro-2-[(2-thienylsulfonyl)amino]phenyl}pyridine-3-sulfonamide;
N-[4-chloro-2-({[4-chloro-3-(trifluoromethyl)phenyl]sulfonyl}amino)phenyl]thiophene-2-sulfonamide;
N-[2-({[4-chloro-3-(trifluoromethyl)phenyl]sulfonyl}amino)phenyl]-1-methyl-1H-imidazole-4-sulfonamide;
N-(2-{[(3-acetylphenyl)sulfonyl]amino}-4,5-dichlorophenyl)thiophene-2-sulfonamide;
N-{4,5-dichloro-2-[(2-thienylsulfonyl)amino]phenyl}-1-methyl-1H-pyrazole-3-sulfonamide;

N-{5-chloro-2-[(2-thienylsulfonyl)amino]phenyl}-1-benzofuran-2-sulfonamide;
N-{4-chloro-2-[(2-thienylsulfonyl)amino]phenyl}-1-benzofuran-2-sulfonamide;
N-(4,5-dichloro-2-{[(3-chloro-2-fluorophenyl)sulfonyl]amino}phenyl)thiophene-2-sulfonamide;
N-[4,5-dichloro-2-({[3-(trifluoromethyl)phenyl]sulfonyl}amino)phenyl]thiophene-2-sulfonamide;
N-(4,5-dichloro-2-{[(3-chlorophenyl)sulfonyl]amino}phenyl)thiophene-2-sulfonamide;
N-(4,5-dichloro-2-{[(2-fluorophenyl)sulfonyl]amino}phenyl)thiophene-2-sulfonamide;
N-[4,5-dichloro-2-({[4-fluoro-3-(trifluoromethyl)phenyl]sulfonyl}amino)phenyl]thiophene-2-sulfonamide;
N-(4,5-dichloro-2-({[(4-fluorophenyl)sulfonyl]amino}phenyl)thiophene-2-sulfonamide;
N,N'-1,2-phenylenedithiophene-2-sulfonamide;
N-[4,5-dichloro-2-({[3-(difluoromethoxy)phenyl]sulfonyl}amino)phenyl]thiophene-2-sulfonamide;
N-(4,5-dichloro-2-{[(3-chloro-4-fluorophenyl)sulfonyl]amino}phenyl)thiophene-2-sulfonamide;
N-(4,5-dichloro-2-{[(3-fluorophenyl)sulfonyl]amino}phenyl)thiophene-2-sulfonamide;
N-{4,5-dichloro-2-[(3-thienylsulfonyl)amino]phenyl}thiophene-2-sulfonamide;
N-(4,5-dichloro-2-{[(3-chloro-4-methylphenyl)sulfonyl]amino}phenyl)thiophene-2-sulfonamide;
N-(4,5-dichloro-2-{[(4-chloro-3-methylphenyl)sulfonyl]amino}phenyl)thiophene-2-sulfonamide;
N-{4,5-dichloro-2-[(2-thienylsulfonyl)amino]phenyl}-1-benzothiophene-3-sulfonamide;
5-chloro-N-{4,5-dichloro-2-[(2-thienylsulfonyl)amino]phenyl}quinoline-8-sulfonamide;
N-(4,5-dichloro-2-{[(3,5-difluorophenyl)sulfonyl]amino}phenyl)thiophene-2-sulfonamide;
N-{4,5-dichloro-2-[(2-thienylsulfonyl)amino]phenyl}furan-3-sulfonamide;
N-{4,5-dichloro-2-[(2-thienylsulfonyl)amino]phenyl}-1-benzofuran-5-sulfonamide;
N-(4,5-dichloro-2-{[(3,4-difluorophenyl)sulfonyl]amino}phenyl)thiophene-2-sulfonamide;
N-{4,5-dichloro-2-[(2-thienylsulfonyl)amino]phenyl}-2,3-dihydro-1-benzofuran-7-sulfonamide;
N-[5-chloro-2-({[4-chloro-3-(trifluoromethyl)phenyl]sulfonyl}amino)-4-methylphenyl]pyridine-3-sulfonamide;
N-(4,5-dichloro-2-({[(2-chlorophenyl)sulfonyl]amino}phenyl)thiophene-2-sulfonamide;
N-[5-chloro-2-({[4-chloro-3-(trifluoromethyl)phenyl]sulfonyl}amino)-4-methylphenyl]-1-methyl-1H-imidazole-4-sulfonamide;
N-{4,5-dichloro-2-[(2-thienylsulfonyl)amino]phenyl}-6-methoxypyridine-3-sulfonamide;
N-{4,5-dichloro-2-[(2-thienylsulfonyl)amino]phenyl}-5-methylthiophene-2-sulfonamide;
N-{4,5-dichloro-2-[(2-thienylsulfonyl)amino]phenyl}-2,3-dihydro-1,4-benzodioxine-6-sulfonamide;
N-(4,5-dichloro-2-{[(2,3-dichlorophenyl)sulfonyl]amino}phenyl)thiophene-2-sulfonamide;
N-(4,5-dichloro-2-{[(3-methylphenyl)sulfonyl]amino}phenyl)thiophene-2-sulfonamide;
N-(4,5-dichloro-2-{[(2-chloro-4-fluorophenyl)sulfonyl]amino}phenyl)thiophene-2-sulfonamide;
N-{4,5-dichloro-2-[(2-thienylsulfonyl)amino]phenyl}-1-methyl-1H-indole-5-sulfonamide;
N-(4,5-dichloro-2-{[(2,5-dichloro-3-thienyl)sulfonyl]amino}phenyl)thiophene-2-sulfonamide.

More preferred compounds of the invention are:
5-chloro-N-{4,5-dichloro-2-[(2-thienylsulfonyl)amino]phenyl}thiophene-2-sulfonamide;
6-chloro-N-{4,5-dichloro-2-[(2-thienylsulfonyl)amino]phenyl}pyridine-3-sulfonamide;
methyl 3-[({2-[(1-benzofuran-2-ylsulfonyl)amino]-4-chlorophenyl}amino)sulfonyl]thiophene-2-carboxylate;
methyl 3-[({4,5-dichloro-2-[(2-thienylsulfonyl)amino]phenyl}amino)sulfonyl]thiophene-2-carboxylate;
N-(2-{[(4-bromo-3-methylphenyl)sulfonyl]amino}-4,5-dichlorophenyl)thiophene-2-sulfonamide;
N-(4,5-dichloro-2-{[(2,4-difluorophenyl)sulfonyl]amino}phenyl)thiophene-2-sulfonamide;
N-(4,5-dichloro-2-{[(2-chlorophenyl)sulfonyl]amino}phenyl)thiophene-2-sulfonamide;
N-(4,5-dichloro-2-{[(2-fluorophenyl)sulfonyl]amino}phenyl)thiophene-2-sulfonamide;
N-(4,5-dichloro-2-{[(3,4-dichlorophenyl)sulfonyl]amino}phenyl)thiophene-2-sulfonamide;
N-(4,5-dichloro-2-{[(3,5-dichloro-2-hydroxyphenyl)sulfonyl]amino}phenyl)thiophene-2-sulfonamide;
N-(4,5-dichloro-2-{[(3-chloro-2-fluorophenyl)sulfonyl]amino}phenyl)thiophene-2-sulfonamide;
N-(4,5-dichloro-2-{[(3-chlorophenyl)sulfonyl]amino}phenyl)thiophene-2-sulfonamide;
N-(4,5-dichloro-2-{[(4-chloro-2-fluorophenyl)sulfonyl]amino}phenyl)thiophene-2-sulfonamide;
N-(4,5-dichloro-2-{[(4-fluorophenyl)sulfonyl]amino}phenyl)thiophene-2-sulfonamide;
N-(5-chloro-2-{[(2,6-dichlorophenyl)sulfonyl]amino}phenyl)-1-benzofuran-2-sulfonamide;
N-(5-chloro-2-{[(2,6-difluorophenyl)sulfonyl]amino}phenyl)-1-benzofuran-2-sulfonamide;
N-(5-chloro-2-{[(3,4-dimethylphenyl)sulfonyl]amino}phenyl)-1-benzofuran-2-sulfonamide;
N-(5-chloro-2-{[(5-methyl-2-thienyl)sulfonyl]amino}phenyl)-1-benzofuran-2-sulfonamide;
N-[3-({[4-chloro-3-(trifluoromethyl)phenyl]sulfonyl}amino)pyridin-2-yl]thiophene-2-sulfonamide;
N-[4,5-dichloro-2-({[3-(trifluoromethyl)phenyl]sulfonyl}amino)phenyl]thiophene-2-sulfonamide;
N-[4,5-dichloro-2-({[4-fluoro-3-(trifluoromethyl)phenyl]sulfonyl}amino)phenyl]thiophene-2-sulfonamide;
N-{2-[(1-benzofuran-2-ylsulfonyl)amino]-4-chlorophenyl}-1H-imidazole-4-sulfonamide;
N-{2-[(1-benzofuran-2-ylsulfonyl)amino]-4-chlorophenyl}-1H-pyrazole-3-sulfonamide;
N-{2-[(1-benzofuran-2-ylsulfonyl)amino]-4-chlorophenyl}-3,5-dimethyl-1H-pyrazole-4-sulfonamide;
N-{2-[(1-benzofuran-2-ylsulfonyl)amino]-4-chlorophenyl}-5-chloro-1,3-dimethyl-1H-pyrazole-4-sulfonamide;
N-{4,5-dichloro-2-[(2-thienylsulfonyl)amino]phenyl}-1-benzofuran-2-sulfonamide;
N-{4,5-dichloro-2-[(2-thienylsulfonyl)amino]phenyl}-1-benzothiophene-2-sulfonamide;
N-{4,5-dichloro-2-[(2-thienylsulfonyl)amino]phenyl}-1-methyl-2,3-dioxoindoline-5-sulfonamide;
N-{4,5-dichloro-2-[(2-thienylsulfonyl)amino]phenyl}-5-methylfuran-2-sulfonamide;
N-{4,5-dichloro-2-[(2-thienylsulfonyl)amino]phenyl}furan-2-sulfonamide;
N-{4-chloro-2-[(2-thienylsulfonyl)amino]phenyl}-1-benzofuran-2-sulfonamide;
N-{5-chloro-2-[(2-thienylsulfonyl)amino]phenyl}-1-benzofuran-2-sulfonamide.

Some compounds of Formula I and some of their intermediates have at least one stereogenic center in their structure.

This stereogenic center may be present in an R or S configuration, said R and S notation is used in correspondence with the rules described in Pure Appli. Chem. (1976), 45, 11-13.

The term “pharmaceutically acceptable salts” refers to salts or complexes that retain the desired biological activity of the above identified compounds and exhibit minimal or no undesired toxicological effects. The “pharmaceutically acceptable salts” according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, Calcium hydroxide, ammonia and the like; or an organic base such as for example, L-Arginine, ethanolamine, betaine, benzathine, morpholine and the like. (Handbook of Pharmaceutical Salts, P. Heinrich Stahal & Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the chemokine receptors.

In another embodiment, there are provided pharmaceutical compositions including at least one compound of the invention in a pharmaceutically acceptable carrier.

In a further embodiment of the invention, there are provided methods for treating disorders associated with modulation of chemokine receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by CCR modulation.

Therapeutic utilities of CCR modulators are skin inflammatory diseases and conditions, including, but are not limited to: rosacea (dilation of the blood vessels just under the skin), sunburn, chronic sun damage, discreet erythemas, psoriasis, atopic dermatitis, menopause-associated hot flashes, hot flashes resulting from orchiectomyatopic dermatitis, photoaging, seborrheic dermatitis, acne, allergic dermatitis, irritant dermatitis, telangiectasia (dilations of previously existing small blood vessels) of the face, rhinophyma (hypertrophy of the nose with follicular dilation), red bulbous nose, acne-like skin eruptions (may ooze or crust), burning or stinging sensation of the face, irritated and bloodshot and watery eyes, cutaneous hyperactivity with dilation of blood vessels of the skin, Lyell’s syndrome, Stevens-Johnson syndrome, erythema multiforme minor, erythema multiforme major and other inflammatory skin diseases, actinic keratoses, arsenic keratoses, inflammatory and non-inflammatory acne, ichthyoses and other keratinization and hyperproliferative disorders of the skin, eczema, wound healing.

Therapeutic utilities of CCR modulators are ocular inflammatory diseases including, but not limited to, uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; uveitis, retinitis, and choroiditis such as acute multifocal placoid pigment epitheliopathy, Behcet’s disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat’s disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt’s disease and fundus flavimaculatus, Best’s disease, pattern dystrophy of the retinal pigmented epithelium, X-linked retinoschisis, Sorsby’s fundus dystrophy, benign concentric maculopathy, Bietti’s crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis.

In still another embodiment of the invention, there are provided methods for treating disorders associated with modulation of chemokine receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular inflammatory diseases including, but not limited to, uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used.

Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Invention compounds and their pharmaceutically-acceptable salts may be administered through different routes, including but not limited to topical eye drops, direct injection, application at the back of the eye or formulations that may further enhance the long duration of actions such as a slow releasing pellet, suspension, gel, or sustained delivery devices such as any suitable drug delivery system (DDS) known in the art. While topical administration is preferred, this compound may also be used in an intraocular implant as described in U.S. U.S. Pat. No. 7,931,909.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of chemokine receptors. Thus, in further embodiments of the invention, there are provided methods for treating a disorder associated with modulation of chemokine receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The synthetic schemes set forth below, illustrate how compounds according to the invention can be made. Those skilled in the art will be able to routinely modify and/or adapt Scheme 1 or Scheme 2 to synthesize any compound of the invention covered by Formula I.

The following abbreviations are used in the general schemes and in the specific examples:

$NH_4HCO_3$ ammonium bicarbonate
$CH_3CN$ acetonitrile
$CH_2Cl_2$ dichloromethane
DMF N,N-dimethylformamide
NaOH sodium hydroxide
MeOH methanol
$CD_3OD$ deuterated methanol
$NH_3$ ammonia
HCl hydrochloric acid
$Na_2SO_4$ sodium sulfate
$NaHCO_3$ sodium bicarbonate
EtOH ethanol
$MgSO_4$ magnesium sulfate
EtOAc ethyl acetate
$CDCl_3$ deuterated chloroform
$CHCl_3$ chloroform
DMSO-$d_6$ deuterated dimethyl sulfoxide
$Et_3N$ triethylamine
DIPEA N,N-Diisopropylethylamine
TFA trifluoroacetic acid
THF tetrahydrofuran
NaH sodium hydride
HOAc acetic acid
DMAP 4-dimethylaminopyridine
$NH_4Cl$ ammonium chloride
$Et_2O$ diethylether
MeLi methylithium
$H_2$ hydrogen (gas)
Pd—C palladium on carbon
Zn zinc Scheme 1

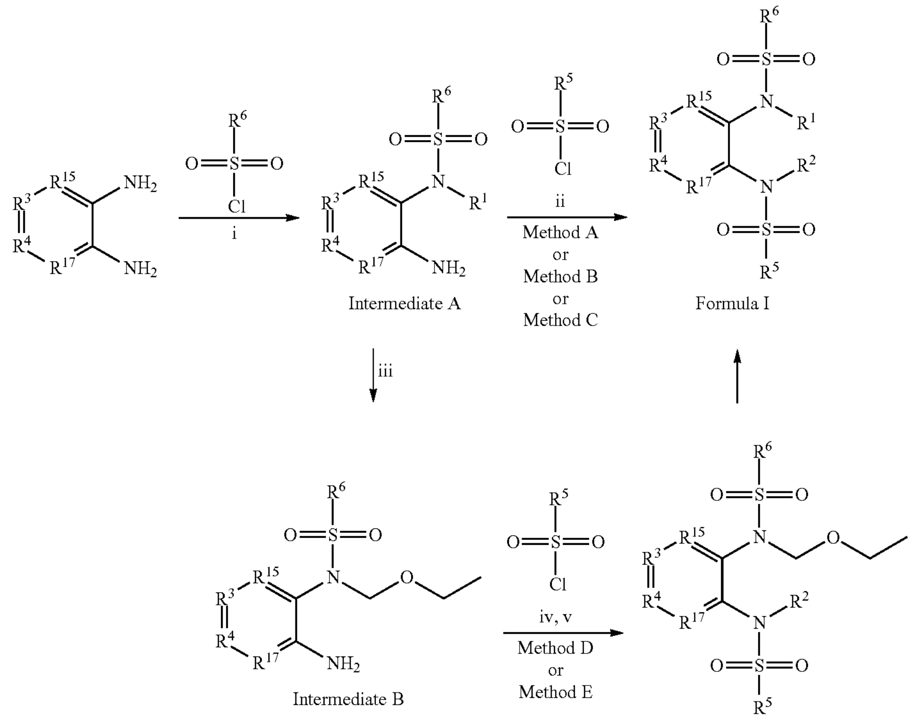

Intermediate A

Formula I

Intermediate B

Intermediate C wherein $R^6$ is 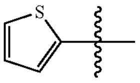

i: 2-thiophenesulfonyl chloride, $CH_2Cl_2$, pyridine, 0° C. to rt. 67%;
ii. sulfonyl chloride, pyridine, 100° C. (30 min) or rt (2 h), ca. 30% on average;
iii: 1-chloromethyl ethyl ether, NaH, THF, 0° C., 63%;
iv: aromatic sulfonyl chlorides: MeLi, THF, 0° C., then sulfonyl chloride, 0° C. to rt, ca. 30%; aliphatic sulfonyl chlorides: $Et_3N$, DMAP, $CHCl_3$, acetone, 50° C., 10-48%;
v: 4M HCl/dioxane, EtOH, rt, ca. 60-90%;

Scheme 2

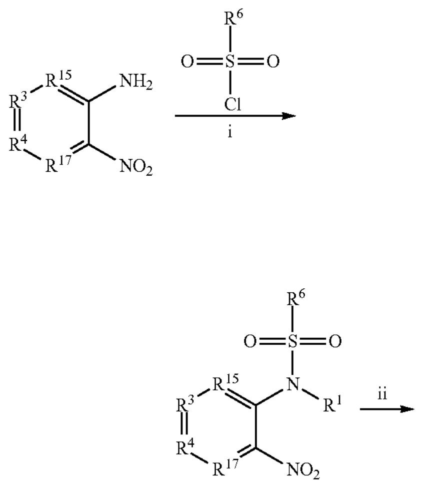

Intermediate D

-continued

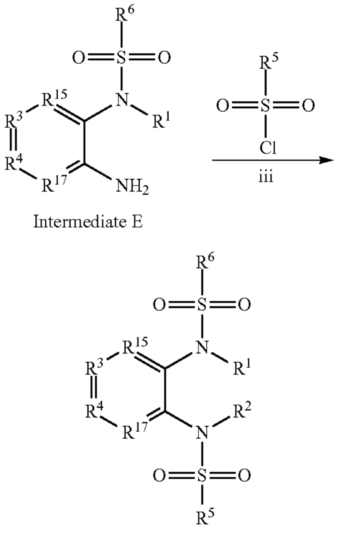

Intermediate E

Formula I

-continued wherein $R^6$ is 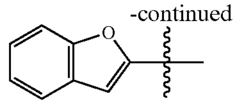

i: NaH, dry DMF, -10° C., 10 min, then 1-benzofuran-2-sulfonyl chloride in DMF, 10 min addition, -10° C., 30 min, 88%;

ii: Zn, sat. aq. $NH_4Cl$, THF, MeOH, r.t., 20 min, 69%;

iii: Sulfonyl chloride, pyridine, 100° C. (30 min) or r.t. (2 h), ca. 38% on average Sulfonamide Intermediate A was prepared starting with an appropriately substituted phenylene diamine. Sulfonamide Intermediate D was prepared starting with an appropriately substituted 2-nitroaniline. Reduction of Intermediate D with zinc dust and saturated aqueous ammonium chloride solution in THF and methanol afforded Intermediate E type. The bis-sulfonamide of Formula I was prepared from Intermediate A or Intermediate E in pyridine at either 100° C. (Method A for aromatic sulfonyl chlorides; or Method B with modified workup for aromatic sulfonyl chlorides containing a carboxylic acid group), or at room temperature (rt) (Method C).

For aliphatic sulfonyl chlorides and for aromatic sulfonyl chlorides that failed using method A, B, or C, the synthesis was modified via Intermediate B and Intermediate C. Protection of the sulfonamide nitrogen of Intermediate A using 1-chloromethyl ethyl ether afforded hemiaminal ether Intermediate B.

Deprotonation of Intermediate B with methyl lithium (MeLi) and subsequent reaction with aromatic sulfonyl chlorides afforded compounds of type Intermediate C, which were deprotected to bis-sulfonamides of Formula I using 4M hydrochloric acid(HCl)/dioxane in the presence of ethanol (both steps combined: Method D).

Reactions of Intermediate B with aliphatic sulfonyl chlorides were performed in the presence of triethylamine and 4-dimethylaminopyridine (DMAP) in chloroform($CHCl_3$)/acetone at 50° C. afforded compounds of type Intermediate C, which were deprotected to bis-sulfonamides of Formula I using 4M hydrochloric acid(HCl)/dioxane in the presence of ethanol (both steps combined: Method E).

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

As will be evident to those skilled in the art, individual isomeric forms can be obtained by separation of mixtures thereof in conventional manner. For example, in the case of diasteroisomeric isomers, chromatographic separation may be employed.

The IUPAC names of the compounds mentioned in the examples were generated with ACD version 8 and some intermediates' and reagents' names used in the examples were generated with software such as Chem Bio Draw Ultra version 12.0 or Auto Nom 2000 from MDL ISIS Draw 2.5 SP1.

In general, characterization of the compounds is performed by nuclear magnetic resonance and/or mass spectrometry. NMR spectra, recorded on Bruker Avance 300, $^1H$-NMR (300 MHz) in the indicated solvent at ambient temperature; chemical shifts in ppm, coupling constants in Hz. HPLC-MS: HPLC-System: Agilent 1100 Series, MS: Thermo Dionex Surveyor MSQ Plus. Column GeminiNX C18, 3 μm, 2.1×50 mm, gradient: 97% A (acidic: 0.1% TFA in water; basic: 1 mM $NH_4HCO_3$ in water pH 10) and 3% B (acidic: 0.085% TFA in $CH_3CN$; basic: $CH_3CN$) for 0.1 min, then in 2.1 min to 3% A and 97% B, then 3% A and 97% B for 0.3 min (flow: 0.8 ml/min); Or column Ascentis express C18, 2.7 μm, 3×50 mm, gradient: 97% A (acidic: 0.1% TEA in water; basic: 1 mM $NH_4(CO_3)_2$ in water pH 10) and 3% B (acidic: 0.085% TFA in $CH_3CN$; basic: $CH_3CN$) for 0.05 min, then in 2.9 min to 3% A and 97% B, then 3% A and 97% B for 0.2 min (flow: 1.3 ml/min); retention times $t_R$ in [min]; UV detection at 254 and 220 nm; ionization method as indicated.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures. Solvents were purchased from commercial sources in appropriate quality and used as received. Air and/or moisture-sensitive reactions were run under an argon or nitrogen atmosphere.

Usually the compounds of the invention were purified by chromatography:

TLC: Merck (silica gel 60 $F_{254}$, 0.25 mm);

Flash chromatography: Fluka silica gel 60 (0.04-0.063 mm) and Interchim Puriflash IR 60 silica gel (0.04-0.063 mm);

MPLC Normal Phase: Solvent system hexane (A)/EtOAc (B), column D: YMC*Gel Silica SL06S50 (0.006-50 μm), 60×200 mm, flow 175 ml/min, program 3 (start with 7% B, then in 12 min 100% B, then 100% B for 5 min), program 7 (start with 25% B, then in 12 min 100% B, then 100% B for 5.5 min);

Normal Phase Preparative HPLC: Macherey-Nagel VP100/21 Nucleosil 50 Å-10 μm, hexane/EtOAc/MeOH gradient.

Reverse Phase Preparative HPLC: Waters Xbridge C18 150×30 mm, 5 μm or Phenomenex GeminiNX C18 axia pack 100×30 mm, 5 μm, water/$CH_3CN$ gradient with 0.1% TFA or 10 mM $NH_4HCO_3$ (pH 10).

The following examples are for illustrative purposes only and are not intended, nor should they be construed as limiting the invention in any manner. Those skilled in the art will appreciate that variations and modifications of the following examples can be made without exceeding the spirit or scope of the invention.

Synthesis of Bis-Sulfonamides of Formula I

Method A

Method A is applied when $R^5$ does not contain a carboxylic acid group. To a solution of Intermediate A (50 mg, 0.155 mmol) in pyridine (1 ml) was added sulfonyl chloride (1.5 eq.) at room temp. The screw cap tube containing the mixture was quickly transferred in a 100° C. hot heating block, the mixture was stirred at 100° C. for 30 min. If the reaction failed according to TLC analysis (or HPLC analysis in cases of doubts), Method C was applied. If TLC analysis (or HPLC analysis in cases of doubt) showed the presence of major amount of starting material, additional sulfonyl chloride (1.5 eq.) was added and stirring at 100° C. was continued for another 30 min.

Half-saturated aq. $NaHCO_3$ solution was added at room temperature and extraction with $CH_2Cl_2$ followed. The organic layer was filtered through a pad of $MgSO_4$ and silica gel, the pad was rinsed with $CH_2Cl_2$/MeOH 9:1 and the filtrate was concentrated. Purification by preparative normal phase HPLC (oversized column: Machery-Nagel VP 150/32 Nucleosil 50-10, hexane/EtOAc/MeOH gradient) afforded the compound of Formula I. If further purification was required, a wash using $Et_2O$ or additional purification by reverse phase preparative HPLC, or depending on the nature of the material, a wash procedure using $Et_2O/CH_2Cl_2$ was performed.

Method B

Method B is applied when $R^5$ contains a carboxylic acid group. The reaction was performed as described in Method A, the workup was modified: Half-saturated aq. $NaHCO_3$ solution was added at room temperature and extraction with $CH_2Cl_2$ followed. The pH was adjusted to 2 by adding adding 4M aq. HCl solution to the aqueous layer. The mixture was extracted with $CH_2Cl_2$ the product is formed as immiscible oil. In this case, the aq. layer was removed, MeOH was added in order to dissolve the oil into the organic layer, the organic layer was filtered through a pad of $MgSO_4$ and silica gel, the pad was rinsed with $CH_2Cl_2$/MeOH 8:2 and the filtrate was concentrated. Purification by preparative reverse phase HPLC (acidic mobile phase) afforded the compound of Formula I. If further purification was needed, a wash procedure using $Et_2O$ (ultrasound bath) followed or additional purification was performed by reverse phase preparative HPLC (acidic mobile phase).

Method C

To a solution of Intermediate A (80 mg, 0.248 mmol) in pyridine (1 ml) was added sulfonyl chloride (1.5 eq.) at room temperature (screw cap tube) The mixture was stirred at room temperature for 2 h. If the reaction failed according to TLC analysis (or HPLC analysis in cases of doubts), Method D was applied. If TLC analysis (or HPLC analysis in cases of doubt) showed the presence of a major amount of starting material, additional sulfonyl chloride (1.5 eq.) was added and stirring at room temp. was continued for 1 h. The workup and purification were performed as described in Method A.

Method D

Deprotonation of Intermediate B with methyl lithium and subsequent reaction with aromatic sulfonyl chlorides afforded Intermediate C type compounds, which were deprotected to give the compound of Formula I using 4M Hydrochloric acid/dioxane in the presence of ethanol.

Method E

Method E is applied when $R^5$ is an aliphatic group. Reactions of Intermediate B with aliphatic sulfonyl chlorides were performed in the presence of triethylamine and 4-dimethylaminopyridine (DMAP) in chloroform($CHCl_3$)/acetone at 50° C. to afford Intermediate C compounds, which were deprotected to give the compound of Formula I using 4M Hydrochloric acid/dioxane in the presence of ethanol.

Preparation of Intermediates

Intermediate 1

N-(2-amino-4,5-dichlorophenyl)thiophene-2-sulfonamide

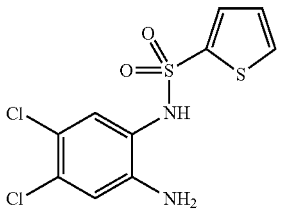 [SMILES: Nc1cc(Cl)c(Cl)cc1NS(=O)(=O)c1cccs1]

To an ice cold solution of 4,5-dichloro-o-phenylenediamine (CAS RN: 5348-42-5), (15.78 g, 89.14 mmol) in $CH_2Cl_2$ (185 ml) and pyridine (45 ml) was added a solution of 2-thiophenesulfonyl chloride (17.1 g, 93.62 mmol, 1.05 eq.) in $CH_2Cl_2$ (40 ml). The mixture (black solution) was stirred and allowed to warm to room temperature overnight (without removal of the cooling bath), then added to EtOAc and washed with sat. aq. $NaHCO_3$ solution. The aq. layer was extracted 2× with EtOAc, the combined organic layers were dried ($Na_2SO_4$) and concentrated. The crude product was combined with the crude product of an analogously performed 10 g scale attempt, chromatography on silica gel (hexane/EtOAc 8:2 to 6:4, chromatography was repeated with mixed fractions using the same eluent) and afforded Intermediate 1 (31.5 g, 67%) as brown solid. $C_{10}H_8Cl_2N_2O_2S_2$ (323.22). MS ($ESI^+$): 325/323 $[M+H]^+$. $^1$H-NMR (DMSO-$d_6$): δ ppm 9.8-9.5 (br. signal, 1H); 7.95 (dd, J=1.4, 5.0, 1H); 7.50 (dd, J=1.4, 3.7, 1H); 7.16 (dd, J=3.8, 5.0, 1H); 6.87, 6.85 (2s, 2×1H); 5.5-5.25 (br. s, 2H).

Intermediate 2

N-(2-amino-4,5-dichlorophenyl)-N-(ethoxymethyl) thiophene-2-sulfonamide

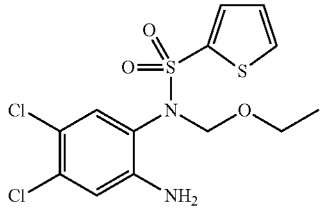 [SMILES: CCOCN(c1cc(Cl)c(Cl)cc1N)S(=O)(=O)c1cccs1]

To an ice cold solution of Intermediate 1 (3.24 g, 10.02 mmol) in THF (90 ml) and DMF (30 ml) was added NaH (ca. 60% in mineral oil, 0.6 g, ca. 15 mmol, 1.5 eq., gas evolution, brown solution). The mixture was stirred at 0° C. for 30 min (dark colored after 5 min), then a solution of 1-chloromethyl ethyl ether (1.02 ml, ca. 1.04 g, 11 mmol, 1.1 eq.) was added dropwise at 0° C. The brown, light green mixture was stirred at 0° C. for 1 h, then sat. aq. $NaHCO_3$ solution (ca. 10 ml) was added at 0° C. The mixture was concentrated (rotary evaporator), water was added and extraction with EtOAc followed. The organic layer was washed with water (2×) and brine, dried ($Na_2SO_4$) and concentrated. The crude product was adsorbed on silica gel ($CH_2Cl_2$/MeOH), chromatography on silica gel (hexane/acetone 90:10 to 88:12 to 86:14 to 84:16 to 82:18 to 80:20) afforded Intermediate 2 (2.4 g, 63%) as brown solid. $C_{13}H_{14}Cl_2N_2O_3S_2$ (381.30). MS (ESI$^+$): 383/381 $[M+H]^+$. $^1$H-NMR (DMSO-$d_6$): δ ppm 8.05 (dd, J=0.5, 4.9, 1H); 7.65 (dd, J=0.5, 3.7, 1H); 7.24 (dd, J=3.8, 5.0, 1H); 6.92, 6.72 (2s, 2×1H); 5.60 (br. s, 2H, exchanged upon treatment with $D_2O$); 5.20-5.05 (br. signal, 1H); 4.78-4.62 (br. signal, 1H); 3.54 (q, J=7.0, 2H); 1.09 (t, J=7.0, 3H).

Intermediate 3

N-(4,5-dichloro-2-(3-chloro-4-fluorophenylsulfonamido)phenyl)-N-(ethoxymethyl)thiophene-2-sulfonamide

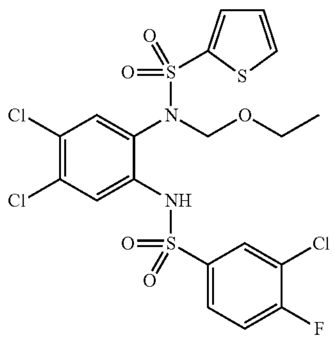 [SMILES: CCOCN(c1cc(Cl)c(Cl)cc1NS(=O)(=O)c1ccc(F)c(Cl)c1)S(=O)(=O)c1cccs1]

Sulfonamide formation according to METHOD D: To an ice cold solution of Intermediate 2 (70 mg, 0.184 mmol) in THF (1 ml) was added dropwise MeLi (1.6M in $Et_2O$, 0.25 ml, ca. 0.4 mmol, 2.2 eq.). The dark green mixture was stirred at 0° C. for 15 min, then a solution of an aromatic sulfonyl chloride for example: 3-chloro-4-fluorobenzenesulfonyl chloride (63.1 mg, 0.275 mmol, 1.5 eq.) in THF (1 ml) was added dropwise at 0° C. The orange solution was stirred at 0° C. for 40 min and at room temp. overnight. MeOH was added at room temp. and the mixture was concentrated. Purification by reverse phase preparative HPLC (acidic mobile phase) afforded Intermediate 3 (37 mg, 35%) as light yellow solid.

$^1$H-NMR (DMSO-$d_6$): δ ppm 10.6-10.35 (br. signal, 1H); 8.14 (dd, J=2.1, 6.7, 1H); 8.08 (dd, J=1.3, 5.0, 1H); 7.94-7.89 (m, 1H); 7.67 (t, J=8.9, 1H); 7.60 (s, 1H); 7.56 (dd, J=1.3, 3.8, 1H); 7.23 (dd, J=3.9, 4.9, 1H); 6.86 (s, 1H); 5.4-5.0 (br. signal, 1H); 4.5-4.1 (br. signal, 1H); 3.41 (partially hidden, partially resolved q, J=7.0, 2H); 1.04 (t, J=7.0, 3H).

Intermediate 4

Benzofuran-2-sulfonic acid (5-chloro-2-nitro-phenyl)-amide

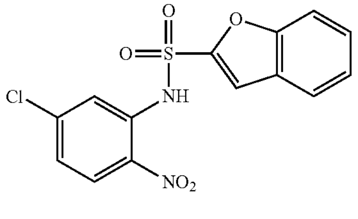 [SMILES: O=[N+]([O-])c1ccc(Cl)cc1NS(=O)(=O)c1cc2ccccc2o1]

To a −10° C. cold yellow solution of 5-chloro-2-nitroaniline (8.00 g, 46.36 mmol) in dry DMF (130 ml) was added sodium hydride 60% (9.27 g, 231.79 mmol) under Ar. The resulting red suspension was stirred at −10° C. for 10 minutes. A solution of 1-benzofuran-2-sulfonyl chloride (12.05 g, 55.63 mmol) in dry DMF (50 ml) was added dropwise with a dropping funnel at −10° C. (10 minutes of addition, exothermic reaction, maximum temperature of addition was 0° C., 5 ml of DMF to rinse the funnel). The resulting orange suspension was stirred at −10° C. for 30 minutes (color changed to brown). The reaction mixture was quenched with half saturated $NaHCO_3$ solution (400 ml) and the product was extracted five times with EtOAc (1×650 ml and 4×300 ml). The combined organic layers were dried over $Na_2SO_4$, filtered and the filtrate evaporated to dryness. The crude product was combined with the crude product of an analogously performed 8 g scale attempt to give 61.82 g of an orange oil which was purified by MPLC (crude was dissolved in $CH_2Cl_2$/MeOH, preabsorption on silica gel, column D, program 3, 5 runs) to afford Intermediate 4 (28.91 g, 88% yield based on combined starting material) as yellow solid.

$C_{14}H_9ClN_2O_6S$ (352.75). HPLC-MS (basic mobile phase, ESI$^-$): $t_R$=1.31 min, 350.7 $[M-H]^-$. $^1$H-NMR (DMSO-$d_6$): 7.70 (ddd, J=0.6, 1.3, 7.8, 1H); 7.60 (dd, J=0.8, 8.3, 1H); 7.52-7.47 (m, 2H); 7.39 (m, 1H); 7.28 (m, 1H); 7.18 (s, 1H); 6.75 (d, J=8.3, 1H).

Intermediate 5

Benzofuran-2-sulfonic acid (2-amino-5-chloro-phenyl)-amide

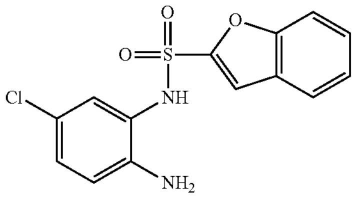 [SMILES: Nc1ccc(Cl)cc1NS(=O)(=O)c1cc2ccccc2o1]

To an orange solution of Intermediate 4 (14.41 g, 40.85 mmol) in THF (55 ml) and MeOH (285 ml) was added saturated aqueous $NH_4Cl$ solution (285 ml, precipitation of starting material) and then Zinc (20.03 g, 306.38 mmol) in a cold water bath (20° C.). The resulting suspension was stirred at room temperature for 20 minutes (color changed from brown to dark green). EtOAc (400 ml) and saturated aqueous $NH_4Cl$ solution (400 ml) were added. The solid in suspension was filtered through a pad of celite and washed with EtOAc (3×250 ml) and saturated aqueous $NH_4Cl$ solution (3×200 ml). The filtrate was shaken and the organic layer was collected, dried over $Na_2SO_4$, filtered and evaporated to dryness. The residue was dissolved in $CH_2Cl_2$, filtered through a pad of silica, washed three times with $CH_2Cl_2$/MeOH 9/1 and evaporated to dryness. The crude product was combined with the crude product of an analogously performed 14.41 g scale attempt to leave 27.23 g of red foam. The crude foam was dissolved in $CH_2Cl_2$/MeOH 99/1 whereupon a solid precipitates. The mixture was evaporated to dryness and re-dissolved in a mixture of EtOAc/MeOH. The remaining solid was filtered off. The filtrate was preabsorbed on silica gel and purified by flash chromatography over silica gel eluted with $CH_2Cl_2$/MeOH from 99/1 to 97/3 to give 20.25 g of impure brown solid. This product was repurified by MPLC (crude was dissolved in $CH_2Cl_2$/MeOH, preabsorption on silica gel, column D, program 7, 5 runs) to afford Intermediate 5 (18.18 g, 69% yield based on combined starting material) as beige solid. $C_{14}H_{11}ClN_2O_3S$ (322.76). HPLC-MS (acidic mobile phase, ESI$^+$): $t_R$=1.93 min, 323/325 $[M+H]^+$. $^1$H-NMR (DMSO-$d_6$): 10.7-9.3 (br. signal, ca. 1H); 7.75 (m, 2H); 7.60-

7.50 (m, 2H); 7.39 (m, 1H); 6.96 (dd, J=2.5, 8.7, 1H); 6.81 (d, J=2.5, 1H); 6.62 (d, J=8.7, 1H), 6.9-5.4 (br. signal, ca. 2H).

Intermediate 6

Benzofuran-2-sulfonic acid (4-chloro-2-nitro-phenyl)-amide

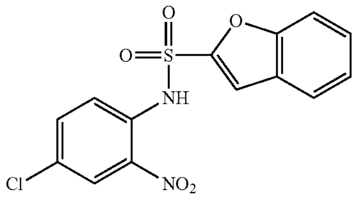 [SMILES: O=[N+]([O-])c1cc(Cl)ccc1NS(=O)(=O)c1cc2ccccc2o1]

To a solution of 4-chloro-2-nitroaniline (CAS RN: 89-63-4) (0.52 g, 3.0 mmol) in pyridine (3.0 ml) was added benzofuran-2-sulfonyl chloride (0.65 g, 3.0 mmol) and the mixture was stirred at room temperature for 64 h. More benzofuran-2-sulfonyl chloride (0.65 g, 3.0 mmol) and pyridine (3.0 ml) were added and the reaction was heated to 100° C. for 4 h, cooled to room temperature, poured onto a mixture of ice and 6M HCl (20 ml). The resulting suspension was filtered, rinsed with $H_2O$, and the cake was dissolved in EtOAc, washed with brine, dried over $Na_2SO_4$, and concentrated to give 1.28 g brown solid. The solid was dissolved in MeOH/THF (40 ml/10 ml), treated with 4 M NaOH (4 ml) at 100° C. for 15 min, and concentrated in vacuo. The residue was quenched with cold 1M HCl, extracted with EtOAc (×2). The combined organic layer was washed with brine, dried over $Na_2SO_4$ and concentrated. Re-crystallization from hot EtOH yielded 0.68 g (64%) of Intermediate 6.

$^1$H-NMR (600 MHz, $CDCl_3$) δ ppm 10.00 (s, 1 H), 8.13 (d, J=2.3 Hz, 1 H), 7.93 (d, J=9.1 Hz, 1 H), 7.64-7.68 (m, 1 H), 7.58 (dd, J=9.0, 2.5 Hz, 1 H), 7.45-7.53 (m, 3 H), 7.34 (ddd, J=7.9, 6.9, 1.0 Hz, 1 H).

Intermediate 7

Benzofuran-2-sulfonic acid (2-amino-4-chloro-phenyl)-amide

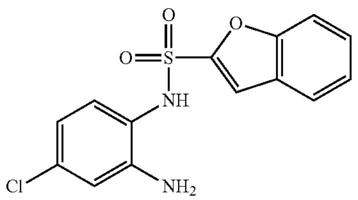

To a suspension of Intermediate 6 (217 mg, 0.61 mmol) in MeOH (25 ml) and saturated aqueous $NH_4Cl$ (25 ml) was added zinc dust (1.0 g, 15.4 mmol). The reaction was stirred at room temperature for 45 min. HOAc (1.0 ml) and zinc dust (1.0 g, 15.4 mmol) were added and the reaction was stirred for another 45 min and was filtered. The filtrate was extracted with EtOAc (×2). The combined organic layer was washed with brine, dried over $Na_2SO_4$, and concentrated. The crude product was purified by flash column chromatography on silica gel (25% EtOAc-hexane) to yield 158 mg (79%) of Intermediate 7.

$^1$H-NMR (600 MHz, $CDCl_3$) δ ppm 7.65 (dt, J=7.4, 0.8 Hz, 1 H), 7.57-7.61 (m, 1 H), 7.50 (ddd, J=8.4, 7.1, 1.2 Hz, 1 H), 7.35 (ddd, J=8.0, 7.3, 0.9 Hz, 1 H), 7.30 (d, J=0.9 Hz, 1 H), 6.70 (d, J=2.3 Hz, 1 H), 6.59 (d, J=8.5 Hz, 1 H), 6.45-6.48 (m, 1 H), 6.32 (s, 1 H), 4.17 (br. s., 2 H).

Intermediate 8

Thiophene-2-sulfonic acid (3-nitro-pyridin-2-yl)-amide

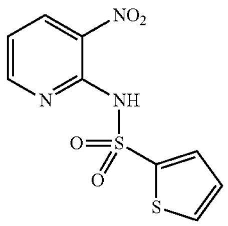 [SMILES: O=[N+]([O-])c1cccnc1NS(=O)(=O)c1cccs1]

To a solution of 2-chloro-3-nitro-pyridine (CAS RN: 5470-18-8, 0.64 g, 4.0 mmol) in DMSO (4 ml) was added thiophene-2-sulfonic acid amide (CAS RN: 6339-87-3, 0.33 g, 2.0 mmol) and $K_2CO_3$ (0.55 g, 4.0 mmol). The mixture was stirred at 60° C. for 24 h, diluted with EtOAc, extracted with 1M HCl, brine, dried over $Na_2SO_4$, and concentrated in vacuo. The crude product was purified by flash column chromatography on silica gel (25%-40% EtOAc in hexanes) to yield Intermediate 8 (0.50 g, 87%) as yellow powder. $^1$H NMR(CHLOROFORM-d) δ ppm: 10.27 (br. s, 1H), 8.63 (dd, J=4.5, 1.6 Hz, 1H), 8.53 (dd, J=8.2, 1.8 Hz, 1H), 8.00 (dd, J=3.8, 1.5 Hz, 1H), 7.67 (dd, J=5.0, 1.5 Hz, 1H), 7.13-7.19 (m, 1H), 7.08-7.12 (m, 1H).

Intermediate 9

Thiophene-2-sulfonic acid (5-chloro-3-nitro-pyridin-2-yl)-amide

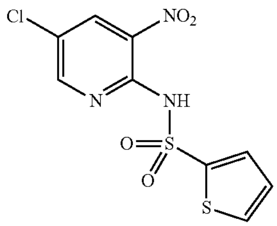 [SMILES: O=[N+]([O-])c1cc(Cl)cnc1NS(=O)(=O)c1cccs1]

To a solution of 2-bromo-5-chloro-3-nitro-pyridine (CAS RN: 75806-86-9, 360 mg, 1.5 mmol) in DMSO (2 ml) was added thiophene-2-sulfonic acid amide (CAS RN: 6339-87-3, 165 mg, 1.0 mmol) and $K_2CO_3$ (276 mg, 2.0 mmol). The mixture was stirred at 60° C. for 24 h, diluted with EtOAc, extracted with 1M HCl, brine, dried over $Na_2SO_4$, and concentrated in vacuo. The crude product was purified by flash column chromatography on silica gel (0%-100% EtOAc in hexanes) to yield Intermediate 9 (245 mg, 77%) as light brown solid.

$^1H$ NMR (METHANOL-$d_4$) δ: 8.57-8.63 (m, 2H), 7.95 (dd, J=4.0, 1.3 Hz, 1H), 7.86 (dd, J=5.0, 1.5 Hz, 1H), 7.14 (dd, J=5.1, 4.0 Hz, 1H).

Intermediate 10

Thiophene-2-sulfonic acid (3-amino-pyridin-2-yl)-amide

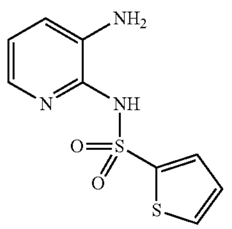 [SMILES: Nc1cccnc1NS(=O)(=O)c1cccs1]

To a solution of Intermediate 8 (175 mg, 0.61 mmol) in MeOH (30 ml) and 1M HCl (2 ml) was added Pd—C (10%, 65 mg, 0.061 mmol). The reaction was pressurized under 45 psi $H_2$ for 3 h using Parr apparatus, filtered, and the filtrate was concentrated in vacuo. The crude product was purified by flash column chromatography on silica gel (50%-100% EtOAc in hexanes, then 2:98 $Et_3N$:EtOAc, then 2:20:80 $Et_3N$:MeOH:$CH_2Cl_2$) to yield Intermediate 10 (157 mg, 84%) as off-white solid.

$^1H$ NMR (CHLOROFORM-d) δ: 7.61 (dd, J=3.7, 1.3 Hz, 1H), 7.44 (dd, J=5.0, 1.2 Hz, 1H), 6.96-7.03 (m, 2H), 6.83 (dd, J=7.6, 1.5 Hz, 1H), 6.56 (dd, J=7.6, 6.2 Hz, 1H).

Intermediate 11

Thiophene-2-sulfonic acid (3-amino-5-chloro-pyridin-2-yl)-amide

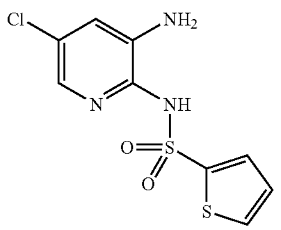 [SMILES: Nc1cc(Cl)cnc1NS(=O)(=O)c1cccs1]

To a solution of Intermediate 9 (111 mg, 0.35 mmol) in MeOH (15 ml) was added aqueous $NH_4Cl$ (15 ml) and zinc dust (0.56 g, 8.7 mmol). The mixture was stirred at room temperature for 2 h, filtered and extracted with EtOAc. The organic layer was washed with brine, dried over $Na_2SO_4$, and concentrated in vacuo. The crude product was purified by flash column chromatography on silica gel (30%-100% EtOAc in hexanes, then 10% MeOH in $CH_2Cl_2$) to yield Intermediate 11 (75 mg, 75%). $C_9H_8ClN_3O_2S_2$ (289.8). MS ($ESI^-$): 288/290/$[M-H]^-$.

Intermediate 12

N-(4,5-dichloro-2-(2-methylpropylsulfonamido)phenyl)-N-(ethoxymethyl)thiophene-2-sulfonamide

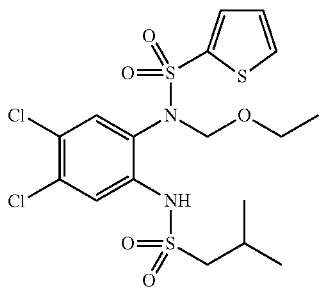 [SMILES: CCOCN(c1cc(Cl)c(Cl)cc1NS(=O)(=O)CC(C)C)S(=O)(=O)c1cccs1]

Sulfonamide formation: To a solution of Intermediate 2 (80 mg, 0.21 mmol) and DMAP (5.1 mg, 0.042 mmol, 0.2 eq.) in $CHCl_3$ (0.8 ml) and acetone (0.8 ml) was added isobutanesulfonyl chloride (32.9 μl, ca. 39 mg, 0.25 mmol, 1.2 eq.) at room temp. followed by $Et_3N$ (87.2 μl, ca. 63 mg, 0.62 mmol, 3 eq.). The orange-brown solution was stirred at 50° C. overnight. Water and EtOAc were added at room temp. and extraction with EtOAc followed. The organic layer was dried ($Na_2SO_4$), filtered and concentrated. Chromatography on silica gel (hexane/$CH_2Cl_2$/$Et_2O$ 5:5:0.5 to 5:5:1) afforded the corresponding type Intermediate 12 product (43 mg, 41%) as light yellow oil.

$^1H$-NMR ($CDCl_3$): δ ppm 7.85 (s, 1H); ca. 7.85-7.84 (partially hidden signal, 1H); 7.74 (dd, J=1.3, 5.0, 1H); 7.54 (dd, J=1.3, 3.8, 1H); 7.15 (dd, J=3.8, 5.0, 1H); 7.00 (s, 1H); 5.05-4.88 (br. signal, 2H); 3.75-3.60 (br. signal, 2H); 3.04 (d, J=6.6, 2H); 2.43-2.30 (heptet, 1H); 1.28 (t, J=7.0, 3H); 1.14 (d, J=6.7, 6H).

Preparation of Specific Compounds of the Invention

Compound 1

N-(4,5-dichloro-2-({[(3-chloro-4-fluorophenyl)sulfonyl]amino}phenyl)thiophene-2-sulfonamide

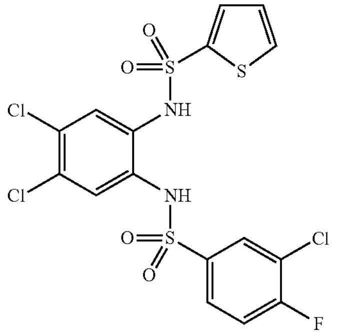 [SMILES: O=S(=O)(Nc1cc(Cl)c(Cl)cc1NS(=O)(=O)c1cccs1)c1ccc(F)c(Cl)c1]

To Intermediate 3 (47 mg, 0.082 mmol) and EtOH (0.2 ml) was added 4M HCl/dioxane (1 ml) at room temp. The solution was stirred for 42 h at room temp. and then concentrated. Chromatography on silica gel ($CH_2Cl_2$/MeOH 9:1) afforded Compound 1 (24.9 mg, 59%) as off-white solid.

$C_{16}H_{10}Cl_3FN_2O_4S_3$ (515.81). HPLC-MS (acidic mobile phase, $ESI^-$): $t_R$=2.14 min, 517/515/513 $[M-H]^-$. $^1H$-NMR (DMSO-$d_6$): δ ppm ca. 10.5-ca. 9 (br. signal, ca. 1H); 7.99-7.95 (m, 2H); 7.74-7.69 (m, 1H); 7.63 (d, J=8.9, 1H); 7.58-7.55 (m, 1H); 7.30 (s, 1H); 7.17 (dd, J=3.8, 5.0, 1H); 7.15 (s, 1H).

Compound 2

N-{4,5-dichloro-2-[(isobutylsulfonyl)amino] phenyl}thiophene-2-sulfonamide

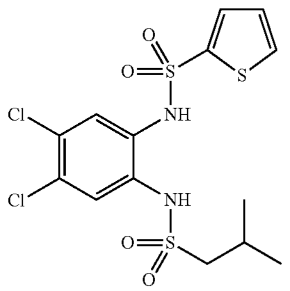 [SMILES: CC(C)CS(=O)(=O)Nc1cc(Cl)c(Cl)cc1NS(=O)(=O)c1cccs1]

To Intermediate 12 (42 mg, 0.084 mmol) in EtOH (0.2 ml) was added 4M HCl/dioxane (2 ml) at room temp. The solution was stirred for 72 h at room temp. and then concentrated. Chromatography on silica gel ($CH_2Cl_2$/MeOH 95:5 to 9:1) afforded Compound 2 (29.8 mg, 80%) as white solid.

$C_{14}H_{16}Cl_2N_2O_4S_3$ (443.39). HPLC-MS (basic mobile phase, $ESI^-$): $t_R$=1.66 min, 443/441 $[M-H]^-$. $^1$H-NMR ($CDCl_3$): δ ppm 7.71 (dd, J=1.3, 5.0, 1H); 7.65 (s, 1H); 7.55 (dd, J=1.3, 3.8, 1H); 7.14 (dd, J=3.8, 5.0, 1H); 7.05 (s, 1H); 6.97, 6.96 (2 partially separated s, 2×1H); 3.02 (d, J=6.6, 2H); 2.42-2.28 (heptet, 1H); 1.14 (d, J=6.6, 6H).

Compound 3

N-(4,5-dichloro-2-{[(3,5-difluorophenyl)sulfonyl] amino}phenyl)thiophene-2-sulfonamide

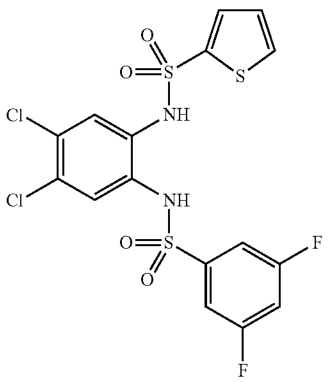 [SMILES: O=S(=O)(Nc1cc(Cl)c(Cl)cc1NS(=O)(=O)c1cccs1)c1cc(F)cc(F)c1]

Preparation according to Method C (18% yield) from Intermediate 1. $C_{16}H_{10}Cl_2F_2N_2O_4S_3$ (499.36).

HPLC-MS (acidic mobile phase, $ESI^-$): $t_R$=2.16 min, 499/497 $[M-H]^-$.

$^1$H-NMR (DMSO-$d_6$): δ ppm ca. 10.4-ca. 9.3 (br. signal, ca. 2H); 8.00 (dd, J=1.3, 5.0, 1H); 7.68 (tt, J=2.3, 9.2, 1H); 7.59 (dd, J=1.3, 3.8, 1H); 7.54-7.43 (m, 2H); 7.31 (s, 1H); 7.18 (dd, J=3.8, 5.0, 1H); 7.13 (s, 1H).

Compound 4

N-{4,5-dichloro-2-[(2-thienylsulfonyl)amino]phenyl}-2,4-dimethyl-1,3-thiazole-5-sulfonamide

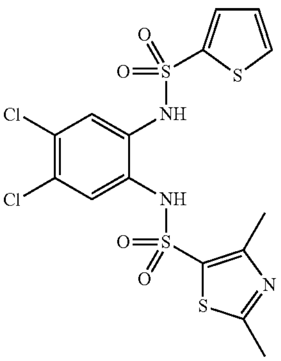 [SMILES: Cc1nc(C)c(S(=O)(=O)Nc2cc(Cl)c(Cl)cc2NS(=O)(=O)c2cccs2)s1]

Preparation according to Method A (10% yield) from Intermediate 1. $C_{16}H_{13}Cl_2N_3O_4S_4$ (498.45).

HPLC-MS (acidic mobile phase, $ESI^-$): $t_R$=1.98 min, 498/496 $[M-H]^-$.

$^1$H-NMR (DMSO-$d_6$): δ ppm 10.3-9.3 (br. signal, ca. 2H); 7.99 (dd, J=1.3, 5.0, 1H); 7.60 (dd, J=1.3, 3.8, 1H); 7.31, 7.27 (2s, 2×1H); 7.18 (dd, J=3.8, 5.0, 1H); 2.62, 2.33 (2s, 2×3H).

Compound 5

N-{4,5-dichloro-2-[(2-thienylsulfonyl)amino]phenyl}-3,5-dimethylisoxazole-4-sulfonamide

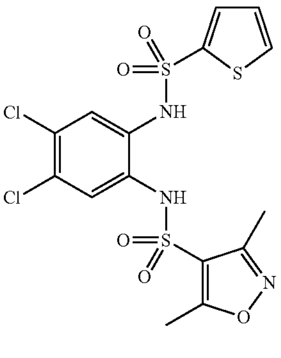 [SMILES: Cc1noc(C)c1S(=O)(=O)Nc1cc(Cl)c(Cl)cc1NS(=O)(=O)c1cccs1]

Preparation according to Method A (18% yield) from Intermediate 1. $C_{15}H_{13}Cl_2N_3O_6S_3$ (482.38).

HPLC-MS (acidic mobile phase, $ESI^-$): $t_R$=2.01 min, 482/480 $[M-H]^-$. $^1$H-NMR (DMSO-$d_6$): δ ppm ca. 10.3-ca. 9.5 (br. signal, ca. 2H); 8.00 (dd, J=1.2, 4.9, 1H); 7.61 (dd, J=1.3, 3.8, 1H); 7.31, 7.21 (2s, 2×1H); 7.19 (dd, J=3.9, 5.0, 1H); 2.40, 2.19 (2s, 2×3H).

Compound 6

N-{4,5-dichloro-2[(2-thienylsulfonyl)amino]phenyl}-2-oxoindoline-5-sulfonamide

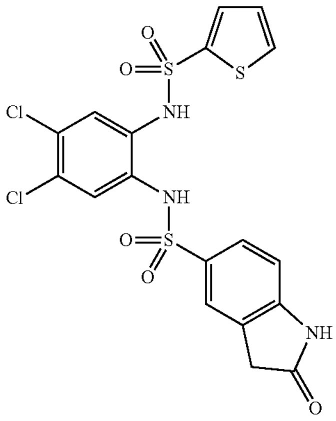 [SMILES: O=C1Cc2cc(S(=O)(=O)Nc3cc(Cl)c(Cl)cc3NS(=O)(=O)c3cccs3)ccc2N1]

Preparation according to Method A (24% yield) from Intermediate 1. $C_{18}H_{13}Cl_2N_3O_6S_3$ (518.41).

HPLC-MS (acidic mobile phase, $ESI^-$): $t_R$=1.88 min, 518/516 $[M-H]^-$.

$^1$H-NMR (DMSO-$d_6$): δ ppm 10.84 (s, 1H); ca. 10.1-ca. 10.65 (br. signal, ca. 1H); ca. 10.65-ca. 9.3 (br. signal, ca. 1H); 7.99 (signal appears as d, "J"=4.9, 1H); 7.60-7.55 (m, 3H); 7.28, 7.19 (2s, 2×1H); 7.17 (dd, J=3.8, 4.9, 1H); 6.93 (d, J=8.7, 1H); 3.55 (s, 2H).

Compound 7

N-{4,5-dichloro-2-[(2-thienylsulfonyl)amino]phenyl}-2-oxo-2,3-dihydro-1,3-benzoxazole-6-sulfonamide

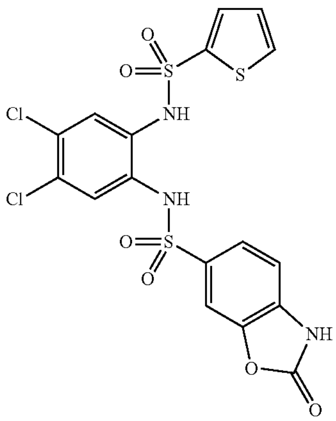 [SMILES: O=c1[nH]c2ccc(S(=O)(=O)Nc3cc(Cl)c(Cl)cc3NS(=O)(=O)c3cccs3)cc2o1]

Preparation according to Method A (31% yield) from Intermediate 1. $C_{17}H_{11}Cl_2N_3O_6S_3$ (520.39).

HPLC-MS (basic mobile phase, $ESI^-$): $t_R$=1.21 min, 520/518 $[M-H]^-$.

$^1$H-NMR (DMSO-$d_6$): δ ppm ca. 12.4-ca. 11.95 (br. signal, 1H); ca. 10.1-ca. 9.3 (br. signal, 2H); 7.98 (dd, J=1.3, 5.0, 1H); 7.65 (d, J=1.6, 1H); 7.56-7.52 (m, 2H); 7.31 (s, 1H); 7.23 (d, J=8.3, 1H); 7.16 (dd, J=3.7, 4.9, 1H); 7.15 (s, 1H).

Compound 8

4-[({4,5-dichloro-2-[(2-thienylsulfonyl)amino]phenyl}amino)sulfonyl]benzoic acid

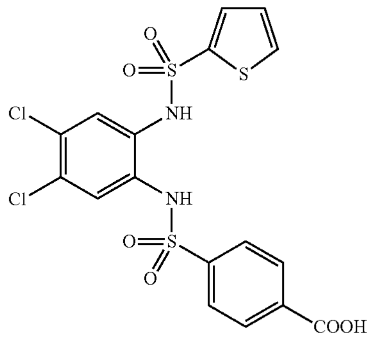 [SMILES: O=C(O)c1ccc(S(=O)(=O)Nc2cc(Cl)c(Cl)cc2NS(=O)(=O)c2cccs2)cc1]

Preparation according to Method A (26% yield) from Intermediate 1. $C_{17}H_{12}Cl_2N_2O_6S_3$ (507.39).

HPLC-MS (acidic mobile phase, $ESI^-$): $t_R$=1.78 min, 507/505 $[M-H]^-$.

$^1$H-NMR (DMSO-$d_6$): δ ppm 10.3-10.05 (br. signal, 1H); 9.58 (s, 1H); 8.06 (s, 1H); 7.88 (partially resolved dd, J=0.9, 5.0, 1H); 7.75 (s, 4H); 7.46-7.45 (m, 2H); 7.06-7.03 (t-like signal, 1H).

Compound 9

5-[({4,5-dichloro-2-[(2-thienylsulfonyl)amino]phenyl}amino)sulfonyl]-2-methoxybenzoic acid

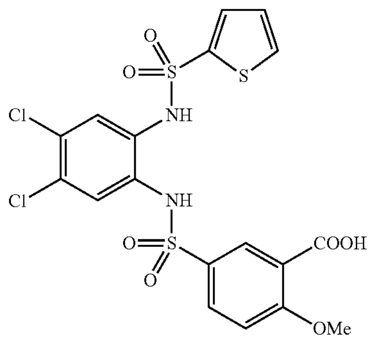 [SMILES: COc1ccc(S(=O)(=O)Nc2cc(Cl)c(Cl)cc2NS(=O)(=O)c2cccs2)cc1C(=O)O]

Preparation according to Method B (31% yield) from Intermediate 1. $C_{18}H_{14}Cl_2N_2O_7S_3$ (537.41).

HPLC-MS (basic mobile phase, $ESI^-$): $t_R$=1.16 min, 537/535 $[M-H]^-$.

$^1$H-NMR (DMSO-$d_6$): δ ppm 10.80 (s, 1H); 10.4-10.15 (br. signal, 1H); 8.73 (s, 1H); 8.30 (d, J=2.3, 1H); 8.05 (dd, J=1.4, 5.0, 1H); 7.81 (dd, J=2.3, 8.6, 1H); 7.55 (dd, J=1.4, 3.8, 1H); 7.26-7.21 (m, 2H); 6.71 (s, 1H); 4.14 (s, 3H).

Compound 10

N-(4,5-dichloro-2-{[(2,4-dimethoxyphenyl)sulfonyl]amino}phenyl)thiophene-2-sulfonamide

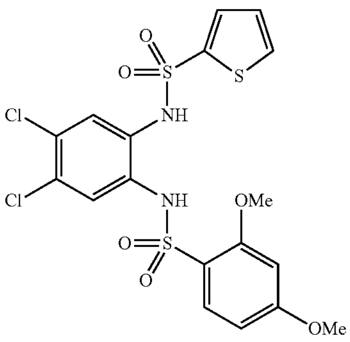 [SMILES: COc1ccc(S(=O)(=O)Nc2cc(Cl)c(Cl)cc2NS(=O)(=O)c2cccs2)c(OC)c1]

Preparation according to Method A (40% yield) from Intermediate 1. $C_{18}H_{16}Cl_2N_2O_6S_3$ (523.43).

HPLC-MS (basic mobile phase, $ESI^-$): $t_R$=1.58 min, 523/521 $[M-H]^-$.

$^1$H-NMR (DMSO-$d_6$): δ ppm ca. 10.1-ca. 9.7 (br. signal, ca. 1H); 9.16 (br. s, 1H); 7.99 (signal appears as partially resolved d, "J"=4.2, 1H); 7.62 (d, J=8.8, 1H); 7.54 (signal appears as partially resolved d, "J"=2.5, 1H); 7.39 (s, 1H); 7.17 (t-like signal, "J"=4.3, 1H); 7.04 (s, 1H); 6.73 (d, J=2.3, 1H); 6.61 (dd, J=2.3, 8.8, 1H); 3.91, 3.83 (2s, 2×3H).

Compound 11

N-[4,5-dichloro-2-({[2-(methylsulfonyl)phenyl]sulfonyl}amino)phenyl]thiophene-2-sulfonamide

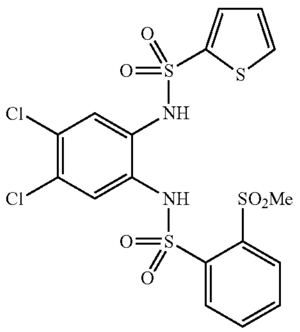 [SMILES: CS(=O)(=O)c1ccccc1S(=O)(=O)Nc1cc(Cl)c(Cl)cc1NS(=O)(=O)c1cccs1]

Preparation: DIPEA (3 eq.), $CH_2Cl_2$, rt (76% yield) from Intermediate 1. $C_{17}H_{14}Cl_2N_2O_6S_4$ (541.47).

HPLC-MS (acidic mobile phase, $ESI^-$): $t_R$=1.99 min, 541/539 $[M-H]^-$.

$^1$H-NMR (DMSO-$d_6$): δ ppm ca. 10.1-ca. 9 (2 br. signals, ca. 2H); 8.27 (partially resolved dd, J=1.2, 7.9, 1H); 8.02-7.94

(m, 3H); 7.89-7.84 (m, 1H); 7.63 (s, 1H); 7.44 (dd, J=1.4, 3.8, 1H); 7.16 (dd, J=3.8, 5.0, 1H); 6.68 (br. s, 1H); 3.51 (s, 3H).

Compound 12

Methyl 4-[({4,5-dichloro-[(2-thienylsulfonyl)amino]phenyl}amino)sulfonyl]benzoate

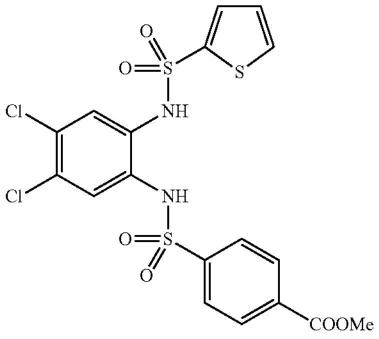 [SMILES: COC(=O)c1ccc(S(=O)(=O)Nc2cc(Cl)c(Cl)cc2NS(=O)(=O)c2cccs2)cc1]

Preparation according to Method A (33% yield) from Intermediate 1. $C_{18}H_{14}Cl_2N_2O_6S_3$ (521.42).

HPLC-MS (basic mobile phase, $ESI^-$): $t_R$=1.58 min, 521/519 $[M-H]^-$.

$^1$H-NMR (DMSO-$d_6$): δ ppm ca. 10.2-ca. 9.5 (br. signal, ca. 2H); 8.12 (d, J=8.6, 2H); 7.98 (dd, J=1.3, 5.0, 1H); 7.87 (d, J=8.7, 2H); 7.55 (dd, J=1.4, 3.8, 1H); 7.24, 7.20 (2s, 2×1H); 7.16 (dd, J=3.8, 5.0, 1H); 3.90 (s, 3H).

Compound 13

N-{4,5-dichloro-2-[(2-thienylsulfonyl)amino]phenyl}-2-oxo-2H-chromene-6-sulfonamide

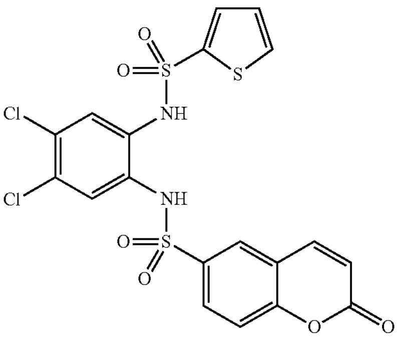 [SMILES: O=c1ccc2cc(S(=O)(=O)Nc3cc(Cl)c(Cl)cc3NS(=O)(=O)c3cccs3)ccc2o1]

Preparation according to Method A (51% yield) from Intermediate 1. $C_{19}H_{12}Cl_2N_2O_6S_3$ (531.41).

HPLC-MS (acidic mobile phase, $ESI^-$): $t_R$=2.04 min, 531/529 $[M-H]^-$.

$^1$H-NMR (DMSO-$d_6$): δ ppm 10.1-9.5 (br. signal, 2H); 8.21 (d, J=2.3, 1H); 8.18 (d, J=9.7, 1H); 7.98 (dd, J=1.3, 5.0, 1H); 7.89 (dd, J=2.3, 8.8, 1H); 7.59-7.55 (m, 2H); 7.33 (s, 1H); 7.16 (dd, J=3.8, 5.0, 1H); 7.15 (s, 1H); 6.64 (d, J=9.6, 1H).

Compound 14

6-chloro-N-{4,5-dichloro-2-[(2-thienylsulfonyl)amino]phenyl}imidazo[2,1-b][1,3]thiazole-5-sulfonamide

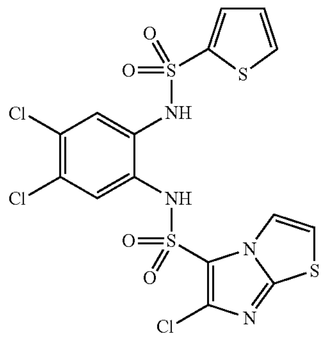 [SMILES: O=S(=O)(Nc1cc(Cl)c(Cl)cc1NS(=O)(=O)c1c(Cl)nc2sccn12)c1cccs1]

Preparation according to Method C (8% yield) from Intermediate 1. $C_{16}H_9Cl_3N_4O_4S_4$ (543.88).

HPLC-MS (acidic mobile phase, $ESI^-$): $t_R$=1.99 min, 545/543/541 $[M-H]^-$.

$^1$H-NMR (DMSO-$d_6$): δ ppm ca. 10.4-ca. 9.3 (br. signal, ca. 1H); 7.98 (dd, J=1.2, 5.0, 1H); 7.91, 7.63 (2d, J=4.5, 2×1H); 7.56 (dd, J=1.3, 3.8, 1H); 7.31 (s, 1H); 7.16 (dd, J=3.9, 4.9, 1H); 7.12 (s, 1H).

Compound 15

N-{4,5-dichloro-2-[(2-thienylsulfonyl)amino]phenyl}-2,5-dimethylfuran-3-sulfonamide

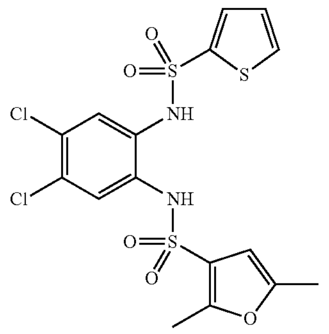 [SMILES: Cc1cc(S(=O)(=O)Nc2cc(Cl)c(Cl)cc2NS(=O)(=O)c2cccs2)c(C)o1]

Preparation according to Method A (40% yield) from Intermediate 1. $C_{16}H_{14}Cl_2N_2O_6S_3$ (481.39).

HPLC-MS (acidic mobile phase, $ESI^-$): $t_R$=2.15 min, 481/479 $[M-H]^-$.

$^1$H-NMR (DMSO-$d_6$): δ ppm ca. 10.1-ca. 9.7 (br. signal, ca. 1H); ca. 9.7-ca. 9.4 (br. signal, 1H); 8.01 (dd, J=1.4, 5.0, 1H); 7.59 (dd, J=1.4, 3.8, 1H); 7.30, 7.28 (2s, 2×1H); 7.18 (dd, J=3.8, 5.0, 1H); 6.15 (signal appears as partially resolved d, "J"=1.0, 1H); 2.28, 2.21 (2s, 2×3H).

Compound 16

N-[4,5-dichloro-2-({[4-(3,5-dimethyl-1H-pyrazol-1-yl)phenyl]sulfonyl}amino)phenyl]thiophene-2-sulfonamide

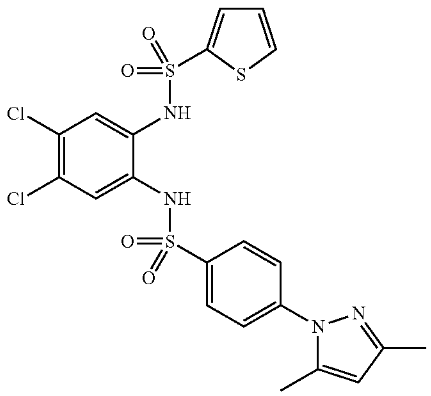 [SMILES: Cc1cc(C)n(-c2ccc(S(=O)(=O)Nc3cc(Cl)c(Cl)cc3NS(=O)(=O)c3cccs3)cc2)n1]

Preparation according to Method A (51% yield) from Intermediate 1. $C_{21}H_{18}Cl_2N_4O_4S_3$ (557.49).

HPLC-MS (basic mobile phase, $ESI^-$): $t_R$=1.61 min, 557/555 $[M-H]^-$.

$^1$H-NMR (DMSO-$d_6$): δ ppm ca. 10-ca. 9.5 (br. signal, 2H); 7.97 (dd, J=1.3, 5.0, 1H); 7.81, 7.75 (2d, J=9.0, 2×2H); 7.56 (dd, J=1.3, 3.8, 1H); 7.27, 7.22 (2s, 2×1H); 7.16 (dd, J=3.8, 5.0, 1H); 6.15 (s, 1H); 2.38, 2.19 (2s, 2×3H).

Compound 17

N-{4,5-dichloro-2-[(2-thienylsulfonyl)amino]phenyl}-1-methyl-1H-pyrazole-3-sulfonamide

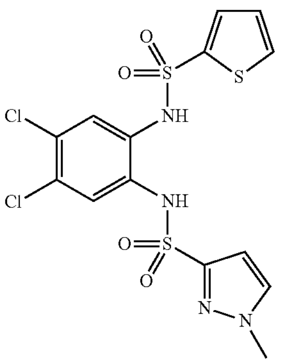 [SMILES: Cn1ccc(S(=O)(=O)Nc2cc(Cl)c(Cl)cc2NS(=O)(=O)c2cccs2)n1]

Preparation according to Method A (57% yield) from Intermediate 1. $C_{14}H_{12}Cl_2N_4O_4S_3$ (467.37).

HPLC-MS (basic mobile phase, $ESI^-$): $t_R$=1.41 min, 467/465 $[M-H]^-$.

$^1$H-NMR (DMSO-$d_6$): δ ppm 10-9.6 (br. signal, 2H); 7.99 (dd, J=1.3, 5.0, 1H); 7.91 (d, J=2.3, 1H); 7.60 (dd, J=1.3, 3.8, 1H); 7.47, 7.32 (2s, 2×1H); 7.17 (dd, J=3.8, 5.0, 1H); 6.64 (d, J=2.3, 1H); 3.93 (s, 3H).

Compound 18

N-{4,5-dichloro-2-[(2-thienylsulfonyl)amino]phenyl}-1-methyl-1H-indole-4-sulfonamide

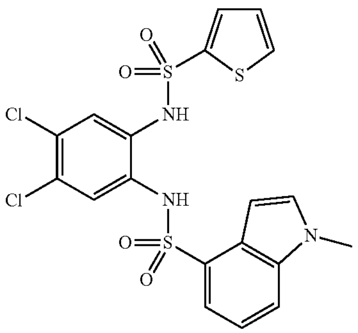 [SMILES: Cn1ccc2c(S(=O)(=O)Nc3cc(Cl)c(Cl)cc3NS(=O)(=O)c3cccs3)cccc21]

Preparation according to Method A, 15 min (45% yield) from Intermediate 1. $C_{19}H_{16}Cl_2N_3O_4S_3$ (516.44).

HPLC-MS (acidic mobile phase, ESI$^-$): $t_R$=2.04 min, 516/514 [M−H]$^-$.

$^1$H-NMR (DMSO-$d_6$): δ ppm ca. 10-ca. 9.5 (br. signal, ca. 2H); 7.96 (dd, J=1.2, 5.0, 1H); 7.82 (d, J=7.8, 1H); 7.59 (d, J=3.1, 1H); 7.52 (partially resolved dd, J=0.8, 7.5, 1H); 7.49 (partially resolved dd, J=1.2, 3.9, 1H); 7.30 (t, J=7.3, 1H); 7.21 (s, 1H); 7.14 (dd, J=3.8, 5.0, 1H); 7.10 (s, 1H); 6.74 (partially resolved dd, J=0.7, 3.1, 1H); 3.86 (s, 3H).

Compound 19

N-(4,5-dichloro-2-{[(2,5-dimethyl-3-thienyl)sulfonyl]amino}phenyl)thiophene-2-sulfonamide

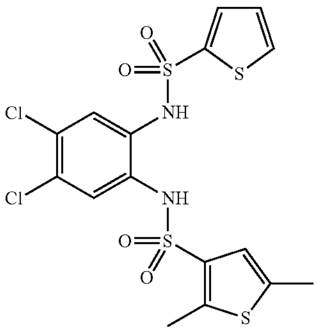 [SMILES: Cc1cc(S(=O)(=O)Nc2cc(Cl)c(Cl)cc2NS(=O)(=O)c2cccs2)c(C)s1]

Preparation according to Method A (44% yield) from Intermediate 1. $C_{16}H_{14}Cl_2N_2O_4S_4$ (497.46).

HPLC-MS (acidic mobile phase, ESI$^-$): $t_R$=2.20 min, 497/495 [M−H].

$^1$H-NMR (DMSO-$d_6$): δ ppm ca. 10.2-ca. 9.3 (2 br. signals, ca. 2H); 8.00 (signal appears as partially resolved d, "J"=4.0, 1H); 7.60 (signal appears as partially resolved d, "J"=2.7, 1H); 7.28 (s, 1H); 7.18 (partially hidden dd, J=3.8, 5.0, 1H); ca. 7.16 (s, 1H); 6.84 (signal appears as partially resolved d, "J"=1.1, 1H); 2.38, 2.35 (2s, 2×3H).

Compound 20

N-{4,5-dichloro-2-[(2-thienylsulfonyl)amino]phenyl}pyridine-3-sulfonamide

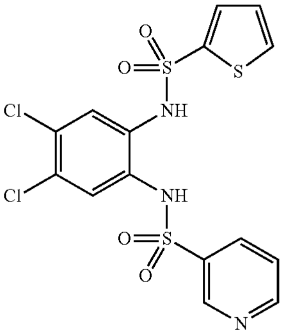 [SMILES: O=S(=O)(Nc1cc(Cl)c(Cl)cc1NS(=O)(=O)c1cccs1)c1cccnc1]

Preparation according to Method A (33% yield) from Intermediate 1. $C_{15}H_{11}Cl_2N_3O_4S_3$ (464.37).

HPLC-MS (acidic mobile phase, ESI$^-$): $t_R$=1.94 min, 464/462 [M−H]$^-$.

$^1$H-NMR (DMSO-$d_6$): δ ppm ca. 10.4-ca. 9.2 (br. signal, ca. 1H); 8.88 (d, J=1.8, 1H); 8.84 (dd, J=1.5, 4.8, 1H); 8.11 (ddd, J=1.7, 2.5, 8.1, 1H); 7.98 (dd, J=1.3, 5.0, 1H); 7.62 (dd, J=4.5, 7.8, 1H); 7.54 (dd, J=1.4, 3.8, 1H); 7.29 (s, 1H); 7.17 (s, 1H); 7.167 (partially hidden dd, J 3.8, 5.0, 1H).

Compound 21

N-{(4,5-dichloro-2-[(3,5-dichloro-4-hydroxyphenyl)sulfonyl]amino}phenyl)thiophene-2-sulfonamide

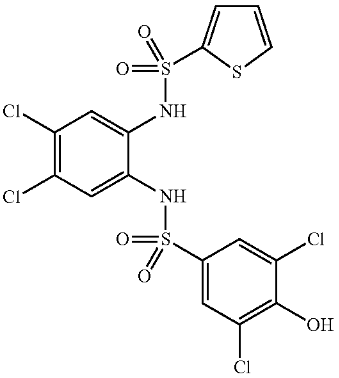 [SMILES: O=S(=O)(Nc1cc(Cl)c(Cl)cc1NS(=O)(=O)c1cccs1)c1cc(Cl)c(O)c(Cl)c1]

Preparation according to Method A (19% yield) from Intermediate 1. $C_{16}H_{10}Cl_4N_{12}O_5S_3$ (548.27).

HPLC-MS (basic mobile phase, ESI$^-$): $t_R$=1.21 min, 549/547/545 [M−H]$^-$.

$^1$H-NMR (DMSO-$d_6$): δ ppm ca. 10.8-ca. 9.1 (br. signal, ca. 2H); 7.99 (dd, J=1.3, 5.0, 1H); 7.69 (s, 2H); 7.56 (dd, J=1.4, 3.8, 1H); 7.30 (s, 1H); 7.17 (dd, J=3.9, 5.0, 1H); 7.15 (s, 1H).

Compound 22

N-{4,5-dichloro-2-[(2-thienylsulfonyl)amino]phenyl}-1,2-dimethyl-1H-imidazole-4-sulfonamide

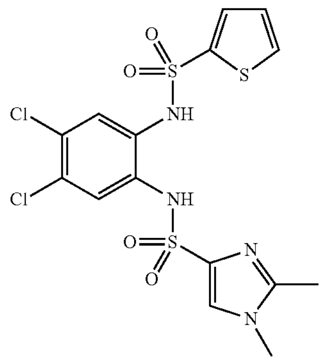 [SMILES: Cc1nc(S(=O)(=O)Nc2cc(Cl)c(Cl)cc2NS(=O)(=O)c2cccs2)cn1C]

Preparation according to Method C (32% yield) from Intermediate 1. $C_{16}H_{14}Cl_2N_4O_4S_3$ (481.40).

HPLC-MS (basic mobile phase, $ESI^-$): $t_R$=1.44 min, 481/479 [M−H].

$^1$H-NMR (DMSO-$d_6$): δ ppm ca. 11-ca. 10 (br. signal, ca. 1H); 9.8-9.5 (br. signal, 1H); 7.98 (signal appears as d, "J"=5.0, 1H); 7.81 (s, 1H); 7.61 (signal appears as d, "J"=3.7, 1H); 7.53, 7.41 (2s, 2×1H); 7.16 (signal appears as t, "J"≈4.4, 1H); 3.60, 2.36 (2s, 2×3H).

Compound 23

N-{4,5-dichloro-2-[(2-thienylsulfonyl)amino]phenyl}-3-methylquinoline-8-sulfonamide

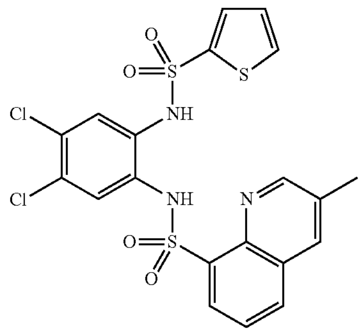 [SMILES: Cc1cnc2c(S(=O)(=O)Nc3cc(Cl)c(Cl)cc3NS(=O)(=O)c3cccs3)cccc2c1]

Preparation according to Method A (30% yield) from Intermediate 1. $C_{20}H_{15}Cl_2N_3O_4S_3$ (528.45).

HPLC-MS (acidic mobile phase, $ESI^-$): $t_R$=2.14 min, 528/526 $[M-H]^-$.

$^1$H-NMR (DMSO-$d_6$): δ ppm ca. 10-ca. 9.6 (br. signal, 2H); 9.04 (partially resolved d, J=1.7, 1H); 8.37 (signal appears as s, 1H); 8.25 (signal appears as t, J=8.5, 2H); 7.95 (signal appears as partially resolved d, "J"=5.2, 1H); 7.73-7.68 (t-like signal, "J"≈7.7, 1H); 7.58 (s, 1H); 7.43 (unresolved "d", "J"=2.5, 1H); 7.14-7.11 (partially resolved t-like signal, "J"≈4.3, 1H); 6.79 (s, 1H); 2.57 (s, 3H).

Compound 24

N-{5-chloro-2[(2-thienylsulfonyl)amino]phenyl}-1-benzofuran-2-sulfonamide

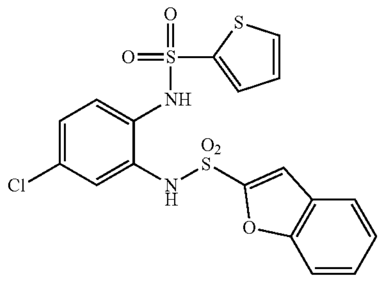 [SMILES: O=S(=O)(Nc1cc(Cl)ccc1NS(=O)(=O)c1cccs1)c1cc2ccccc2o1]

To a solution of N-(2-amino-4-chlorophenyl)thiophene-2-sulfonamide (CAS RN: 926205-90-5) (140 mg, ~0.47 mmol) in pyridine (2.5 ml) was added benzofuran-2-sulfonyl chloride (102 mg, 0.47 mmol) and the mixture was stirred at room temperature for 16 h. More benzofuran-2-sulfonyl chloride (51 mg, 0.24 mmol) was added and the reaction was stirred for another 24 h, concentrated in vacuo to remove most of solvent. The residual thick syrup was quenched with 6M HCl and diluted with $H_2O$. The resulting suspension was filtered and washed with $H_2O$ (×3). The crude product was purified by flash column chromatography on silica gel (25-50% EtOAc-hexane) to yield 43 mg of product slightly contaminated with impurities. This material was triturated with $CH_2Cl_2$ to form a sandy colored solid, which was filtered and rinsed with minimal amount of $CH_2Cl_2$ to yield 23 mg (10%) of Compound 24.

1H-NMR (600 MHz, $CD_3OD$) δ ppm 7.73 (dd, J=5.0, 1.5 Hz, 1 H), 7.70-7.72 (m, 1 H), 7.60-7.63 (m, 1 H), 7.51 (ddd, J=8.5, 7.2, 1.3 Hz, 1 H), 7.41 (dd, J=3.8, 1.2 Hz, 1 H), 7.37 (dd, J=1.9, 0.7 Hz, 1 H), 7.34-7.36 (m, 1 H), 7.29 (d, J=2.3 Hz, 1 H), 7.07 (dd, J=8.8, 2.3 Hz, 1 H), 7.05 (dd, J=5.0, 3.8 Hz, 1 H), 6.95 (d, J=8.5 Hz, 1 H), 4.57 (br. s., 2 H).

Compound 25

N-{4-chloro-2[(2-thienylsulfonyl)amino]phenyl}-1-benzofuran-2-sulfonamide

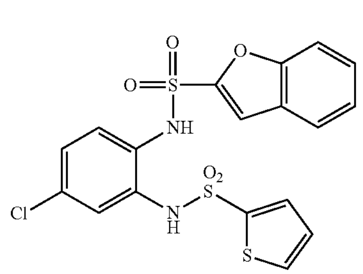 [SMILES: O=S(=O)(Nc1ccc(Cl)cc1NS(=O)(=O)c1cccs1)c1cc2ccccc2o1]

To a solution of Intermediate 7 (158 mg, 0.49 mmol) in pyridine (3.0 ml) was added thiophene-2-sulfonyl chloride (90 mg, 0.49 mmol) and the mixture was stirred at room temperature for 16 h. The solvent was removed in vacuo and the residue was purified by flash column chromatography on silica gel (25-50% EtOAc-hexane) to yield 64 mg of the desired product slightly contaminated with impurities. Further purification with preparative TLC (50% EtOAc-hexane) yielded 52 mg (23%) of Compound 25.

$^1$H-NMR (600 MHz, $CD_3OD$) δ ppm 7.76 (dd, J=5.0, 1.2 Hz, 1 H), 7.69 (dd, J=7.9, 1.2 Hz, 1 H), 7.62 (dd, J=8.5, 0.6 Hz, 1 H), 7.51 (ddd, J=8.4, 7.3, 1.3 Hz, 1 H), 7.46 (dd, J=3.8, 1.5 Hz, 1 H), 7.32-7.37 (m, 2 H), 7.13-7.16 (m, 1 H), 7.06-7.11 (m, 3 H).

Compound 26

N-{2-[(1-benzofuran-2-ylsulfonyl)amino]-4-chlorophenyl}-2,2-dimethylchromane-6-sulfonamide

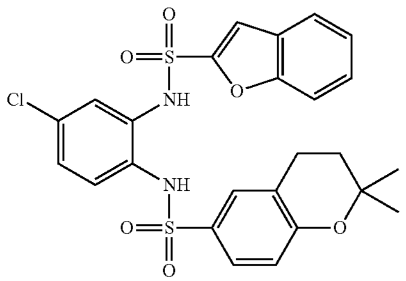 [SMILES: CC1(C)CCc2cc(S(=O)(=O)Nc3ccc(Cl)cc3NS(=O)(=O)c3cc4ccccc4o3)ccc2O1]

Preparation: Method A (63% yield) from Intermediate 5. $C_{25}H_{23}ClN_2O_6S_2$ (547.04).

HPLC-MS (basic mobile phase, $ESI^-$): $t_R$=1.55 min, 547/545 $[M-H]^-$.

$^1$H-NMR (DMSO-$d_6$): δ ppm 10.5-9.8 (br. signal, ca. 1H); 9.28 (s, 1H); 7.79 (partially resolved dd, J=0.4, 7.6, 1H); 7.72 (dd, J=0.8, 8.4, 1H); 7.66 (s, 1H); 7.56 (m, 1H); 7.50 (d, J=2.3, 1H); 7.41 (m, 1H); 7.32 (dd, J=2.4, 8.7, 1H); 7.20-7.10 (m, 2H); 7.08 (partially resolved dd, J=0.4, 8.7, 1H); 6.75 (d, J=8.7, 1H); 2.74 (t, J=6.6, 2H); 1.76 (t, J=6.6, 2H); 1.27 (s, 6H).

Compound 27

N-{2-[(1-benzofuran-2-ylsulfonyl)amino]-4-chlorophenyl}-2-methyl-1,3-benzothiazole-6-sulfonamide

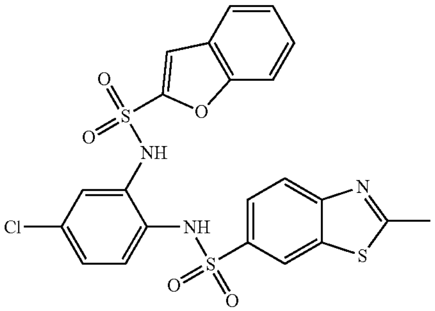 [SMILES: Cc1nc2ccc(S(=O)(=O)Nc3ccc(Cl)cc3NS(=O)(=O)c3cc4ccccc4o3)cc2s1]

Preparation: Method A (60% yield) from Intermediate 5. $C_{22}H_{16}ClN_3O_6S_3$ (534.03).

HPLC-MS (basic mobile phase, $ESI^-$): $t_R$=1.36 min, 532/534 $[M-H]^-$.

$^1$H-NMR (DMSO-$d_6$): δ ppm 10.4-9.8 (br. signal, ca. 1H); 9.8-9.6 (broad signal, ca. 1H); 9.59 (s, 1H); 8.50 (d, J=1.6, 1H); 7.98 (d, J=8.6, 1H); 7.80-7.70 (m, 3H); 7.62 (s, 1H); 7.56 (m, 1H); 7.40 (m, 1H); 7.14-7.10 (m, 2H); 7.00 (dd, partially resolved, J=1.3, 8.5, 1H); 2.84 (s, 3H).

Compound 28

N-[5-chloro-2-({[3-(2-methylpyrimidin-4-yl)phenyl]sulfonyl}amino)phenyl]-1-benzofuran-2-sulfonamide

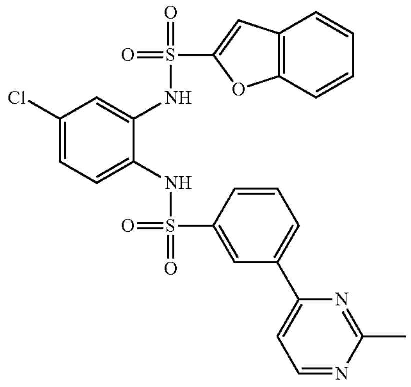 [SMILES: Cc1nccc(-c2cccc(S(=O)(=O)Nc3ccc(Cl)cc3NS(=O)(=O)c3cc4ccccc4o3)c2)n1]

Preparation: Method A (20% yield) from Intermediate 5. $C_{25}H_{19}ClN_4O_5S_2$ (555.03).

HPLC-MS (acidic mobile phase, $ESI^+$): $t_R$=2.11 min, 555/557 $[M+H]^+$.

$^1$H-NMR (DMSO-$d_6$): δ ppm 10.6-9.8 (br. signal, ca. 1H); 9.8-9.5 (br. signal, ca. 1H); 8.81 (d, J=5.3, 1H); 8.56 (t, J=1.6, 1H); 8.40 (d, J=7.9, 1H); 7.89 (d, J=5.3, 1H); 7.82 (m, 1H); 7.76 (d, J=7.6, 1H); 7.68 (m, 2H); 7.62 (s, 1H); 7.54 (m, 1H); 7.39 (m, 1H); 7.18-7.14 (m, 2H); 7.06 (d, J=9.1, 1H); 2.70 (s, 3H).

Compound 29

N-{5-chloro-2-[(isobutylsulfonyl)amino]phenyl}-1-benzofuran-2-sulfonamide

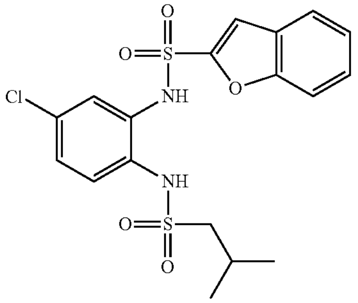 [SMILES: CC(C)CS(=O)(=O)Nc1ccc(Cl)cc1NS(=O)(=O)c1cc2ccccc2o1]

Preparation: Method A (11% yield) from Intermediate 5. $C_{18}H_{19}ClN_2O_5S_2$ (442.94).

HPLC-MS (basic mobile phase, $ESI^-$): $t_R$=1.86 min, 441/443 $[M-H]^-$.

$^1$H-NMR (DMSO-$d_6$): δ ppm 10.8-9.8 (br. signal, ca. 1H); 8.91 (s, 1H); 7.78 (d, J=7.7, 1H); 7.72 (d, J=8.4, 1H); 7.66 (s, 1H); 7.56 (m, 1H); 7.44-7.36 (m, 2H); 7.27 (d, J=8.9, 1H);

7.23 (d, J=2.4, 1H); 2.84 (d, J=6.5, 2H); 2.04 (septuplet, J=6.7, 1H); 0.91 (d, J=6.7, 6H).

Compound 30

N-{2-[(1-benzofuran-2-ylsulfonyl)amino]-4-chlorophenyl}isoquinoline-5-sulfonamide

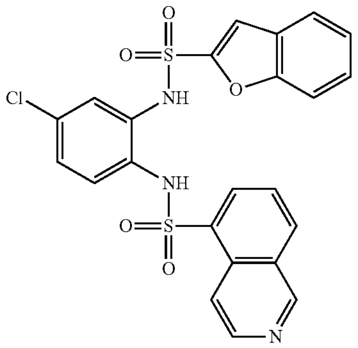 [SMILES: O=S(=O)(Nc1cc(Cl)ccc1NS(=O)(=O)c1cccc2cnccc12)c1cc2ccccc2o1]

Preparation: Method A (51% yield) from Intermediate 5. $C_{23}H_{16}ClN_3O_6S_2$ (513.97).

HPLC-MS (acidic mobile phase, $ESI^+$): $t_R$=1.86 min, 514/516 $[M+H]^+$.

$^1$H-NMR (DMSO-$d_6$): δ ppm 10.4-9.6 (br. signal, ca. 2H); 9.47 (d, J=0.7, 1H); 8.65 (d, J=6.2, 1H); 8.45 (d, J=8.2, 1H); 8.37 (d, J=6.1, 1H); 8.25 (dd, J=1.2, 7.4, 1H); 7.76 (m, 2H); 7.69 (dd, J=0.7, 8.4, 1H); 7.59 (s, 1H); 7.54 (m, 1H); 7.39 (m, 1H); 7.08-7.03 (m, 2H); 6.87 (d, J=8.7, 1H).

Compound 31

N-(5-chloro-2-{[(2,4-dimethoxyphenyl)sulfonyl]amino}phenyl)-1-benzofuran-2-sulfonamide

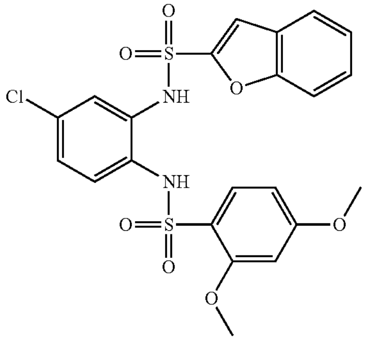 [SMILES: COc1ccc(S(=O)(=O)Nc2ccc(Cl)cc2NS(=O)(=O)c2cc3ccccc3o2)c(OC)c1]

Preparation: Method A (54% yield) from Intermediate 5. $C_{22}H_{19}ClN_2O_7S_2$ (522.98).

MS ($ESI^+$): 523 $[M+H]^+$.

$^1$H-NMR (DMSO-$d_6$): δ ppm 10.6-9.8 (br. signal, ca. 1H); 9.02 (s, 1H); 7.78 (d, J=7.6, 1H); 7.71 (d, J=8.4, 1H); 7.65 (s, 1H); 7.55 (m, 2H); 7.40 (t, J=7.5, 1H); 7.15 (s, 2H); 7.01 (t partially resolved, J=1.2, 1H); 6.71 (d, J=2.2, 1H); 6.56 (dd, J=2.3, 8.8, 1H); 3.91 (s, 3H); 3.81 (s, 3H).

Compound 32 ethyl 5-[({2-[(1-benzofuran-2-ylsulfonyl)amino]-4-chlorophenyl}amino)sulfonyl]-3-furoate

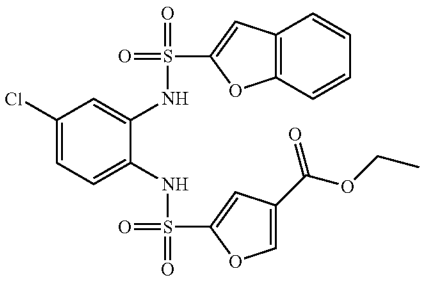 [SMILES: CCOC(=O)c1coc(S(=O)(=O)Nc2ccc(Cl)cc2NS(=O)(=O)c2cc3ccccc3o2)c1]

Preparation: Method C (16% yield) from Intermediate 5. $C_{21}H_{17}ClN_2O_8S_2$ (524.95).

HPLC-MS (acidic mobile phase, $ESI^-$): $t_R$=2.30 min, 523/525 $[M-H]^-$.

$^1$H-NMR (DMSO-$d_6$): δ ppm 10.9-9.5 (br. signal, ca. 2H); 8.61 (d, J=0.9, 1H); 7.79 (d, J=7.4, 1H); 1.71 (dd, J=0.7, 8.4, 1H); 7.67 (s, 1H); 7.55 (m, 1H); 7.40 (m, 1H); 7.26-7.21 (m, 2H); 7.19 (d, J=2.2, 1H); 7.13 (d, J=8.6, 1H); 4.25 (quartet, J=7.1, 2H); 1.27 (t, J=7.1, 3H).

Compound 33

N-(5-chloro-2-{[(2,5-dichloro-3-thienyl)sulfonyl]amino}phenyl)-1-benzofuran-2-sulfonamide

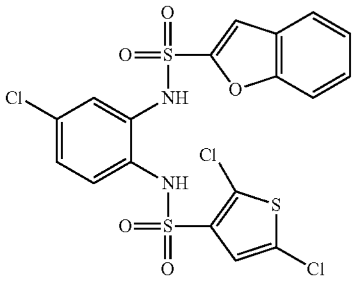 [SMILES: O=S(=O)(Nc1cc(Cl)ccc1NS(=O)(=O)c1cc(Cl)sc1Cl)c1cc2ccccc2o1]

Preparation: Method C (30% yield) from Intermediate 5. $C_{18}H_{11}Cl_3N_2O_5S_3$ (537.84).

HPLC-MS (basic mobile phase, $ESI^-$): $t_R$=1.70 min, 535/537 $[M-H]^-$.

$^1$H-NMR (DMSO-$d_6$): δ ppm 10.6-9.4 (br. signal, ca. 2H); 7.80 (dd, J=0.7, 7.8, 1H); 7.73-7.69 (m, 2H); 7.55 (m, 1H); 7.40 (m, 1H); 7.33-7.20 (m, 3H); 7.09 (d, J=8.7, 1H).

Compound 34

N-{2-[(1-benzofuran-2-ylsulfonyl)amino]-4-chlorophenyl}-5,6-dichloropyridine-3-sulfonamide

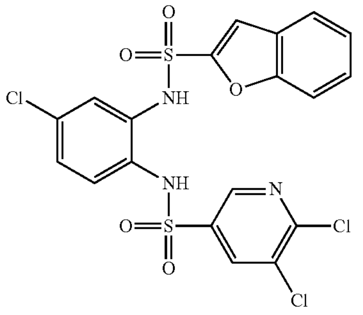

Preparation: Method C (28% yield) from Intermediate 5. $C_{19}H_{12}Cl_3N_3O_6S_2$ (532.80).

HPLC-MS (acidic mobile phase, ESI$^+$): $t_R$=2.36 min, 532/534 [M+H]$^+$.

$^1$H-NMR (DMSO-$d_6$): δ ppm 10.7-9.5 (br. signal, ca. 2H); 8.60 (d, J=2.2, 1H); 8.37 (d, J=2.2, 1H); 7.80 (d, J=7.4, 1H); 7.72 (dd, J=0.7, 8.4, 1H); 7.67 (s, 1H); 7.56 (m, 1H); 7.40 (m, 1H); 7.22 (m, 2H); 7.04 (dd partially resolved, J=0.5, 2.3, 1H).

Compound 35

5-[({2-[(1-benzofuran-2-ylsulfonyl)amino]-4-chlorophenyl}amino)sulfonyl]-2-methoxybenzoic acid

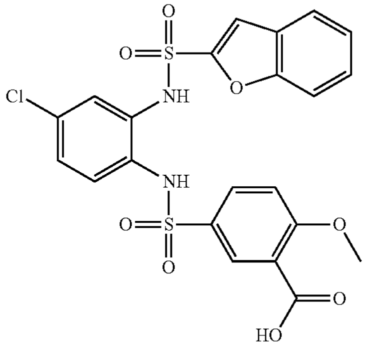 [SMILES: COc1ccc(S(=O)(=O)Nc2ccc(Cl)cc2NS(=O)(=O)c2cc3ccccc3o2)cc1C(=O)O]

Preparation: Method B (17% yield) from Intermediate 5. $C_{22}H_{17}ClN_2O_8S_2$ (536.96).

HPLC-MS (acidic mobile phase, ESI$^+$): $t_R$=1.68 min, 537/539 [M+H]$^+$.

$^1$H-NMR (DMSO-$d_6$): δ ppm 11.0-10.7 (br. signal, ca. 1H); 10.67 (s, 1H); 8.42 (d, J=8.9, 1H); 8.29 (d, J=2.3, 1H); 7.78 (m, 2H); 7.66-7.62 (m, 2H); 1.53 (m, 1H); 7.44-7.36 (m, 2H); 7.23 (d, J=8.7, 1H); 6.77 (d, J=2.5, 1H); 4.14 (s, 3H).

Compound 36

5-[({2-[(1-benzofuran-2-ylsulfonyl)amino]-4-chlorophenyl}amino)sulfonyl]-2-ethoxybenzoic acid

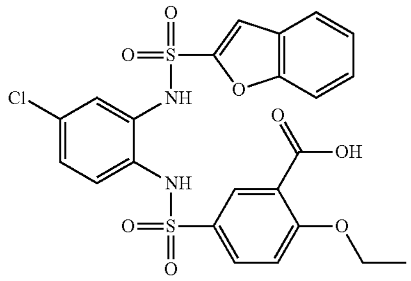 [SMILES: CCOc1ccc(S(=O)(=O)Nc2ccc(Cl)cc2NS(=O)(=O)c2cc3ccccc3o2)cc1C(=O)O]

Preparation: Method B (27% yield) from Intermediate 5. $C_{23}H_{19}ClN_2O_8S_2$ (550.99).

HPLC-MS (acidic mobile phase, ESI$^+$): $t_R$=1.77 min, 551/553 [M+H]$^+$.

$^1$H-NMR (DMSO-$d_6$): δ ppm 10.9-10.6 (br. signal, ca. 1H); 10.48 (s, 1H); 8.31 (d, J=8.9, 1H); 8.25 (d, J=2.3, 1H); 7.79-7.75 (m, 2H); 7.66-7.59 (m, 2H); 7.53 (m, 1H); 7.43-7.36 (m, 2H); 7.22 (d, J=8.7, 1H); 6.78 (d, J=2.5, 1H); 4.44 (quartet, J=7.0, 2H); 1.47 (t, J=6.9, 3H).

Compound 37

N-[3-({[4-chloro-3-(trifluoromethyl)phenyl]sulfonyl}amino)pyridin-2-yl]thiophene-2-sulfonamide

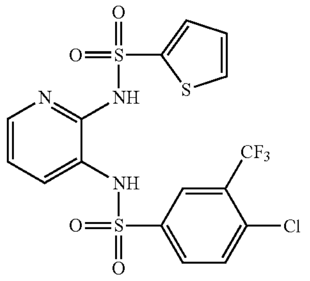 [SMILES: O=S(=O)(Nc1cccnc1NS(=O)(=O)c1cccs1)c1ccc(Cl)c(C(F)(F)F)c1]

To a solution Intermediate 10 (72 mg, 0.28 mmol) in pyridine (2 ml) was added 4-chloro-3-trifluoromethyl-benzenesulfonyl chloride (49 μl, 0.28 mmol) and the reaction was stirred at room temperature for 3 days, concentrated in vacuo. The crude product was purified by flash column chromatography on silica gel (50%-75% EtOAc in hexanes) to yield Compound 37 (26 mg, 18%).

$^1$H NMR (acetone-d6) δ ppm: 8.27 (d, J=2.1 Hz, 1H), 8.14 (dd, J=8.4, 2.2 Hz, 1H), 7.97 (dd, J=7.6, 1.5 Hz, 1H), 7.83 (dd, J=6.4, 1.5 Hz, 1H), 7.78 (d, J=8.2 Hz, 1H), 7.71 (dd, J=5.0, 1.5 Hz, 1H), 7.51 (dd, J=3.7, 1.3 Hz, 1H), 7.05 (dd, J=5.0, 3.5 Hz, 1H), 6.88 (dd, J=7.8, 6.3 Hz, 1H).

Compound 38

N-[5-chloro-3-({[4-chloro-3-(trifluoromethyl)phenyl]sulfonyl}amino)pyridin-2-yl]thiophene-2-sulfonamide

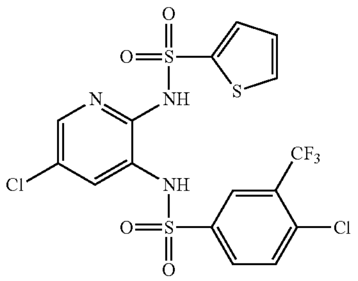 [SMILES: O=S(=O)(Nc1cc(Cl)cnc1NS(=O)(=O)c1cccs1)c1ccc(Cl)c(C(F)(F)F)c1]

To a solution of Intermediate 11 (75 mg, 0.26 mmol) in pyridine (2 ml) was added 4-chloro-3-trifluoromethyl-benzenesulfonyl chloride (143 mg, 0.52 mmol) and the reaction was stirred at 100° C. for 6 h, concentrated in vacuo. The crude product was purified by flash column chromatography on silica gel (50%-100% EtOAc in hexanes), followed by PTLC (EtOAc) to yield Compound 38 (24 mg, 17%).

$^1$H NMR (acetone-d6) δ ppm: 8.52 (d, J=8.5 Hz, 1H), 8.47 (s, 1H), 7.88-8.01 (m, 1H), 7.69 (d, J=8.2 Hz, 1H), 7.58 (d, J=4.7 Hz, 1H), 7.42-7.51 (m, 1H), 7.17-7.28 (m, 1H), 6.91-7.01 (m, 1H).

The synthetic methods used in the preparation of the other compounds of the invention is summarized in Table 1. Compounds 39 through 261 where prepared starting from Intermediate 1. Compound 262 was prepared from Intermediate 7. Compound 263 through 484 were prepared starting from Intermediate 5.

TABLE 1

| Comp. No. | Structure | IUPAC compound name | Synthesis |
|---|---|---|---|
| 39 | 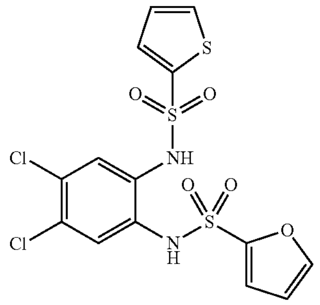 [SMILES: O=S(=O)(Nc1cc(Cl)c(Cl)cc1NS(=O)(=O)c1cccs1)c1ccco1] | N-{4,5-dichloro-2-[(2-thienylsulfonyl)amino]phenyl}-furan-2-sulfonamide | Method C |
| 40 | 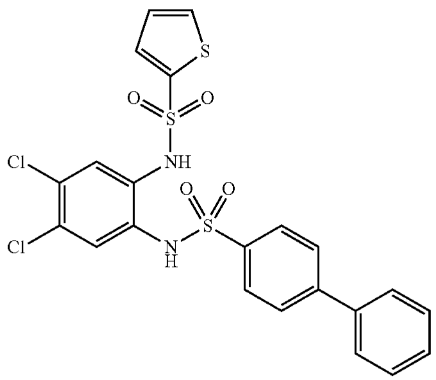 [SMILES: O=S(=O)(Nc1cc(Cl)c(Cl)cc1NS(=O)(=O)c1cccs1)c1ccc(-c2ccccc2)cc1] | N-{2-[(biphenyl-4-ylsulfonyl)amino]-4,5-dichlorophenyl}thiophene-2-sulfonamide | Method A |
| 41 | 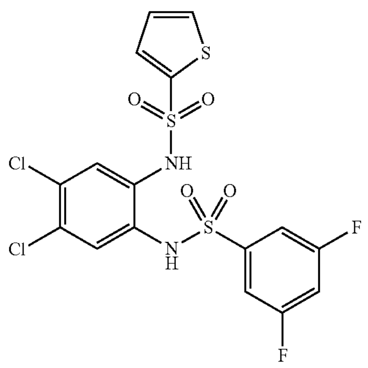 [SMILES: O=S(=O)(Nc1cc(Cl)c(Cl)cc1NS(=O)(=O)c1cccs1)c1cc(F)cc(F)c1] | N-(4,5-dichloro-2-{[(3,5-difluorophenyl)sulfonyl]amino}phenyl)thiophene-2-sulfonamide | Method C |

TABLE 1-continued

| Comp. No. | Structure | IUPAC compound name | Synthesis |
|---|---|---|---|
| 42 | 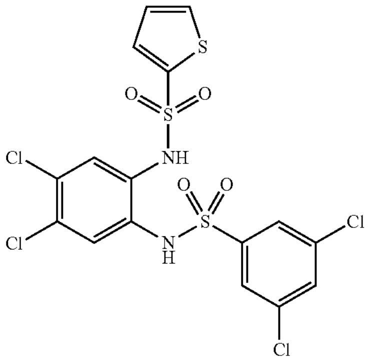 [SMILES: O=S(=O)(Nc1cc(Cl)c(Cl)cc1NS(=O)(=O)c1cccs1)c1cc(Cl)cc(Cl)c1] | N-(4,5-dichloro-2-{[(3,5-dichlorophenyl)sulfonyl] amino}phenyl)thiophene-2-sulfonamide | Method C |
| 43 | 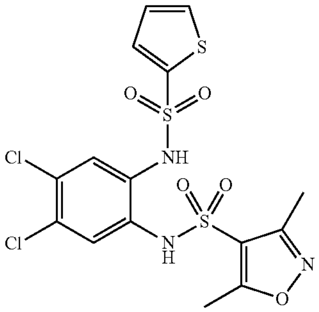 [SMILES: Cc1noc(C)c1S(=O)(=O)Nc1cc(Cl)c(Cl)cc1NS(=O)(=O)c1cccs1] | N-{4,5-dichloro-2-[(2-thienylsulfonyl)amino] phenyl}-3,5-dimethylisoxazole-4-sulfonamide | Method A |
| 44 | 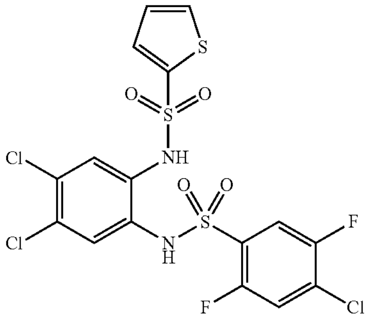 [SMILES: O=S(=O)(Nc1cc(Cl)c(Cl)cc1NS(=O)(=O)c1cc(F)c(Cl)cc1F)c1cccs1] | N-(4,5-dichloro-2-{[(4-chloro-2,5-difluorophenyl)sulfonyl] amino}phenyl)thiophene-2-sulfonamide | Method C |
| 45 | 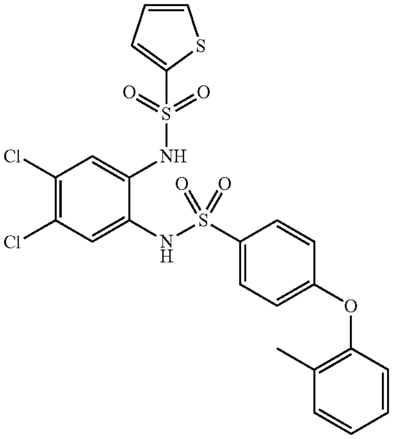 [SMILES: Cc1ccccc1Oc1ccc(S(=O)(=O)Nc2cc(Cl)c(Cl)cc2NS(=O)(=O)c2cccs2)cc1] | N-[4,5-dichloro-2-({[4-(2-methylphenoxy)phenyl] sulfonyl}amino)phenyl]thiophene-2-sulfonamide | Method A |

TABLE 1-continued

| Comp. No. | Structure | IUPAC compound name | Synthesis |
|---|---|---|---|
| 46 | 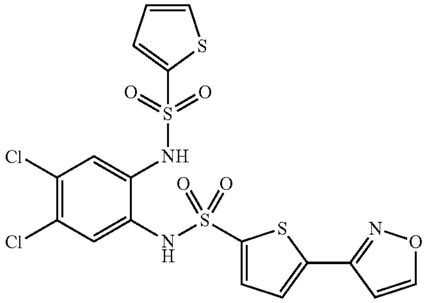 [SMILES: O=S(=O)(Nc1cc(Cl)c(Cl)cc1NS(=O)(=O)c1ccc(-c2ccon2)s1)c1cccs1] | N-{4,5-dichloro-2-[(2-thienylsulfonyl)amino]phenyl}-5-isoxazol-3-ylthiophene-2-sulfonamide | Method C |
| 47 | 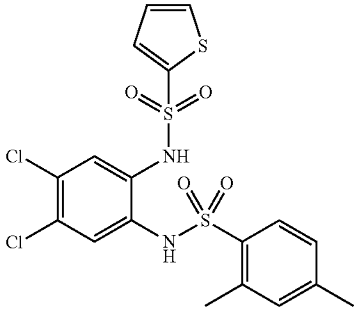 [SMILES: Cc1ccc(S(=O)(=O)Nc2cc(Cl)c(Cl)cc2NS(=O)(=O)c2cccs2)c(C)c1] | N-(4,5-dichloro-2-{[(2,4-dimethylphenyl)sulfonyl]amino}phenyl)thiophene-2-sulfonamide | Method A |
| 48 | 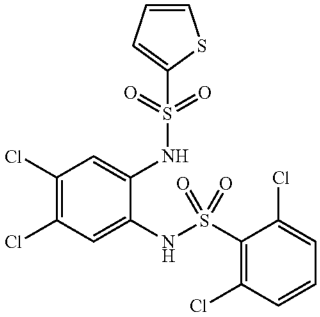 [SMILES: O=S(=O)(Nc1cc(Cl)c(Cl)cc1NS(=O)(=O)c1c(Cl)cccc1Cl)c1cccs1] | N-(4,5-dichloro-2-{[(2,6-dichlorophenyl)sulfonyl]amino}phenyl)thiophene-2-sulfonamide | Method A |
| 49 | 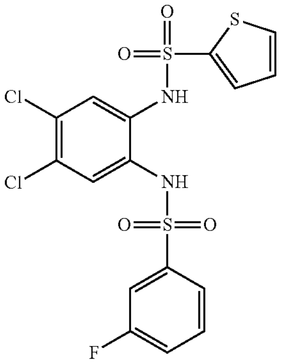 [SMILES: O=S(=O)(Nc1cc(Cl)c(Cl)cc1NS(=O)(=O)c1cccs1)c1cccc(F)c1] | N-(4,5-dichloro-2-{[(3-fluorophenyl)sulfonyl]amino}phenyl)thiophene-2-sulfonamide | Method A |

TABLE 1-continued
| Comp. No. | Structure | IUPAC compound name | Synthesis |
|---|---|---|---|
| 50 | 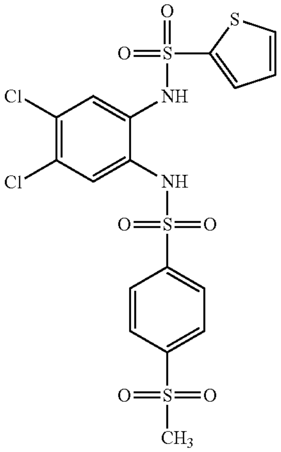 [SMILES: CS(=O)(=O)c1ccc(S(=O)(=O)Nc2cc(Cl)c(Cl)cc2NS(=O)(=O)c2cccs2)cc1] | N-[4,5-dichloro-2-({[4-(methylsulfonyl)phenyl]sulfonyl}phenyl]thiophene-2-sulfonamide | Method A |
| 51 | 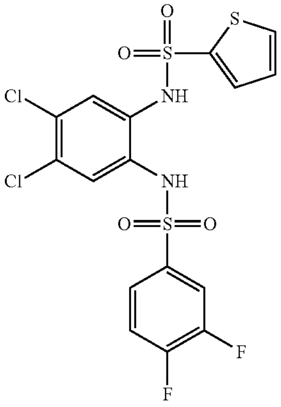 [SMILES: O=S(=O)(Nc1cc(Cl)c(Cl)cc1NS(=O)(=O)c1cccs1)c1ccc(F)c(F)c1] | N-(4,5-dichloro-2-{[(3,4-difluorophenyl)sulfonyl]amino}phenyl)thiophene-2-sulfonamide | Method C |
| 52 | 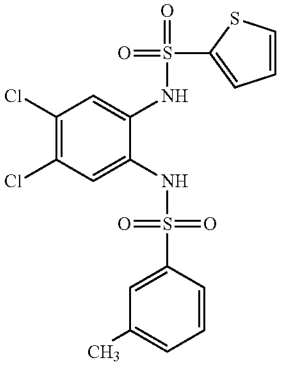 [SMILES: Cc1cccc(S(=O)(=O)Nc2cc(Cl)c(Cl)cc2NS(=O)(=O)c2cccs2)c1] | N-(4,5-dichloro-2-{[(3-methylphenyl)sulfonyl]amino}phenyl)thiophene-2-sulfonamide | Method A |

TABLE 1-continued
| Comp. No. | Structure | IUPAC compound name | Synthesis |
|---|---|---|---|
| 53 | 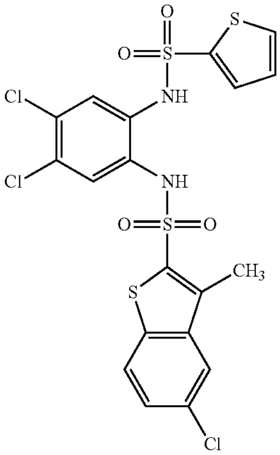 [SMILES: Cc1c(S(=O)(=O)Nc2cc(Cl)c(Cl)cc2NS(=O)(=O)c2cccs2)sc2ccc(Cl)cc12] | 5-chloro-N-{4,5-dichloro-2-[(2-thienylsulfonyl)amino] phenyl}-3-methyl-1-benzothiophene-2-sulfonamide | Method C |
| 54 | 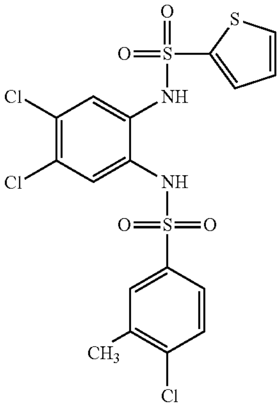 [SMILES: Cc1cc(S(=O)(=O)Nc2cc(Cl)c(Cl)cc2NS(=O)(=O)c2cccs2)ccc1Cl] | N-(4,5-dichloro-2-{[(4-chloro-3-methylphenyl)sulfonyl] amino}phenyl)thiophene-2-sulfonamide | Method A |
| 55 | 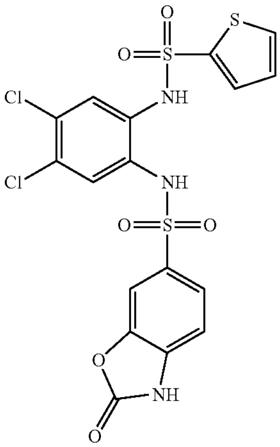 [SMILES: O=c1[nH]c2ccc(S(=O)(=O)Nc3cc(Cl)c(Cl)cc3NS(=O)(=O)c3cccs3)cc2o1] | N-{4,5-dichloro-2-[(2-thienylsulfonyl)amino] phenyl}-2-oxo-2,3-dihydro-1,3-benzoxazole-6-sulfonamide | Method A |

TABLE 1-continued
| Comp. No. | Structure | IUPAC compound name | Synthesis |
|---|---|---|---|
| 56 | 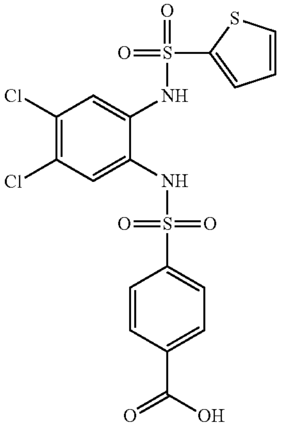 [SMILES: O=C(O)c1ccc(S(=O)(=O)Nc2cc(Cl)c(Cl)cc2NS(=O)(=O)c2cccs2)cc1] | 4-[({4,5-dichloro-2-[(2-thienylsulfonyl)amino]phenyl}amino)sulfonyl]benzoic acid | Method A |
| 57 | 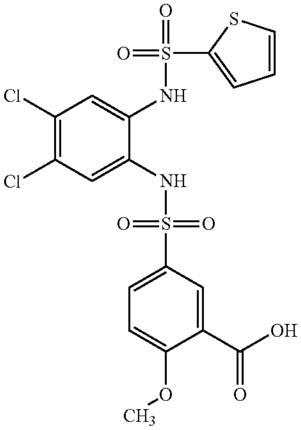 [SMILES: COc1ccc(S(=O)(=O)Nc2cc(Cl)c(Cl)cc2NS(=O)(=O)c2cccs2)cc1C(=O)O] | 5-[({4,5-dichloro-2-[(2-thienylsulfonyl)amino]phenyl}amino)sulfonyl]-2-methoxybenzoic acid | Method B |
| 58 | 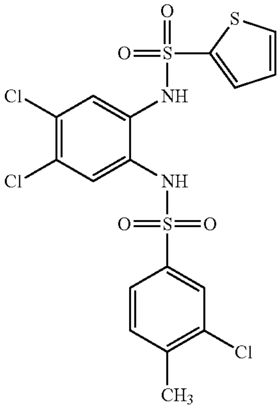 [SMILES: Cc1ccc(S(=O)(=O)Nc2cc(Cl)c(Cl)cc2NS(=O)(=O)c2cccs2)cc1Cl] | N-(4,5-dichloro-2-{[(3-chloro-4-methylphenyl)sulfonyl]amino}phenyl)thiophene-2-sulfonamide | Method A |

TABLE 1-continued
| Comp. No. | Structure | IUPAC compound name | Synthesis |
|---|---|---|---|
| 59 | 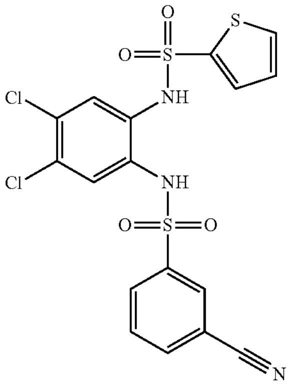 [SMILES: N#Cc1cccc(S(=O)(=O)Nc2cc(Cl)c(Cl)cc2NS(=O)(=O)c2cccs2)c1] | N-(4,5-dichloro-2-{[(3-cyanophenyl)sulfonyl]amino}phenyl)thiophene-2-sulfonamide | Method C |
| 60 | 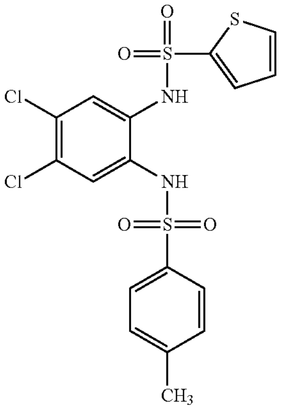 [SMILES: Cc1ccc(S(=O)(=O)Nc2cc(Cl)c(Cl)cc2NS(=O)(=O)c2cccs2)cc1] | N-(4,5-dichloro-2-{[(4-methylphenyl)sulfonyl]amino}phenyl)thiophene-2-sulfonamide | Method A |
| 61 | 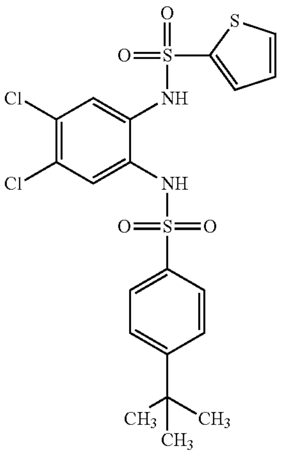 [SMILES: CC(C)(C)c1ccc(S(=O)(=O)Nc2cc(Cl)c(Cl)cc2NS(=O)(=O)c2cccs2)cc1] | N-(2-{[(4-tert-butylphenyl)sulfonyl]amino}-4,5-dichlorophenyl)thiophene-2-sulfonamide | Method A |

TABLE 1-continued
| Comp. No. | Structure | IUPAC compound name | Synthesis |
|---|---|---|---|
| 62 | 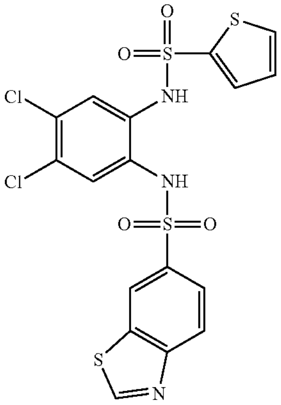 [SMILES: O=S(=O)(Nc1cc(Cl)c(Cl)cc1NS(=O)(=O)c1cccs1)c1ccc2ncsc2c1] | N-{4,5-dichloro-2-[(2-thienylsulfonyl)amino]phenyl}-1,3-benzothiazole-6-sulfonamide | Method A |
| 63 | 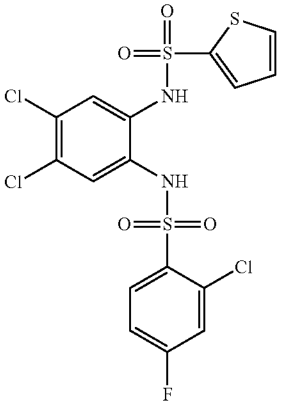 [SMILES: O=S(=O)(Nc1cc(Cl)c(Cl)cc1NS(=O)(=O)c1ccc(F)cc1Cl)c1cccs1] | N-(4,5-dichloro-2-{[(2-chloro-4-fluorophenyl}sulfonyl]amino}phenyl)thiophene-2-sulfonamide | Method A |
| 64 | 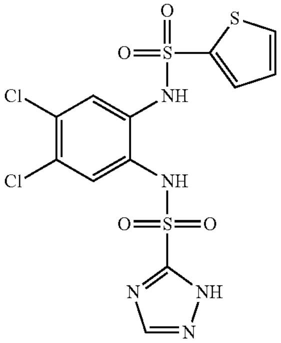 [SMILES: O=S(=O)(Nc1cc(Cl)c(Cl)cc1NS(=O)(=O)c1cccs1)c1ncn[nH]1] | N-{4,5-dichloro-2-[(2-thienylsulfonyl)amino]phenyl}-1H-1,2,4-triazole-5-sulfonamide | Method A |

TABLE 1-continued
| Comp. No. | Structure | IUPAC compound name | Synthesis |
|---|---|---|---|
| 65 | 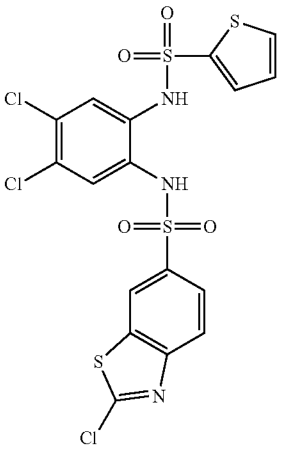 [SMILES: O=S(=O)(Nc1cc(Cl)c(Cl)cc1NS(=O)(=O)c1cccs1)c1ccc2nc(Cl)sc2c1] | 2-chloro-N-{4,5-dichloro-2-[(2-thienylsulfonyl)amino]phenyl}-1,3-benzothiazole-6-sulfonamide | Method A |
| 66 | 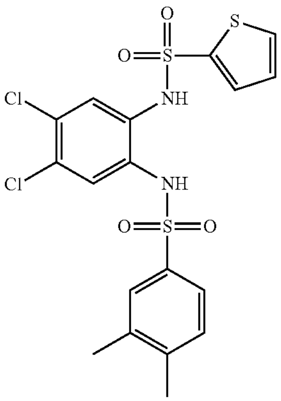 [SMILES: Cc1ccc(S(=O)(=O)Nc2cc(Cl)c(Cl)cc2NS(=O)(=O)c2cccs2)cc1C] | N-(4,5-dichloro-2-{[(3,4-dimethylphenyl)sulfonyl]amino}phenyl)thiophene-2-sulfonamide | Method A |
| 67 | 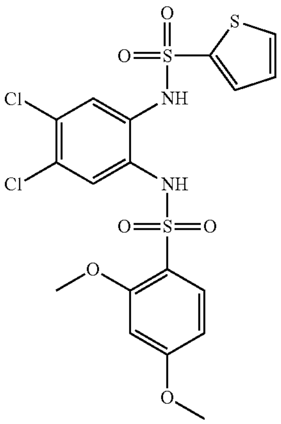 [SMILES: COc1ccc(S(=O)(=O)Nc2cc(Cl)c(Cl)cc2NS(=O)(=O)c2cccs2)c(OC)c1] | N-(4,5-dichloro-2-{[(2,4-dimethoxyphenyl)sulfonyl]amino}phenyl)thiophene-2-sulfonamide | Method A |

TABLE 1-continued
| Comp. No. | Structure | IUPAC compound name | Synthesis |
|---|---|---|---|
| 68 | 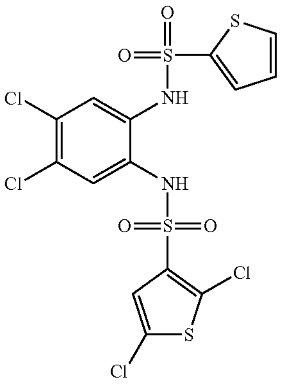 [SMILES: O=S(=O)(Nc1cc(Cl)c(Cl)cc1NS(=O)(=O)c1cc(Cl)sc1Cl)c1cccs1] | N-(4,5-dichloro-2-{[(2,5-dichloro-3-thienyl)sulfonyl]amino}phenyl)thiophene-2-sulfonamide | Method C |
| 69 | 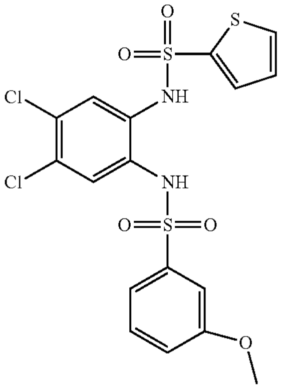 [SMILES: COc1cccc(S(=O)(=O)Nc2cc(Cl)c(Cl)cc2NS(=O)(=O)c2cccs2)c1] | N-(4,5-dichloro-2-{[(3-methoxyphenyl)sulfonyl]amino}phenyl)thiophene-2-sulfonamide | Method A |
| 70 | 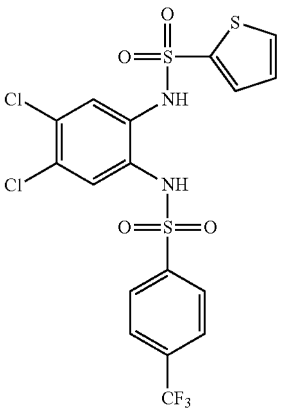 [SMILES: O=S(=O)(Nc1cc(Cl)c(Cl)cc1NS(=O)(=O)c1cccs1)c1ccc(C(F)(F)F)cc1] | N-[4,5-dichloro-2-({[4-(trifluoromethyl)phenyl]sulfonyl}amino)phenyl]thiophene-2-sulfonamide | Method C |

TABLE 1-continued
| Comp. No. | Structure | IUPAC compound name | Synthesis |
|---|---|---|---|
| 71 | 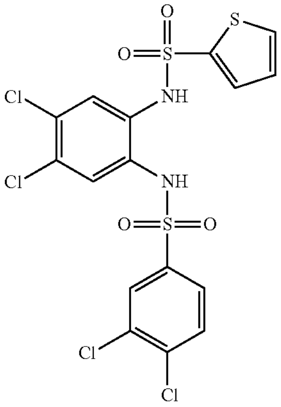 | N-(4,5-dichloro-2-{[(3,4-dichlorophenyl)sulfonyl]amino}phenyl)thiophene-2-sulfonamide | Method C |
| 72 | 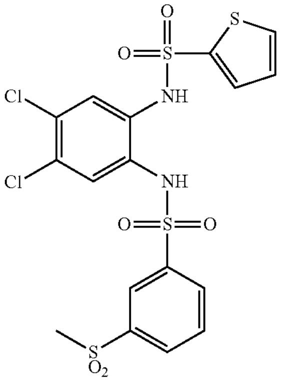 [SMILES: CS(=O)(=O)c1cccc(S(=O)(=O)Nc2cc(Cl)c(Cl)cc2NS(=O)(=O)c2cccs2)c1] | N-[4,5-dichloro-2-({[3-(methylsulfonyl)phenyl]sulfonyl}amino)phenyl]thiophene-2-sulfonamide | Method A |
| 73 | 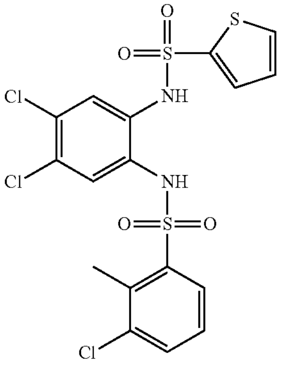 [SMILES: Cc1c(Cl)cccc1S(=O)(=O)Nc1cc(Cl)c(Cl)cc1NS(=O)(=O)c1cccs1] | N-(4,5-dichloro-2-{[(3-chloro-2-methylphenyl)sulfonyl]amino}phenyl)thiophene-2-sulfonamide | Method A |

TABLE 1-continued
| Comp. No. | Structure | IUPAC compound name | Synthesis |
|---|---|---|---|
| 74 | 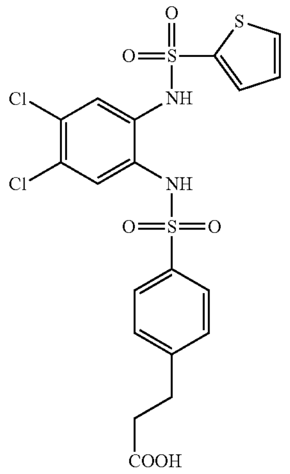 [SMILES: O=C(O)CCc1ccc(S(=O)(=O)Nc2cc(Cl)c(Cl)cc2NS(=O)(=O)c2cccs2)cc1] | 3-{4-[({4,5-dichloro-2-[(2-thienylsulfonyl)amino]phenyl}amino)sulfonyl]phenyl}propanoic acid | Method B |
| 75 | 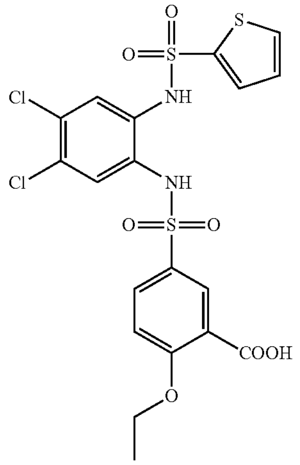 [SMILES: CCOc1ccc(S(=O)(=O)Nc2cc(Cl)c(Cl)cc2NS(=O)(=O)c2cccs2)cc1C(=O)O] | 5-[({4,5-dichloro-2-[(2-thienylsulfonyl)amino]phenyl}amino)sulfonyl]-2-ethoxybenzoic acid | Method B |
| 76 | 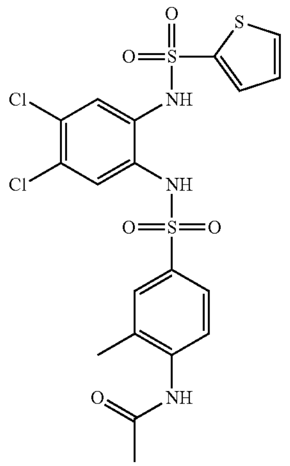 [SMILES: CC(=O)Nc1ccc(S(=O)(=O)Nc2cc(Cl)c(Cl)cc2NS(=O)(=O)c2cccs2)cc1C] | N-{4-[({4,5-dichloro-2-[(2-thienylsulfonyl)amino]phenyl}amino)sulfonyl]-2-methylphenyl}acetamide | Method A |

TABLE 1-continued

| Comp. No. | Structure | IUPAC compound name | Synthesis |
| --- | --- | --- | --- |
| 77 | 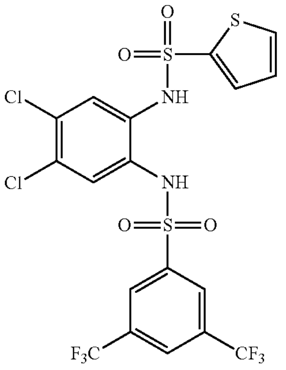 [SMILES: O=S(=O)(Nc1cc(Cl)c(Cl)cc1NS(=O)(=O)c1cccs1)c1cc(C(F)(F)F)cc(C(F)(F)F)c1] | N-[2-({[3,5-bis(trifluoromethyl)phenyl] sulfonyl}amino)-4,5-dichlorophenyl]thiophene-2-sulfonamide | Method C |
| 76 | 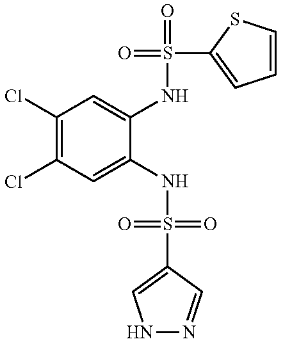 [SMILES: O=S(=O)(Nc1cc(Cl)c(Cl)cc1NS(=O)(=O)c1cccs1)c1cn[nH]c1] | N-{4,5-dichloro-2-[(2-thienylsulfonyl)amino]phenyl}-1H-pyrazole-4-sulfonamide | Method C |
| 77 | 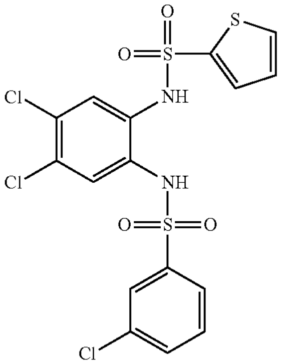 | N-(4,5-dichloro-2-{[(3-chlorophenyl)sulfonyl] amino}phenyl)thiophene-2-sulfonamide | Method A |
| 78 | 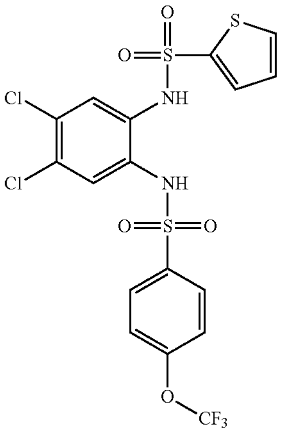 | N-[4,5-dichloro-2-({[4-(trifluoromethoxy)phenyl] sulfonyl}amino)phenyl]thio-phene-2-sulfonamide | Method C |

TABLE 1-continued
| Comp. No. | Structure | IUPAC compound name | Synthesis |
|---|---|---|---|
| 79 | 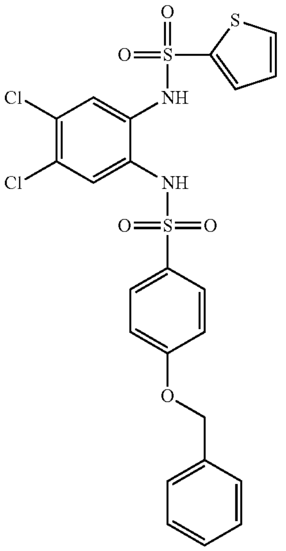 [SMILES: O=S(=O)(Nc1cc(Cl)c(Cl)cc1NS(=O)(=O)c1cccs1)c1ccc(OCc2ccccc2)cc1] | N-[2-({[4-(benzyloxy)phenyl]sulfonyl}amino)-4,5-dichlorophenyl}thiophene-2-sulfonamide | Method A |
| 80 | 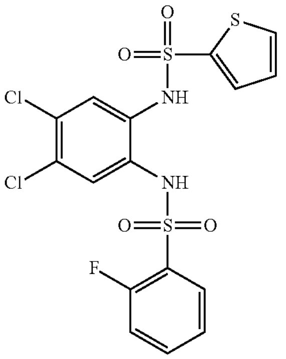 [SMILES: O=S(=O)(Nc1cc(Cl)c(Cl)cc1NS(=O)(=O)c1ccccc1F)c1cccs1] | N-(4,5-dichloro-2-{[(2-fluorophenyl)sulfonyl]amino}phenyl)thiophene-2-sulfonamide | Method A |
| 81 | 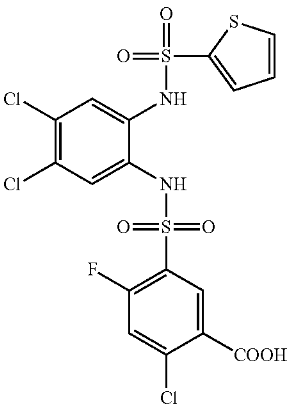 [SMILES: O=C(O)c1cc(S(=O)(=O)Nc2cc(Cl)c(Cl)cc2NS(=O)(=O)c2cccs2)c(F)cc1Cl] | 2-chloro-5-[({4,5-dichloro-2-[(2-thienylsulfonyl)amino]phenyl}amino)sulfonyl}-4-fluorobenzoic acid | Method B |

TABLE 1-continued

| Comp. No. | Structure | IUPAC compound name | Synthesis |
|---|---|---|---|
| 82 | 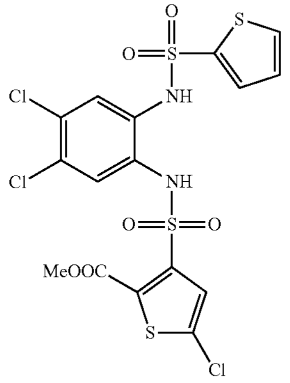 [SMILES: COC(=O)c1sc(Cl)cc1S(=O)(=O)Nc1cc(Cl)c(Cl)cc1NS(=O)(=O)c1cccs1] | methyl 5-chloro-3-[({4,5-dichloro-2-[(2-thienylsulfonyl)amino]phenyl}amino)sulfonyl]thiophene-2-carboxylate | Method A |
| 83 | 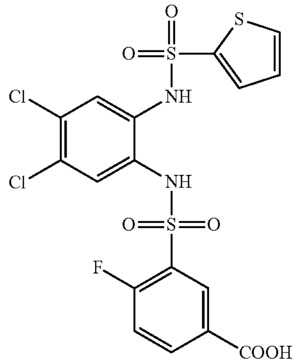 [SMILES: O=C(O)c1ccc(F)c(S(=O)(=O)Nc2cc(Cl)c(Cl)cc2NS(=O)(=O)c2cccs2)c1] | 3-[({4,5-dichloro-2-[(2-thienylsulfonyl)amino]phenyl}amino)sulfonyl]-4-fluorobenzoic acid | Method B |
| 84 | 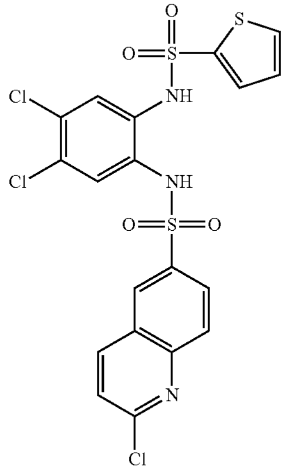 [SMILES: O=S(=O)(Nc1cc(Cl)c(Cl)cc1NS(=O)(=O)c1cccs1)c1ccc2nc(Cl)ccc2c1] | 2-chloro-N-{4,5-dichloro-2-[(2-thienylsulfonyl)amino]phenyl}quinoline-6-sulfonamide | Method C |
| 85 | 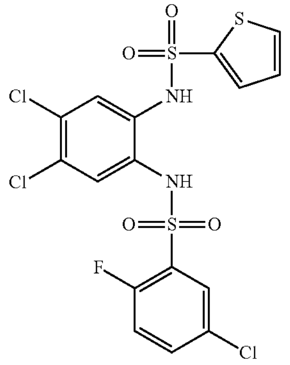 | N-(4,5-dichloro-2-{[(5-chloro-2-fluorophenyl)sulfonyl]amino}phenyl)thiophene-2-sulfonamide | Method A |

TABLE 1-continued
| Comp. No. | Structure | IUPAC compound name | Synthesis |
|---|---|---|---|
| 86 | 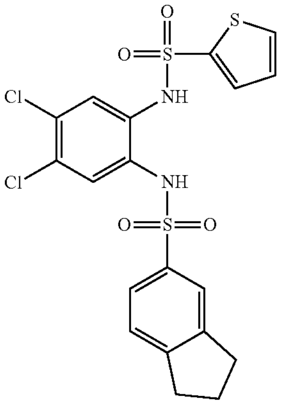 [SMILES: O=S(=O)(Nc1cc(Cl)c(Cl)cc1NS(=O)(=O)c1cccs1)c1ccc2c(c1)CCC2] | N-{4,5-dichloro-2-[(2,3-dihydro-1H-inden-5-ylsulfonyl)amino]phenyl}thiophene-2-sulfonamide | Method A |
| 87 | 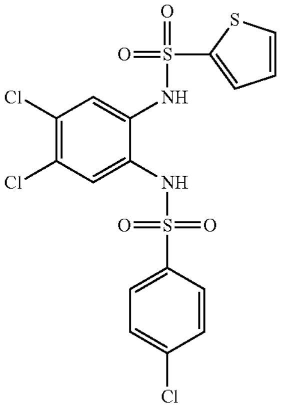 | N-(4,5-dichloro-2-{[(4-chlorophenyl)sulfonyl]amino}phenyl)thiophene-2-sulfonamide | Method A |
| 88 | 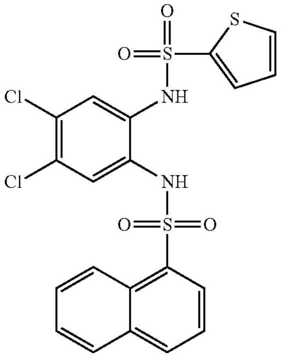 [SMILES: O=S(=O)(Nc1cc(Cl)c(Cl)cc1NS(=O)(=O)c1cccc2ccccc12)c1cccs1] | N-{4,5-dichloro-2-[(1-naphthylsulfonyl)amino]phenyl}thiophene-2-sulfonamide | Method A |

TABLE 1-continued

| Comp. No. | Structure | IUPAC compound name | Synthesis |
|---|---|---|---|
| 89 | 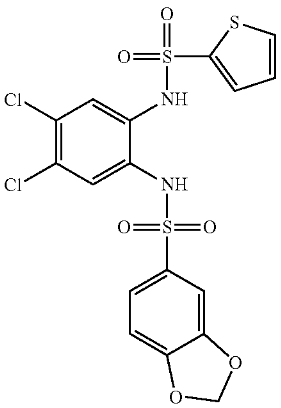 [SMILES: O=S(=O)(Nc1cc(Cl)c(Cl)cc1NS(=O)(=O)c1cccs1)c1ccc2c(c1)OCO2] | N-{4,5-dichloro-2-[(2-thienylsulfonyl)amino]phenyl}-1,3-benzodioxole-5-sulfonamide | Method A |
| 90 | 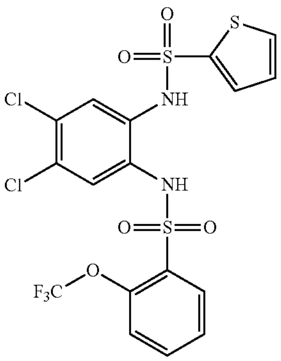 [SMILES: O=S(=O)(Nc1cc(Cl)c(Cl)cc1NS(=O)(=O)c1ccccc1OC(F)(F)F)c1cccs1] | N-[4,5-dichloro-2-({[2-(trifluoromethoxy)phenyl]sulfonyl}amino)phenyl]thiophene-2-sulfonamide | Method A |
| 91 | 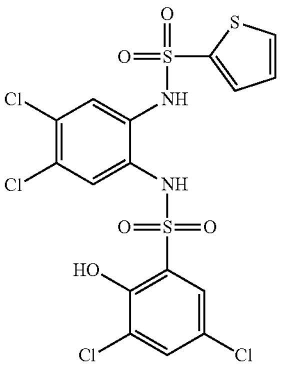 [SMILES: O=S(=O)(Nc1cc(Cl)c(Cl)cc1NS(=O)(=O)c1cc(Cl)cc(Cl)c1O)c1cccs1] | N-(4,5-dichloro-2-{[(3,5-dichloro-2-hydroxyphenyl)sulfonyl]amino}phenyl)thiophene-2-sulfonamide | Method A |
| 92 | 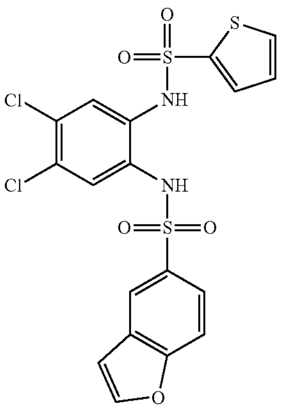 [SMILES: O=S(=O)(Nc1cc(Cl)c(Cl)cc1NS(=O)(=O)c1cccs1)c1ccc2occc2c1] | N-{4,5-dichloro-2-[(2-thienylsulfonyl)amino]phenyl}-1-benzofuran-5-sulfonamide | Method A |

TABLE 1-continued

| Comp. No. | Structure | IUPAC compound name | Synthesis |
|---|---|---|---|
| 93 | 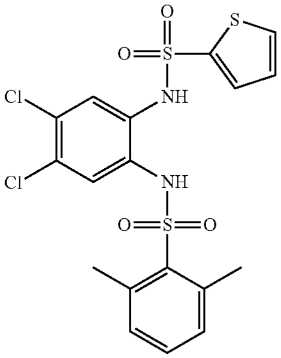 [SMILES: Cc1cccc(C)c1S(=O)(=O)Nc1cc(Cl)c(Cl)cc1NS(=O)(=O)c1cccs1] | N-(4,5-dichloro-2-{[(2,6-dimethylphenyl)sulfonyl] amino}phenyl)thiophene-2-sulfonamide | Method A |
| 94 | 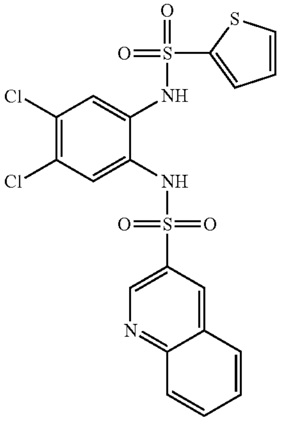 [SMILES: O=S(=O)(Nc1cc(Cl)c(Cl)cc1NS(=O)(=O)c1cccs1)c1cnc2ccccc2c1] | N-{4,5-dichloro-2-[(2-thienylsulfonyl)amino] phenyl}quinoline-3-sulfonamide | Method A |
| 95 | 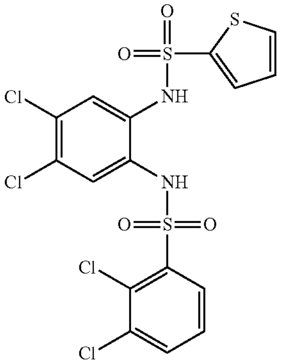 [SMILES: O=S(=O)(Nc1cc(Cl)c(Cl)cc1NS(=O)(=O)c1cccc(Cl)c1Cl)c1cccs1] | N-(4,5-dichloro-2-{[(2,3-dichlorophenyl)sulfonyl] amino}phenyl)thiophene-2-sulfonamide | Method A |
| 96 | 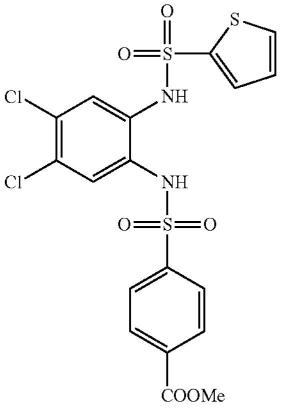 [SMILES: COC(=O)c1ccc(S(=O)(=O)Nc2cc(Cl)c(Cl)cc2NS(=O)(=O)c2cccs2)cc1] | methyl 4-[({4,5-dichloro-2-[(2-thienylsulfonyl)amino] phenyl}amino)sulfonyl] benzoate | Method A |

TABLE 1-continued

| Comp. No. | Structure | IUPAC compound name | Synthesis |
|---|---|---|---|
| 97 | 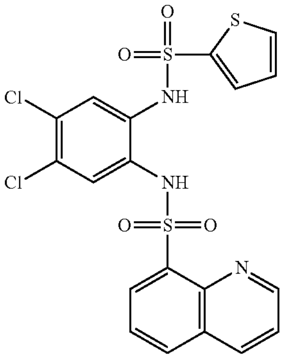 [SMILES: O=S(=O)(Nc1cc(Cl)c(Cl)cc1NS(=O)(=O)c1cccc2cccnc12)c1cccs1] | N-{4,5-dichloro-2-[(2-thienylsulfonyl)amino]phenyl}quinoline-8-sulfonamide | Method A |
| 98 | 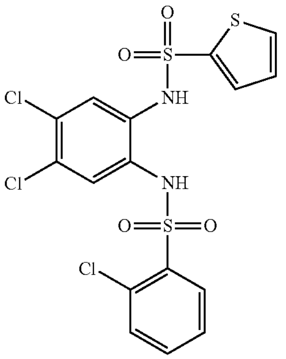 | N-(4,5-dichloro-2-{[(2-chlorophenyl)sulfonyl]amino}phenyl)thiophene-2-sulfonamide | Method A |
| 99 | 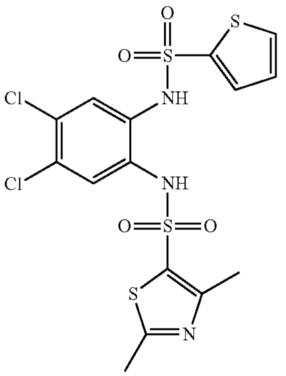 [SMILES: Cc1nc(C)c(S(=O)(=O)Nc2cc(Cl)c(Cl)cc2NS(=O)(=O)c2cccs2)s1] | N-{4,5-dichloro-2-[(2-thienylsulfonyl)amino]phenyl}-2,4-dimethyl-1,3-thiazole-5-sulfonamide | Method A |
| 100 | 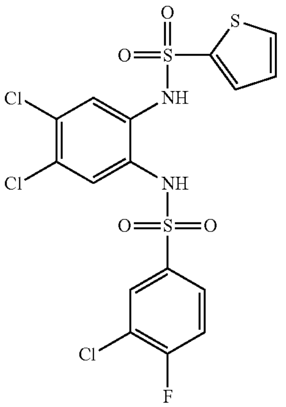 [SMILES: O=S(=O)(Nc1cc(Cl)c(Cl)cc1NS(=O)(=O)c1cccs1)c1ccc(F)c(Cl)c1] | N-(4,5-dichloro-2-{[(3-chloro-4-fluorophenyl)sulfonyl]amino}phenyl)thiophene-2-sulfonamide | Method D |

TABLE 1-continued

| Comp. No. | Structure | IUPAC compound name | Synthesis |
|---|---|---|---|
| 101 | 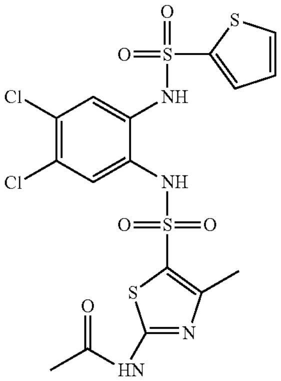 [SMILES: CC(=O)Nc1nc(C)c(S(=O)(=O)Nc2cc(Cl)c(Cl)cc2NS(=O)(=O)c2cccs2)s1] | N-{5-[({4,5-dichloro-2-[(2-thienylsulfonyl)amino] phenyl}amino)sulfonyl]-4-methyl-1,3-thiazol-2-yl}acetamide | Method A |
| 102 | 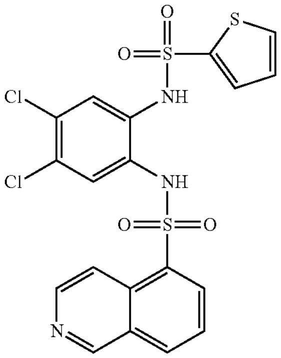 [SMILES: O=S(=O)(Nc1cc(Cl)c(Cl)cc1NS(=O)(=O)c1cccc2cnccc12)c1cccs1] | N-{4,5-dichloro-2-[(2-thienylsulfonyl)amino]phenyl} isoquinoline-5-sulfonamide | Method A |
| 103 | 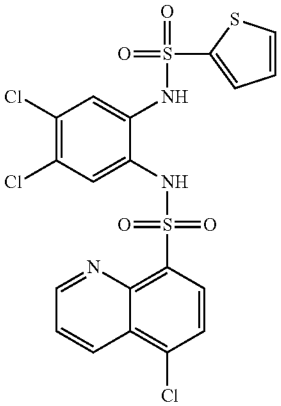 [SMILES: O=S(=O)(Nc1cc(Cl)c(Cl)cc1NS(=O)(=O)c1ccc(Cl)c2cccnc12)c1cccs1] | 5-chloro-N-{4,5-dichloro-2-[(2-thienylsulfonyl)amino] phenyl}quinoline-8-sulfonamide | Method A |
| 105 | 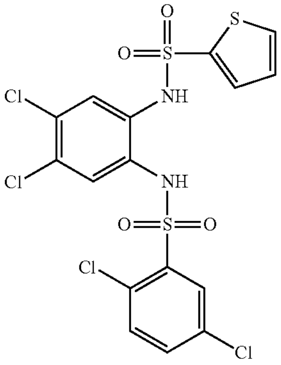 [SMILES: O=S(=O)(Nc1cc(Cl)c(Cl)cc1NS(=O)(=O)c1cc(Cl)ccc1Cl)c1cccs1] | N-(4,5-dichloro-2-{[(2,5-dichlorophenyl)sulfonyl] amino}phenyl)thiophene-2-sulfonamide | Method A |

TABLE 1-continued
| Comp. No. | Structure | IUPAC compound name | Synthesis |
|---|---|---|---|
| 106 | 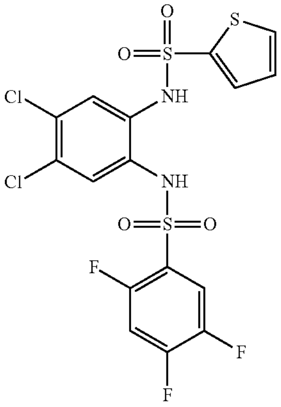 | N-(4,5-dichloro-2-{[(2,4,5-trifluorophenyl)sulfonyl] amino}phenyl)thiophene-2-sulfonamide | Method C |
| 107 | 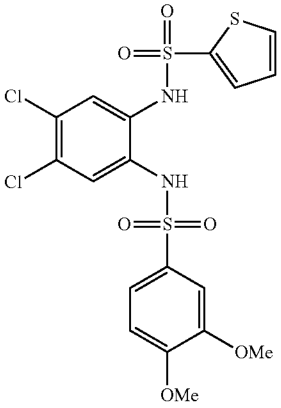 [SMILES: COc1ccc(S(=O)(=O)Nc2cc(Cl)c(Cl)cc2NS(=O)(=O)c2cccs2)cc1OC] | N-(4,5-dichloro-2-{[(3,4-dimethoxyphenyl)sulfonyl] amino}phenyl)thiophene-2-sulfonamide | Method A |
| 108 | 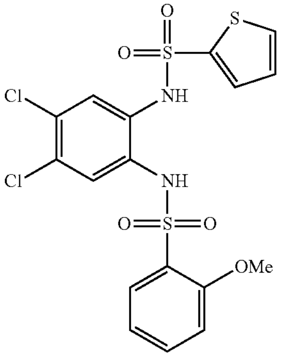 [SMILES: COc1ccccc1S(=O)(=O)Nc1cc(Cl)c(Cl)cc1NS(=O)(=O)c1cccs1] | N-(4,5-dichloro-2-{[(2-methoxyphenyl)sulfonyl] amino}phenyl)thiophene-2-sulfonamide | Method A |

TABLE 1-continued

| Comp. No. | Structure | IUPAC compound name | Synthesis |
|---|---|---|---|
| 109 | 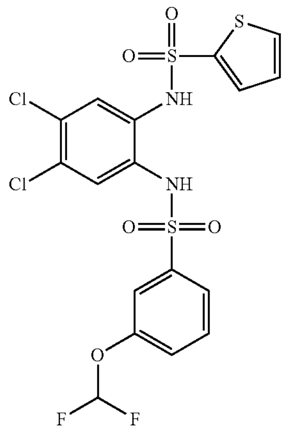 [SMILES: O=S(=O)(Nc1cc(Cl)c(Cl)cc1NS(=O)(=O)c1cccs1)c1cccc(OC(F)F)c1] | N-[4,5-dichloro-2-({[3-(difluoromethoxy)phenyl] sulfonyl}amino)phenyl]thiophene-2-sulfonamide | Method A |
| 110 | 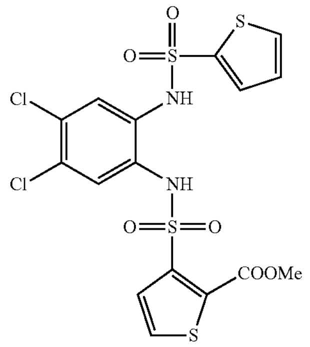 [SMILES: COC(=O)c1sccc1S(=O)(=O)Nc1cc(Cl)c(Cl)cc1NS(=O)(=O)c1cccs1] | methyl 3-[({4,5-dichloro-2-[(2-thienylsulfonyl)amino]phenyl}amino)sulfonyl]thiophene-2-carboxylate | Method A |
| 111 | 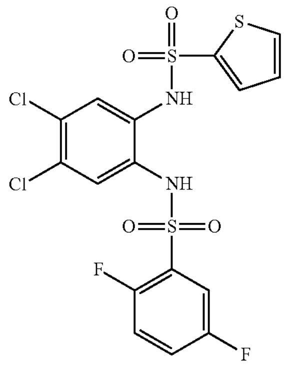 [SMILES: O=S(=O)(Nc1cc(Cl)c(Cl)cc1NS(=O)(=O)c1cc(F)ccc1F)c1cccs1] | N-(4,5-dichloro-2-{[(2,5-difluorophenyl)sulfonyl] amino}phenyl)thiophene-2-sulfonamide | Method A |
| 112 | 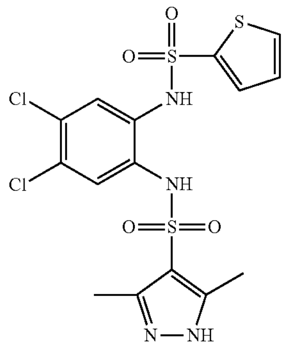 [SMILES: Cc1n[nH]c(C)c1S(=O)(=O)Nc1cc(Cl)c(Cl)cc1NS(=O)(=O)c1cccs1] | N-{4,5-dichloro-2-[(2-thienylsulfonyl)amino] phenyl}-3,5-dimethyl-1H-pyrazole-4-sulfonamide | Method A |

TABLE 1-continued
| Comp. No. | Structure | IUPAC compound name | Synthesis |
|---|---|---|---|
| 113 | 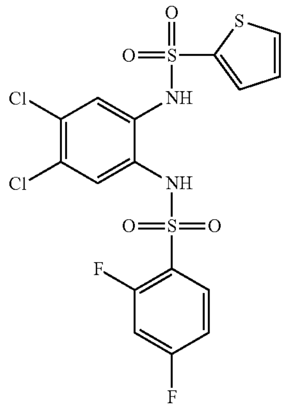 [SMILES: O=S(=O)(Nc1cc(Cl)c(Cl)cc1NS(=O)(=O)c1ccc(F)cc1F)c1cccs1] | N-(4,5-dichloro-2-{[(2,4-difluorophenyl)sulfonyl]amino}phenyl)thiophene-2-sulfonamide | Method A |
| 114 | 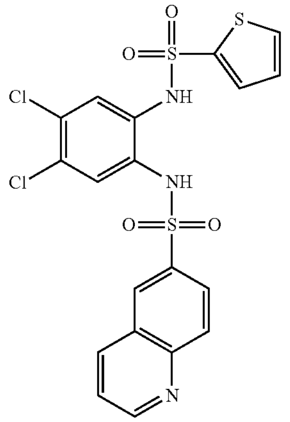 [SMILES: O=S(=O)(Nc1cc(Cl)c(Cl)cc1NS(=O)(=O)c1cccs1)c1ccc2ncccc2c1] | N-{4,5-dichloro-2-[(2-thienylsulfonyl)amino]phenyl}quinoline-6-sulfonamide | Method A |
| 115 | 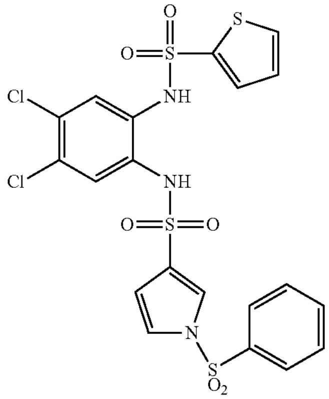 [SMILES: O=S(=O)(Nc1cc(Cl)c(Cl)cc1NS(=O)(=O)c1cccs1)c1ccn(S(=O)(=O)c2ccccc2)c1] | N-{4,5-dichloro-2-[(2-thienylsulfonyl)amino]phenyl}-1-(phenylsulfonyl)-1H-pyrrole-3-sulfonamide | Method A |

TABLE 1-continued

| Comp. No. | Structure | IUPAC compound name | Synthesis |
|---|---|---|---|
| 116 | 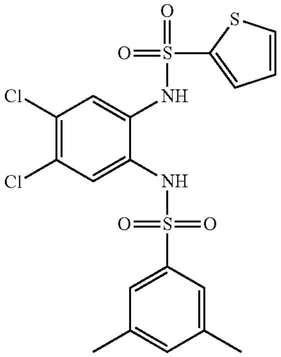 [SMILES: Cc1cc(C)cc(S(=O)(=O)Nc2cc(Cl)c(Cl)cc2NS(=O)(=O)c2cccs2)c1] | N-(4,5-dichloro-2-{[(3,5-dimethylphenyl)sulfonyl] amino}phenyl)thiophene-2-sulfonamide | Method A |
| 117 | 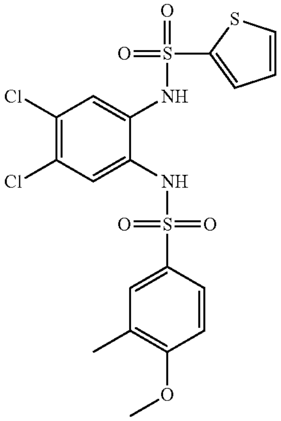 [SMILES: COc1ccc(S(=O)(=O)Nc2cc(Cl)c(Cl)cc2NS(=O)(=O)c2cccs2)cc1C] | N-(4,5-dichloro-2-{[(4-methoxy-3-methylphenyl)sulfonyl] amino}phenyl)thiophene-2-sulfonamide | Method A |
| 118 | 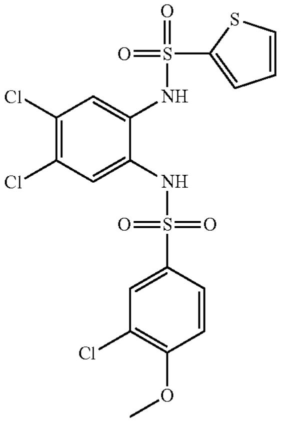 [SMILES: COc1ccc(S(=O)(=O)Nc2cc(Cl)c(Cl)cc2NS(=O)(=O)c2cccs2)cc1Cl] | N-(4,5-dichloro-2-{[(3-chloro-4-methoxyphenyl)sulfonyl] amino}phenyl)thiophene-2-sulfonamide | Method A |
| 119 | 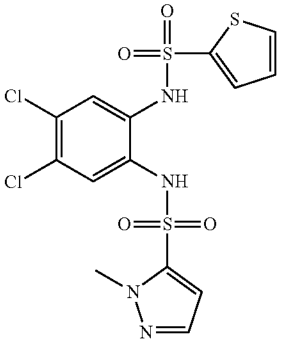 [SMILES: Cn1nccc1S(=O)(=O)Nc1cc(Cl)c(Cl)cc1NS(=O)(=O)c1cccs1] | N-{4,5-dichloro-2-[(2-thienylsulfonyl)amino] phenyl}-1-methyl-1H-pyrazole-5-sulfonamiee | Method A |

TABLE 1-continued
| Comp. No. | Structure | IUPAC compound name | Synthesis |
|---|---|---|---|
| 120 | 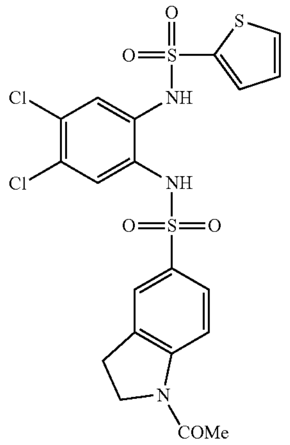 | 1-acetyl-N-{4,5-dichloro-2-[(2-thienylsulfonyl)amino]phenyl}indoline-5-sulfonamide | Method A |
| 121 | 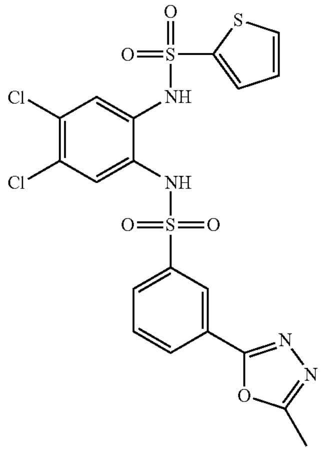 [SMILES: Cc1nnc(-c2cccc(S(=O)(=O)Nc3cc(Cl)c(Cl)cc3NS(=O)(=O)c3cccs3)c2)o1] | N-[4,5-dichloro-2-({[3-(5-methyl-1,3,4-oxadiazol-2-yl)phenyl]sulfonyl}amino)phenyl]thiophene-2-sulfonamide | Method A |
| 122 | 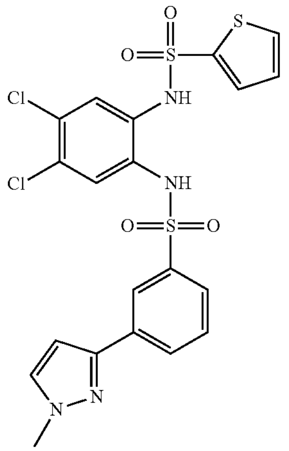 [SMILES: Cn1ccc(-c2cccc(S(=O)(=O)Nc3cc(Cl)c(Cl)cc3NS(=O)(=O)c3cccs3)c2)n1] | N-[4,5-dichloro-2-({[3-(1-methyl-1H-pyrazol-3-yl)phenyl]sulfonyl}amino)phenyl]thiophene-2-sulfonamide | Method A |

TABLE 1-continued
| Comp. No. | Structure | IUPAC compound name | Synthesis |
|---|---|---|---|
| 123 | 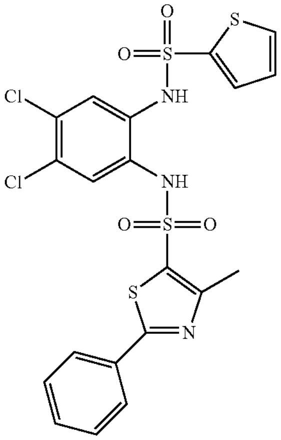 [SMILES: Cc1nc(-c2ccccc2)sc1S(=O)(=O)Nc1cc(Cl)c(Cl)cc1NS(=O)(=O)c1cccs1] | N-{4,5-dichloro-2-[(2-thienylsulfonyl)amino]phenyl}-4-methyl-2-phenyl-1,3-thiazole-5-sulfonamide | Method A |
| 124 | 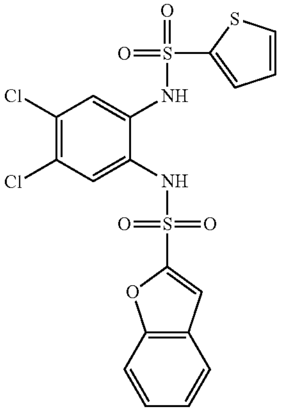 [SMILES: O=S(=O)(Nc1cc(Cl)c(Cl)cc1NS(=O)(=O)c1cccs1)c1cc2ccccc2o1] | N-{4,5-dichloro-2-[(2-thienylsulfonyl)amino]phenyl}-1-benzofuran-2-sulfonamide | Method A |
| 125 | 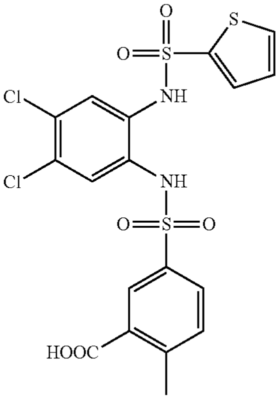 [SMILES: Cc1ccc(S(=O)(=O)Nc2cc(Cl)c(Cl)cc2NS(=O)(=O)c2cccs2)cc1C(=O)O] | 5-[({4,5-dichloro-2-[(2-thienylsulfonyl)amino]phenyl}amino)sulfonyl]-2-methylbenzoic acid | Method B |

TABLE 1-continued
| Comp. No. | Structure | IUPAC compound name | Synthesis |
|---|---|---|---|
| 126 | 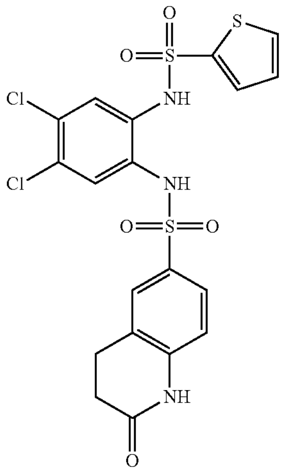 [SMILES: O=C1CCc2cc(S(=O)(=O)Nc3cc(Cl)c(Cl)cc3NS(=O)(=O)c3cccs3)ccc2N1] | N-{4,5-dichloro-2-[(2-thienylsulfonyl)amino] phenyl}-2-oxo-1,2,3,4-tetrahydroquinoline-6-sulfonamide | Method C |
| 127 | 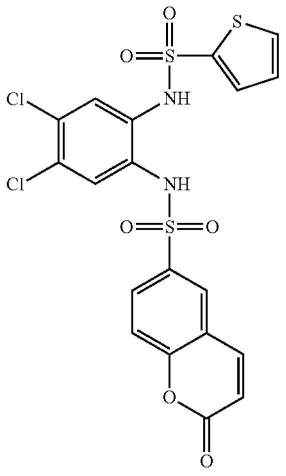 [SMILES: O=c1ccc2cc(S(=O)(=O)Nc3cc(Cl)c(Cl)cc3NS(=O)(=O)c3cccs3)ccc2o1] | N-{4,5-dichloro-2-[(2-thienylsulfonyl)amino] phenyl}-2-oxo-2H-chromene-6-sulfonamide | Method A |
| 128 | 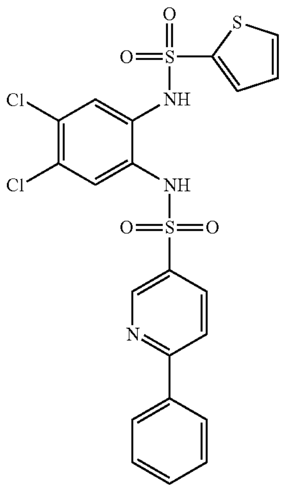 [SMILES: O=S(=O)(Nc1cc(Cl)c(Cl)cc1NS(=O)(=O)c1cccs1)c1ccc(-c2ccccc2)nc1] | N-{4,5-dichloro-2-[(2-thienylsulfonyl)amino] phenyl}-6-phenylpyridine-3-sulfonamide | Method C |

TABLE 1-continued
| Comp. No. | Structure | IUPAC compound name | Synthesis |
|---|---|---|---|
| 129 | 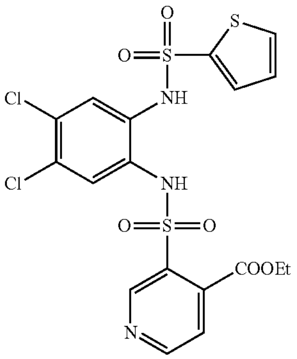 [SMILES: CCOC(=O)c1ccncc1S(=O)(=O)Nc1cc(Cl)c(Cl)cc1NS(=O)(=O)c1cccs1] | ethyl 3-[({4,5-dichloro-2-[(2-thienylsulfonyl)amino]phenyl}amino)sulfonyl]isonicotinate | Method A |
| 130 | 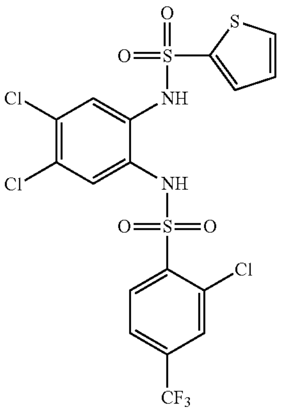 [SMILES: O=S(=O)(Nc1cc(Cl)c(Cl)cc1NS(=O)(=O)c1ccc(C(F)(F)F)cc1Cl)c1cccs1] | N-[4,5-dichloro-2-({[2-chloro-4-(trifluoromethyl)phenyl]sulfonyl}amino)phenyl]thiophene-2-sulfonamide | Method C |
| 131 | 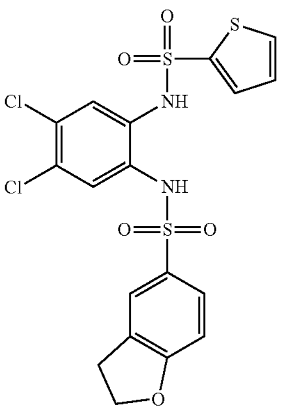 [SMILES: O=S(=O)(Nc1cc(Cl)c(Cl)cc1NS(=O)(=O)c1cccs1)c1ccc2c(c1)CCO2] | N-{4,5-dichloro-2-[(2-thienylsulfonyl)amino]phenyl}-2,3-dihydro-1-benzofuran-5-sulfonamide | Method C |

TABLE 1-continued
| Comp. No. | Structure | IUPAC compound name | Synthesis |
| --- | --- | --- | --- |
| 132 | 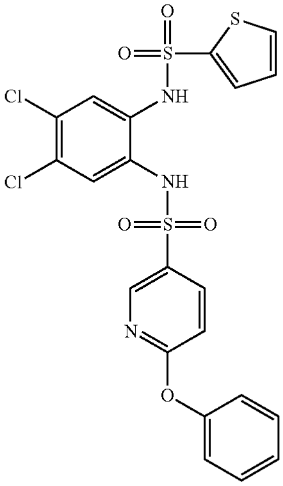 [SMILES: O=S(=O)(Nc1cc(Cl)c(Cl)cc1NS(=O)(=O)c1cccs1)c1ccc(Oc2ccccc2)nc1] | N-{4,5-dichloro-2-[(2-thienylsulfonyl)amino]phenyl}-6-phenoxypyridine-3-sulfonamide | Method A |
| 133 | 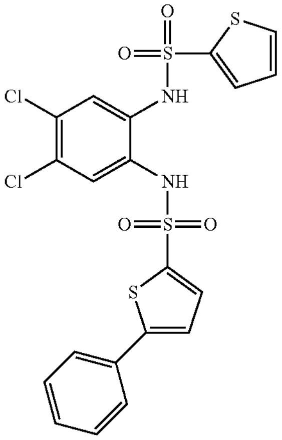 [SMILES: O=S(=O)(Nc1cc(Cl)c(Cl)cc1NS(=O)(=O)c1ccc(-c2ccccc2)s1)c1cccs1] | N-{4,5-dichloro-2-[(2-thienylsulfonyl)amino] phenyl}-5-phenylthiophene-2-sulfonamide | Method C |
| 134 | 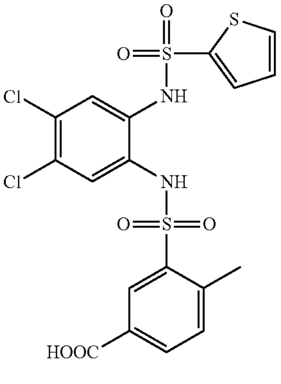 [SMILES: Cc1ccc(C(=O)O)cc1S(=O)(=O)Nc1cc(Cl)c(Cl)cc1NS(=O)(=O)c1cccs1] | 3-[({4,5-dichloro-2-[(2-thienylsulfonyl)amino] phenyl}amino)sulfonyl]-4-methylbenzoic acid | Method B |

TABLE 1-continued
| Comp. No. | Structure | IUPAC compound name | Synthesis |
|---|---|---|---|
| 135 | 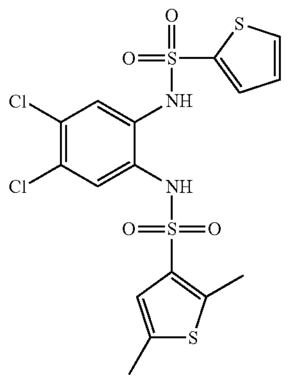 [SMILES: Cc1cc(S(=O)(=O)Nc2cc(Cl)c(Cl)cc2NS(=O)(=O)c2cccs2)c(C)s1] | N-(4,5-dichloro-2-{[(2,5-dimethyl-3-thienyl)sulfonyl]amino}phenyl)thiophene-2-sulfonamide | Method A |
| 136 | 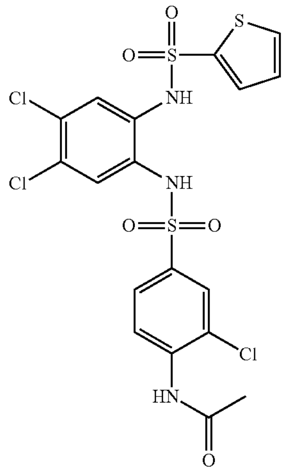 [SMILES: CC(=O)Nc1ccc(S(=O)(=O)Nc2cc(Cl)c(Cl)cc2NS(=O)(=O)c2cccs2)cc1Cl] | N-{2-chloro-4-[({4,5-dichloro-2-[(2-thienylsulfonyl)amino]phenyl}amino)sulfonyl]phenyl}acetamide | Method C |
| 137 | 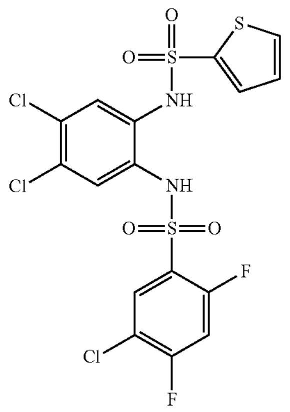 [SMILES: O=S(=O)(Nc1cc(Cl)c(Cl)cc1NS(=O)(=O)c1cc(Cl)c(F)cc1F)c1cccs1] | N-(4,5-dichloro-2-{[(5-chloro-2,4-difluorophenyl)sulfonyl]amino}phenyl)thiophene-2-sulfonamide | Method C |

TABLE 1-continued
| Comp. No. | Structure | IUPAC compound name | Synthesis |
|---|---|---|---|
| 138 | 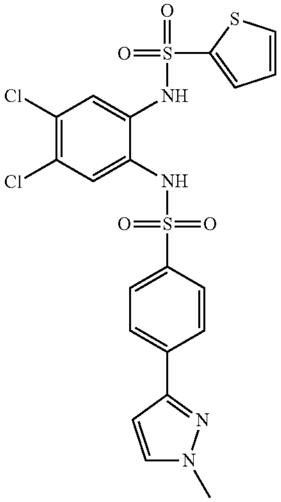 [SMILES: Cn1ccc(-c2ccc(S(=O)(=O)Nc3cc(Cl)c(Cl)cc3NS(=O)(=O)c3cccs3)cc2)n1] | N-[4,5-dichloro-2-({[4-(1-methyl-1H-pyrazol-3-yl)phenyl]sulfonyl}amino) phenyl]thiophene-2-sulfonamide | Method A |
| 139 | 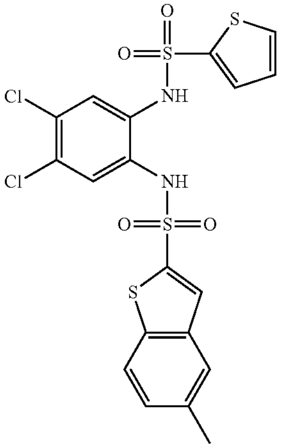 [SMILES: Cc1ccc2sc(S(=O)(=O)Nc3cc(Cl)c(Cl)cc3NS(=O)(=O)c3cccs3)cc2c1] | N-{4,5-dichloro-2-[(2-thienylsulfonyl)amino] phenyl}-5-methyl-1-benzothiophene-2-sulfonamide | Method A |
| 140 | 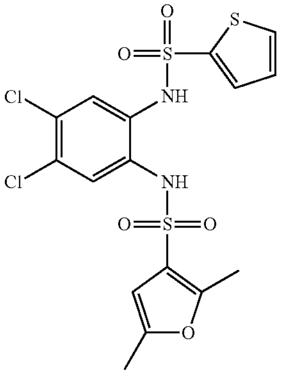 [SMILES: Cc1cc(S(=O)(=O)Nc2cc(Cl)c(Cl)cc2NS(=O)(=O)c2cccs2)c(C)o1] | N-{4,5-dichloro-2-[(2-thienylsulfonyl)amino]phenyl}-2,5-dimethylfuran-3-sulfonamide | Method A |

TABLE 1-continued
| Comp. No. | Structure | IUPAC compound name | Synthesis |
|---|---|---|---|
| 141 | 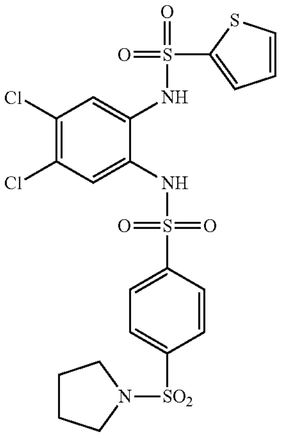 [SMILES: O=S(=O)(Nc1cc(Cl)c(Cl)cc1NS(=O)(=O)c1cccs1)c1ccc(S(=O)(=O)N2CCCC2)cc1] | N-[4,5-dichloro-2-({[4-(pyrrolidin-1-ylsulfonyl)phenyl]sulfonyl}amino)phenyl]thiophene-2-sulfonamide | Method C |
| 142 | 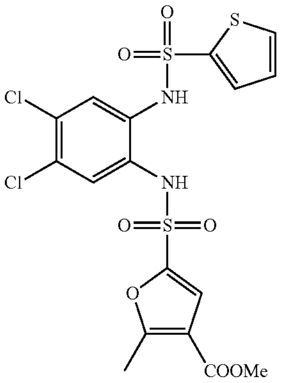 [SMILES: COC(=O)c1cc(S(=O)(=O)Nc2cc(Cl)c(Cl)cc2NS(=O)(=O)c2cccs2)oc1C] | methyl 5-[({4,5-dichloro-2-[(2-thienylsulfonyl)amino]phenyl}amino)sulfonyl]-2-methyl-3-furoate | Method C |
| 143 | 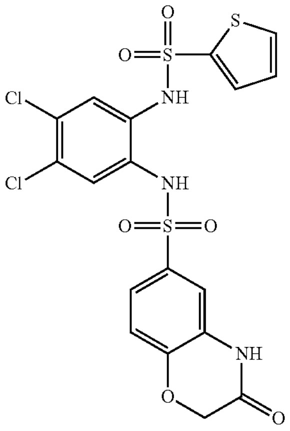 [SMILES: O=C1COc2ccc(S(=O)(=O)Nc3cc(Cl)c(Cl)cc3NS(=O)(=O)c3cccs3)cc2N1] | N-{4,5-dichloro-2-[(2-thienylsulfonyl)amino]phenyl}-3-oxo-3,4-dihydro-2H-1,4-benzoxazine-6-sulfonamide | Method A |

TABLE 1-continued
| Comp. No. | Structure | IUPAC compound name | Synthesis |
|---|---|---|---|
| 144 | 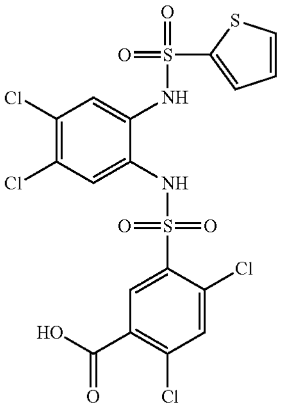 [SMILES: O=C(O)c1cc(S(=O)(=O)Nc2cc(Cl)c(Cl)cc2NS(=O)(=O)c2cccs2)c(Cl)cc1Cl] | 2,4-dichloro-5-[({4,5-dichloro-2-[(2-thienylsulfonyl)amino] phenyl}amino)sulfonyl]benzoic acid | Method B |
| 145 | 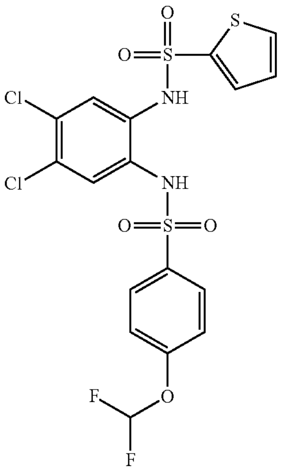 [SMILES: O=S(=O)(Nc1cc(Cl)c(Cl)cc1NS(=O)(=O)c1cccs1)c1ccc(OC(F)F)cc1] | N-[4,5-dichloro-2-({[4-(difluoromethoxy)phenyl] sulfonyl}amino)phenyl]thio-phene-2-sulfonamide | Method A |
| 146 | 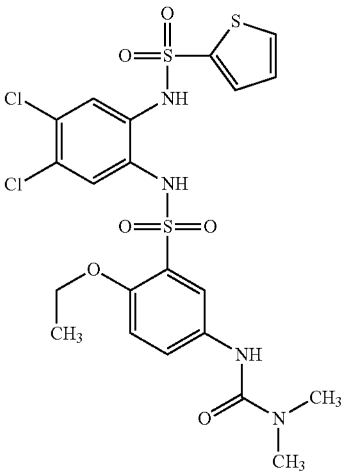 [SMILES: CCOc1ccc(NC(=O)N(C)C)cc1S(=O)(=O)Nc1cc(Cl)c(Cl)cc1NS(=O)(=O)c1cccs1] | N-(4,5-dichloro-2-{[(5-{[(dimethylamino)carbonyl] amino}-2-ethoxyphenyl)sulfonyl] amino}phenyl)thiophene-2-sulfonamide | Method A |

TABLE 1-continued

| Comp. No. | Structure | IUPAC compound name | Synthesis |
|---|---|---|---|
| 147 | 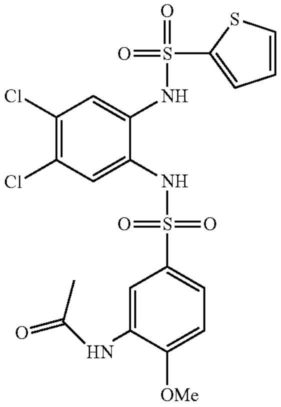 [SMILES: COc1ccc(S(=O)(=O)Nc2cc(Cl)c(Cl)cc2NS(=O)(=O)c2cccs2)cc1NC(C)=O] | N-{5-[({4,5-dichloro-2-[(2-thienylsulfonyl)amino]phenyl}amino)sulfonyl]-2-methoxyphenyl}acetamide | Method A |
| 148 | 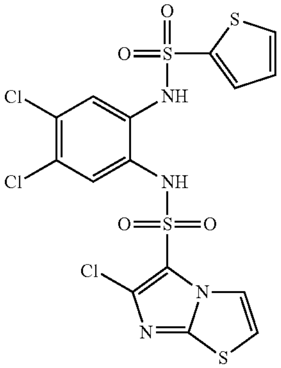 [SMILES: O=S(=O)(Nc1cc(Cl)c(Cl)cc1NS(=O)(=O)c1c(Cl)nc2sccn12)c1cccs1] | 6-chloro-N-{4,5-dichloro-2-[(2-thienylsulfonyl)amino]phenyl}imidazo[2,1-b][1,3]thiazole-5-sulfonamide | Method C |
| 149 | 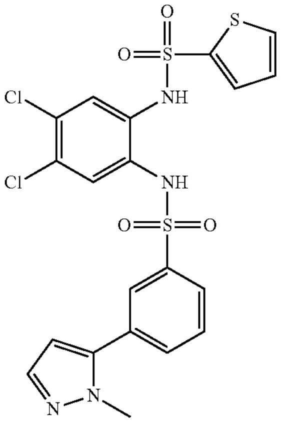 [SMILES: Cn1nccc1-c1cccc(S(=O)(=O)Nc2cc(Cl)c(Cl)cc2NS(=O)(=O)c2cccs2)c1] | N-[4,5-dichloro-2-({[3-(1-methyl-1H-pyrazol-5-yl)phenyl]sulfonyl}amino)phenyl]thiophene-2-sulfonamide | Method A |
| 150 | 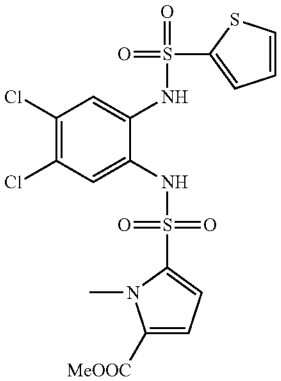 [SMILES: COC(=O)c1ccc(S(=O)(=O)Nc2cc(Cl)c(Cl)cc2NS(=O)(=O)c2cccs2)n1C] | methyl 5-[({4,5-dichloro-2-[(2-thienylsulfonyl)amino]phenyl}amino)sulfonyl]-1-methyl-1H-pyrrole-2-carboxylate | Method A |

TABLE 1-continued
| Comp. No. | Structure | IUPAC compound name | Synthesis |
|---|---|---|---|
| 151 | 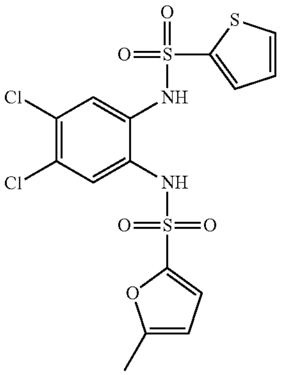 [SMILES: Cc1ccc(S(=O)(=O)Nc2cc(Cl)c(Cl)cc2NS(=O)(=O)c2cccs2)o1] | N-{4,5-dichloro-2-[(2-thienylsulfonyl)amino]phenyl}-5-methylfuran-2-sulfonamide | Method A |
| 152 | 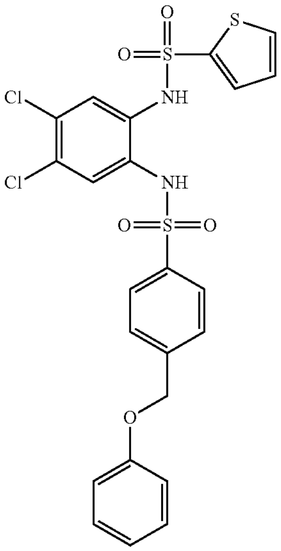 [SMILES: O=S(=O)(Nc1cc(Cl)c(Cl)cc1NS(=O)(=O)c1cccs1)c1ccc(COc2ccccc2)cc1] | N-[4,5-dichloro-2-({[4-(phenoxymethyl)phenyl]sulfonyl}amino)phenyl]thiophene-2-sulfonamide | Method A |
| 153 | 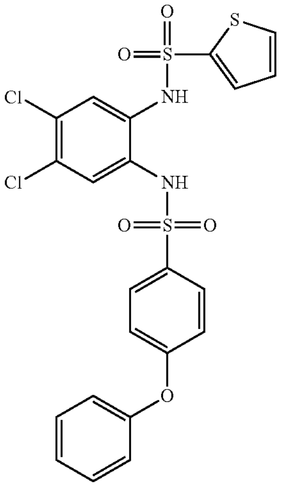 [SMILES: O=S(=O)(Nc1cc(Cl)c(Cl)cc1NS(=O)(=O)c1cccs1)c1ccc(Oc2ccccc2)cc1] | N-(4,5-dichloro-2-{[(4-phenoxyphenyl)sulfonyl]amino}phenyl)thiophene-2-sulfonamide | Method A |

TABLE 1-continued
| Comp. No. | Structure | IUPAC compound name | Synthesis |
|---|---|---|---|
| 154 | 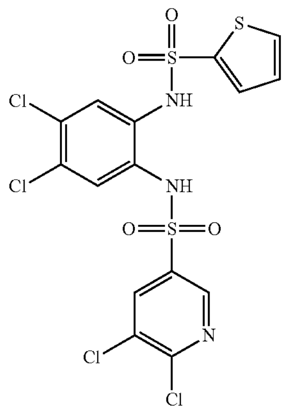 [SMILES: O=S(=O)(Nc1cc(Cl)c(Cl)cc1NS(=O)(=O)c1cccs1)c1cnc(Cl)c(Cl)c1] | 5,6-dichloro-N-{4,5-dichloro-2-[(2-thienylsulfonyl)amino]phenyl}pyridine-3-sulfonamide | Method C |
| 155 | 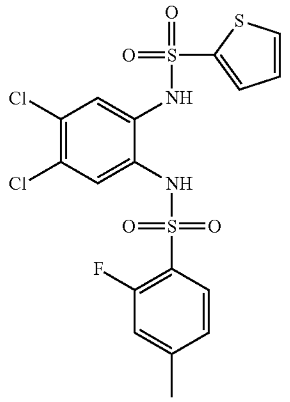 [SMILES: Cc1ccc(S(=O)(=O)Nc2cc(Cl)c(Cl)cc2NS(=O)(=O)c2cccs2)c(F)c1] | N-(4,5-dichloro-2-{[(2-fluoro-4-methylphenyl)sulfonyl]amino}phenyl)thiophene-2-sulfonamide | Method A |
| 156 | 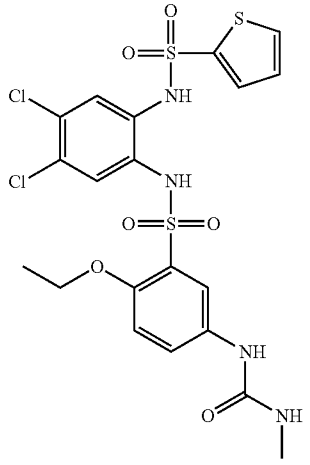 [SMILES: CCOc1ccc(NC(=O)NC)cc1S(=O)(=O)Nc1cc(Cl)c(Cl)cc1NS(=O)(=O)c1cccs1] | N-(4,5-dichloro-2-{[(2-ethoxy-5-{[(methylamino)carbonyl]amino}phenyl)sulfonyl]amino}phenyl)thiophene-2-sulfonamide | Method A |

TABLE 1-continued
| Comp. No. | Structure | IUPAC compound name | Synthesis |
|---|---|---|---|
| 157 | 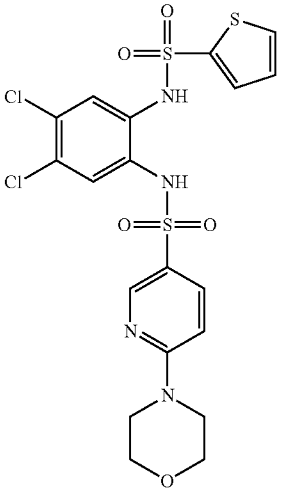 [SMILES: O=S(=O)(Nc1cc(Cl)c(Cl)cc1NS(=O)(=O)c1cccs1)c1ccc(N2CCOCC2)nc1] | N-{4,5-dichloro-2-[(2-thienylsulfonyl)amino]phenyl}-6-morpholin-4-ylpyridine-3-sulfonamide | Method A |
| 158 | 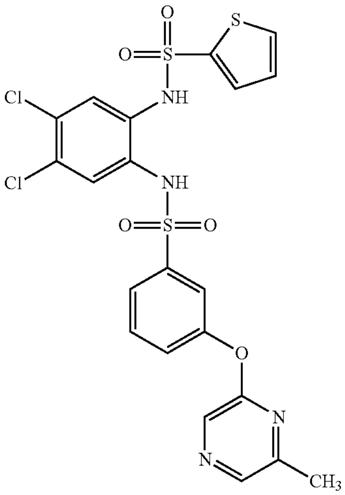 [SMILES: Cc1cncc(Oc2cccc(S(=O)(=O)Nc3cc(Cl)c(Cl)cc3NS(=O)(=O)c3cccs3)c2)n1] | N-{4,5-dichloro-2-[({3-[(6-methylpyrazin-2-yl)oxy]phenyl}sulfonyl)amino]phenyl}thiophene-2-sulfonamide | Method A |
| 159 | 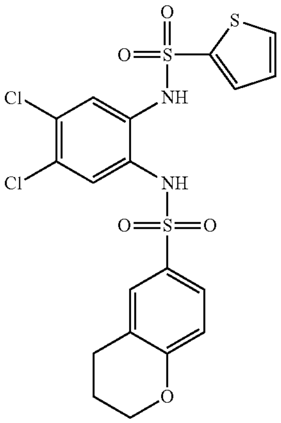 [SMILES: O=S(=O)(Nc1cc(Cl)c(Cl)cc1NS(=O)(=O)c1cccs1)c1ccc2c(c1)CCCO2] | N-{4,5-dichloro-2-[(2-thienylsulfonyl)amino]phenyl}chromane-6-sulfonamide | Method A |

TABLE 1-continued
| Comp. No. | Structure | IUPAC compound name | Synthesis |
|---|---|---|---|
| 160 | 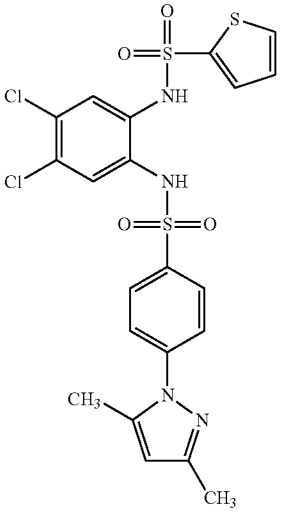 [SMILES: Cc1cc(C)n(-c2ccc(S(=O)(=O)Nc3cc(Cl)c(Cl)cc3NS(=O)(=O)c3cccs3)cc2)n1] | N-[4,5-dichloro-2-({[4-(3,5-dimethyl-1H-pyrazol-1-yl)phenyl]sulfonyl}amino) phenyl]thiophene-2-sulfonamide | Method A |
| 161 | 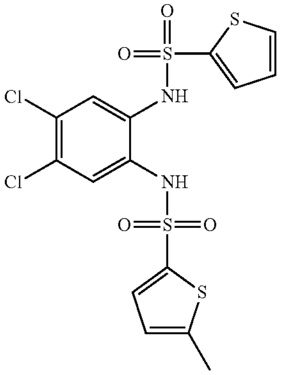 [SMILES: Cc1ccc(S(=O)(=O)Nc2cc(Cl)c(Cl)cc2NS(=O)(=O)c2cccs2)s1] | N-{4,5-dichloro-2-[(2-thienylsulfonyl)amino] phenyl}-5-methylthiophene-2-sulfonamide | Method A |
| 162 | 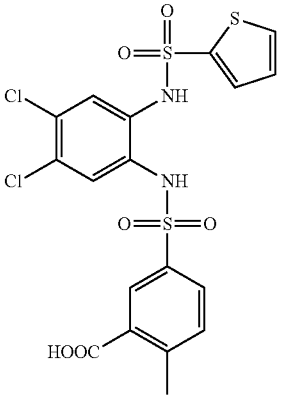 [SMILES: Cc1ccc(S(=O)(=O)Nc2cc(Cl)c(Cl)cc2NS(=O)(=O)c2cccs2)cc1C(=O)O] | N-[({4,5-dichloro-2-[(2-thienylsulfonyl)amino]phenyl} amino)sulfonyl]-2-hydroxybenzoic acid | Method B |

TABLE 1-continued
| Comp. No. | Structure | IUPAC compound name | Synthesis |
|---|---|---|---|
| 163 | 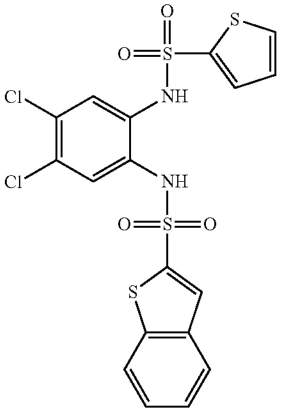 [SMILES: O=S(=O)(Nc1cc(Cl)c(Cl)cc1NS(=O)(=O)c1cc2ccccc2s1)c1cccs1] | N-{4,5-dichloro-2-[(2-thienylsulfonyl)amino]phenyl}-1-benzothiophene-2-sulfonamide | Method C |
| 164 | 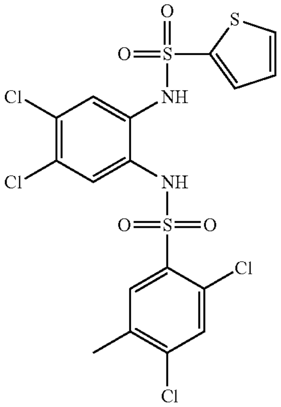 [SMILES: Cc1cc(S(=O)(=O)Nc2cc(Cl)c(Cl)cc2NS(=O)(=O)c2cccs2)c(Cl)cc1Cl] | N-(4,5-dichloro-2-{[(2,4-dichloro-5-methylphenyl)sulfonyl]amino}phenyl)thiophene-2-sulfonamide | Method A |
| 165 | 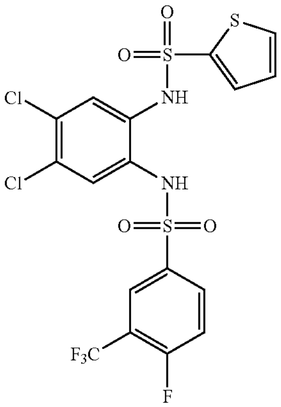 [SMILES: O=S(=O)(Nc1cc(Cl)c(Cl)cc1NS(=O)(=O)c1cccs1)c1ccc(F)c(C(F)(F)F)c1] | N-[4,5-dichloro-2-({[4-fluoro-3-(trifluoromethyl)phenyl]sulfonyl}amino)phenyl]thiophene-2-sulfonamide | Method C |

TABLE 1-continued
| Comp. No. | Structure | IUPAC compound name | Synthesis |
| --- | --- | --- | --- |
| 166 | 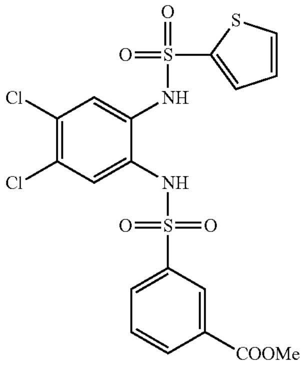 [SMILES: COC(=O)c1cccc(S(=O)(=O)Nc2cc(Cl)c(Cl)cc2NS(=O)(=O)c2cccs2)c1] | methyl 3-[({4,5-dichloro-2-[(2-thienylsulfonyl)amino] phenyl}amino)sulfonyl] benzoate | Method C |
| 167 | 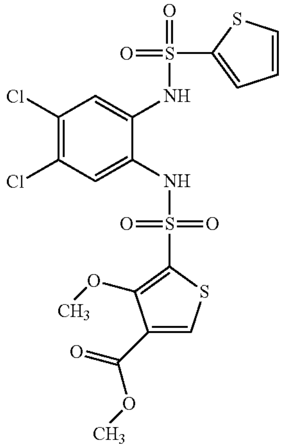 [SMILES: COC(=O)c1csc(S(=O)(=O)Nc2cc(Cl)c(Cl)cc2NS(=O)(=O)c2cccs2)c1OC] | methyl 5-[({4,5-dichloro-2-[(2-thienylsulfonyl)amino] phenyl}amino)sulfonyl]-4-methoxythiophene-3-carboxylate | Method C |
| 168 | 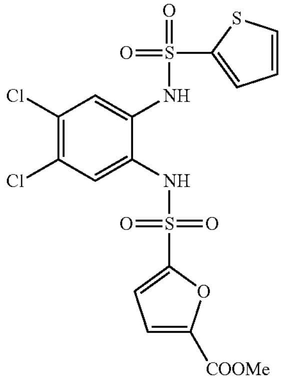 [SMILES: COC(=O)c1ccc(S(=O)(=O)Nc2cc(Cl)c(Cl)cc2NS(=O)(=O)c2cccs2)o1] | methyl 5-[({4,5-dichloro-2-[(2-thienylsulfonyl)amino]phenyl}amino)sulfonyl]-2-furoate | Method C |

TABLE 1-continued
| Comp. No. | Structure | IUPAC compound name | Synthesis |
|---|---|---|---|
| 169 | 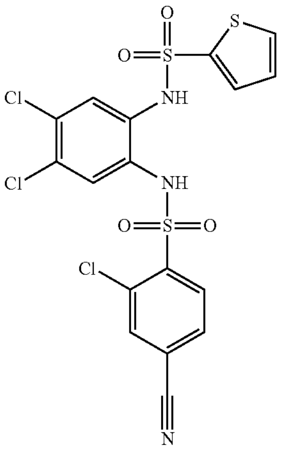 [SMILES: N#Cc1ccc(S(=O)(=O)Nc2cc(Cl)c(Cl)cc2NS(=O)(=O)c2cccs2)c(Cl)c1] | N-(4,5-dichloro-2-{[(2-chloro-4-cyanophenyl)sulfonyl]amino}phenyl)thiophene-2-sulfonamide | Method C |
| 170 | 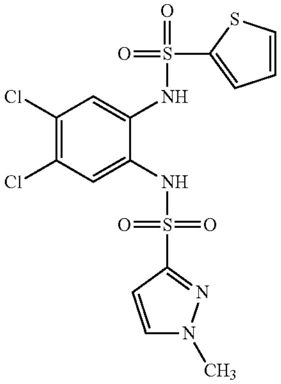 [SMILES: Cn1ccc(S(=O)(=O)Nc2cc(Cl)c(Cl)cc2NS(=O)(=O)c2cccs2)n1] | N-{4,5-dichloro-2-[(2-thienylsulfonyl)amino]phenyl}-1-methyl-1H-pyrazole-3-sulfonamide | Method A |
| 171 | 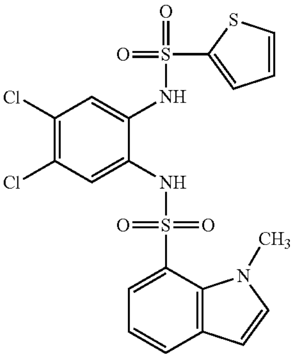 [SMILES: Cn1ccc2cccc(S(=O)(=O)Nc3cc(Cl)c(Cl)cc3NS(=O)(=O)c3cccs3)c21] | N-{4,5-dichloro-2-[(2-thienylsulfonyl)amino]phenyl}-1-methyl-1H-indole-7-sulfonamide | Method A |

TABLE 1-continued
| Comp. No. | Structure | IUPAC compound name | Synthesis |
|---|---|---|---|
| 172 | 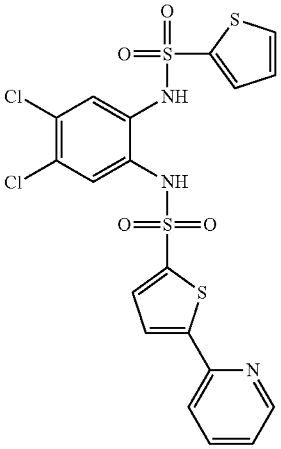 [SMILES: O=S(=O)(Nc1cc(Cl)c(Cl)cc1NS(=O)(=O)c1ccc(-c2ccccn2)s1)c1cccs1] | N-{4,5-dichloro-2-[(2-thienylsulfonyl)amino]phenyl}-5-pyridin-2-ylthiophene-2-sulfonamide | Method A |
| 173 | 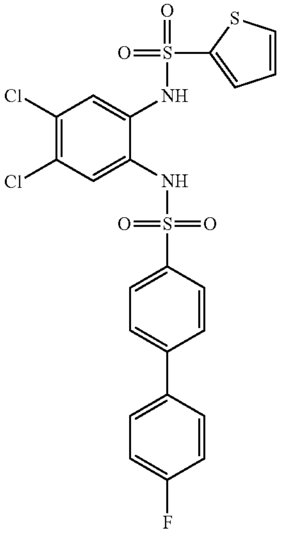 [SMILES: O=S(=O)(Nc1cc(Cl)c(Cl)cc1NS(=O)(=O)c1cccs1)c1ccc(-c2ccc(F)cc2)cc1] | N-(4,5-dichloro-2-{[(4'-fluorobiphenyl-4-yl)sulfonyl]amino}phenyl)thiophene-2-sulfonamide | Method A |
| 174 | 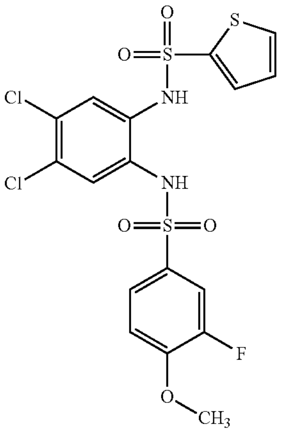 [SMILES: COc1ccc(S(=O)(=O)Nc2cc(Cl)c(Cl)cc2NS(=O)(=O)c2cccs2)cc1F] | N-(4,5-dichloro-2-{[(3-fluoro-4-methoxyphenyl)sulfonyl]amino}phenyl)thiophene-2-sulfonamide | Method A |

TABLE 1-continued
| Comp. No. | Structure | IUPAC compound name | Synthesis |
|---|---|---|---|
| 175 | 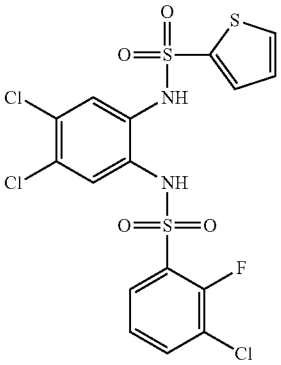 [SMILES: O=S(=O)(Nc1cc(Cl)c(Cl)cc1NS(=O)(=O)c1cccc(Cl)c1F)c1cccs1] | N-(4,5-dichloro-2-{[(3-chloro-2-fluorophenyl)sulfonyl]amino}phenyl)thiophene-2-sulfonamide | Method C |
| 176 | 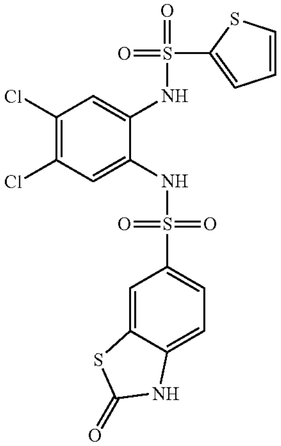 [SMILES: O=c1[nH]c2ccc(S(=O)(=O)Nc3cc(Cl)c(Cl)cc3NS(=O)(=O)c3cccs3)cc2s1] | N-{4,5-dichloro-2-[(2-thienylsulfonyl)amino]phenyl}-2-oxo-2,3-dihydro-1,3-benzothiazole-6-sulfonamide | Method A |
| 177 | 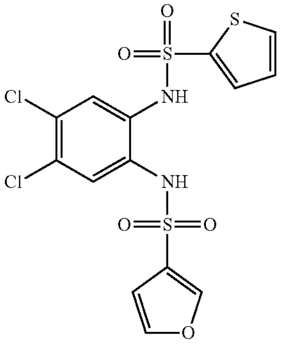 [SMILES: O=S(=O)(Nc1cc(Cl)c(Cl)cc1NS(=O)(=O)c1cccs1)c1ccoc1] | N-{4,5-dichloro-2-[(2-thienylsulfonyl)amino]phenyl}furan-3-sulfonamide | Method A |

TABLE 1-continued
| Comp. No. | Structure | IUPAC compound name | Synthesis |
|---|---|---|---|
| 178 | 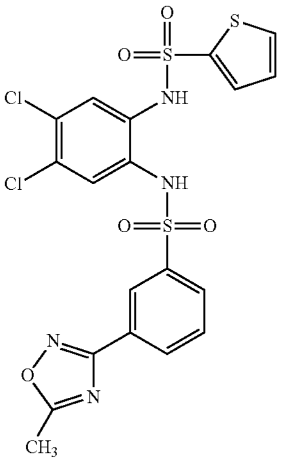 [SMILES: Cc1nc(-c2cccc(S(=O)(=O)Nc3cc(Cl)c(Cl)cc3NS(=O)(=O)c3cccs3)c2)no1] | N-[4,5-dichloro-2-({[3-(5-methyl-1,2,4-oxadiazol-3-yl)phenyl]sulfonyl}amino) phenyl]thiophene-2-sulfonamide | Method A |
| 179 | 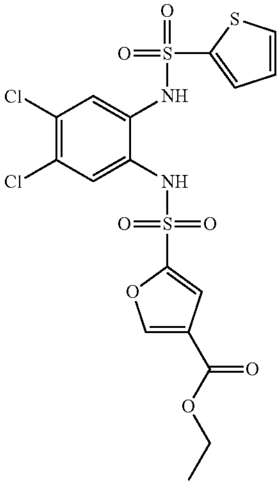 [SMILES: CCOC(=O)c1coc(S(=O)(=O)Nc2cc(Cl)c(Cl)cc2NS(=O)(=O)c2cccs2)c1] | ethyl 5-[({4,5-dichloro-2-[(2-thienylsulfonyl)amino)phenyl} amino)sulfonyl]-3-furoate | Method C |
| 180 | 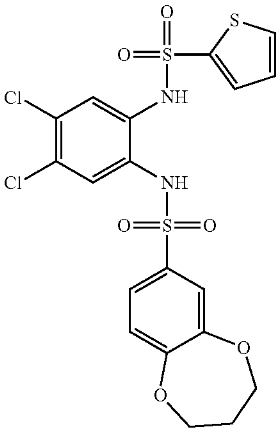 [SMILES: O=S(=O)(Nc1cc(Cl)c(Cl)cc1NS(=O)(=O)c1cccs1)c1ccc2c(c1)OCCCO2] | N-{4,5-dichloro-2-[(2-thienylsulfonyl)amino]phenyl)-3,4-dihydro-2H-1,5-benzodioxepine-7-sulfonamide | Method A |

TABLE 1-continued
| Comp. No. | Structure | IUPAC compound name | Synthesis |
| --- | --- | --- | --- |
| 181 | 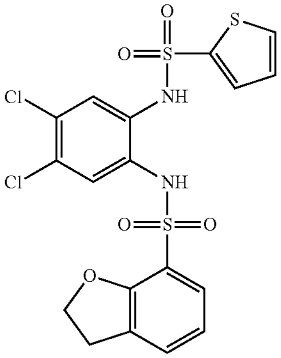 [SMILES: O=S(=O)(Nc1cc(Cl)c(Cl)cc1NS(=O)(=O)c1cccc2c1OCC2)c1cccs1] | N-{4,5-dichloro-2-[(2-thienylsulfonyl)amino]phenyl}-2,3-dihydro-1-benzofuran-7-sulfonamide | Method A |
| 182 | 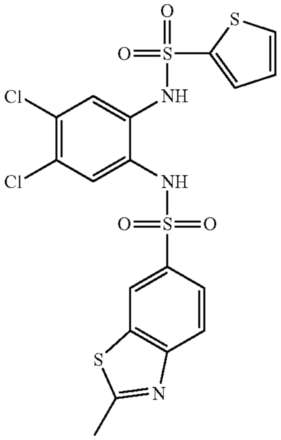 [SMILES: Cc1nc2ccc(S(=O)(=O)Nc3cc(Cl)c(Cl)cc3NS(=O)(=O)c3cccs3)cc2s1] | N-{4,5-dichloro-2-[(2-thienylsulfonyl)amino]phenyl}-2-methyl-1,3-benzothiophene-6-sulfonamide | Method A |
| 183 | 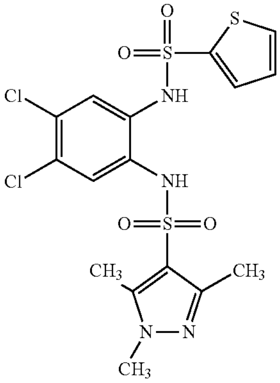 [SMILES: Cc1nn(C)c(C)c1S(=O)(=O)Nc1cc(Cl)c(Cl)cc1NS(=O)(=O)c1cccs1] | N-{4,5-dichloro-2-[(2-thienylsulfonyl)amino]phenyl}-1,3,5-trimethyl-1H-pyrazole-4-sulfonamide | Method A |

TABLE 1-continued
| Comp. No. | Structure | IUPAC compound name | Synthesis |
|---|---|---|---|
| 184 | 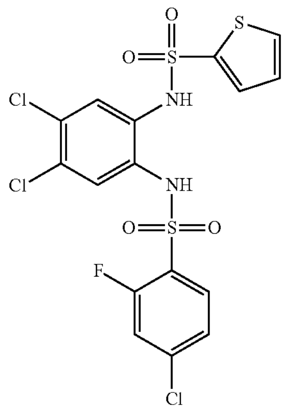 [SMILES: O=S(=O)(Nc1cc(Cl)c(Cl)cc1NS(=O)(=O)c1ccc(Cl)cc1F)c1cccs1] | N-(4,5-dichloro-2-{[(4-chloro-2-fluorophenyl)sulfonyl]amino}phenyl)thiophene-2-sulfonamide | Method C |
| 185 | 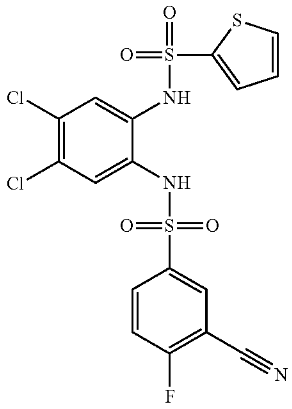 [SMILES: N#Cc1cc(S(=O)(=O)Nc2cc(Cl)c(Cl)cc2NS(=O)(=O)c2cccs2)ccc1F] | N-(4,5-dichloro-2-{[(3-cyano-4-fluorophenyl)sulfonyl]amino}phenyl)thiophene-2-sulfonamide | Method C |
| 186 | 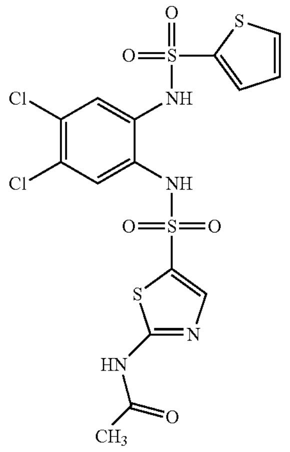 [SMILES: CC(=O)Nc1ncc(S(=O)(=O)Nc2cc(Cl)c(Cl)cc2NS(=O)(=O)c2cccs2)s1] | N-{5-[({4,5-dichloro-2-[(2-thienylsulfonyl)amino]phenyl}amino)sulfonyl]-1,3-thiazol-2-yl}acetamide | Method A |

TABLE 1-continued
| Comp. No. | Structure | IUPAC compound name | Synthesis |
|---|---|---|---|
| 187 | 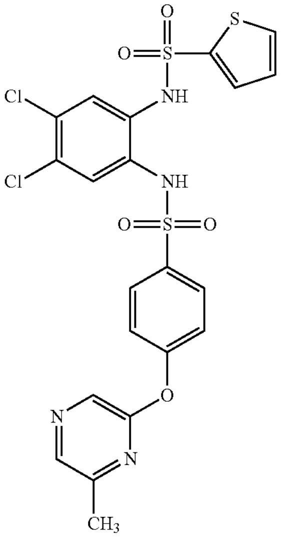 [SMILES: Cc1cncc(Oc2ccc(S(=O)(=O)Nc3cc(Cl)c(Cl)cc3NS(=O)(=O)c3cccs3)cc2)n1] | N-{4,5-dichloro-2-[({4-[(6-methylpyrazin-2-yl)oxy]phenyl}sulfonyl) amino]phenyl}thiophene-2-sulfonamide | Method A |
| 188 | 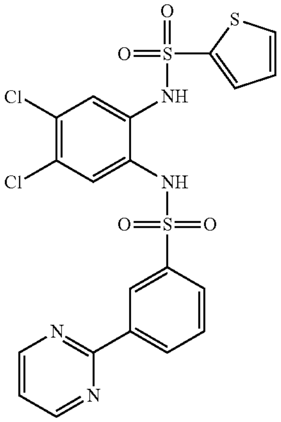 [SMILES: O=S(=O)(Nc1cc(Cl)c(Cl)cc1NS(=O)(=O)c1cccs1)c1cccc(-c2ncccn2)c1] | N-(4,5-dichloro-2-{[(3-pyrimidin-2-ylphenyl)sulfonyl]amino} phenyl)thiophene-2-sulfonamide | Method A |
| 189 | 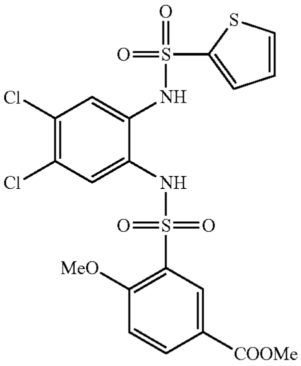 [SMILES: COC(=O)c1ccc(OC)c(S(=O)(=O)Nc2cc(Cl)c(Cl)cc2NS(=O)(=O)c2cccs2)c1] | methyl 3-[({4,5-dichloro-2-[(2-thienylsulfonyl)amino]phenyl} amino)sulfonyl]-4-methoxybenzoate | Method A |

TABLE 1-continued

| Comp. No. | Structure | IUPAC compound name | Synthesis |
|---|---|---|---|
| 190 | 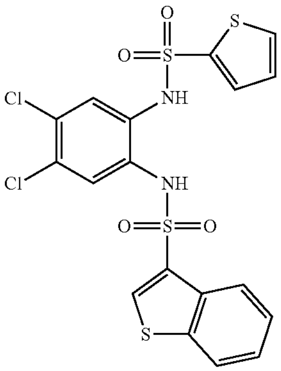 [SMILES: O=S(=O)(Nc1cc(Cl)c(Cl)cc1NS(=O)(=O)c1csc2ccccc12)c1cccs1] | N-{4,5-dichloro-2-[(2-thienylsulfonyl)amino]phenyl}-1-benzothiophene-3-sulfonamide | Method A |
| 191 | 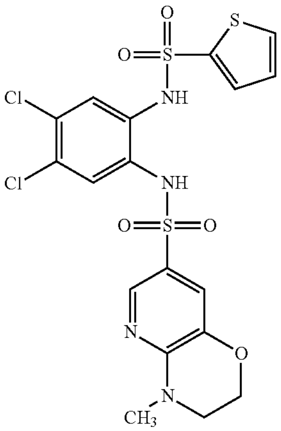 [SMILES: CN1CCOc2cc(S(=O)(=O)Nc3cc(Cl)c(Cl)cc3NS(=O)(=O)c3cccs3)cnc21] | N-{4,5-dichloro-2-[(2-thienylsulfonyl)amino]phenyl}-4-methyl-3,4-dihydro-2H-pyrido[3,2-b][1,4]oxazine-7-sulfonamide | Method A |
| 192 | 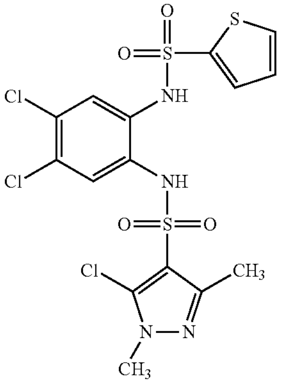 [SMILES: Cc1nn(C)c(Cl)c1S(=O)(=O)Nc1cc(Cl)c(Cl)cc1NS(=O)(=O)c1cccs1] | 5-chloro-N-{4,5-dichloro-2-[(2-thienylsulfonyl)amino]phenyl}-1,3-dimethyl-1H-pyrazole-4-sulfonamide | Method A |
| 193 | 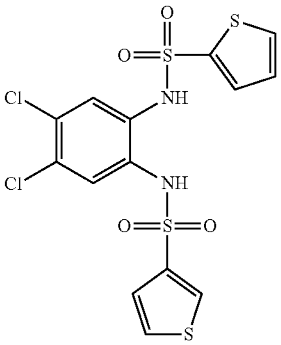 [SMILES: O=S(=O)(Nc1cc(Cl)c(Cl)cc1NS(=O)(=O)c1cccs1)c1ccsc1] | N-{4,5-dichloro-2-[(3-thienylsulfonyl)amino]phenyl}thiophene-2-sulfonamide | Method A |

TABLE 1-continued
| Comp. No. | Structure | IUPAC compound name | Synthesis |
|---|---|---|---|
| 194 | 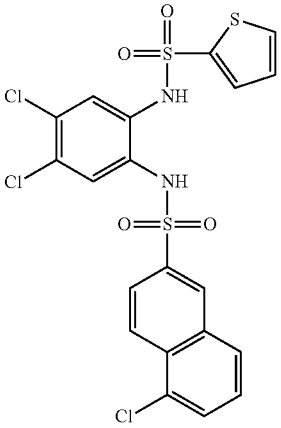 [SMILES: O=S(=O)(Nc1cc(Cl)c(Cl)cc1NS(=O)(=O)c1cccs1)c1ccc2c(Cl)cccc2c1] | N-(4,5-dichloro-2-{[(5-chloro-2-naphthyl)sulfonyl]amino}phenyl)thiophene-2-sulfonamide | Method A |
| 195 | 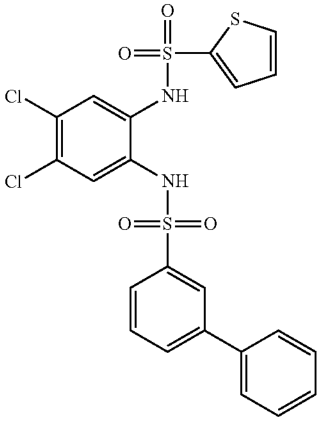 [SMILES: O=S(=O)(Nc1cc(Cl)c(Cl)cc1NS(=O)(=O)c1cccs1)c1cccc(-c2ccccc2)c1] | N-{2-[(biphenyl-3-ylsulfonyl)amino]-4,5-dichlorophenyl}thiophene-2-sulfonamide | Method A |
| 196 | 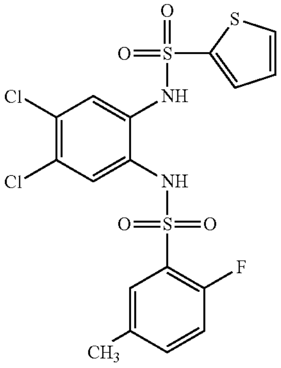 [SMILES: Cc1ccc(F)c(S(=O)(=O)Nc2cc(Cl)c(Cl)cc2NS(=O)(=O)c2cccs2)c1] | N-(4,5-dichloro-2-{[(2-fluoro-5-methylphenyl)sulfonyl]amino}phenyl)thiophene-2-sulfonamide | Method A |

TABLE 1-continued
| Comp. No. | Structure | IUPAC compound name | Synthesis |
|---|---|---|---|
| 197 | 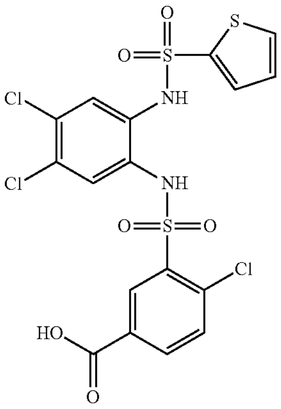 [SMILES: O=C(O)c1ccc(Cl)c(S(=O)(=O)Nc2cc(Cl)c(Cl)cc2NS(=O)(=O)c2cccs2)c1] | 4-chloro-3-[({4,5-dichloro-2-[(2-thienylsulfonyl)amino] phenyl}amino)sulfonyl]benzoic acid | Method A |
| 198 | 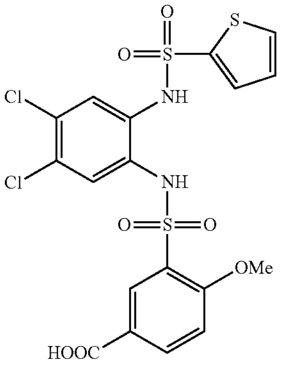 [SMILES: COc1ccc(C(=O)O)cc1S(=O)(=O)Nc1cc(Cl)c(Cl)cc1NS(=O)(=O)c1cccs1] | 3-[({4,5-dichloro-2-[(2-thienylsulfonyl)amino]phenyl} amino)sulfonyl]-4-methoxybenzoic acid | Method B |
| 199 | 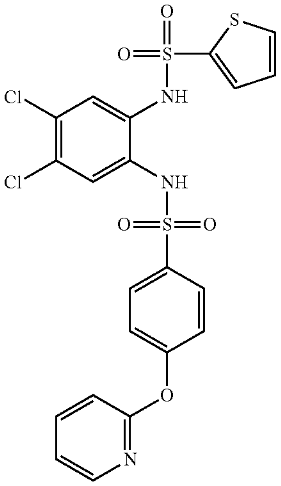 [SMILES: O=S(=O)(Nc1cc(Cl)c(Cl)cc1NS(=O)(=O)c1cccs1)c1ccc(Oc2ccccn2)cc1] | N-[4,5-dichloro-2-({[4-(pyridin-2-yloxy)phenyl]sulfonyl}amino) phenyl]thiophene-2-sulfonamide | Method C |

TABLE 1-continued
| Comp. No. | Structure | IUPAC compound name | Synthesis |
|---|---|---|---|
| 200 | 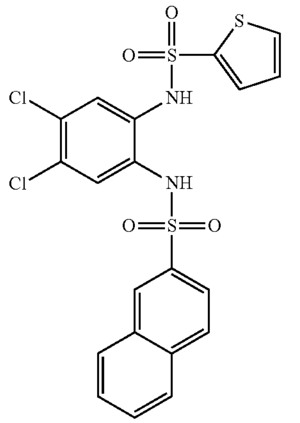 [SMILES: O=S(=O)(Nc1cc(Cl)c(Cl)cc1NS(=O)(=O)c1cccs1)c1ccc2ccccc2c1] | N-{4,5-dichloro-2-[(2-naphthylsulfonyl)amino]phenyl}thiophene-2-sulfonamide | Method C |
| 201 | 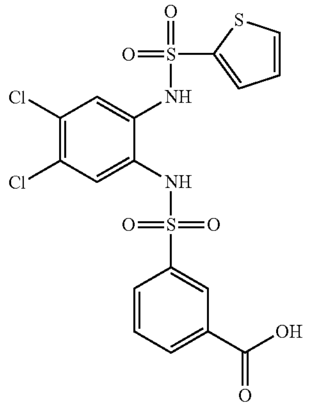 [SMILES: O=C(O)c1cccc(S(=O)(=O)Nc2cc(Cl)c(Cl)cc2NS(=O)(=O)c2cccs2)c1] | 3-[({4,5-dichloro-2-[(2-thienylsulfonyl)amino]phenyl}amino)sulfonyl]benzoic acid | Method B |
| 202 | 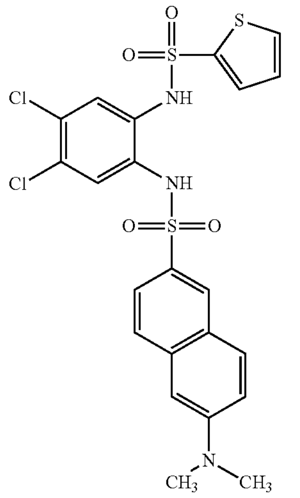 [SMILES: CN(C)c1ccc2cc(S(=O)(=O)Nc3cc(Cl)c(Cl)cc3NS(=O)(=O)c3cccs3)ccc2c1] | N-[4,5-dichloro-2-({[6-(dimethylamino)-2-naphthyl]sulfonyl}amino)phenyl]thiophene-2-sulfonamide | Method A |

TABLE 1-continued
| Comp. No. | Structure | IUPAC compound name | Synthesis |
|---|---|---|---|
| 203 | 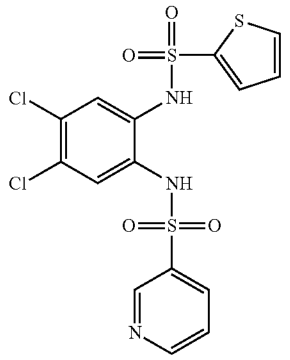 [SMILES: O=S(=O)(Nc1cc(Cl)c(Cl)cc1NS(=O)(=O)c1cccs1)c1cccnc1] | N-{4,5-dichloro-2-[(2-thienylsulfonyl)amino]phenyl}pyridine-3-sulfonamide | Method A |
| 204 | 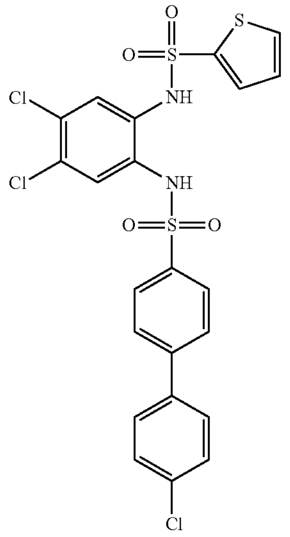 [SMILES: O=S(=O)(Nc1cc(Cl)c(Cl)cc1NS(=O)(=O)c1cccs1)c1ccc(-c2ccc(Cl)cc2)cc1] | N-(4,5-dichloro-2-{[(4'-chlorobiphenyl-4-yl)sulfonyl]amino}phenyl)thiophene-2-sulfonamide | Method A |
| 205 | 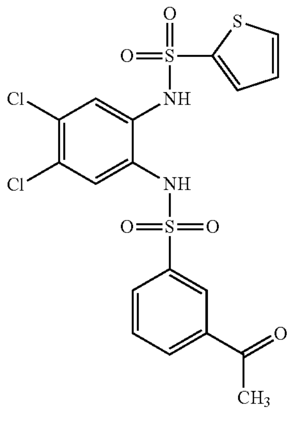 [SMILES: CC(=O)c1cccc(S(=O)(=O)Nc2cc(Cl)c(Cl)cc2NS(=O)(=O)c2cccs2)c1] | N-(2-{[(3-acetylphenyl)sulfonyl]amino}-4,5-dichlorophenyl)thiophene-2-sulfonamide | Method A |

TABLE 1-continued
| Comp. No. | Structure | IUPAC compound name | Synthesis |
|---|---|---|---|
| 206 | 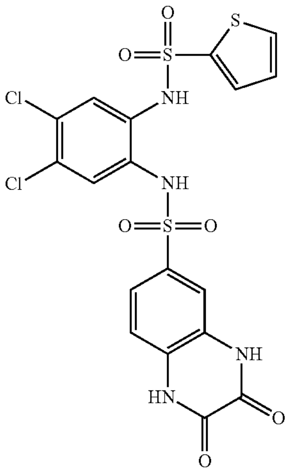 [SMILES: O=c1[nH]c2ccc(S(=O)(=O)Nc3cc(Cl)c(Cl)cc3NS(=O)(=O)c3cccs3)cc2[nH]c1=O] | N-{4,5-dichloro-2-[(2-thienylsulfonyl)amino]phenyl}-2,3-dioxo-1,2,3,4-tetrahydroquinoxaline-6-sulfonamide | Method A |
| 207 | 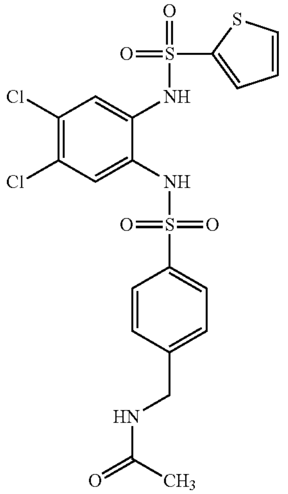 [SMILES: CC(=O)NCc1ccc(S(=O)(=O)Nc2cc(Cl)c(Cl)cc2NS(=O)(=O)c2cccs2)cc1] | N-{4-[({4,5-dichloro-2-[(2-thienylsulfonyl)amino]phenyl}amino)sulfonyl]benzyl}acetamide | Method A |
| 208 | 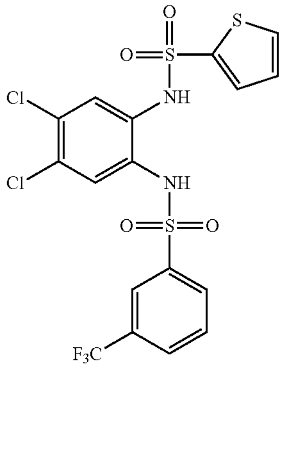 [SMILES: O=S(=O)(Nc1cc(Cl)c(Cl)cc1NS(=O)(=O)c1cccs1)c1cccc(C(F)(F)F)c1] | N-[4,5-dichloro-2-({[3-(trifluoromethyl)phenyl]sulfonyl}amino)phenyl]thiophene-2-sulfonamide | Method C |

TABLE 1-continued
| Comp. No. | Structure | IUPAC compound name | Synthesis |
|---|---|---|---|
| 209 | 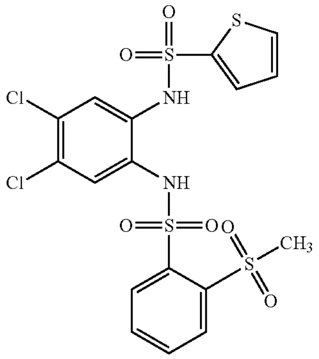 [SMILES: CS(=O)(=O)c1ccccc1S(=O)(=O)Nc1cc(Cl)c(Cl)cc1NS(=O)(=O)c1cccs1] | N-[4,5-dichloro-2-({[2-(methylsulfonyl)phenyl]sulfonyl}amino)phenyl]thiophene-2-sulfonamide | Method E |
| 210 | 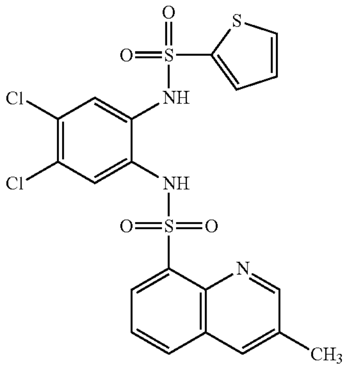 [SMILES: Cc1cnc2c(S(=O)(=O)Nc3cc(Cl)c(Cl)cc3NS(=O)(=O)c3cccs3)cccc2c1] | N-{4,5-dichloro-2-[(2-thienylsulfonyl)amino]phenyl}-3-methylquinoline-8-sulfonamide | Method A |
| 211 | 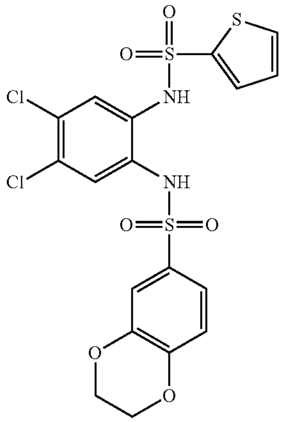 [SMILES: O=S(=O)(Nc1cc(Cl)c(Cl)cc1NS(=O)(=O)c1cccs1)c1ccc2c(c1)OCCO2] | N-{4,5-dichloro-2-[(2-thienylsulfonyl)amino]phenyl}-2,3-dihydro-1,4-benzodioxine-6-sulfonamide | Method A |

TABLE 1-continued
| Comp. No. | Structure | IUPAC compound name | Synthesis |
|---|---|---|---|
| 212 | 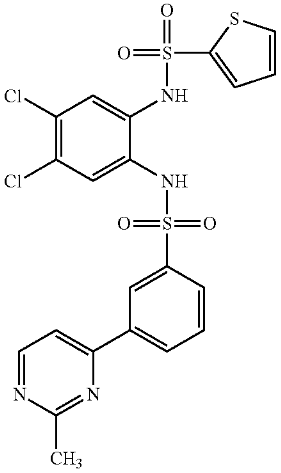 [SMILES: Cc1nccc(-c2cccc(S(=O)(=O)Nc3cc(Cl)c(Cl)cc3NS(=O)(=O)c3cccs3)c2)n1] | N-[4,5-dichloro-2-({[3-(2-methylpyrimidin-4-yl)phenyl]sulfonyl}amino) phenyl]thiophene-2-sulfonamide | Method A |
| 213 | 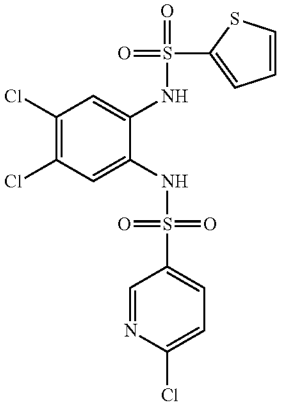 [SMILES: O=S(=O)(Nc1cc(Cl)c(Cl)cc1NS(=O)(=O)c1cccs1)c1ccc(Cl)nc1] | 6-chloro-N-{4,5-dichloro-2-[(2-thienylsulfonyl)amino] phenyl)pyridine-3-sulfonamide | Method C |
| 214 | 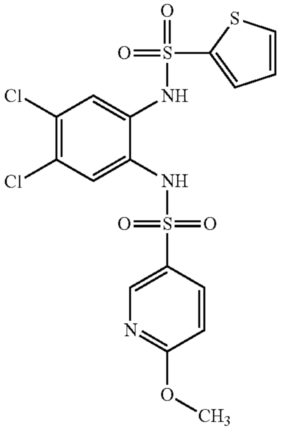 [SMILES: COc1ccc(S(=O)(=O)Nc2cc(Cl)c(Cl)cc2NS(=O)(=O)c2cccs2)cn1] | N-{4,5-dichloro-2-[(2-thienylsulfonyl)amino] phenyl}-6-methoxypyridine-3-sulfonamide | Method A |

TABLE 1-continued
| Comp. No. | Structure | IUPAC compound name | Synthesis |
|---|---|---|---|
| 215 | 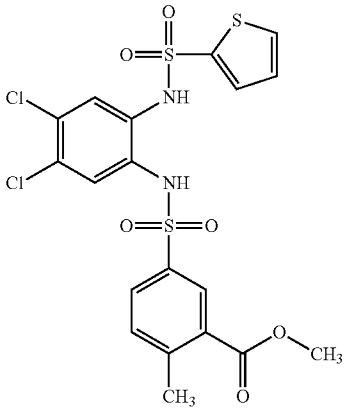 [SMILES: COC(=O)c1cc(S(=O)(=O)Nc2cc(Cl)c(Cl)cc2NS(=O)(=O)c2cccs2)ccc1C] | methyl 5-[({4,5-dichloro-2-[(2-thienylsulfonyl)amino]phenyl}amino)sulfonyl]-2-methylbenzoate | Method A |
| 216 | 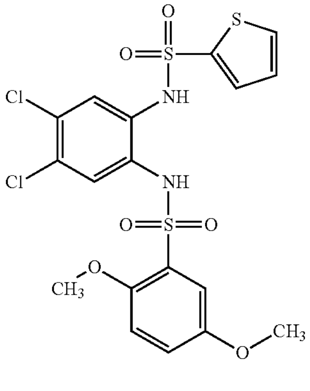 [SMILES: COc1ccc(OC)c(S(=O)(=O)Nc2cc(Cl)c(Cl)cc2NS(=O)(=O)c2cccs2)c1] | N-(4,5-dichloro-2-{[(2,5-dimethoxyphenyl)sulfonyl]amino}phenyl)thiophene-2-sulfonamide | Method A |
| 217 | 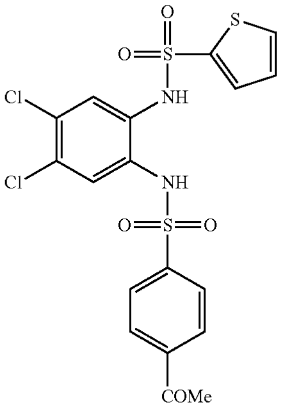 | N-(2-{[(4-acetylphenyl)sulfonyl]amino}-4,5-dichlorophenyl)thiophene-2-sulfonamide | Method A |

TABLE 1-continued
| Comp. No. | Structure | IUPAC compound name | Synthesis |
|---|---|---|---|
| 218 | 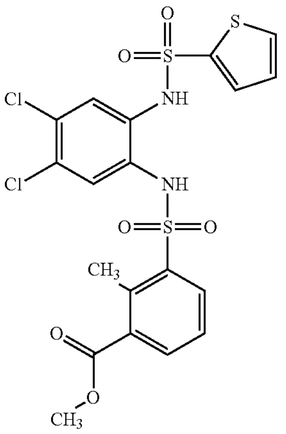 [SMILES: COC(=O)c1cccc(S(=O)(=O)Nc2cc(Cl)c(Cl)cc2NS(=O)(=O)c2cccs2)c1C] | methyl 3-[({4,5-dichloro-2-[(2-thienylsulfonyl)amino]phenyl}amino)sulfonyl]-2-methylbenzoate | Method A |
| 219 | 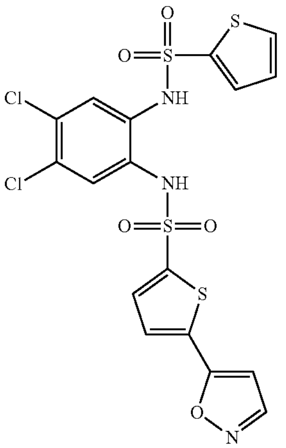 [SMILES: O=S(=O)(Nc1cc(Cl)c(Cl)cc1NS(=O)(=O)c1ccc(-c2ccno2)s1)c1cccs1] | N-{4,5-dichloro-2-[(2-thienylsulfonyl)amino]phenyl}-5-isoxazol-5-ylthiophene-2-sulfonamide | Method C |
| 220 | 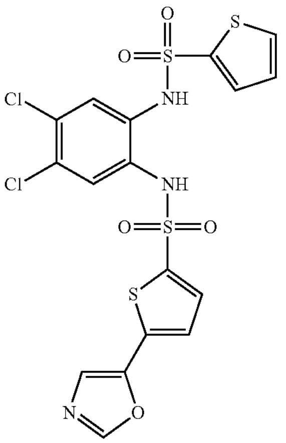 [SMILES: O=S(=O)(Nc1cc(Cl)c(Cl)cc1NS(=O)(=O)c1ccc(-c2cnco2)s1)c1cccs1] | N-{4,5-dichloro-2-[(2-thienylsulfonyl)amino]phenyl}-5-(1,3-oxazol-5-yl)thiophene-2-sulfonamide | Method C |

TABLE 1-continued

| Comp. No. | Structure | IUPAC compound name | Synthesis |
|---|---|---|---|
| 221 | 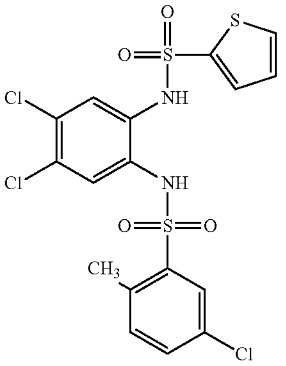 [SMILES: Cc1ccc(Cl)cc1S(=O)(=O)Nc1cc(Cl)c(Cl)cc1NS(=O)(=O)c1cccs1] | N-{4,5-dichloro-2-{[(5-chloro-2-methylphenyl)sulfonyl]amino}phenyl)thiophene-2-sulfonamide | Method A |
| 222 | 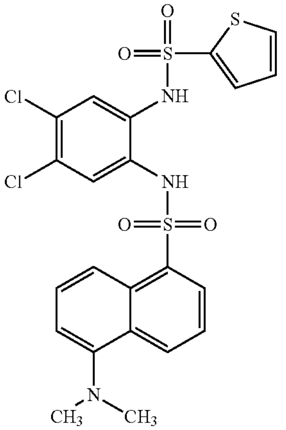 [SMILES: CN(C)c1cccc2c(S(=O)(=O)Nc3cc(Cl)c(Cl)cc3NS(=O)(=O)c3cccs3)cccc12] | N-[4,5-dichloro-2-({[5-(dimethylamino)-1-naphthyl]sulfonyl}amino)phenyl]thiophene-2-sulfonamide | Method A |
| 223 | 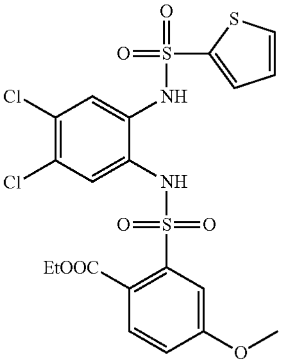 [SMILES: CCOC(=O)c1ccc(OC)cc1S(=O)(=O)Nc1cc(Cl)c(Cl)cc1NS(=O)(=O)c1cccs1] | methyl 2-[({4,5-dichloro-2-[(2-thienylsulfonyl)amino]phenyl}amino)sulfonyl]-4-methoxybenzoate | Method A |
| 224 | 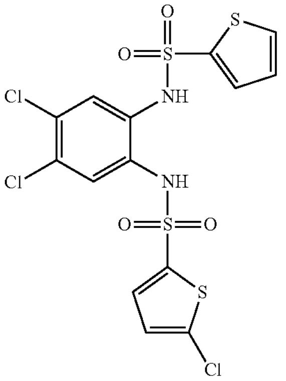 [SMILES: O=S(=O)(Nc1cc(Cl)c(Cl)cc1NS(=O)(=O)c1ccc(Cl)s1)c1cccs1] | 5-chloro-N-{4,5-dichloro-2-[(2-thienylsulfonyl)amino]phenyl}thiophene-2-sulfonamide | Method C |

TABLE 1-continued

| Comp. No. | Structure | IUPAC compound name | Synthesis |
|---|---|---|---|
| 225 | 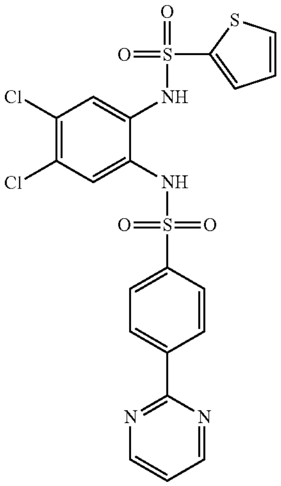 [SMILES: O=S(=O)(Nc1cc(Cl)c(Cl)cc1NS(=O)(=O)c1cccs1)c1ccc(-c2ncccn2)cc1] | N-(4,5-dihydro-2-{[(4-pyrimidin-2-ylphenyl)sulfonyl]amino}phenyl)thiophene-2-sulfonamide | Method A |
| 226 | 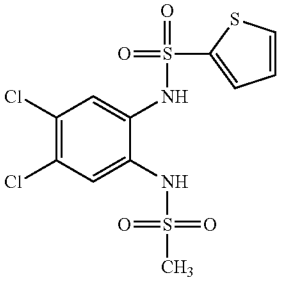 [SMILES: CS(=O)(=O)Nc1cc(Cl)c(Cl)cc1NS(=O)(=O)c1cccs1] | N-{4,5-dichloro-2-[(methylsulfonyl)amino]phenyl}thiophene-2-sulfonamide | Method E |
| 227 | 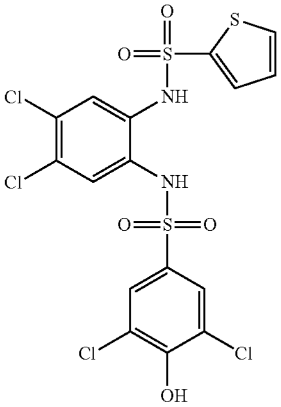 [SMILES: O=S(=O)(Nc1cc(Cl)c(Cl)cc1NS(=O)(=O)c1cccs1)c1cc(Cl)c(O)c(Cl)c1] | N-(4,5-dichloro-2-{[(3,5-dichloro-4-hydroxyphenyl)sulfonyl]amino}phenyl)thiophene-2-sulfonamide | Method A |
| 228 | 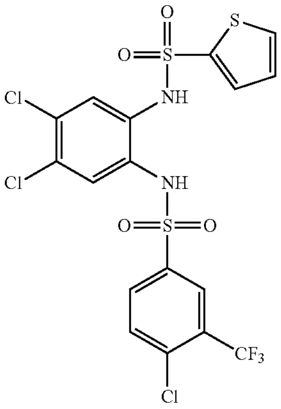 [SMILES: O=S(=O)(Nc1cc(Cl)c(Cl)cc1NS(=O)(=O)c1cccs1)c1ccc(Cl)c(C(F)(F)F)c1] | N-[4,5-dichloro-2-({[4-chloro-3-(trifluoromethyl)phenyl]sulfonyl}amino)phenyl]thiophene-2-sulfonamide | Method C |

TABLE 1-continued
| Comp. No. | Structure | IUPAC compound name | Synthesis |
|---|---|---|---|
| 229 | 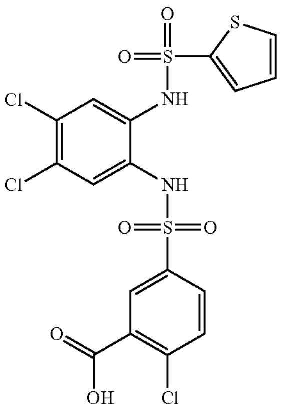 [SMILES: O=C(O)c1cc(S(=O)(=O)Nc2cc(Cl)c(Cl)cc2NS(=O)(=O)c2cccs2)ccc1Cl] | 2-chloro-5-[({4,5-dichloro-2-[(2-thienylsulfonyl)amino] phenyl}amino)sulfonyl]benzoic acid | Method B |
| 230 | 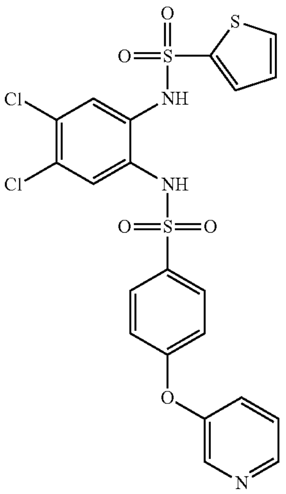 [SMILES: O=S(=O)(Nc1cc(Cl)c(Cl)cc1NS(=O)(=O)c1cccs1)c1ccc(Oc2cccnc2)cc1] | N-[4,5-dichloro-2-({[4-(pyridin-3-yloxy)phenyl]sulfonyl} amino)phenyl]thiophene-2-sulfonamide | Method C |
| 231 | 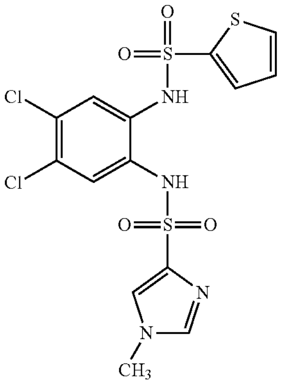 [SMILES: Cn1cnc(S(=O)(=O)Nc2cc(Cl)c(Cl)cc2NS(=O)(=O)c2cccs2)c1] | N-{4,5-dichloro-2-[(2-thienylsulfonyl)amino]phenyl}-1-methyl-1H-imidazole-4-sulfonamide | Method A |

TABLE 1-continued

| Comp. No. | Structure | IUPAC compound name | Synthesis |
|---|---|---|---|
| 232 | 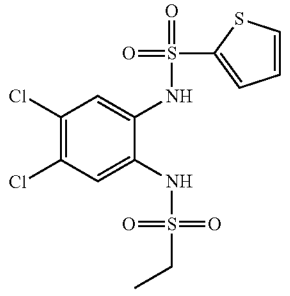 [SMILES: CCS(=O)(=O)Nc1cc(Cl)c(Cl)cc1NS(=O)(=O)c1cccs1] | N-{4,5-dichloro-2-[(ethylsulfonyl)amino]phenyl}thiophene-2-sulfonamide | Method E |
| 233 | 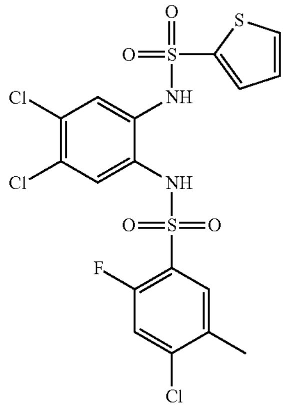 [SMILES: Cc1cc(S(=O)(=O)Nc2cc(Cl)c(Cl)cc2NS(=O)(=O)c2cccs2)c(F)cc1Cl] | N-(4,5-dichloro-2-{[(4-chloro-2-fluoro-5-methylphenyl)sulfonyl]amino}phenyl)thiophene-2-sulfonamide | Method C |
| 234 | 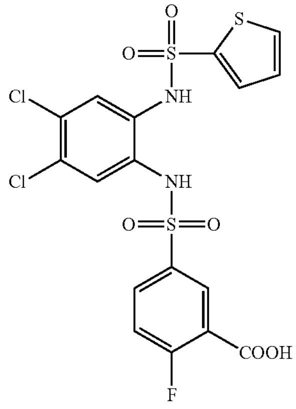 [SMILES: O=C(O)c1cc(S(=O)(=O)Nc2cc(Cl)c(Cl)cc2NS(=O)(=O)c2cccs2)ccc1F] | N-[({4,5-dichloro-2-[(2-thienylsulfonyl)amino]phenyl}amino)sulfonyl]-2-fluorobenzoic acid | Method B |
| 235 | 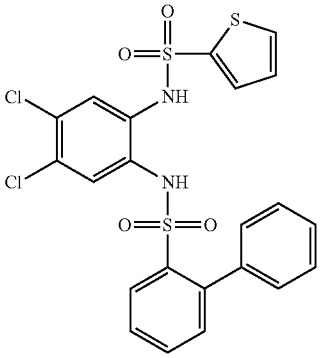 [SMILES: O=S(=O)(Nc1cc(Cl)c(Cl)cc1NS(=O)(=O)c1ccccc1-c1ccccc1)c1cccs1] | N-{2-[(biphenyl-2-ylsulfonyl)amino]-4,5-dichlorophenyl}thiophene-2-sulfonamide | Method A |

TABLE 1-continued

| Comp. No. | Structure | IUPAC compound name | Synthesis |
| --- | --- | --- | --- |
| 236 | 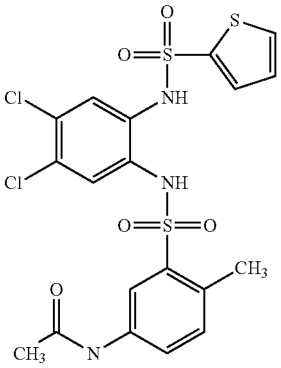 [SMILES: CC(=O)Nc1ccc(C)c(S(=O)(=O)Nc2cc(Cl)c(Cl)cc2NS(=O)(=O)c2cccs2)c1] | N-{3-[({4,5-dichloro-2-[(2-thienylsulfonyl)amino]phenyl}amino)sulfonyl]-4-methylphenyl}acetamide | Method A |
| 237 | 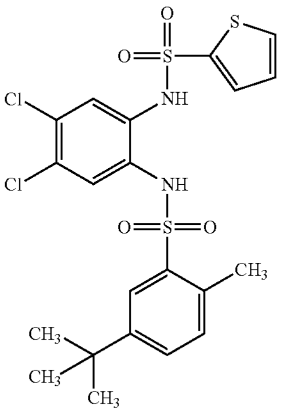 [SMILES: Cc1ccc(C(C)(C)C)cc1S(=O)(=O)Nc1cc(Cl)c(Cl)cc1NS(=O)(=O)c1cccs1] | N-(2-{[(5-tert-butyl-2-methylphenyl)sulfonyl]amino}-4,5-dichlorophenyl)thiophene-2-sulfonamide | Method C |
| 238 | 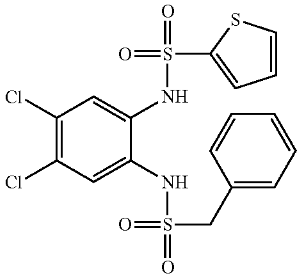 [SMILES: O=S(=O)(Cc1ccccc1)Nc1cc(Cl)c(Cl)cc1NS(=O)(=O)c1cccs1] | N-{2-[(benzylsulfonyl)amino]-4,5-dichlorophenyl}thiophene-2-sulfonamide | Method E |
| 239 | 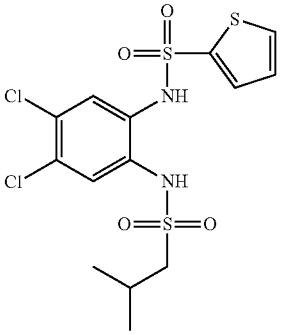 [SMILES: CC(C)CS(=O)(=O)Nc1cc(Cl)c(Cl)cc1NS(=O)(=O)c1cccs1] | N-{4,5-dichloro-2-[(isobutylsulfonyl)amino]phenyl}thiophene-2-sulfonamide | Method E |

TABLE 1-continued
| Comp. No. | Structure | IUPAC compound name | Synthesis |
|---|---|---|---|
| 240 | 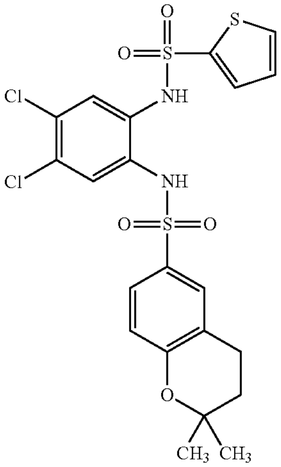 [SMILES: CC1(C)CCc2cc(S(=O)(=O)Nc3cc(Cl)c(Cl)cc3NS(=O)(=O)c3cccs3)ccc2O1] | N-{4,5-dichloro-2-[(2-thienylsulfonyl)amino]phenyl}-2,2-dimethylchromane-6-sulfonamide | Method A |
| 241 | 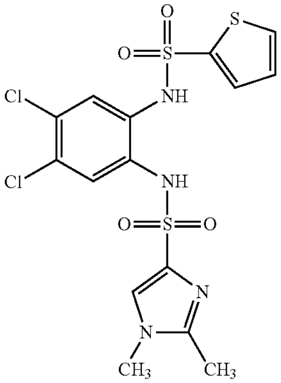 [SMILES: Cc1nc(S(=O)(=O)Nc2cc(Cl)c(Cl)cc2NS(=O)(=O)c2cccs2)cn1C] | N-{4,5-dichloro-2-[(2-thienylsulfonyl)amino]phenyl}-1,2-dimethyl-1H-imidazole-4-sulfonamide | Method C |
| 242 | 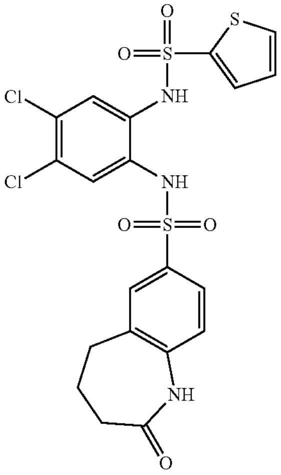 [SMILES: O=C1CCCc2cc(S(=O)(=O)Nc3cc(Cl)c(Cl)cc3NS(=O)(=O)c3cccs3)ccc2N1] | N-{4,5-dichloro-2-[(2-thienylsulfonyl)amino]phenyl}-2-oxo-2,3,4,5-tetrahydro-1H-1-benzazepine-7-sulfonamide | Method A |

TABLE 1-continued
| Comp. No. | Structure | IUPAC compound name | Synthesis |
|---|---|---|---|
| 243 | 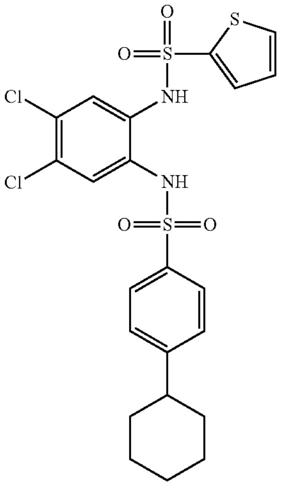 [SMILES: O=S(=O)(Nc1cc(Cl)c(Cl)cc1NS(=O)(=O)c1cccs1)c1ccc(C2CCCCC2)cc1] | N-(4,5-dichloro-2-{[(4-cyclohexylphenyl)sulfonyl]amino}phenyl)thiophene-2-sulfonamide | Method A |
| 244 | 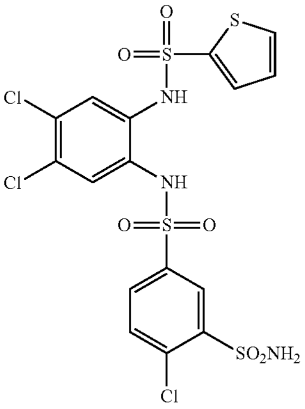 [SMILES: NS(=O)(=O)c1cc(S(=O)(=O)Nc2cc(Cl)c(Cl)cc2NS(=O)(=O)c2cccs2)ccc1Cl] | 4-chloro-N~1~-{4,5-dichloro-2-[(2-thienylsulfonyl)amino]phenyl}benzene-1,3-disulfonamide | Method A |
| 245 | 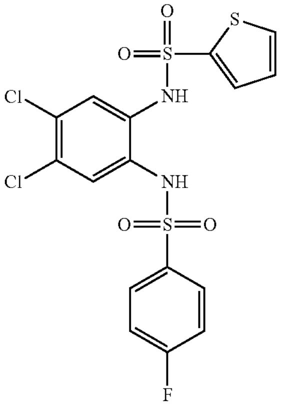 [SMILES: O=S(=O)(Nc1cc(Cl)c(Cl)cc1NS(=O)(=O)c1cccs1)c1ccc(F)cc1] | N-(4,5-dichloro-2-{[(4-fluorophenyl)sulfonyl]amino}phenyl)thiophene-2-sulfonamide | Method A |

TABLE 1-continued

| Comp. No. | Structure | IUPAC compound name | Synthesis |
|---|---|---|---|
| 246 | 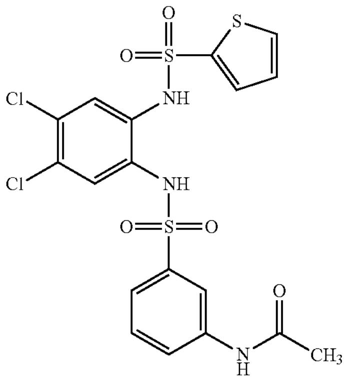 [SMILES: CC(=O)Nc1cccc(S(=O)(=O)Nc2cc(Cl)c(Cl)cc2NS(=O)(=O)c2cccs2)c1] | N-{3-[({4,5-dichloro-2-[(2-thienylsulfonyl)amino]phenyl}amino)sulfonyl]phenyl}acetamide | Method C |
| 247 | 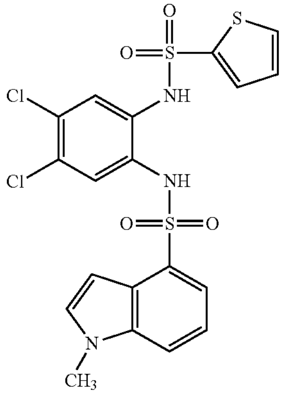 [SMILES: Cn1ccc2c(S(=O)(=O)Nc3cc(Cl)c(Cl)cc3NS(=O)(=O)c3cccs3)cccc21] | N-{4,5-dichloro-2-[(2-thienylsulfonyl)amino]phenyl}-1-methyl-1H-indole-4-sulfonamide | Method A |
| 248 | 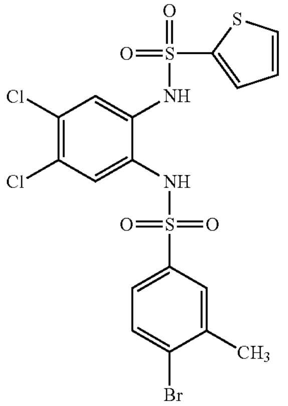 [SMILES: Cc1cc(S(=O)(=O)Nc2cc(Cl)c(Cl)cc2NS(=O)(=O)c2cccs2)ccc1Br] | N-(2-{[(4-bromo-3-methylphenyl)sulfonyl]amino}-4,5-dichlorophenyl)thiophene-2-sulfonamide | Method A |
| 249 | 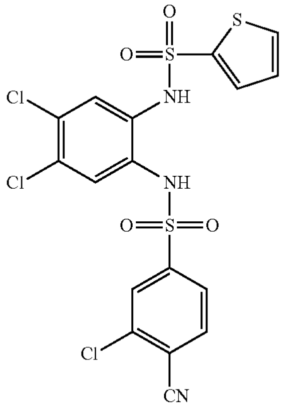 [SMILES: N#Cc1ccc(S(=O)(=O)Nc2cc(Cl)c(Cl)cc2NS(=O)(=O)c2cccs2)cc1Cl] | N-(4,5-dichloro-2-{[(3-chloro-4-cyanophenyl)sulfonyl]amino}phenyl)thiophene-2-sulfonamide | Method C |

TABLE 1-continued
| Comp. No. | Structure | IUPAC compound name | Synthesis |
|---|---|---|---|
| 250 | 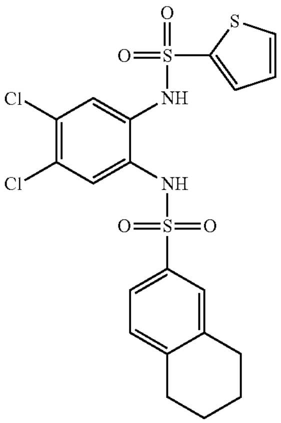 [SMILES: O=S(=O)(Nc1cc(Cl)c(Cl)cc1NS(=O)(=O)c1cccs1)c1ccc2c(c1)CCCC2] | N-{4,5-dichloro-2-[(5,6,7,8-tetrahydronaphthalen-2-ylsulfonyl)amino]phenyl}thiophene-2-sulfonamide | Method A |
| 251 | 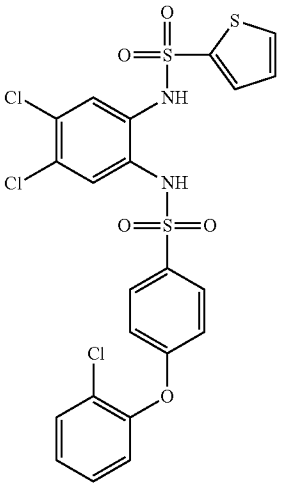 [SMILES: O=S(=O)(Nc1cc(Cl)c(Cl)cc1NS(=O)(=O)c1cccs1)c1ccc(Oc2ccccc2Cl)cc1] | N-[4,5-dichloro-2-({[4-(2-chlorophenoxy)phenyl]sulfonyl}amino)phenyl]thiophene-2-sulfonamide | Method A |
| 252 | 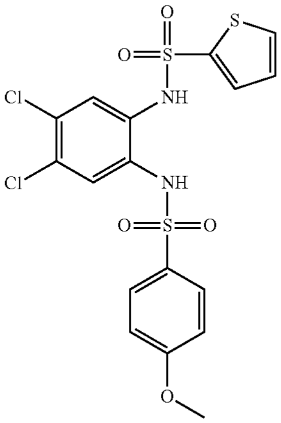 [SMILES: COc1ccc(S(=O)(=O)Nc2cc(Cl)c(Cl)cc2NS(=O)(=O)c2cccs2)cc1] | N-(4,5-dichloro-2-{[(4-methoxyphenyl)sulfonyl]amino}phenyl)thiophene-2-sulfonamide | Method A |

TABLE 1-continued
| Comp. No. | Structure | IUPAC compound name | Synthesis |
| --- | --- | --- | --- |
| 253 | 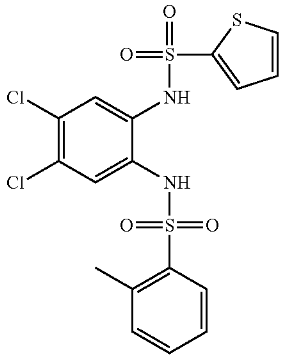 [SMILES: Cc1ccccc1S(=O)(=O)Nc1cc(Cl)c(Cl)cc1NS(=O)(=O)c1cccs1] | N-(4,5-dichloro-2-{[(2-methylphenyl)sulfonyl]amino}phenyl)thiophene-2-sulfonamide | Method A |
| 254 | 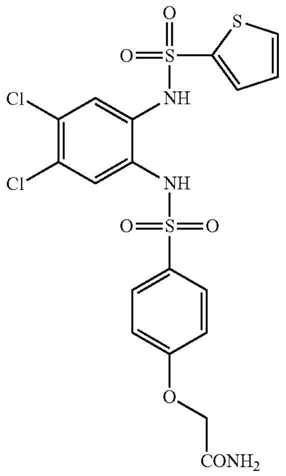 [SMILES: NC(=O)COc1ccc(S(=O)(=O)Nc2cc(Cl)c(Cl)cc2NS(=O)(=O)c2cccs2)cc1] | 2-{4-[({4,5-dichloro-2-[(2-thienylsulfonyl)amino]phenyl}amino)sulfonyl]phenoxy}acetamide | Method C |
| 255 | 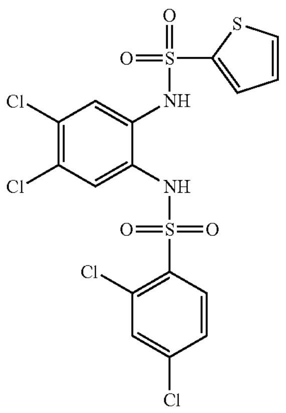 [SMILES: O=S(=O)(Nc1cc(Cl)c(Cl)cc1NS(=O)(=O)c1ccc(Cl)cc1Cl)c1cccs1] | N-(4,5-dichloro-2-{[(2,4-dichlorophenyl)sulfonyl]amino}phenyl)thiophene-2-sulfonamide | Method A |

TABLE 1-continued
| Comp. No. | Structure | IUPAC compound name | Synthesis |
|---|---|---|---|
| 256 | 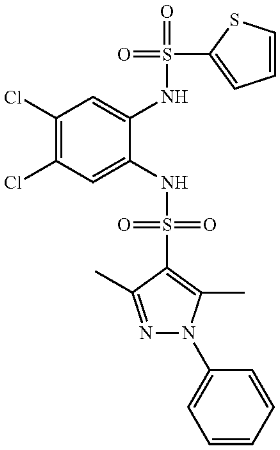 [SMILES: Cc1nn(-c2ccccc2)c(C)c1S(=O)(=O)Nc1cc(Cl)c(Cl)cc1NS(=O)(=O)c1cccs1] | N-{4,5-dichloro-2-[(2-thienylsulfonyl)amino] phenyl}-3,5-dimethyl-1-phenyl-1H-pyrazole-4-sulfonamide | Method A |
| 257 | 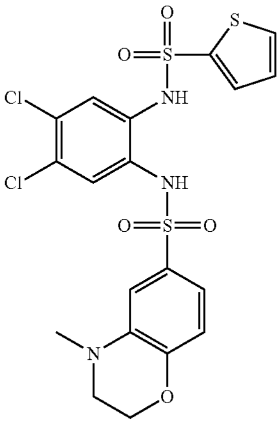 [SMILES: CN1CCOc2ccc(S(=O)(=O)Nc3cc(Cl)c(Cl)cc3NS(=O)(=O)c3cccs3)cc21] | N-{4,5-dichloro-2-[(2-thienylsulfonyl)amino]phenyl}-4-methyl-3,4-dihydro-2H-1,4-benzoxazine-6-sulfonamide | Method A |
| 258 | 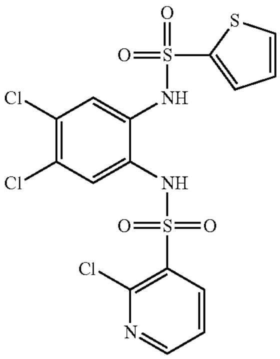 [SMILES: O=S(=O)(Nc1cc(Cl)c(Cl)cc1NS(=O)(=O)c1cccnc1Cl)c1cccs1] | 2-chloro-N-{4,5-dichloro-2-[(2-thienylsulfonyl)amino]phenyl} pyridine-3-sulfonamide | Method A |

TABLE 1-continued

| Comp. No. | Structure | IUPAC compound name | Synthesis |
|---|---|---|---|
| 259 | 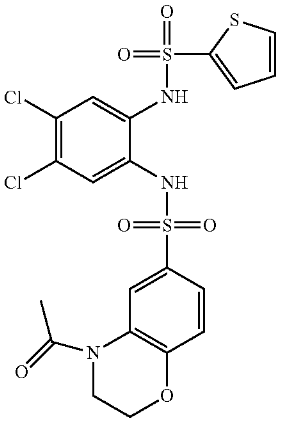 [SMILES: CC(=O)N1CCOc2ccc(S(=O)(=O)Nc3cc(Cl)c(Cl)cc3NS(=O)(=O)c3cccs3)cc21] | 4-acetyl-N-{4,5-dichloro-2-[(2-thienylsulfonyl)amino]phenyl}-3,4-dihydro-2H-1,4-benzoxazine-6-sulfonamide | Method A |
| 260 | 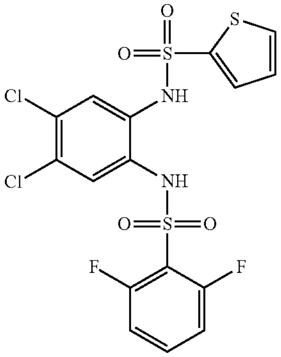 [SMILES: O=S(=O)(Nc1cc(Cl)c(Cl)cc1NS(=O)(=O)c1c(F)cccc1F)c1cccs1] | N-(4,5-dichloro-2-{[(2,6-difluorophenyl)sulfonyl]amino}phenyl)thiophene-2-sulfonamide | Method A |
| 261 | 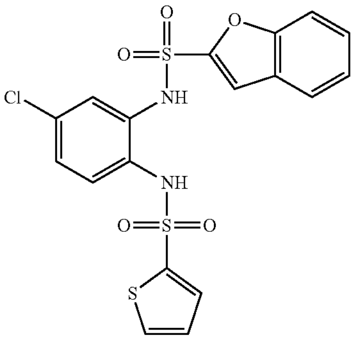 [SMILES: O=S(=O)(Nc1cc(Cl)ccc1NS(=O)(=O)c1cccs1)c1cc2ccccc2o1] | N-{5-chloro-2-[(2-thienylsulfonyl)amino]phenyl}-1-benzofuran-2-sulfonamide | Method A |
| 262 | 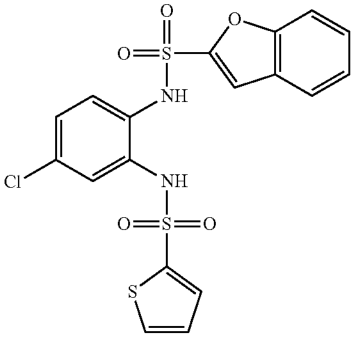 [SMILES: O=S(=O)(Nc1ccc(Cl)cc1NS(=O)(=O)c1cccs1)c1cc2ccccc2o1] | N-{4-chloro-2-[(2-thienylsulfonyl)amino]phenyl}-1-benzofuran-2-sulfonamide | Method A |

TABLE 1-continued

| Comp. No. | Structure | IUPAC compound name | Synthesis |
|---|---|---|---|
| 263 | 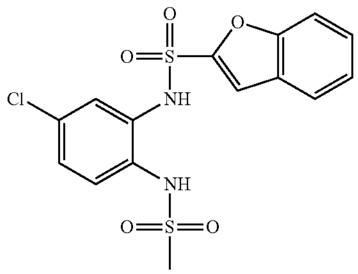 [SMILES: CS(=O)(=O)Nc1ccc(Cl)cc1NS(=O)(=O)c1cc2ccccc2o1] | N-{5-chloro-2-[(methylsulfonyl)amino]phenyl}-1-benzofuran-2-sulfonamide | Method A |
| 264 | 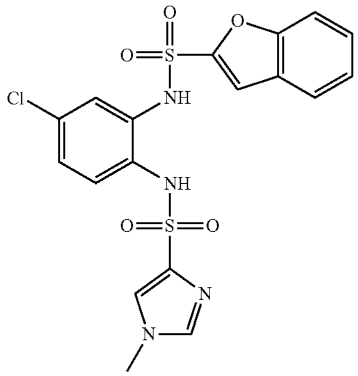 [SMILES: Cn1cnc(S(=O)(=O)Nc2ccc(Cl)cc2NS(=O)(=O)c2cc3ccccc3o2)c1] | N-{2-[(1-benzofuran-2-ylsulfonyl)amino]-4-chlorophenyl}-1-methyl-1H-imidazole-4-sulfonamide | Method A |
| 265 | 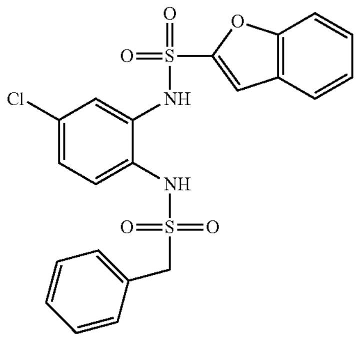 [SMILES: O=S(=O)(Cc1ccccc1)Nc1ccc(Cl)cc1NS(=O)(=O)c1cc2ccccc2o1] | N-{2-[(benzylsulfonyl)amino]-5-chlorophenyl}-1-benzofuran-2-sulfonamide | Method A |
| 266 | 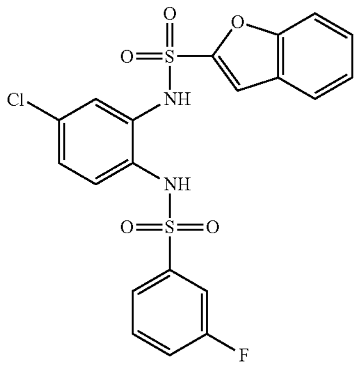 [SMILES: O=S(=O)(Nc1ccc(Cl)cc1NS(=O)(=O)c1cc2ccccc2o1)c1cccc(F)c1] | N-(5-chloro-2-{[(3-fluorophenyl)sulfonyl]amino}phenyl)-1-benzofuran-2-sulfonamide | Method A |

TABLE 1-continued

| Comp. No. | Structure | IUPAC compound name | Synthesis |
| --- | --- | --- | --- |
| 267 | 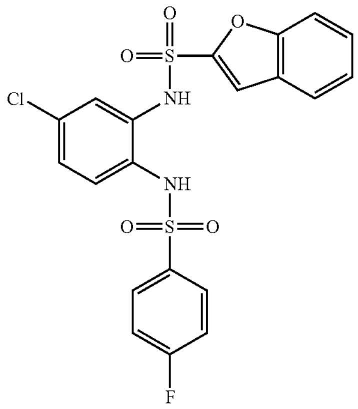 [SMILES: O=S(=O)(Nc1ccc(Cl)cc1NS(=O)(=O)c1cc2ccccc2o1)c1ccc(F)cc1] | N-(5-chloro-2-{[(4-fluorophenyl)sulfonyl] amino}phenyl)-1-benzofuran-2-sulfonamide | Method A |
| 268 | 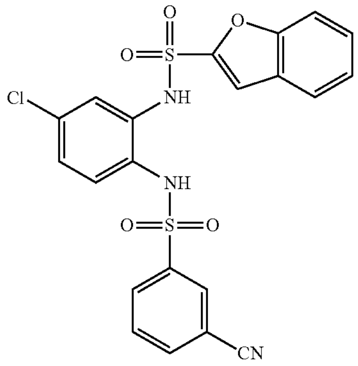 [SMILES: N#Cc1cccc(S(=O)(=O)Nc2ccc(Cl)cc2NS(=O)(=O)c2cc3ccccc3o2)c1] | N-(5-chloro-2-{[(3-cyanophenyl)sulfonyl] amino}phenyl)-1-benzofuran-2-sulfonamide | Method A |
| 269 | 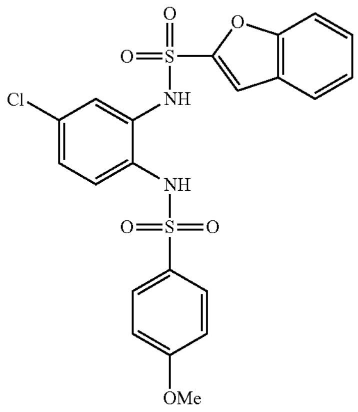 [SMILES: COc1ccc(S(=O)(=O)Nc2ccc(Cl)cc2NS(=O)(=O)c2cc3ccccc3o2)cc1] | N-(5-chloro-2-{[(4-methoxyphenyl)sulfonyl] amino}phenyl)-1-benzofuran-2-sulfonamide | Method A |
| 270 | 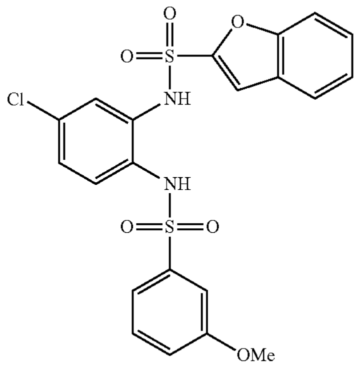 [SMILES: COc1cccc(S(=O)(=O)Nc2ccc(Cl)cc2NS(=O)(=O)c2cc3ccccc3o2)c1] | N-(5-chloro-2-{[(3-methoxyphenyl)sulfonyl] amino}phenyl)-1-benzofuran-2-sulfonamide | Method A |

TABLE 1-continued

| Comp. No. | Structure | IUPAC compound name | Synthesis |
|---|---|---|---|
| 271 | 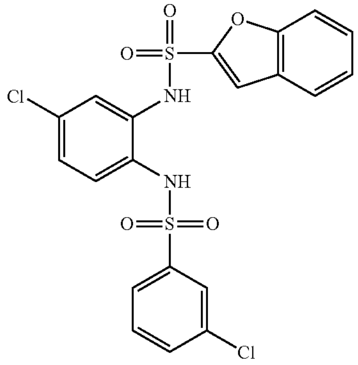 [SMILES: O=S(=O)(Nc1ccc(Cl)cc1NS(=O)(=O)c1cc2ccccc2o1)c1cccc(Cl)c1] | N-(5-chloro-2-{[(3-chlorophenyl)sulfonyl]amino}phenyl)-1-benzofuran-2-sulfonamide | Method A |
| 272 | 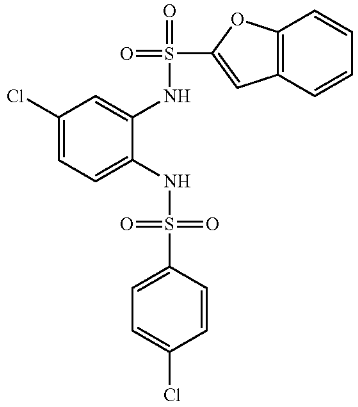 [SMILES: O=S(=O)(Nc1ccc(Cl)cc1NS(=O)(=O)c1cc2ccccc2o1)c1ccc(Cl)cc1] | N-(5-chloro-2-{[(4-chlorophenyl)sulfonyl]amino}phenyl)-1-benzofuran-2-sulfonamide | Method A |
| 273 | 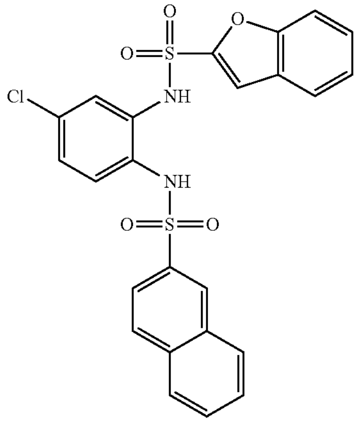 [SMILES: O=S(=O)(Nc1ccc(Cl)cc1NS(=O)(=O)c1cc2ccccc2o1)c1ccc2ccccc2c1] | N-{5-chloro-2-[(2-naphthylsulfonyl)amino]phenyl}-1-benzofuran-2-sulfonamide | Method A |
| 274 | 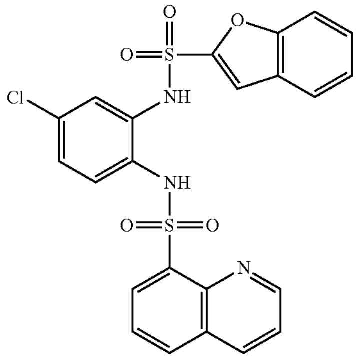 [SMILES: O=S(=O)(Nc1cc(Cl)ccc1NS(=O)(=O)c1cccc2cccnc12)c1cc2ccccc2o1] | N-{2-[(1-benzofuran-2-ylsulfonyl)amino]-4-chlorophenyl}quinoline-8-sulfonamide | Method A |

TABLE 1-continued
| Comp. No. | Structure | IUPAC compound name | Synthesis |
|---|---|---|---|
| 275 | 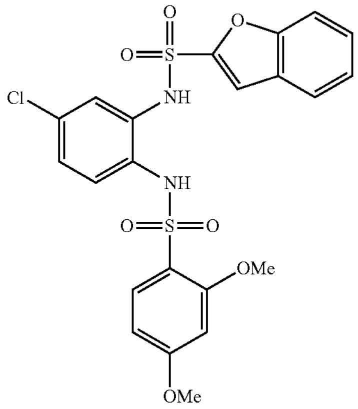 [SMILES: COc1ccc(S(=O)(=O)Nc2ccc(Cl)cc2NS(=O)(=O)c2cc3ccccc3o2)c(OC)c1] | N-(5-chloro-2-{[(3,4-dimethoxyphenyl)sulfonyl]amino}phenyl)-1-benzofuran-2-sulfonamide | Method A |
| 276 | 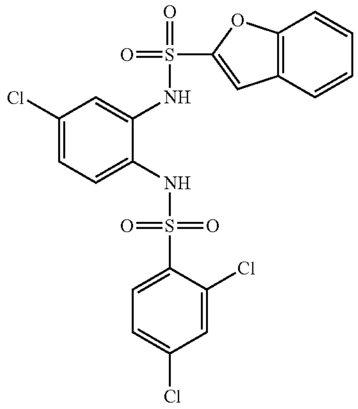 [SMILES: O=S(=O)(Nc1cc(Cl)ccc1NS(=O)(=O)c1ccc(Cl)cc1Cl)c1cc2ccccc2o1] | N-(5-chloro-2-{[(2,4-dichlorophenyl)sulfonyl]amino}phenyl)-1-benzofuran-2-sulfonamide | Method A |
| 277 | 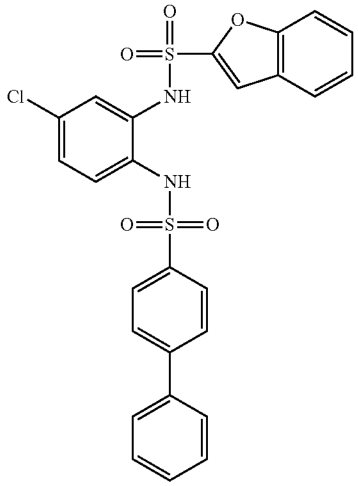 [SMILES: O=S(=O)(Nc1ccc(Cl)cc1NS(=O)(=O)c1cc2ccccc2o1)c1ccc(-c2ccccc2)cc1] | N-{2-[(biphenyl-4-ylsulfonyl)amino]-5-chlorophenyl}-1-benzofuran-2-sulfonamide | Method A |

TABLE 1-continued
| Comp. No. | Structure | IUPAC compound name | Synthesis |
|---|---|---|---|
| 278 | 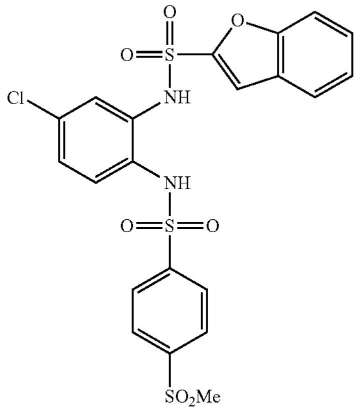 [SMILES: CS(=O)(=O)c1ccc(S(=O)(=O)Nc2ccc(Cl)cc2NS(=O)(=O)c2cc3ccccc3o2)cc1] | N-[5-chloro-2-({[4-(methylsulfonyl)phenyl]sulfonyl}amino)phenyl]-1-benzofuran-2-sulfonamide | Method A |
| 279 | 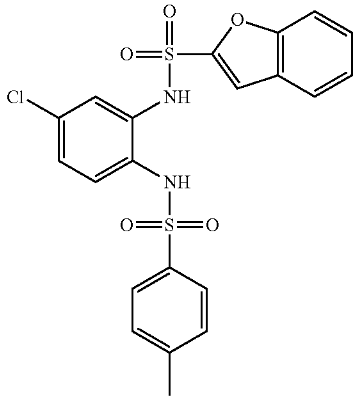 [SMILES: Cc1ccc(S(=O)(=O)Nc2ccc(Cl)cc2NS(=O)(=O)c2cc3ccccc3o2)cc1] | N-(5-chloro-2-{[(4-methylphenyl)sulfonyl]amino}phenyl)-1-benzofuran-2-sulfonamide | Method A |
| 280 | 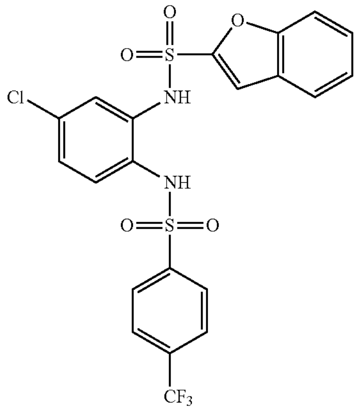 [SMILES: O=S(=O)(Nc1ccc(Cl)cc1NS(=O)(=O)c1cc2ccccc2o1)c1ccc(C(F)(F)F)cc1] | N-[5-chloro-2-({[4-(trifluoromethyl)phenyl]sulfonyl}amino)phenyl]-1-benzofuran-2-sulfonamide | Method A |

TABLE 1-continued

| Comp. No. | Structure | IUPAC compound name | Synthesis |
|---|---|---|---|
| 281 | 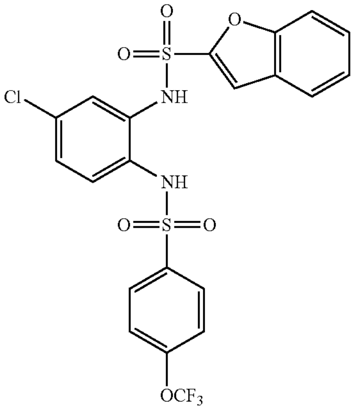 [SMILES: O=S(=O)(Nc1ccc(Cl)cc1NS(=O)(=O)c1cc2ccccc2o1)c1ccc(OC(F)(F)F)cc1] | N-[5-chloro-2-({[4-(trifluoromethoxyphenyl]sulfonyl}amino)phenyl]-1-benzofuran-2-sulfonamide | Method A |
| 282 | 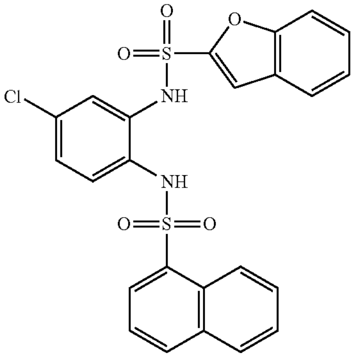 [SMILES: O=S(=O)(Nc1cc(Cl)ccc1NS(=O)(=O)c1cccc2ccccc12)c1cc2ccccc2o1] | N-{5-chloro-2-[(1-naphthylsulfonyl)amino]phenyl}-1-benzofuran-2-sulfonamide | Method A |
| 283 | 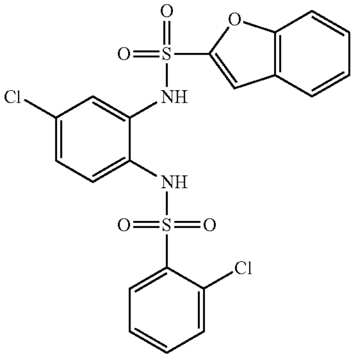 [SMILES: O=S(=O)(Nc1cc(Cl)ccc1NS(=O)(=O)c1ccccc1Cl)c1cc2ccccc2o1] | N-(5-chloro-2-{[(2-chlorophenyl)sulfonyl]amino}phenyl)-1-benzofuran-2-sulfonamide | Method A |
| 284 | 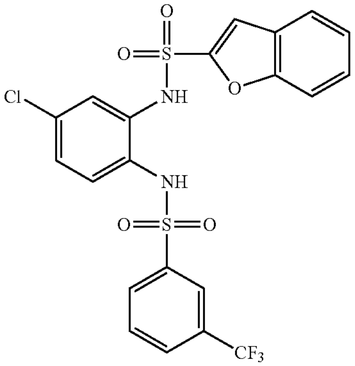 [SMILES: O=S(=O)(Nc1ccc(Cl)cc1NS(=O)(=O)c1cc2ccccc2o1)c1cccc(C(F)(F)F)c1] | N-[5-chloro-2-({[3-(trifluoromethyl)phenyl]sulfonyl}amino)phenyl]-1-benzofuran-2-sulfonamide | Method A |

TABLE 1-continued

| Comp. No. | Structure | IUPAC compound name | Synthesis |
|---|---|---|---|
| 285 | 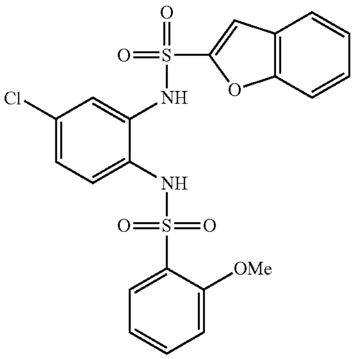 [SMILES: COc1ccccc1S(=O)(=O)Nc1ccc(Cl)cc1NS(=O)(=O)c1cc2ccccc2o1] | N-(5-chloro-2-{[(2-methoxyphenyl)sulfonyl]amino}phenyl)-1-benzofuran-2-sulfonamide | Method A |
| 286 | 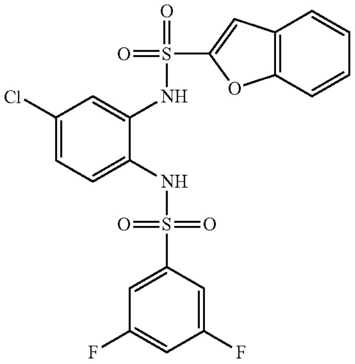 [SMILES: O=S(=O)(Nc1ccc(Cl)cc1NS(=O)(=O)c1cc2ccccc2o1)c1cc(F)cc(F)c1] | N-(5-chloro-2-{[(3,5-difluorophenyl)sulfonyl]amino}phenyl)-1-benzofuran-2-sulfonamide | Method A |
| 287 | 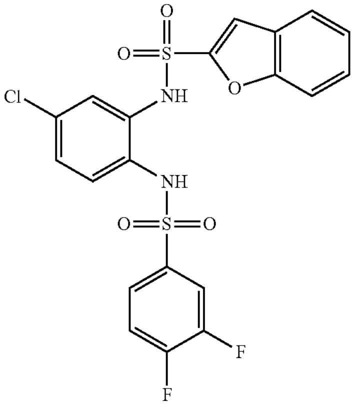 [SMILES: O=S(=O)(Nc1ccc(Cl)cc1NS(=O)(=O)c1cc2ccccc2o1)c1ccc(F)c(F)c1] | N-(5-chloro-2-{[(3,4-difluorophenyl)sulfonyl]amino}phenyl)-1-benzofuran-2-sulfonamide | Method A |
| 288 | 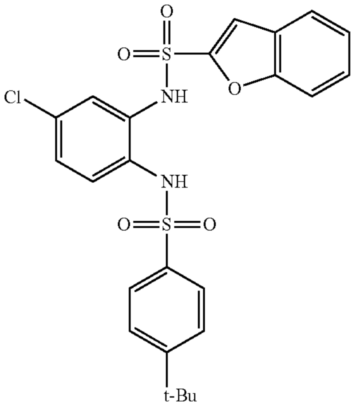 [SMILES: CC(C)(C)c1ccc(S(=O)(=O)Nc2ccc(Cl)cc2NS(=O)(=O)c2cc3ccccc3o2)cc1] | N-(2-{[(4-tert-butylphenyl)sulfonyl]amino}-5-chlorophenyl)-1-benzofuran-2-sulfonamide | Method A |

TABLE 1-continued
| Comp. No. | Structure | IUPAC compound name | Synthesis |
|---|---|---|---|
| 289 | 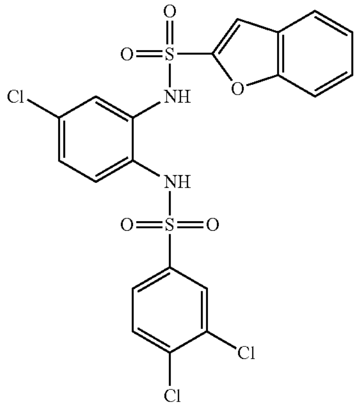 [SMILES: O=S(=O)(Nc1ccc(Cl)cc1NS(=O)(=O)c1cc2ccccc2o1)c1ccc(Cl)c(Cl)c1] | N-(5-chloro-2-{[(3,4-dichlorophenyl)sulfonyl]amino}phenyl)-1-benzofuran-2-sulfonamide | Method A |
| 290 | 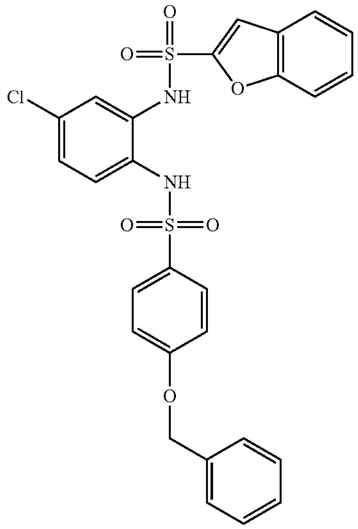 [SMILES: O=S(=O)(Nc1ccc(Cl)cc1NS(=O)(=O)c1cc2ccccc2o1)c1ccc(OCc2ccccc2)cc1] | N-[2-({[4-(benzyloxy)phenyl]sulfonyl}amino)-5-chlorophenyl]-1-benzofuran-2-sulfonamide | Method A |
| 291 | 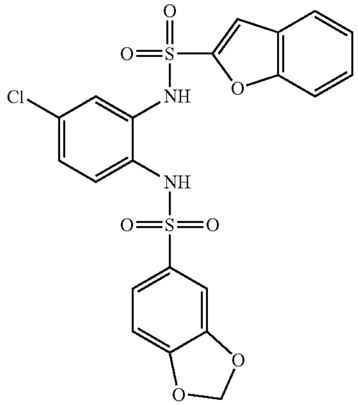 [SMILES: O=S(=O)(Nc1ccc(Cl)cc1NS(=O)(=O)c1cc2ccccc2o1)c1ccc2c(c1)OCO2] | N-{2-[(1-benzofuran-2-ylsulfonyl)amino]-4-chlorophenyl}-1,3-benzodioxin-5-sulfonamide | Method A |

TABLE 1-continued

| Comp. No. | Structure | IUPAC compound name | Synthesis |
|---|---|---|---|
| 292 | 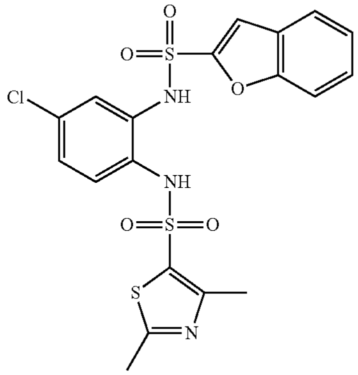 [SMILES: Cc1nc(C)c(S(=O)(=O)Nc2ccc(Cl)cc2NS(=O)(=O)c2cc3ccccc3o2)s1] | N-{2-[(1-benzofuran-2-ylsulfonyl)amino]-4-chlorophenyl}-2,4-dimethyl-1,3-thiazole-5-sulfonamide | Method A |
| 292 | 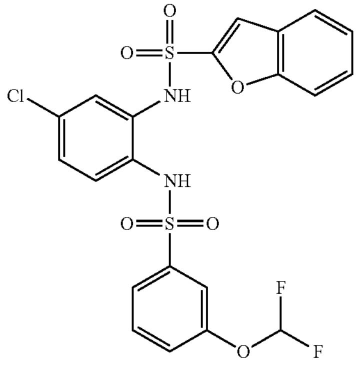 [SMILES: O=S(=O)(Nc1ccc(Cl)cc1NS(=O)(=O)c1cc2ccccc2o1)c1cccc(OC(F)F)c1] | N-[5-chloro-2-({[3-(difluoromethoxy)phenyl] sulfonyl}amino)phenyl]-1-benzofuran-2-sulfonamide | Method A |
| 293 | 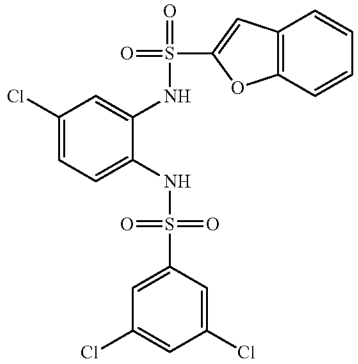 [SMILES: O=S(=O)(Nc1ccc(Cl)cc1NS(=O)(=O)c1cc2ccccc2o1)c1cc(Cl)cc(Cl)c1] | N-(5-chloro-2-{[(3,5-dichlorophenyl)sulfonyl] amino}phenyl)-1-benzofuran-2-sulfonamide | Method A |
| 294 | 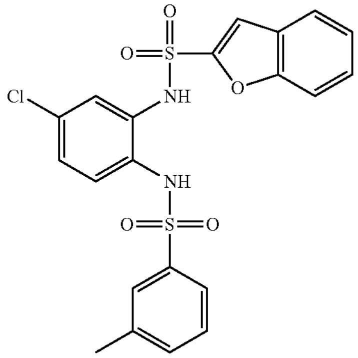 [SMILES: Cc1cccc(S(=O)(=O)Nc2ccc(Cl)cc2NS(=O)(=O)c2cc3ccccc3o2)c1] | N-(5-chloro-2-{[(3-methylphenyl)sulfonyl] amino}phenyl)-1-benzofuran-2-sulfonamide | Method A |

TABLE 1-continued

| Comp. No. | Structure | IUPAC compound name | Synthesis |
|---|---|---|---|
| 295 | 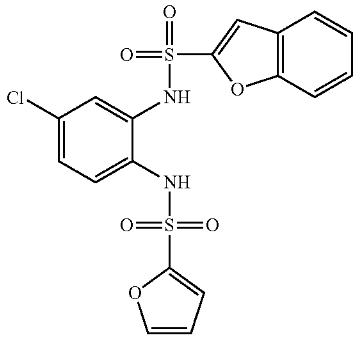 [SMILES: O=S(=O)(Nc1ccc(Cl)cc1NS(=O)(=O)c1cc2ccccc2o1)c1ccco1] | N-{5-chloro-2-[(2-furylsulfonyl)amino]phenyl}-1-benzofuran-2-sulfonamide | Method A |
| 296 | 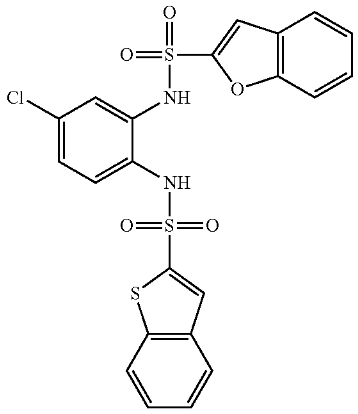 [SMILES: O=S(=O)(Nc1cc(Cl)ccc1NS(=O)(=O)c1cc2ccccc2s1)c1cc2ccccc2o1] | N-{2-[(1-benzothien-3-ylsulfonyl)amino]-5-chlorophenyl}-1-benzofuran-2-sulfonamide | Method A |
| 297 | 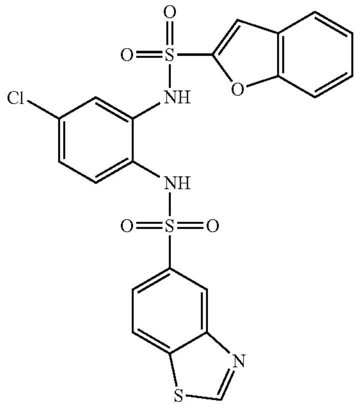 [SMILES: O=S(=O)(Nc1ccc(Cl)cc1NS(=O)(=O)c1cc2ccccc2o1)c1ccc2scnc2c1] | N-{2-[(1-benzofuran-3-ylsulfonyl)amino]-4-chlorophenyl}-1,3-benzothiazole-6-sulfonamide | Method A |
| 298 | 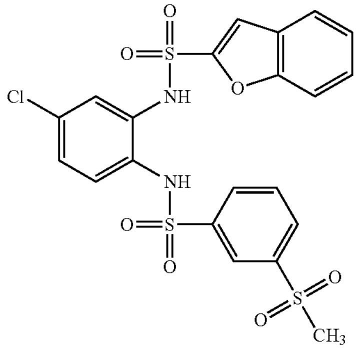 [SMILES: CS(=O)(=O)c1cccc(S(=O)(=O)Nc2ccc(Cl)cc2NS(=O)(=O)c2cc3ccccc3o2)c1] | N-[5-chloro-2-({[3-(methylsulfonyl)phenyl]sulfonyl}amino)phenyl]-1-benzofuran-2-sulfonamide | Method A |

TABLE 1-continued

| Comp. No. | Structure | IUPAC compound name | Synthesis |
| --- | --- | --- | --- |
| 299 | 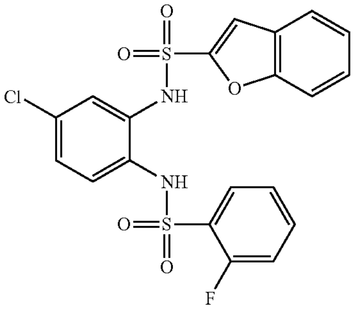 [SMILES: O=S(=O)(Nc1cc(Cl)ccc1NS(=O)(=O)c1ccccc1F)c1cc2ccccc2o1] | N-(5-chloro-2-{[(2-fluorophenyl)sulfonyl]amino}phenyl)-1-benzofuran-2-sulfonamide | Method A |
| 300 | 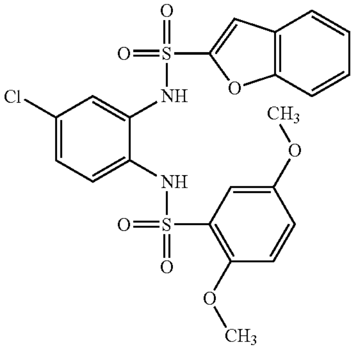 [SMILES: COc1ccc(OC)c(S(=O)(=O)Nc2ccc(Cl)cc2NS(=O)(=O)c2cc3ccccc3o2)c1] | N-(5-chloro-2-{[(2,5-dimethoxyphenyl)sulfonyl]amino}phenyl)-1-benzofuran-2-sulfonamide | Method A |
| 301 | 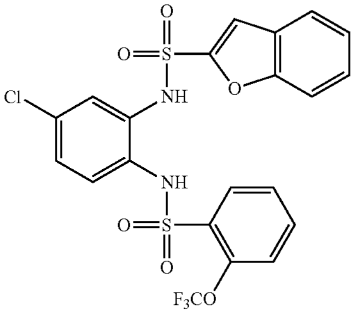 [SMILES: O=S(=O)(Nc1cc(Cl)ccc1NS(=O)(=O)c1ccccc1OC(F)(F)F)c1cc2ccccc2o1] | N-[5-chloro-2-({[2-(trifluoromethoxy)phenyl]sulfonyl}amino)phenyl]-1-benzofuran-2-sulfonamide | Method A |
| 302 | 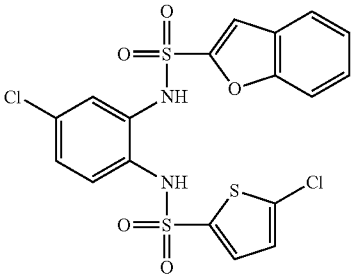 [SMILES: O=S(=O)(Nc1cc(Cl)ccc1NS(=O)(=O)c1ccc(Cl)s1)c1cc2ccccc2o1] | N-(5-chloro-2-{[(5-chloro-2-thienyl)sulfonyl]amino}phenyl)-1-benzofuran-2-sulfonamide | Method A |
| 303 | 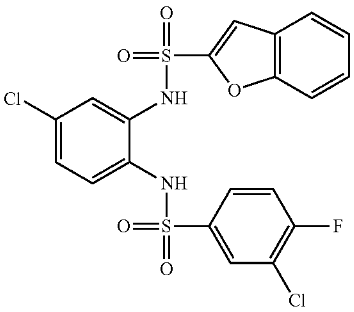 [SMILES: O=S(=O)(Nc1ccc(Cl)cc1NS(=O)(=O)c1cc2ccccc2o1)c1ccc(F)c(Cl)c1] | N-(5-chloro-2-{[(3-chloro-4-fluorophenyl)sulfonyl]amino}phenyl)-1-benzofuran-2-sulfonamide | Method A |

TABLE 1-continued

| Comp. No. | Structure | IUPAC compound name | Synthesis |
|---|---|---|---|
| 304 | 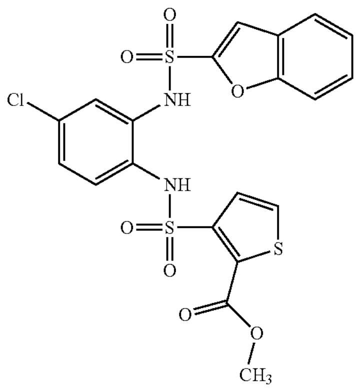 [SMILES: COC(=O)c1sccc1S(=O)(=O)Nc1ccc(Cl)cc1NS(=O)(=O)c1cc2ccccc2o1] | methyl 3-[({2-[(1-benzofuran-2-ylsulfonyl)amino]-4-chlorophenyl}amino)sulfonyl] thiophene-2-carboxylate | Method A |
| 305 | 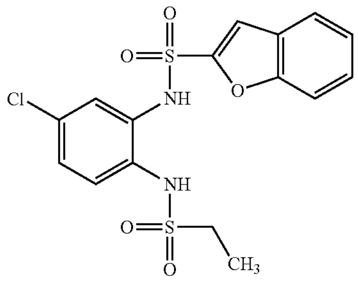 [SMILES: CCS(=O)(=O)Nc1ccc(Cl)cc1NS(=O)(=O)c1cc2ccccc2o1] | N-{5-chloro-2-[(ethylsulfonyl)amino] phenyl}-1-benzofuran-2-sulfonamide | Method A |
| 306 | 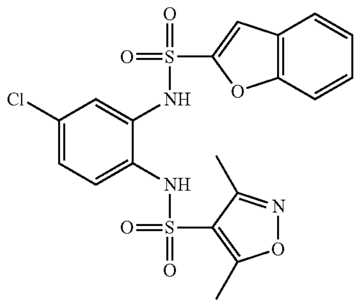 [SMILES: Cc1noc(C)c1S(=O)(=O)Nc1ccc(Cl)cc1NS(=O)(=O)c1cc2ccccc2o1] | N-{2-[(1-benzofuran-2-ylsulfonyl)amino]-4-chlorophenyl}-3,5-dimethylisoxazole-4-sulfonamide | Method A |
| 307 | 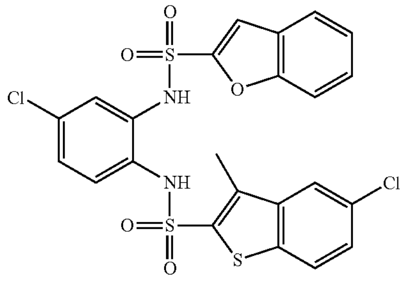 [SMILES: Cc1c(S(=O)(=O)Nc2ccc(Cl)cc2NS(=O)(=O)c2cc3ccccc3o2)sc2ccc(Cl)cc12] | N-(5-chloro-2-{[(5-chloro-3-methyl-1-benzothien-2-yl)sulfonyl]amino}phenyl)-1-benzofuran-2-sulfonamide | Method A |
| 308 | 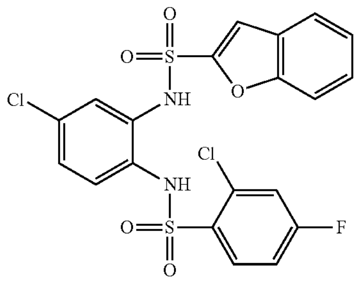 [SMILES: O=S(=O)(Nc1cc(Cl)ccc1NS(=O)(=O)c1ccc(F)cc1Cl)c1cc2ccccc2o1] | N-(5-chloro-2-{[(2-chloro-4-fluorophenyl)sulfonyl] amino}phenyl)-1-benzofuran-2-sulfonamide | Method A |

TABLE 1-continued

| Comp. No. | Structure | IUPAC compound name | Synthesis |
|---|---|---|---|
| 309 | 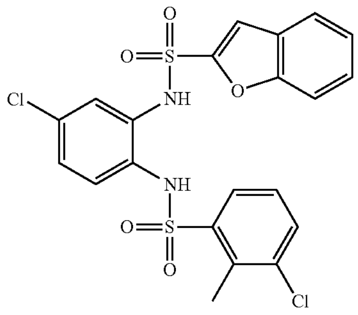 [SMILES: Cc1c(Cl)cccc1S(=O)(=O)Nc1ccc(Cl)cc1NS(=O)(=O)c1cc2ccccc2o1] | N-(5-chloro-2-{[(3-chloro-2-methylphenyl)sulfonyl]amino}phenyl)-1-benzofuran-2-sulfonamide | Method A |
| 310 | 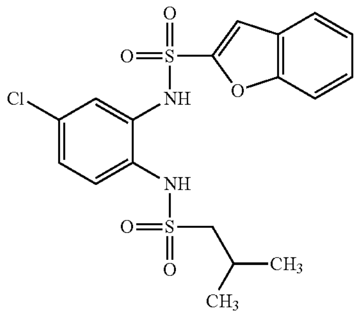 [SMILES: CC(C)CS(=O)(=O)Nc1ccc(Cl)cc1NS(=O)(=O)c1cc2ccccc2o1] | N-{5-chloro-2-[(isobutylsulfonyl)amino]phenyl}-1-benzofuran-2-sulfonamide | Method A |
| 311 | 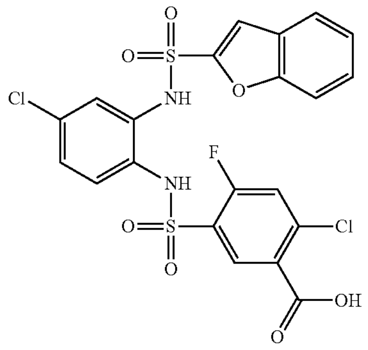 [SMILES: O=C(O)c1cc(S(=O)(=O)Nc2ccc(Cl)cc2NS(=O)(=O)c2cc3ccccc3o2)c(F)cc1Cl] | 5-[({2-[(1-benzofuran-2-ylsulfonyl)amino]-4-chlorophenyl}amino)sulfonyl]-2-chloro-4-fluorobenzoic acid | Method B |
| 312 | 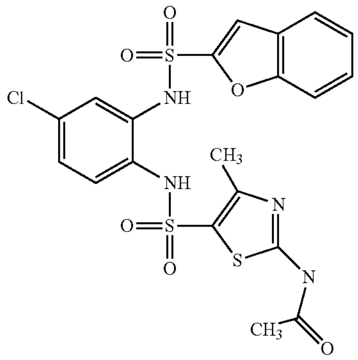 [SMILES: CC(=O)Nc1nc(C)c(S(=O)(=O)Nc2ccc(Cl)cc2NS(=O)(=O)c2cc3ccccc3o2)s1] | N-{5-[({2-[(1-benzofuran-2-ylsulfonyl)amino]-4-chlorophenyl}amino)sulfonyl]-4-methyl-1,3-thiazol-2-yl}acetamide | Method A |

TABLE 1-continued

| Comp. No. | Structure | IUPAC compound name | Synthesis |
| --- | --- | --- | --- |
| 313 | 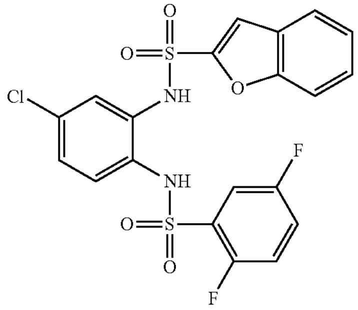 [SMILES: O=S(=O)(Nc1cc(Cl)ccc1NS(=O)(=O)c1cc(F)ccc1F)c1cc2ccccc2o1] | N-(5-chloro-2-{[(2,5-difluorophenyl)sulfonyl]amino}phenyl)-1-benzofuran-2-sulfonamide | Method A |
| 314 | 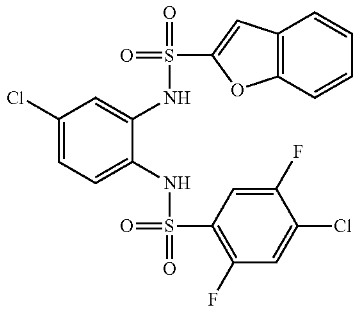 [SMILES: O=S(=O)(Nc1cc(Cl)ccc1NS(=O)(=O)c1cc(F)c(Cl)cc1F)c1cc2ccccc2o1] | N-(5-chloro-2-{[(4-chloro-2,5-difluorophenyl)sulfonyl]amino}phenyl)-1-benzofuran-2-sulfonamide | Method A |
| 315 | 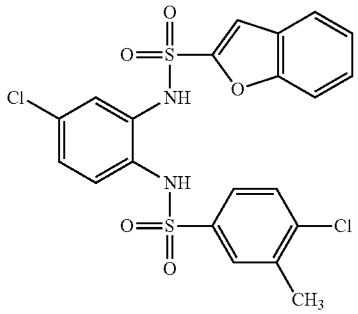 [SMILES: Cc1cc(S(=O)(=O)Nc2ccc(Cl)cc2NS(=O)(=O)c2cc3ccccc3o2)ccc1Cl] | N-(5-chloro-2-{[(4-chloro-3-methylphenyl)sulfonyl]amino}phenyl)-1-benzofuran-2-sulfonamide | Method A |
| 316 | 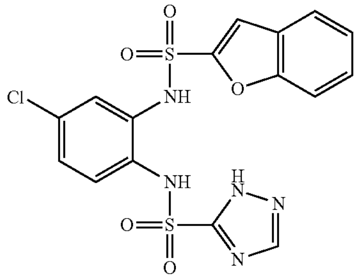 [SMILES: O=S(=O)(Nc1ccc(Cl)cc1NS(=O)(=O)c1cc2ccccc2o1)c1ncn[nH]1] | N-{2-[(1-benzofuran-2-ylsulfonyl)amino]-4-chlorophenyl}-1H-1,2,4-triazole-5-sulfonamide | Method A |
| 317 | 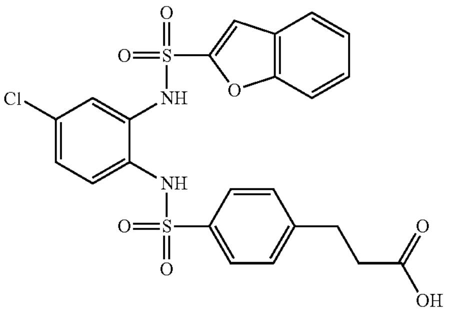 [SMILES: O=C(O)CCc1ccc(S(=O)(=O)Nc2ccc(Cl)cc2NS(=O)(=O)c2cc3ccccc3o2)cc1] | 3-{4-[({2-[(1-benzofuran-2-ylsulfonyl)amino]-4-chlorophenyl}amino)sulfonyl]phenyl}propanoic acid | Method B |

TABLE 1-continued

| Comp. No. | Structure | IUPAC compound name | Synthesis |
|---|---|---|---|
| 318 | 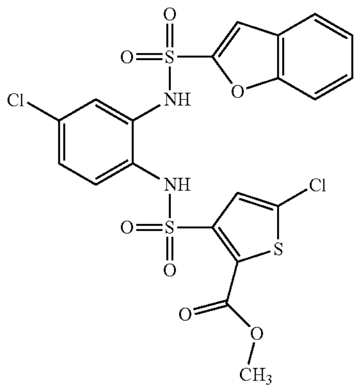 [SMILES: COC(=O)c1sc(Cl)cc1S(=O)(=O)Nc1ccc(Cl)cc1NS(=O)(=O)c1cc2ccccc2o1] | methyl 3-[({2-[(1-benzofuran-2-ylsulfonyl)amino]-4-chlorophenyl}amino)sulfonyl]-5-chlorothiophene-2-carboxylate | Method A |
| 319 | 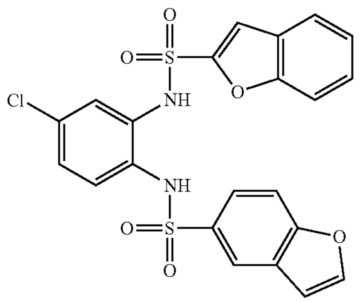 [SMILES: O=S(=O)(Nc1ccc(Cl)cc1NS(=O)(=O)c1cc2ccccc2o1)c1ccc2occc2c1] | N-{2-[(1-benzofuran-5-ylsulfonyl)amino]-5-chlorophenyl}-1-benzofuran-2-sulfonamide | Method A |
| 320 | 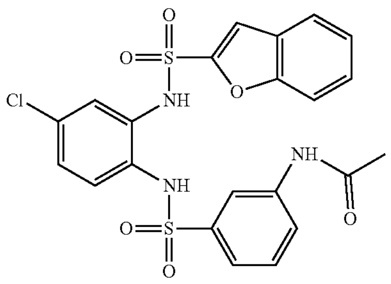 [SMILES: CC(=O)Nc1cccc(S(=O)(=O)Nc2ccc(Cl)cc2NS(=O)(=O)c2cc3ccccc3o2)c1] | N-{3-[({2-[(1-benzofuran-2-ylsulfonyl)amino]-4-chlorophenyl}amino)sulfonyl]phenyl}acetamide | Method A |
| 321 | 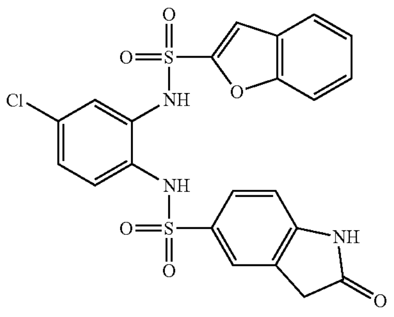 [SMILES: O=C1Cc2cc(S(=O)(=O)Nc3ccc(Cl)cc3NS(=O)(=O)c3cc4ccccc4o3)ccc2N1] | N-{2-[(1-benzofuran-2-ylsulfonyl)amino]-4-chlorophenyl}-2-oxoindoline-5-sulfonamide | Method A |

TABLE 1-continued

| Comp. No. | Structure | IUPAC compound name | Synthesis |
|---|---|---|---|
| 322 | 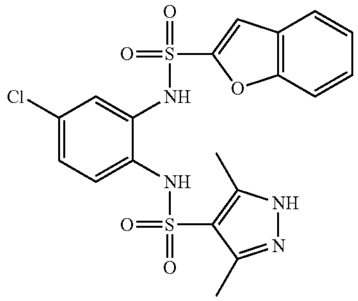 [SMILES: Cc1n[nH]c(C)c1S(=O)(=O)Nc1ccc(Cl)cc1NS(=O)(=O)c1cc2ccccc2o1] | N-{2-[(1-benzofuran-2-ylsulfonyl)amino]-4-chlorophenyl}-3,5-dimethyl-1H-pyrazole-4-sulfonamide | Method A |
| 323 | 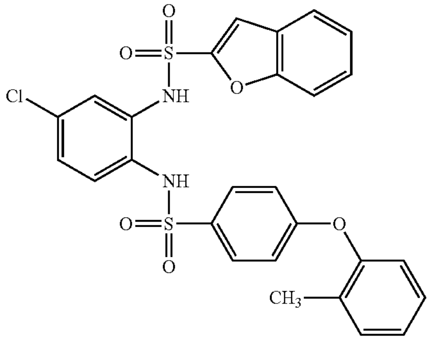 [SMILES: Cc1ccccc1Oc1ccc(S(=O)(=O)Nc2ccc(Cl)cc2NS(=O)(=O)c2cc3ccccc3o2)cc1] | N-[5-chloro-2-({[4-(2-methylphenoxy)phenyl] sulfonyl}amino)phenyl]-1-benzofuran-2-sulfonamide | Method A |
| 324 | 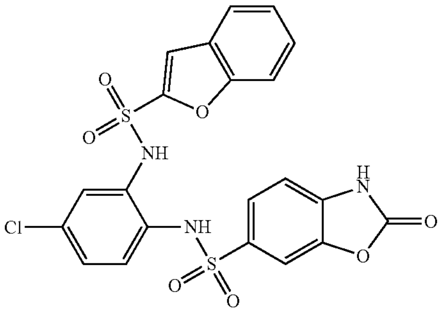 [SMILES: O=c1[nH]c2ccc(S(=O)(=O)Nc3ccc(Cl)cc3NS(=O)(=O)c3cc4ccccc4o3)cc2o1] | N-{2-[(1-benzofuran-2-ylsulfonyl)amino]-4-chlorophenyl}-2-oxo-2,3-dihydro-1,3-benzoxazole-6-sulfonamide | Method A |
| 325 | 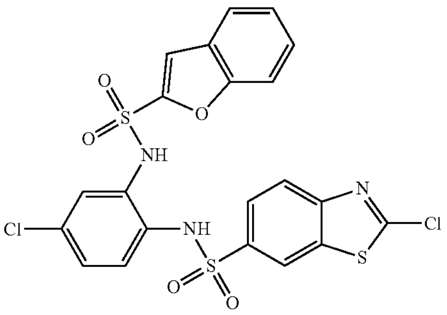 [SMILES: O=S(=O)(Nc1ccc(Cl)cc1NS(=O)(=O)c1cc2ccccc2o1)c1ccc2nc(Cl)sc2c1] | N-{2-[(1-benzofuran-3-ylsulfonyl)amino]-4-chlorophenyl}-2-chloro-1,3-benzothiazole-6-sulfonamide | Method C |
| 326 | 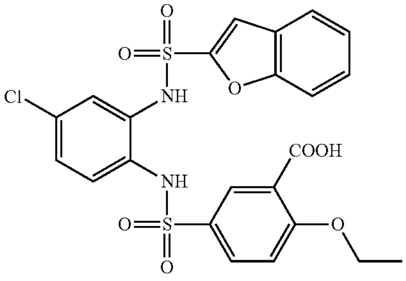 [SMILES: CCOc1ccc(S(=O)(=O)Nc2ccc(Cl)cc2NS(=O)(=O)c2cc3ccccc3o2)cc1C(=O)O] | 5-[({2-[(1-benzofuran-2-ylsulfonyl)amino]-4-chlorophenyl}amino)sulfonyl]-2-ethoxybenzoic acid | Method B |

TABLE 1-continued

| Comp. No. | Structure | IUPAC compound name | Synthesis |
|---|---|---|---|
| 327 | 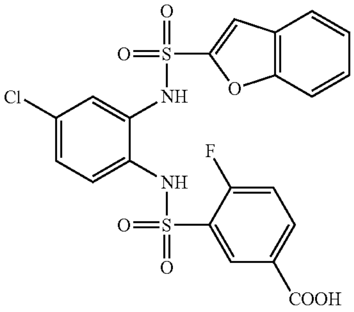 [SMILES: O=C(O)c1ccc(F)c(S(=O)(=O)Nc2ccc(Cl)cc2NS(=O)(=O)c2cc3ccccc3o2)c1] | 3-[({2-[(1-benzofuran-2-ylsulfonyl)amino]-4-chlorophenyl}amino)sulfonyl]-4-fluorobenzoic acid | Method B |
| 328 | 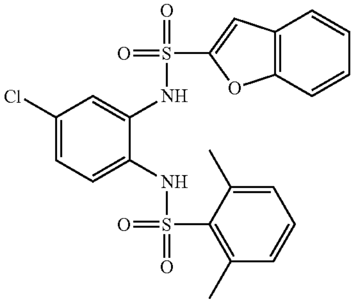 [SMILES: Cc1cccc(C)c1S(=O)(=O)Nc1ccc(Cl)cc1NS(=O)(=O)c1cc2ccccc2o1] | N-(5-chloro-2-{[(2,6-dimethylphenyl)sulfonyl]amino}phenyl)-1-benzofuran-2-sulfonamide | Method A |
| 329 | 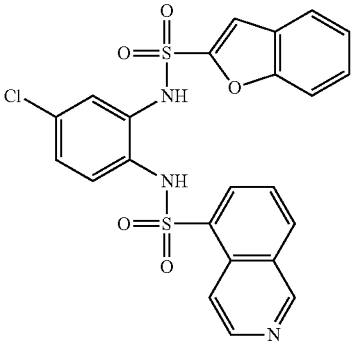 [SMILES: O=S(=O)(Nc1cc(Cl)ccc1NS(=O)(=O)c1cccc2cnccc12)c1cc2ccccc2o1] | N-{2-[(1-benzofuran-2-ylsulfonyl)amino]-4-chlorophenyl}isoquinoline-5-sulfonamide | Method A |
| 330 | 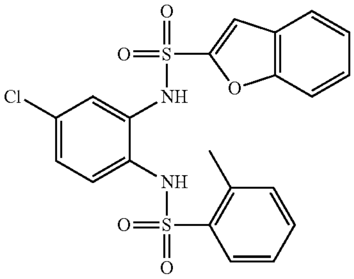 [SMILES: Cc1ccccc1S(=O)(=O)Nc1ccc(Cl)cc1NS(=O)(=O)c1cc2ccccc2o1] | N-(5-chloro-2-{[(2-methylphenyl)sulfonyl]amino}phenyl)-1-benzofuran-2-sulfonamide | Method A |
| 331 | 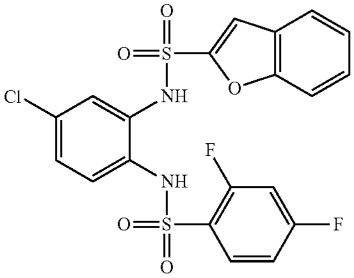 [SMILES: O=S(=O)(Nc1cc(Cl)ccc1NS(=O)(=O)c1ccc(F)cc1F)c1cc2ccccc2o1] | N-(5-chloro-2-{[(2,4-difluorophenyl)sulfonyl]amino}phenyl)-1-benzofuran-2-sulfonamide | Method A |

TABLE 1-continued

| Comp. No. | Structure | IUPAC compound name | Synthesis |
|---|---|---|---|
| 332 | 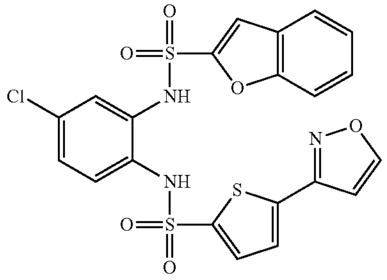 [SMILES: O=S(=O)(Nc1cc(Cl)ccc1NS(=O)(=O)c1ccc(-c2ccon2)s1)c1cc2ccccc2o1] | N-(5-chloro-2-{[(5-isoxazol-3-yl-2-thienyl)sulfonyl]amino}phenyl)-1-benzofuran-2-sulfonamide | Method A |
| 333 | 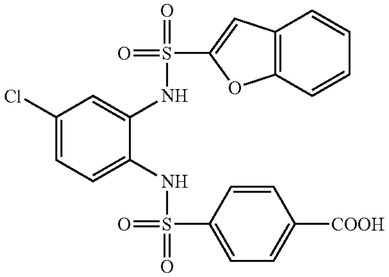 [SMILES: O=C(O)c1ccc(S(=O)(=O)Nc2ccc(Cl)cc2NS(=O)(=O)c2cc3ccccc3o2)cc1] | 4-[({2-[(1-benzofuran-2-ylsulfonyl)amino]-4-chlorophenyl}amino)sulfonyl]benzoic acid | Method B |
| 334 | 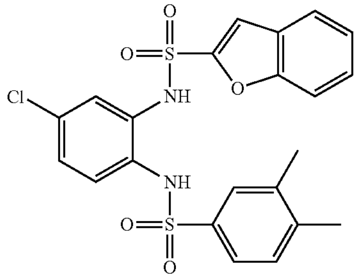 [SMILES: Cc1ccc(S(=O)(=O)Nc2ccc(Cl)cc2NS(=O)(=O)c2cc3ccccc3o2)cc1C] | N-(5-chloro-2-{[(3,4-dimethylphenyl)sulfonyl]amino}phenyl)-1-benzofuran-2-sulfonamide | Method A |
| 335 | 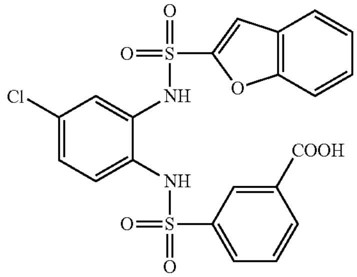 [SMILES: O=C(O)c1cccc(S(=O)(=O)Nc2ccc(Cl)cc2NS(=O)(=O)c2cc3ccccc3o2)c1] | 3-[({2-[(1-benzofuran-2-ylsulfonyl)amino]-4-chlorophenyl}amino)sulfonyl]benzoic acid | Method B |
| 336 | 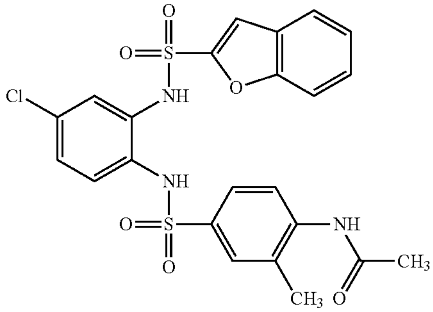 [SMILES: CC(=O)Nc1ccc(S(=O)(=O)Nc2ccc(Cl)cc2NS(=O)(=O)c2cc3ccccc3o2)cc1C] | N-(4-[({2-[(1-benzofuran-2-ylsulfonyl}amino]-4-chlorophenyl}amino)sulfonyl]-2-methylphenyl}acetamide | Method A |

TABLE 1-continued

| Comp. No. | Structure | IUPAC compound name | Synthesis |
|---|---|---|---|
| 337 | 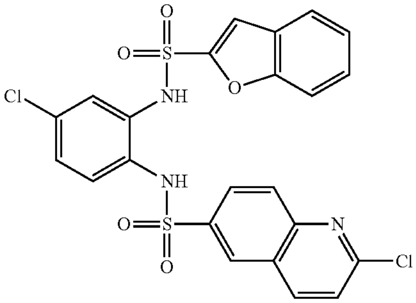 [SMILES: O=S(=O)(Nc1ccc(Cl)cc1NS(=O)(=O)c1cc2ccccc2o1)c1ccc2nc(Cl)ccc2c1] | N-{2-[(1-benzofuran-2-ylsulfonyl)amino]-4-chlorophenyl}-2-chloroquinoline-6-sulfonamide | Method C |
| 338 | 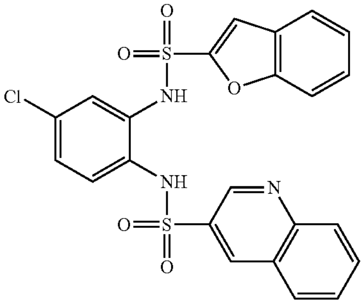 [SMILES: O=S(=O)(Nc1ccc(Cl)cc1NS(=O)(=O)c1cc2ccccc2o1)c1cnc2ccccc2c1] | N-{2-[(1-benzofuran-2-ylsulfonyl)amino]-4-chlorophenyl}quinoline-3-sulfonamide | Method A |
| 339 | 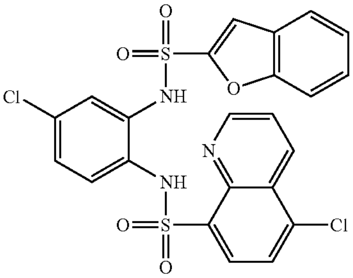 [SMILES: O=S(=O)(Nc1cc(Cl)ccc1NS(=O)(=O)c1ccc(Cl)c2cccnc12)c1cc2ccccc2o1] | N-{2-[(1-benzofuran-2-ylsulfonyl)amino]-4-chlorophenyl}-5-chloroquinoline-6-sulfonamide | Method A |
| 340 | 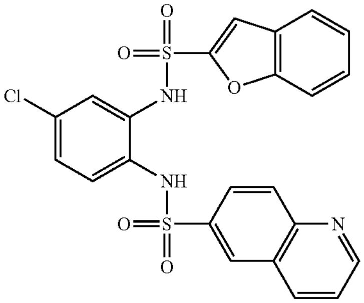 [SMILES: O=S(=O)(Nc1ccc(Cl)cc1NS(=O)(=O)c1cc2ccccc2o1)c1ccc2ncccc2c1] | N-{2-[(1-benzofuran-2-ylsulfonyl)amino]-4-chlorophenyl}quinoline-6-sulfonamide | Method A |
| 341 | 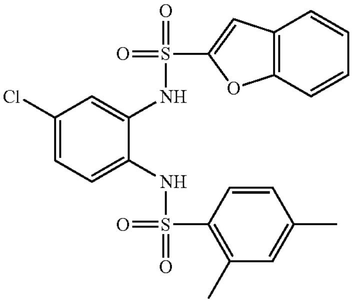 [SMILES: Cc1ccc(S(=O)(=O)Nc2ccc(Cl)cc2NS(=O)(=O)c2cc3ccccc3o2)c(C)c1] | N-(5-chloro-2-{[(2,4-dimethylphenyl)sulfonyl]amino}phenyl)-1-benzofuran-2-sulfonamide | Method A |

TABLE 1-continued

| Comp. No. | Structure | IUPAC compound name | Synthesis |
|---|---|---|---|
| 342 | 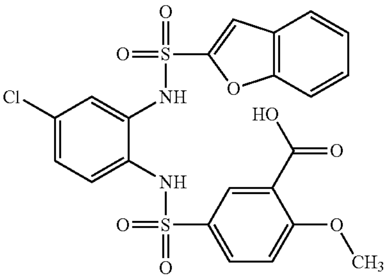 [SMILES: COc1ccc(S(=O)(=O)Nc2ccc(Cl)cc2NS(=O)(=O)c2cc3ccccc3o2)cc1C(=O)O] | 5-[({2-[(1-benzofuran-2-ylsulfonyl)amino]-4-chlorophenyl}amino)sulfonyl]-2-methoxybenzoic acid | Method B |
| 343 | 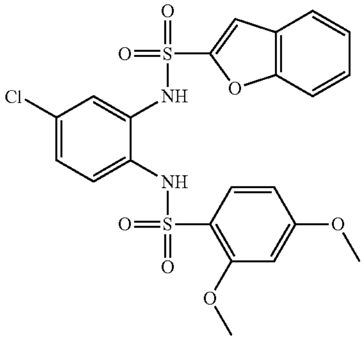 [SMILES: COc1ccc(S(=O)(=O)Nc2ccc(Cl)cc2NS(=O)(=O)c2cc3ccccc3o2)c(OC)c1] | N-(5-chloro-2-{[(2,4-dimethoxyphenyl)sulfonyl]amino}phenyl)-1-benzofuran-2-sulfonamide | Method A |
| 344 | 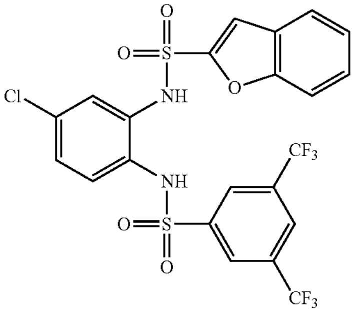 [SMILES: O=S(=O)(Nc1ccc(Cl)cc1NS(=O)(=O)c1cc2ccccc2o1)c1cc(C(F)(F)F)cc(C(F)(F)F)c1] | N-[2-({[3,5-bis(trifluoromethyl)phenyl]sulfonyl}amino)-5-chlorophenyl]-1-benzofuran-2-sulfonamide | Method C |
| 345 | 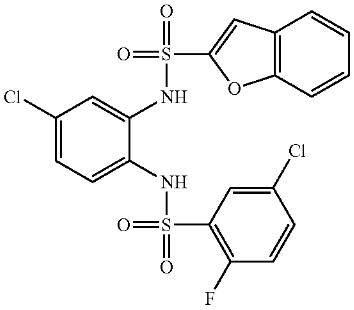 [SMILES: O=S(=O)(Nc1cc(Cl)ccc1NS(=O)(=O)c1cc(Cl)ccc1F)c1cc2ccccc2o1] | N-(5-chloro-2-{[(5-chloro-2-fluorophenyl)sulfonyl]amino}phenyl)-1-benzofuran-2-sulfonamide | Method A |
| 346 | 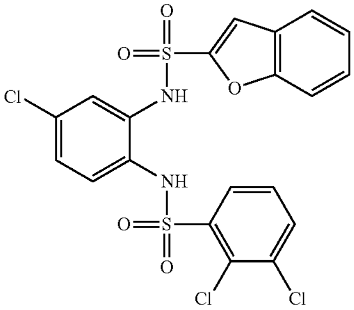 [SMILES: O=S(=O)(Nc1cc(Cl)ccc1NS(=O)(=O)c1cccc(Cl)c1Cl)c1cc2ccccc2o1] | N-(5-chloro-2-{[(2,3-dichlorophenyl)sulfonyl]amino}phenyl)-1-benzofuran-2-sulfonamide | Method A |

TABLE 1-continued

| Comp. No. | Structure | IUPAC compound name | Synthesis |
|---|---|---|---|
| 347 | 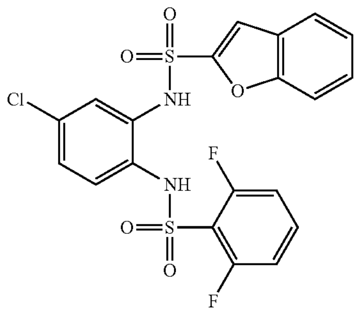 [SMILES: O=S(=O)(Nc1cc(Cl)ccc1NS(=O)(=O)c1c(F)cccc1F)c1cc2ccccc2o1] | N-(5-chloro-2-{[(2,6-difluorophenyl)sulfonyl]amino}phenyl)-1-benzofuran-2-sulfonamide | Method A |
| 348 | 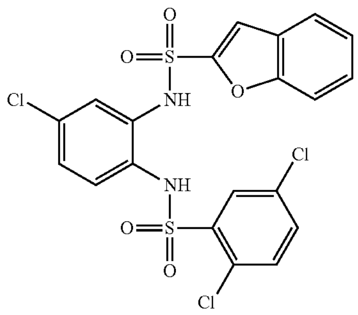 [SMILES: O=S(=O)(Nc1cc(Cl)ccc1NS(=O)(=O)c1cc(Cl)ccc1Cl)c1cc2ccccc2o1] | N-(5-chloro-2-{[(2,5-dichlorophenyl)sulfonyl]amino}phenyl)-1-benzofuran-2-sulfonamide | Method A |
| 349 | 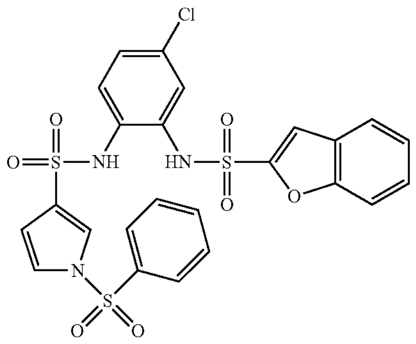 [SMILES: O=S(=O)(Nc1ccc(Cl)cc1NS(=O)(=O)c1cc2ccccc2o1)c1ccn(S(=O)(=O)c2ccccc2)c1] | N-{2-[(1-benzofuran-2-ylsulfonyl)amino]-4-chlorophenyl}-1-(phenylsulfonyl)-1H-pyrrole-3-sulfonamide | Method A |
| 350 | 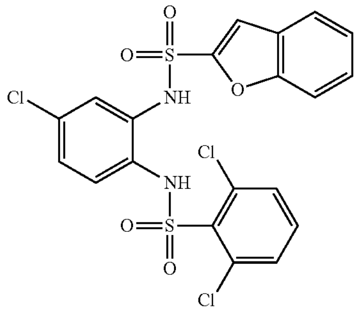 [SMILES: O=S(=O)(Nc1cc(Cl)ccc1NS(=O)(=O)c1c(Cl)cccc1Cl)c1cc2ccccc2o1] | N-(5-chloro-2-{[(2,6-dichlorophenyl)sulfonyl]amino}phenyl)-1-benzofuran-2-sulfonamide | Method A |

TABLE 1-continued

| Comp. No. | Structure | IUPAC compound name | Synthesis |
|---|---|---|---|
| 351 | 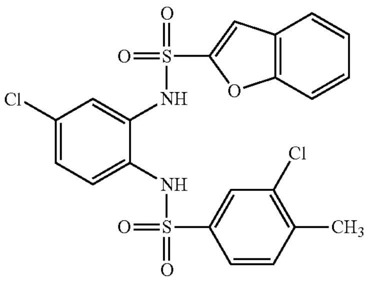 [SMILES: Cc1ccc(S(=O)(=O)Nc2ccc(Cl)cc2NS(=O)(=O)c2cc3ccccc3o2)cc1Cl] | N-(5-chloro-2-{[(3-chloro-4-methylphenyl)sulfonyl]amino}phenyl)-1-benzofuran-2-sulfonamide | Method A |
| 352 | 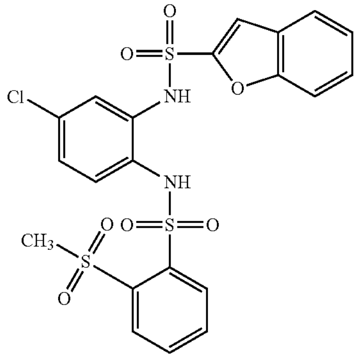 [SMILES: CS(=O)(=O)c1ccccc1S(=O)(=O)Nc1ccc(Cl)cc1NS(=O)(=O)c1cc2ccccc2o1] | N-[5-chloro-2-({[2-(methylsulfonyl)phenyl]sulfonyl}amino)phenyl]-1-benzofuran-2-sulfonamide | Method A |
| 353 | 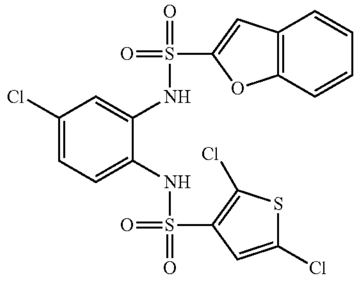 [SMILES: O=S(=O)(Nc1cc(Cl)ccc1NS(=O)(=O)c1cc(Cl)sc1Cl)c1cc2ccccc2o1] | N-(5-chloro-2-{[(2,5-dichloro-3-thienyl)sulfonyl]amino}phenyl)-1-benzofuran-2-sulfonamide | Method C |
| 354 | 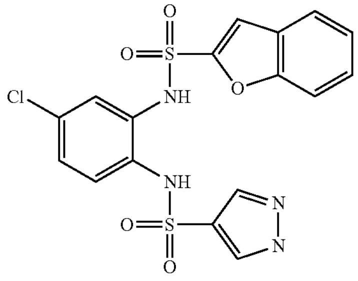 [SMILES: O=S(=O)(Nc1ccc(Cl)cc1NS(=O)(=O)c1cc2ccccc2o1)c1cn[nH]c1] | N-{2-[(1-benzofuran-2-ylsulfonyl)amino]-4-chlorophenyl}-1H-pyrazole-4-sulfonamide | Method A |
| 355 | 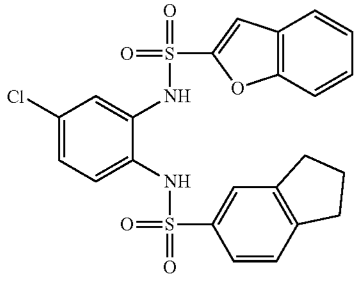 [SMILES: O=S(=O)(Nc1ccc(Cl)cc1NS(=O)(=O)c1cc2ccccc2o1)c1ccc2c(c1)CCC2] | N-{5-chloro-2-[(2,3-dihydro-1H-inden-5-ylsulfonyl)amino]phenyl}-1-benzofuran-2-sulfonamide | Method A |

TABLE 1-continued

| Comp. No. | Structure | IUPAC compound name | Synthesis |
| --- | --- | --- | --- |
| 356 | 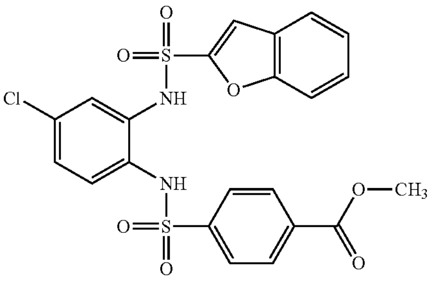 [SMILES: COC(=O)c1ccc(S(=O)(=O)Nc2ccc(Cl)cc2NS(=O)(=O)c2cc3ccccc3o2)cc1] | methyl 4-[({2-[(1-benzofuran-2-ylsulfonyl)amino]-4-chlorophenyl}amino)sulfonyl] benzoate | Method A |
| 357 | 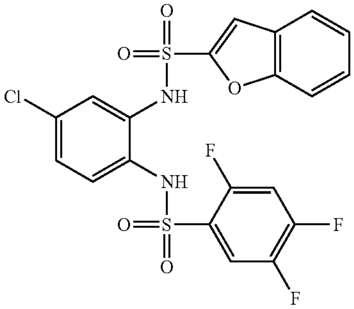 [SMILES: O=S(=O)(Nc1cc(Cl)ccc1NS(=O)(=O)c1cc(F)c(F)cc1F)c1cc2ccccc2o1] | N-(5-chloro-2-{[(2,4,5-trifluorophenyl)sulfonyl] amino}phenyl)-1-benzofuran-2-sulfonamide | Method A |
| 358 | 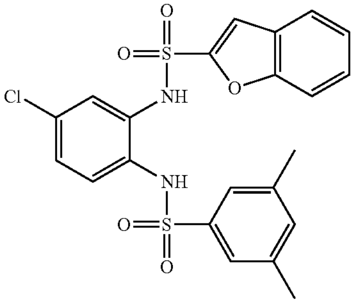 [SMILES: Cc1cc(C)cc(S(=O)(=O)Nc2ccc(Cl)cc2NS(=O)(=O)c2cc3ccccc3o2)c1] | N-(5-chloro-2-{[(3,5-dimethylphenyl)sulfonyl] amino}phenyl)-1-benzofuran-2-sulfonamide | Method A |
| 359 | 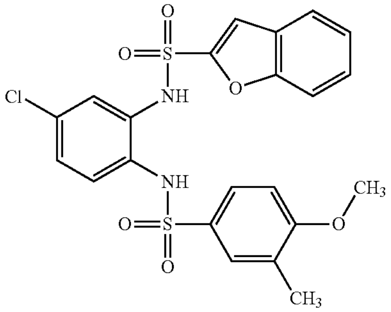 [SMILES: COc1ccc(S(=O)(=O)Nc2ccc(Cl)cc2NS(=O)(=O)c2cc3ccccc3o2)cc1C] | N-(5-chloro-2-{[(4-methoxy-3-methylphenyl)sulfonyl] amino}phenyl)-1-benzofuran-2-sulfonamide | Method A |
| 360 | 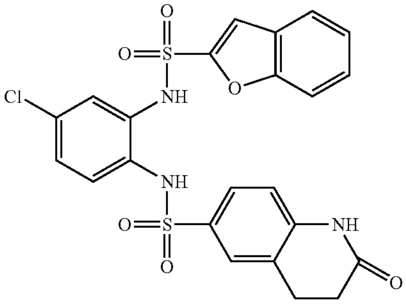 [SMILES: O=C1CCc2cc(S(=O)(=O)Nc3ccc(Cl)cc3NS(=O)(=O)c3cc4ccccc4o3)ccc2N1] | N-{2-[(1-benzofuran-2-ylsulfonyl)amino]-4-chlorophenyl}-2-oxo-1,2,3,4-tetrahydroisoquinoline-6-sulfonamide | Method A |

TABLE 1-continued

| Comp. No. | Structure | IUPAC compound name | Synthesis |
|---|---|---|---|
| 361 | 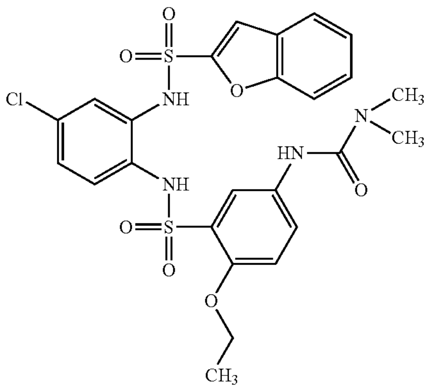 [SMILES: CCOc1ccc(NC(=O)N(C)C)cc1S(=O)(=O)Nc1ccc(Cl)cc1NS(=O)(=O)c1cc2ccccc2o1] | N-(5-chloro-2-{[(5-{[(dimethylamino)carbonyl] amino}-2-ethoxyphenyl)sulfonyl] amino}phenyl)-1-benzofuran-2-sulfonamide | Method A |
| 362 | 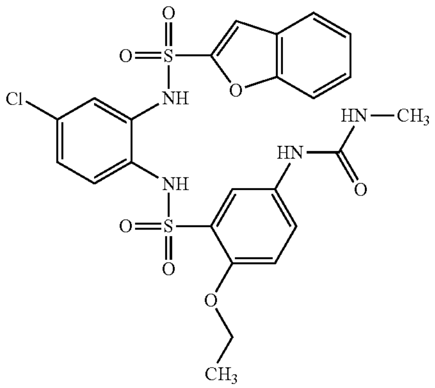 [SMILES: CCOc1ccc(NC(=O)NC)cc1S(=O)(=O)Nc1ccc(Cl)cc1NS(=O)(=O)c1cc2ccccc2o1] | N-(5-chloro-2-{[(2-ethoxy-5-{[(methylamino)carbonyl] amino}phenyl)sulfonyl] amino}phenyl)-1-benzofuran-2-sulfonamide | Method A |
| 363 | 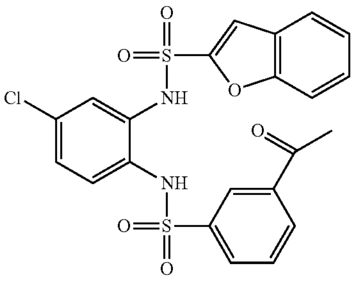 [SMILES: CC(=O)c1cccc(S(=O)(=O)Nc2ccc(Cl)cc2NS(=O)(=O)c2cc3ccccc3o2)c1] | N-(2-{[(4-acetylphenyl)sulfonyl] amino}-5-chlorophenyl)-1-benzofuran-2-sulfonamide | Method A |
| 364 | 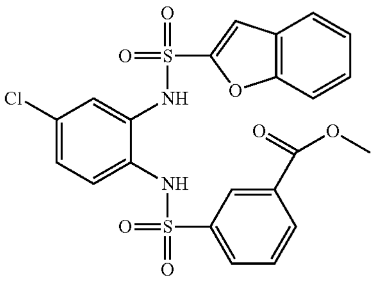 [SMILES: COC(=O)c1cccc(S(=O)(=O)Nc2ccc(Cl)cc2NS(=O)(=O)c2cc3ccccc3o2)c1] | methyl 3-[({2-[(1-benzofuran-2-ylsulfonyl)amino]-4-chlorophenyl}amino)sulfonyl] benzoate | Method A |

TABLE 1-continued

| Comp. No. | Structure | IUPAC compound name | Synthesis |
|---|---|---|---|
| 365 | 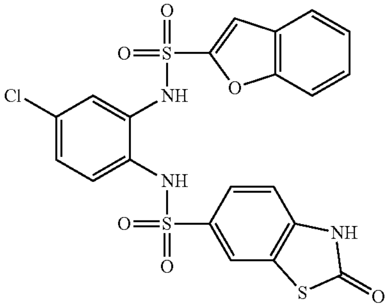 [SMILES: O=c1[nH]c2ccc(S(=O)(=O)Nc3ccc(Cl)cc3NS(=O)(=O)c3cc4ccccc4o3)cc2s1] | N-{2-[(1-benzofuran-2-ylsulfonyl)amino]-4-chlorophenyl}-2-oxo-2,3-dihydro-1,3-benzothiazole-6-sulfonamide | Method A |
| 366 | 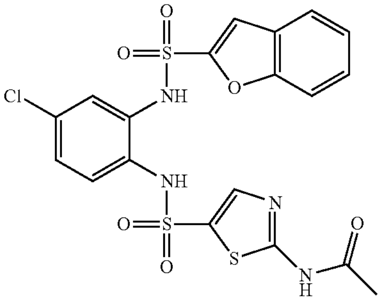 [SMILES: CC(=O)Nc1ncc(S(=O)(=O)Nc2ccc(Cl)cc2NS(=O)(=O)c2cc3ccccc3o2)s1] | N-{5-[({2-[(1-benzofuran-2-ylsulfonyl)amino]-4-chlorophenyl}amino)sulfonyl]-1,3-thiazol-2-yl}acetamide | Method A |
| 367 | 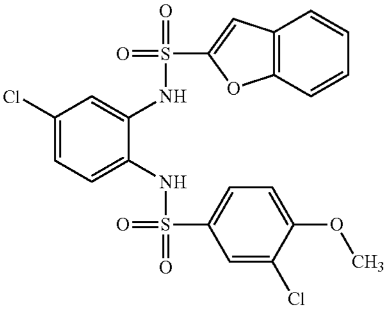 [SMILES: COc1ccc(S(=O)(=O)Nc2ccc(Cl)cc2NS(=O)(=O)c2cc3ccccc3o2)cc1Cl] | N-(5-chloro-2-{[(3-chloro-4-methoxyphenyl)sulfonyl]amino}phenyl)-1-benzofuran-2-sulfonamide | Method A |
| 368 | 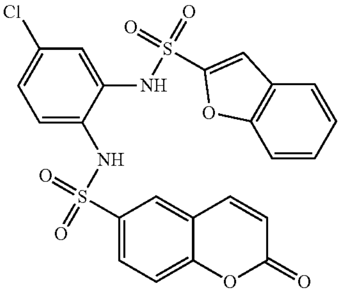 [SMILES: O=c1ccc2cc(S(=O)(=O)Nc3ccc(Cl)cc3NS(=O)(=O)c3cc4ccccc4o3)ccc2o1] | N-{2-[(1-benzofuran-2-ylsulfonyl)amino]-4-chlorophenyl}-2-oxo-2H-chromene-6-sulfonamide | Method A |
| 369 | 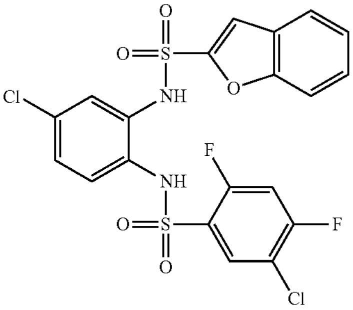 [SMILES: O=S(=O)(Nc1cc(Cl)ccc1NS(=O)(=O)c1cc(Cl)c(F)cc1F)c1cc2ccccc2o1] | N-(5-chloro-2-{[(5-chloro-2,4-difluorophenyl)sulfonyl]amino}phenyl)-1-benzofuran-2-sulfonamide | Method A |

TABLE 1-continued

| Comp. No. | Structure | IUPAC compound name | Synthesis |
|---|---|---|---|
| 370 | 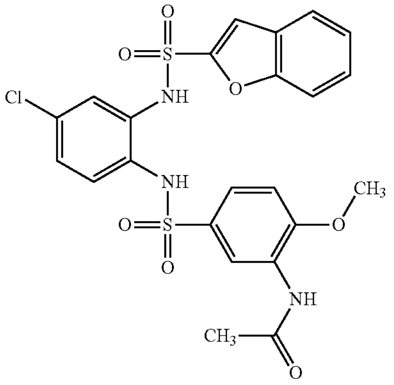 [SMILES: COc1ccc(S(=O)(=O)Nc2ccc(Cl)cc2NS(=O)(=O)c2cc3ccccc3o2)cc1NC(C)=O] | N-{5-[({2-[(1-benzofuran-2-ylsulfonyl)amino]-4-chlorophenyl}amino)sulfonyl]-2-methoxyphenyl}acetamide | Method A |
| 371 | 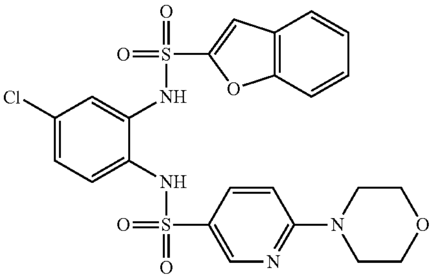 [SMILES: O=S(=O)(Nc1ccc(Cl)cc1NS(=O)(=O)c1cc2ccccc2o1)c1ccc(N2CCOCC2)nc1] | N-{2-[(1-benzofuran-2-ylsulfonyl)amino]-4-chlorophenyl}-6-morpholin-4-ylpyridine-3-sulfonamide | Method A |
| 372 | 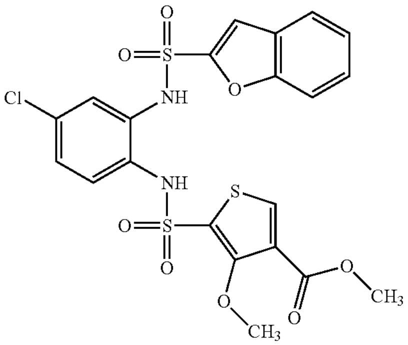 [SMILES: COC(=O)c1csc(S(=O)(=O)Nc2ccc(Cl)cc2NS(=O)(=O)c2cc3ccccc3o2)c1OC] | methyl 5-[({2-[(1-benzofuran-2-ylsulfonyl)amino]-4-chlorophenyl}amino)sulfonyl]-4-methoxythiophene-2-carboxylate | Method C |
| 373 | 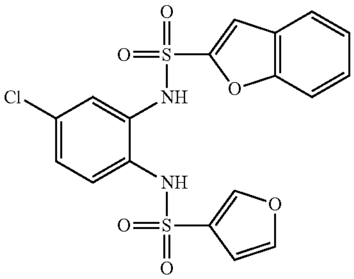 [SMILES: O=S(=O)(Nc1ccc(Cl)cc1NS(=O)(=O)c1cc2ccccc2o1)c1ccoc1] | N-{5-chloro-2-[(3-furylsulfonyl)amino]phenyl}-1-benzofuran-2-sulfonamide | Method C |

TABLE 1-continued

| Comp. No. | Structure | IUPAC compound name | Synthesis |
|---|---|---|---|
| 374 | 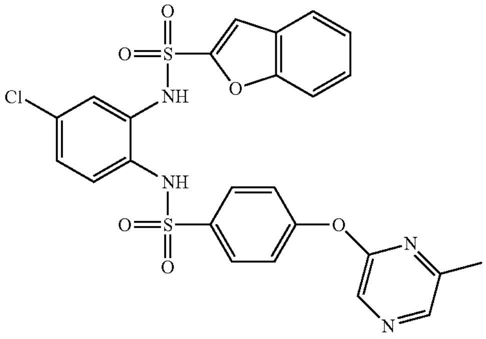 [SMILES: Cc1cncc(Oc2ccc(S(=O)(=O)Nc3ccc(Cl)cc3NS(=O)(=O)c3cc4ccccc4o3)cc2)n1] | N-{5-chloro-2-[({4-[(6-methylpyrazin-2-yl)oxy]phenyl}sulfonyl)amino]phenyl}-1-benzofuran-2-sulfonamide | Method A |
| 375 | 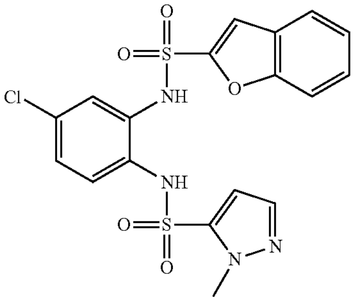 [SMILES: Cn1nccc1S(=O)(=O)Nc1ccc(Cl)cc1NS(=O)(=O)c1cc2ccccc2o1] | N-{2-[(1-benzofuran-2-ylsulfonyl)amino]-4-chlorophenyl}-1-methyl-1H-pyrazole-5-sulfonamide | Method C |
| 376 | 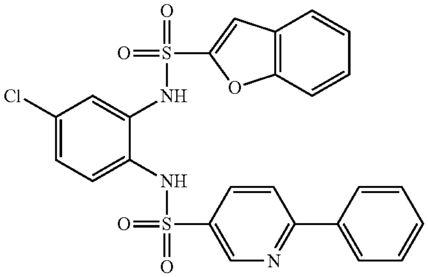 [SMILES: O=S(=O)(Nc1ccc(Cl)cc1NS(=O)(=O)c1cc2ccccc2o1)c1ccc(-c2ccccc2)nc1] | N-{2-[(1-benzofuran-2-ylsulfonyl)amino]-4-chlorophenyl}-6-phenylpyridine-3-sulfonamide | Method C |
| 377 | 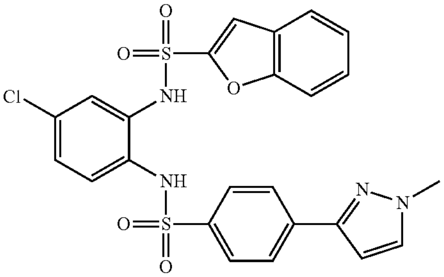 [SMILES: Cn1ccc(-c2ccc(S(=O)(=O)Nc3ccc(Cl)cc3NS(=O)(=O)c3cc4ccccc4o3)cc2)n1] | N-{5-chloro-2-({[4-(1-methyl-1H-pyrazol-3-yl)phenyl]sulfonyl}amino)phenyl]-1-benzofuran-2-sulfonamide | Method A |
| 378 | 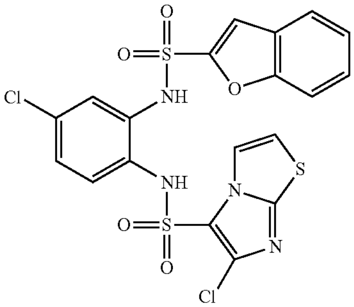 [SMILES: O=S(=O)(Nc1cc(Cl)ccc1NS(=O)(=O)c1c(Cl)nc2sccn12)c1cc2ccccc2o1] | N-{2-[(1-benzofuran-2-ylsulfonyl)amino]-4-chlorophenyl}-6-chloroimidazo[2,1-b][1,3]thiazole-5-sulfonamide | Method C |

TABLE 1-continued

| Comp. No. | Structure | IUPAC compound name | Synthesis |
|---|---|---|---|
| 379 | 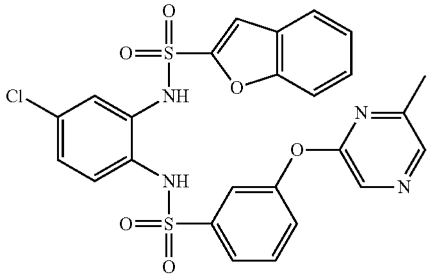 [SMILES: Cc1cncc(Oc2cccc(S(=O)(=O)Nc3ccc(Cl)cc3NS(=O)(=O)c3cc4ccccc4o3)c2)n1] | N-{5-chloro-2-[({3-[(6-methylpyrazin-2-yl)oxy]phenyl}sulfonyl}amino]phenyl}-1-benzofuran-2-sulfonamide | Method A |
| 380 | 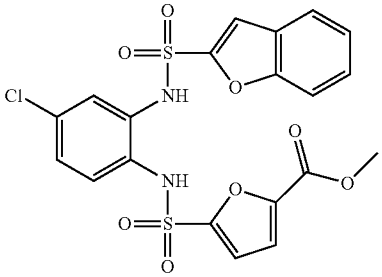 [SMILES: COC(=O)c1ccc(S(=O)(=O)Nc2ccc(Cl)cc2NS(=O)(=O)c2cc3ccccc3o2)o1] | methyl 5-[({2-[(1-benzofuran-2-ylsulfonyl)amino]-4-chlorophenyl}amino)sulfonyl]-2-furoate | Method C |
| 381 | 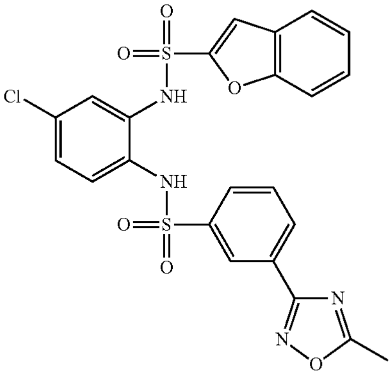 [SMILES: Cc1nc(-c2cccc(S(=O)(=O)Nc3ccc(Cl)cc3NS(=O)(=O)c3cc4ccccc4o3)c2)no1] | N-[5-chloro-2-({[3-(5-methyl-1,2,4-oxadiazol-3-yl)phenyl]sulfonyl}amino)phenyl]-1-benzofuran-2-sulfonamide | Method A |
| 382 | 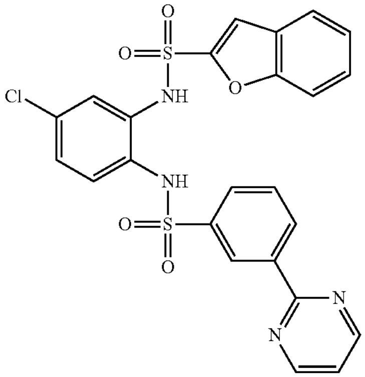 [SMILES: O=S(=O)(Nc1ccc(Cl)cc1NS(=O)(=O)c1cc2ccccc2o1)c1cccc(-c2ncccn2)c1] | N-(5-chloro-2-{[(3-pyrimidin-2-ylphenyl)sulfonyl]amino}phenyl)-1-benzofuran-2-sulfonamide | Method A |

TABLE 1-continued

| Comp. No. | Structure | IUPAC compound name | Synthesis |
|---|---|---|---|
| 383 | 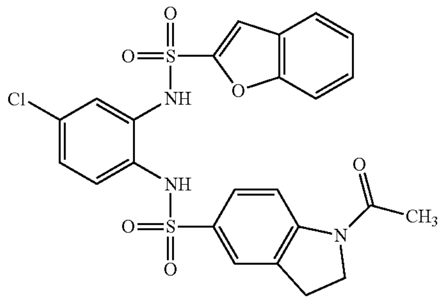 [SMILES: CC(=O)N1CCc2cc(S(=O)(=O)Nc3ccc(Cl)cc3NS(=O)(=O)c3cc4ccccc4o3)ccc21] | 1-acetyl-N-{2-[(1-benzofuran-2-ylsulfonyl)amino]-4-chlorophenyl}indole-5-sulfonamide | Method C |
| 384 | 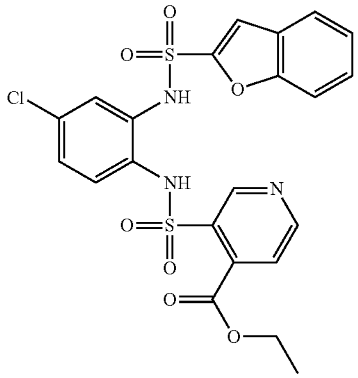 [SMILES: CCOC(=O)c1ccncc1S(=O)(=O)Nc1ccc(Cl)cc1NS(=O)(=O)c1cc2ccccc2o1] | ethyl 3-[({2-[(1-benzofuran-2-ylsulfonyl)amino]-4-chlorophenyl}amino)sulfonyl] isonicotinate | Method A |
| 385 | 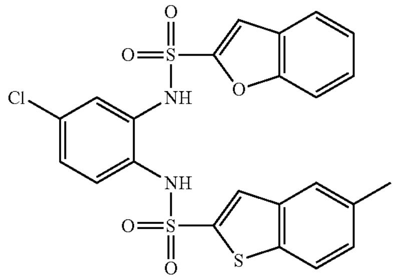 [SMILES: Cc1ccc2sc(S(=O)(=O)Nc3ccc(Cl)cc3NS(=O)(=O)c3cc4ccccc4o3)cc2c1] | N-(5-chloro-2-{[(5-methyl-1-benzofuran-2-yl)sulfonyl]amino}phenyl)-1-benzofuran-2-sulfonamide | Method A |
| 386 | 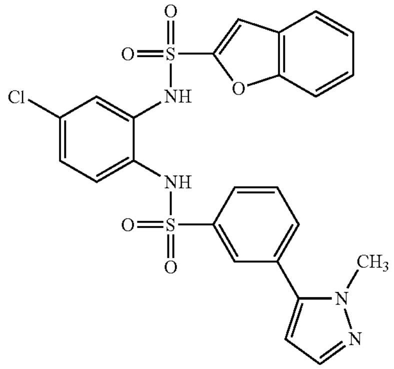 [SMILES: Cn1nccc1-c1cccc(S(=O)(=O)Nc2ccc(Cl)cc2NS(=O)(=O)c2cc3ccccc3o2)c1] | N-[5-chloro-2-({[3-(1-methyl-1H-pyrazol-5-yl)phenyl]sulfonyl}amino) phenyl]-1-benzofuran-2-sulfonamide | Method A |

TABLE 1-continued

| Comp. No. | Structure | IUPAC compound name | Synthesis |
|---|---|---|---|
| 387 | 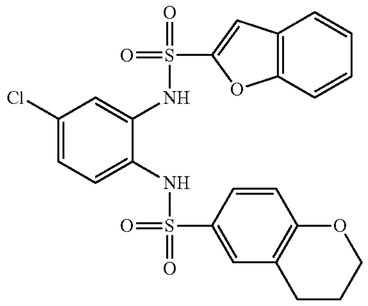 [SMILES: O=S(=O)(Nc1ccc(Cl)cc1NS(=O)(=O)c1cc2ccccc2o1)c1ccc2c(c1)CCCO2] | N-{2-[(1-benzofuran-2-ylsulfonyl)amino]-4-chlorophenyl}chromane-6-sulfonamide | Method A |
| 388 | 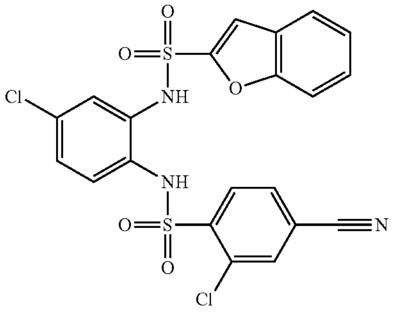 [SMILES: N#Cc1ccc(S(=O)(=O)Nc2ccc(Cl)cc2NS(=O)(=O)c2cc3ccccc3o2)c(Cl)c1] | N-(5-chloro-2-{[(2-chloro-4-cyanophenyl)sulfonyl]amino}phenyl)-1-benzofuran-2-sulfonamide | Method A |
| 389 | 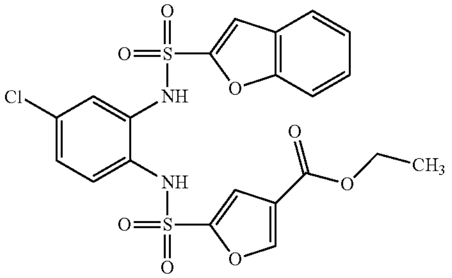 [SMILES: CCOC(=O)c1coc(S(=O)(=O)Nc2ccc(Cl)cc2NS(=O)(=O)c2cc3ccccc3o2)c1] | ethyl 5-[({2-[(1-benzofuran-2-ylsulfonyl)amino]-4-chlorophenyl}amino)sulfonyl]-3-furoate | Method C |
| 390 | 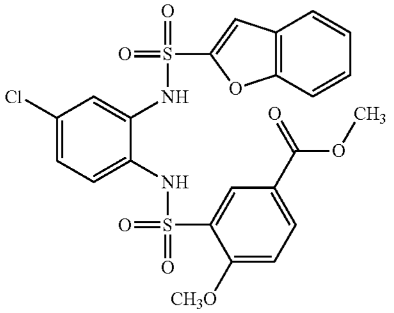 | methyl 3-[({2-[(1-benzofuran-2-ylsulfonyl)amino]-4-chlorophenyl}amino)sulfonyl]-4-methoxybenzoate | Method A |
| 391 | 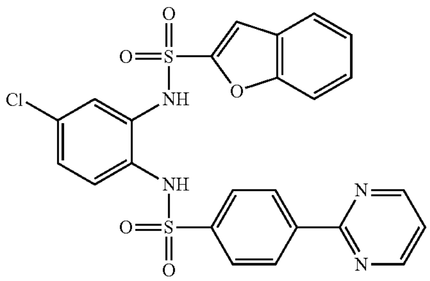 [SMILES: O=S(=O)(Nc1ccc(Cl)cc1NS(=O)(=O)c1cc2ccccc2o1)c1ccc(-c2ncccn2)cc1] | N-(5-chloro-2-{[(4-pyrimidin-2-ylphenyl)sulfonyl]amino}phenyl)-1-benzofuran-2-sulfonamide | Method A |

TABLE 1-continued

| Comp. No. | Structure | IUPAC compound name | Synthesis |
|---|---|---|---|
| 392 | 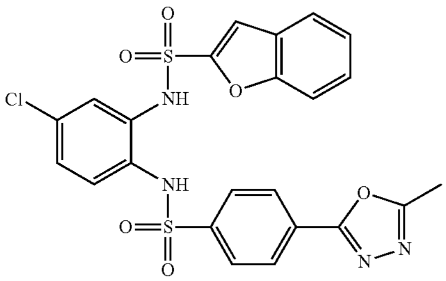 [SMILES: Cc1nnc(-c2ccc(S(=O)(=O)Nc3ccc(Cl)cc3NS(=O)(=O)c3cc4ccccc4o3)cc2)o1] | N-[5-chloro-2-({[3-(5-methyl-1,3,4-oxadiazol-2-yl)phenyl]sulfonyl}amino) phenyl]-1-benzofuran-2-sulfonamide | Method C |
| 393 | 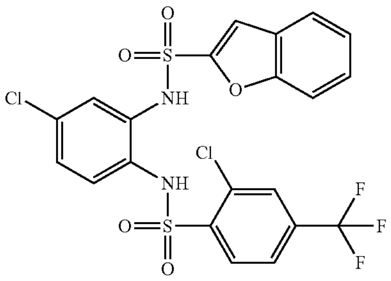 [SMILES: O=S(=O)(Nc1cc(Cl)ccc1NS(=O)(=O)c1ccc(C(F)(F)F)cc1Cl)c1cc2ccccc2o1] | N-[5-chloro-2-({[2-chloro-4-(trifluoromethyl)phenyl] sulfonyl}amino)phenyl]-1-benzofuran-2-sulfonamide | Method A |
| 394 | 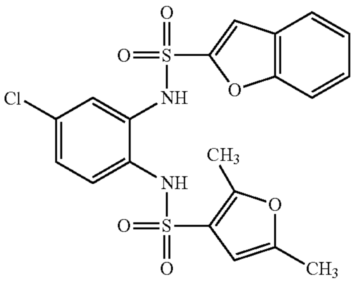 [SMILES: Cc1cc(S(=O)(=O)Nc2ccc(Cl)cc2NS(=O)(=O)c2cc3ccccc3o2)c(C)o1] | N-(5-chloro-2-{[(2,5-dimethyl-3-furyl)sulfonyl]amino} phenyl)-1-benzofuran-2-sulfonamide | Method A |
| 395 | 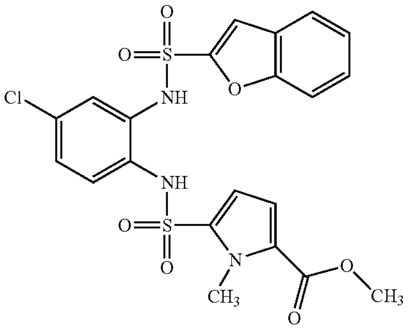 [SMILES: COC(=O)c1ccc(S(=O)(=O)Nc2ccc(Cl)cc2NS(=O)(=O)c2cc3ccccc3o2)n1C] | methyl 5-[({2-[(1-benzofuran-2-ylsulfonyl)amino]-4-chlorophenyl}amino)sulfonyl]-1-methyl-1H-pyrrole-2-carboxylate | Method A |
| 396 | 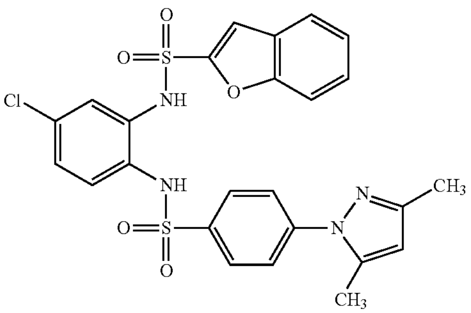 [SMILES: Cc1cc(C)n(-c2ccc(S(=O)(=O)Nc3ccc(Cl)cc3NS(=O)(=O)c3cc4ccccc4o3)cc2)n1] | N-[5-chloro-2-({[4-(3,5-dimethyl-1H-pyrazol-1-yl)phenyl]sulfonyl}amino) phenyl]-1-benzofuran-2-sulfonamide | Method A |

TABLE 1-continued

| Comp. No. | Structure | IUPAC compound name | Synthesis |
|---|---|---|---|
| 397 | 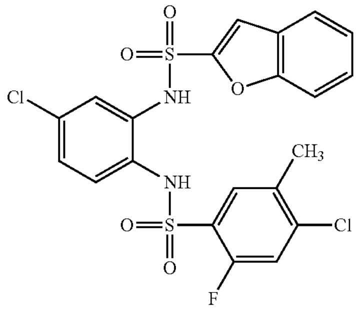 [SMILES: Cc1cc(S(=O)(=O)Nc2ccc(Cl)cc2NS(=O)(=O)c2cc3ccccc3o2)c(F)cc1Cl] | N-(5-chloro-2-{[(4-chloro-2-fluoro-5-methylphenyl)sulfonyl]amino}phenyl)-1-benzofuran-2-sulfonamide | Method A |
| 398 | 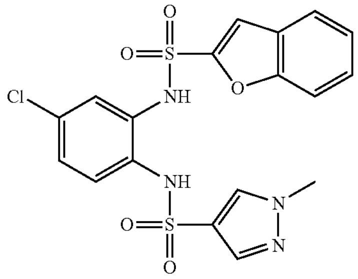 [SMILES: Cn1cc(S(=O)(=O)Nc2ccc(Cl)cc2NS(=O)(=O)c2cc3ccccc3o2)cn1] | N-{2-[(1-benzofuran-2-ylsulfonyl)amino]-4-chlorophenyl}-1-methyl-1H-pyrazole-3-sulfonamide | Method A |
| 399 | 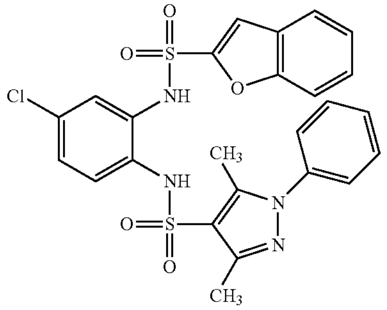 [SMILES: Cc1nn(-c2ccccc2)c(C)c1S(=O)(=O)Nc1ccc(Cl)cc1NS(=O)(=O)c1cc2ccccc2o1] | N-{2-[(1-benzofuran-2-ylsulfonyl)amino]-4-chlorophenyl}-3,5-dimethyl-1-phenyl-1H-pyrazole-4-sulfonamide | Method A |
| 400 | 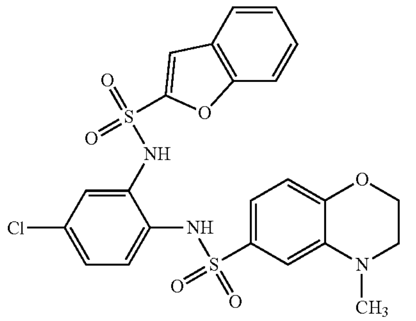 [SMILES: CN1CCOc2ccc(S(=O)(=O)Nc3ccc(Cl)cc3NS(=O)(=O)c3cc4ccccc4o3)cc21] | N-{2-[(1-benzofuran-2-ylsulfonyl)amino]-4-chlorophenyl}-4-methyl-3,4-dihydro-2H-1,4-benzoxazine-6-sulfonamide | Method A |
| 401 | 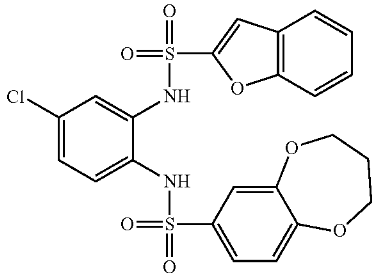 [SMILES: O=S(=O)(Nc1ccc(Cl)cc1NS(=O)(=O)c1cc2ccccc2o1)c1ccc2c(c1)OCCCO2] | N-{2-[(1-benzofuran-2-ylsulfonyl)amino]-4-chlorophenyl}-3,4-dihydro-2H-1,5-benzodioxepine-7-sulfonamide | Method A |

TABLE 1-continued

| Comp. No. | Structure | IUPAC compound name | Synthesis |
|---|---|---|---|
| 402 | 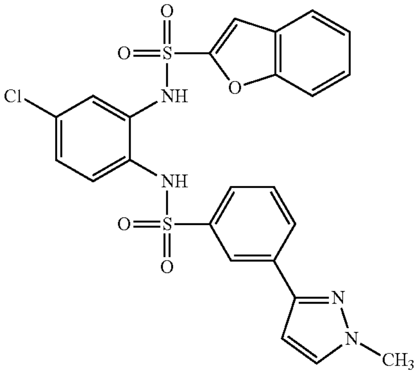 [SMILES: Cn1ccc(-c2cccc(S(=O)(=O)Nc3ccc(Cl)cc3NS(=O)(=O)c3cc4ccccc4o3)c2)n1] | N-[5-chloro-2-({[3-(1-methyl-1H-pyrazol-3-yl)phenyl]sulfonyl}amino) phenyl]-1-benzofuran-2-sulfonamide | Method A |
| 403 | 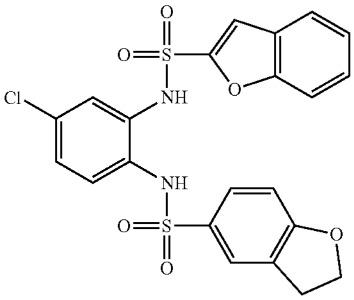 [SMILES: O=S(=O)(Nc1ccc(Cl)cc1NS(=O)(=O)c1cc2ccccc2o1)c1ccc2c(c1)CCO2] | N-{5-chloro-2-[(2,3-dihydro-1-benzofuran-5-ylsulfonyl)amino]phenyl}-1-benzofuran-2-sulfonamide | Method A |
| 404 | 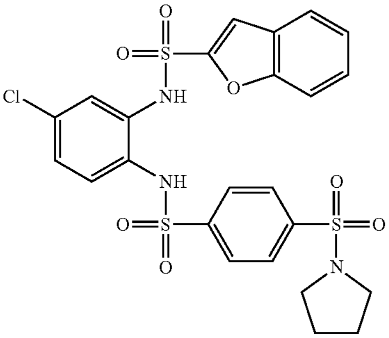 [SMILES: O=S(=O)(Nc1ccc(Cl)cc1NS(=O)(=O)c1cc2ccccc2o1)c1ccc(S(=O)(=O)N2CCCC2)cc1] | N-[5-chloro-2-({[4-(pyrrolidin-1-ylsulfonyl)phenyl]sulfonyl} amino)phenyl]-1-benzofuran-2-sulfonamide | Method A |
| 405 | 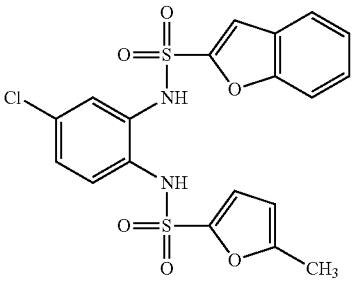 [SMILES: Cc1ccc(S(=O)(=O)Nc2ccc(Cl)cc2NS(=O)(=O)c2cc3ccccc3o2)o1] | N-(5-chloro-2-{[(5-methyl-2-furyl)sulfonyl]amino}phenyl)-1-benzofuran-2-sulfonamide | Method A |

TABLE 1-continued

| Comp. No. | Structure | IUPAC compound name | Synthesis |
|---|---|---|---|
| 406 | 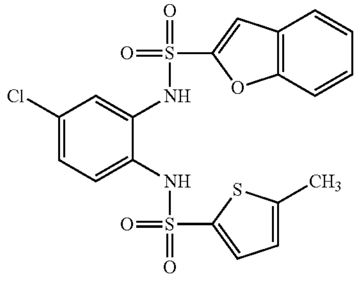 [SMILES: Cc1ccc(S(=O)(=O)Nc2ccc(Cl)cc2NS(=O)(=O)c2cc3ccccc3o2)s1] | N-(5-chloro-2-{[(5-methyl-2-thienyl)sulfonyl]amino}phenyl)-1-benzofuran-2-sulfonamide | Method A |
| 407 | 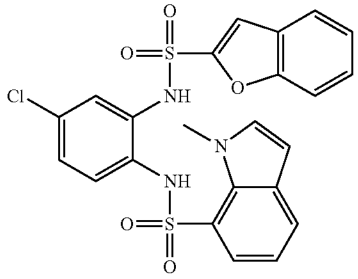 [SMILES: Cn1ccc2cccc(S(=O)(=O)Nc3ccc(Cl)cc3NS(=O)(=O)c3cc4ccccc4o3)c21] | N-{2-[(1-benzofuran-2-ylsulfonyl)amino]-4-chlorophenyl}-1-methyl-1H-indole-7-sulfonamide | Method A |
| 408 | 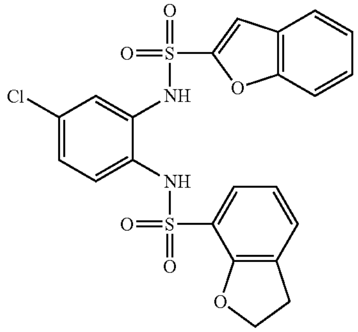 [SMILES: O=S(=O)(Nc1cc(Cl)ccc1NS(=O)(=O)c1cccc2c1OCC2)c1cc2ccccc2o1] | N-{5-chloro-2-[(2,3-dihydro-1-benzofuran-7-ylsulfonyl)amino]phenyl}-1-benzofuran-2-sulfonamide | Method A |
| 409 | 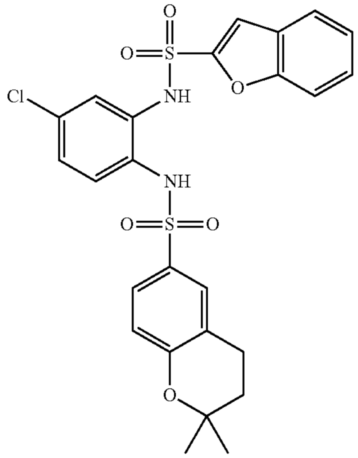 [SMILES: CC1(C)CCc2cc(S(=O)(=O)Nc3ccc(Cl)cc3NS(=O)(=O)c3cc4ccccc4o3)ccc2O1] | N-{2-[(1-benzofuran-2-ylsulfonyl)amino]-4-chlorophenyl}-2,2-dimethylchromane-6-sulfonamide | Method A |

TABLE 1-continued

| Comp. No. | Structure | IUPAC compound name | Synthesis |
|---|---|---|---|
| 410 | 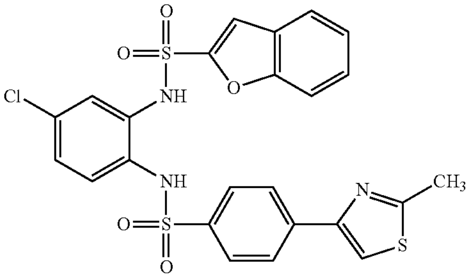 [SMILES: Cc1nc(-c2ccc(S(=O)(=O)Nc3ccc(Cl)cc3NS(=O)(=O)c3cc4ccccc4o3)cc2)cs1] | N-[5-chloro-2-({[4-(2-methyl-1,3-thiazol-4-yl)phenyl]sulfonyl}amino)phenyl]-1-benzofuran-2-sulfonamide | Method A |
| 411 | 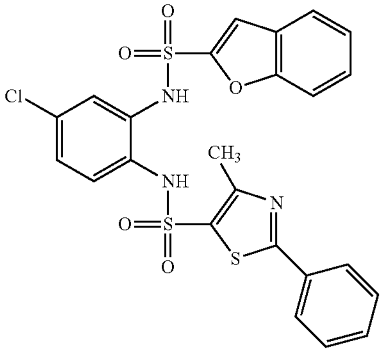 [SMILES: Cc1nc(-c2ccccc2)sc1S(=O)(=O)Nc1ccc(Cl)cc1NS(=O)(=O)c1cc2ccccc2o1] | N-{2-[(1-benzofuran-2-ylsulfonyl)amino]-4-chlorophenyl}-4-methyl-2-phenyl-1,3-thiazole-5-sulfonamide | Method A |
| 412 | 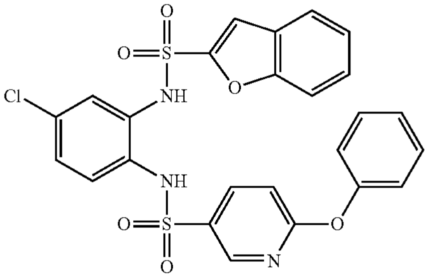 [SMILES: O=S(=O)(Nc1ccc(Cl)cc1NS(=O)(=O)c1cc2ccccc2o1)c1ccc(Oc2ccccc2)nc1] | N-{2-[(1-benzofuran-2-ylsulfonyl)amino]-4-chlorophenyl}-6-phenoxypyridine-3-sulfonamide | Method A |
| 413 | 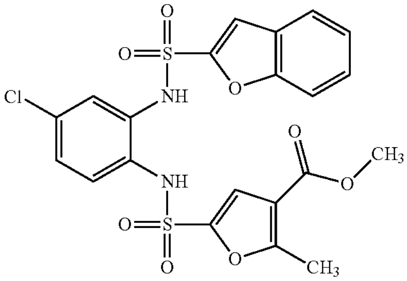 [SMILES: COC(=O)c1cc(S(=O)(=O)Nc2ccc(Cl)cc2NS(=O)(=O)c2cc3ccccc3o2)oc1C] | methyl 5-[({2-[(1-benzofuran-2-ylsulfonyl)amino]-4-chlorophenyl}amino)sulfonyl]-2-methyl-3-furoate | Method A |
| 414 | 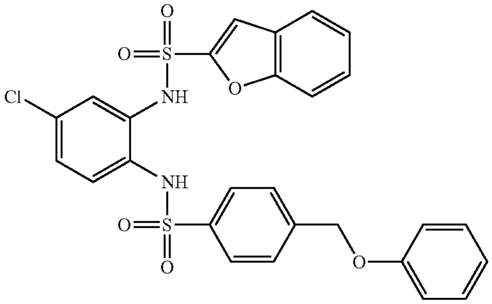 [SMILES: O=S(=O)(Nc1ccc(Cl)cc1NS(=O)(=O)c1cc2ccccc2o1)c1ccc(COc2ccccc2)cc1] | N-[5-chloro-2-({[4-(phenoxymethyl)phenyl]sulfonyl}amino)phenyl]-1-benzofuran-2-sulfonamide | Method A |

TABLE 1-continued

| Comp. No. | Structure | IUPAC compound name | Synthesis |
| --- | --- | --- | --- |
| 415 | 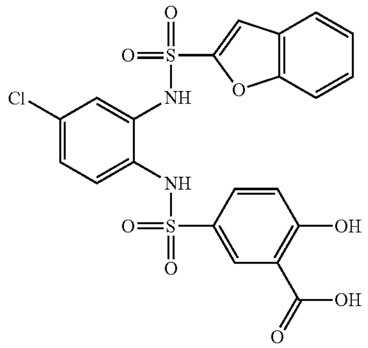 [SMILES: O=C(O)c1cc(S(=O)(=O)Nc2ccc(Cl)cc2NS(=O)(=O)c2cc3ccccc3o2)ccc1O] | 5-[({2-[(1-benzofuran-2-ylsulfonyl)amino]-4-chlorophenyl}amino)sulfonyl]-2-hydroxybenzoic acid | Method B |
| 416 | 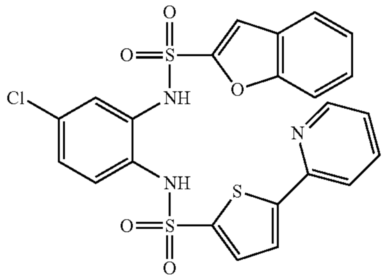 [SMILES: O=S(=O)(Nc1cc(Cl)ccc1NS(=O)(=O)c1ccc(-c2ccccn2)s1)c1cc2ccccc2o1] | N-(5-chloro-2-{[(5-pyridin-2-yl-2-thienyl)sulfonyl]amino}phenyl)-1-benzofuran-2-sulfonamide | Method A |
| 417 | 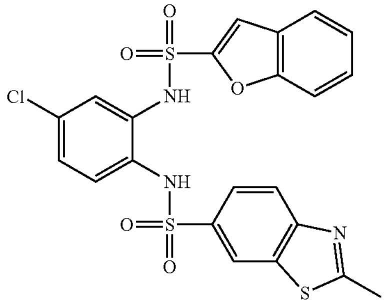 [SMILES: Cc1nc2ccc(S(=O)(=O)Nc3ccc(Cl)cc3NS(=O)(=O)c3cc4ccccc4o3)cc2s1] | N-{2-[(1-benzofuran-2-ylsulfonyl)amino]-4-chlorophenyl}-2-methyl-1,3-benzothiazole-6-sulfonamide | Method A |
| 418 | 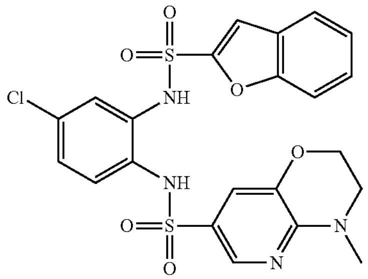 [SMILES: CN1CCOc2cc(S(=O)(=O)Nc3ccc(Cl)cc3NS(=O)(=O)c3cc4ccccc4o3)cnc21] | N-{2-[(1-benzofuran-2-ylsulfonyl)amino]-4-chlorophenyl}-4-methyl-3,4-dihydro-2H-pyrido[3,2-b][1,4]oxazine-7-sulfonamide | Method A |
| 419 | 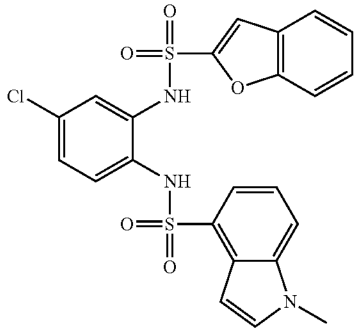 [SMILES: Cn1ccc2c(S(=O)(=O)Nc3ccc(Cl)cc3NS(=O)(=O)c3cc4ccccc4o3)cccc21] | N-{2-[(1-benzofuran-2-ylsulfonyl)amino]-4-chlorophenyl}-1-methyl-1H-indole-4-sulfonamide | Method A |

TABLE 1-continued

| Comp. No. | Structure | IUPAC compound name | Synthesis |
| --- | --- | --- | --- |
| 420 | 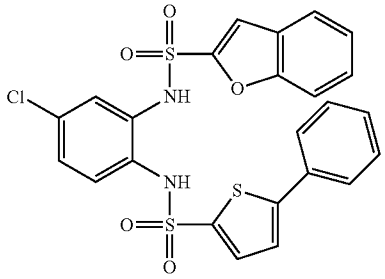 [SMILES: O=S(=O)(Nc1cc(Cl)ccc1NS(=O)(=O)c1ccc(-c2ccccc2)s1)c1cc2ccccc2o1] | N-(5-chloro-2-{[(5-phenyl-2-thienyl)sulfonyl]amino}phenyl)-1-benzofuran-2-sulfonamide | Method A |
| 421 | 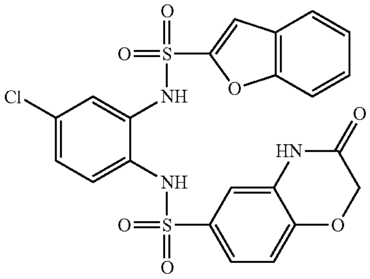 [SMILES: O=C1COc2ccc(S(=O)(=O)Nc3ccc(Cl)cc3NS(=O)(=O)c3cc4ccccc4o3)cc2N1] | N-{2-[(1-benzofuran-2-ylsulfonyl)amino]-4-chlorophenyl}-3-oxo-3,4-dihydro-2H-1,4-benzoxazine-6-sulfonamide | Method A |
| 422 | 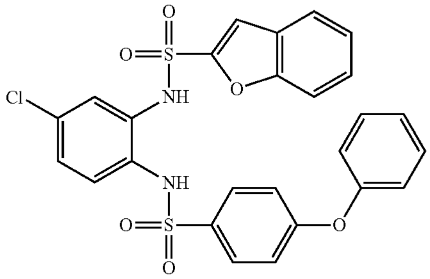 [SMILES: O=S(=O)(Nc1ccc(Cl)cc1NS(=O)(=O)c1cc2ccccc2o1)c1ccc(Oc2ccccc2)cc1] | N-(5-chloro-2-{[(4-phenoxyphenyl)sulfonyl]amino}phenyl)-1-benzofuran-2-sulfonamide | Method A |
| 423 | 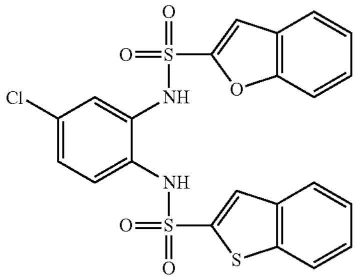 [SMILES: O=S(=O)(Nc1cc(Cl)ccc1NS(=O)(=O)c1cc2ccccc2s1)c1cc2ccccc2o1] | N-{2-[(1-benzothien-2-ylsulfonyl)amino]-5-chlorophenyl}-1-benzofuran-2-sulfonamide | Method A |
| 424 | 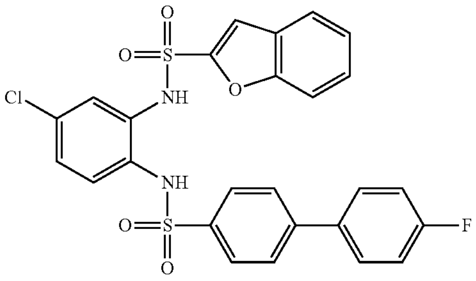 [SMILES: O=S(=O)(Nc1ccc(Cl)cc1NS(=O)(=O)c1cc2ccccc2o1)c1ccc(-c2ccc(F)cc2)cc1] | N-(5-chloro-2-{[(4'-fluorobiphenyl-4-yl)sulfonyl]amino}phenyl)-1-benzofuran-2-sulfonamide | Method A |

TABLE 1-continued

| Comp. No. | Structure | IUPAC compound name | Synthesis |
|---|---|---|---|
| 425 | 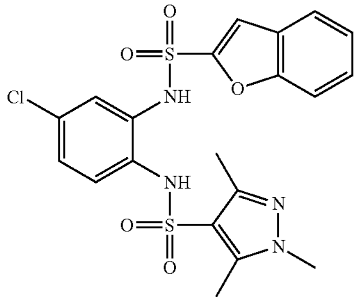 [SMILES: Cc1nn(C)c(C)c1S(=O)(=O)Nc1ccc(Cl)cc1NS(=O)(=O)c1cc2ccccc2o1] | N-{2-[(1-benzofuran-2-ylsulfonyl)amino]-4-chlorophenyl}-1,3,5-trimethyl-1H-pyrazole-4-sulfonamide | Method A |
| 426 | 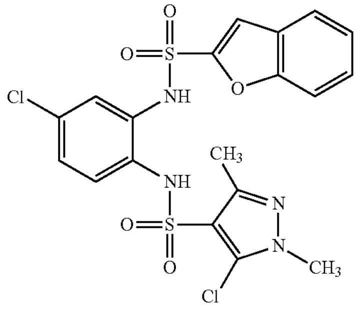 [SMILES: Cc1nn(C)c(Cl)c1S(=O)(=O)Nc1ccc(Cl)cc1NS(=O)(=O)c1cc2ccccc2o1] | N-{2-[(1-benzofuran-2-ylsulfonyl)amino]-4-chlorophenyl}-5-chloro-1,3-dimethyl-1H-pyrazole-4-sulfonamide | Method A |
| 427 | 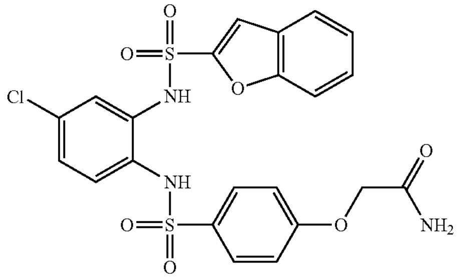 [SMILES: NC(=O)COc1ccc(S(=O)(=O)Nc2ccc(Cl)cc2NS(=O)(=O)c2cc3ccccc3o2)cc1] | 2-{4-[({2-[(1-benzofuran-2-ylsulfonyl)amino]-4-chlorpophenyl}amino)sulfonyl]phenoxy}acetamide | Method A |
| 428 | 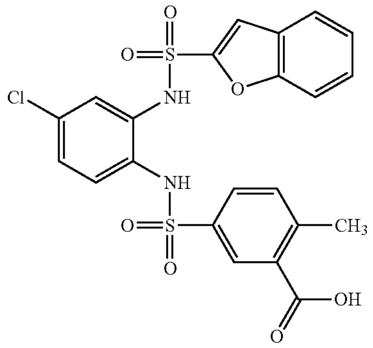 [SMILES: Cc1ccc(S(=O)(=O)Nc2ccc(Cl)cc2NS(=O)(=O)c2cc3ccccc3o2)cc1C(=O)O] | 5-[({2-[(1-benzofuran-2-ylsulfonyl)amino]-4-chlorophenyl}amino)sulfonyl]-2-methylbenzoic acid | Method B |

TABLE 1-continued

| Comp. No. | Structure | IUPAC compound name | Synthesis |
|---|---|---|---|
| 429 | 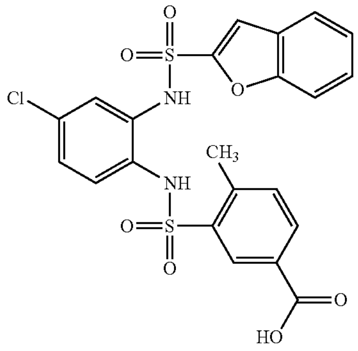 [SMILES: Cc1ccc(C(=O)O)cc1S(=O)(=O)Nc1ccc(Cl)cc1NS(=O)(=O)c1cc2ccccc2o1] | 3-[({2-[(1-benzofuran-2-ylsulfonyl)amino]-4-chlorophenyl}amino)sulfonyl]-4-methylbenzoic acid | Method B |
| 430 | 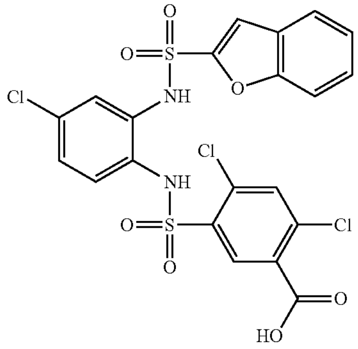 [SMILES: O=C(O)c1cc(S(=O)(=O)Nc2ccc(Cl)cc2NS(=O)(=O)c2cc3ccccc3o2)c(Cl)cc1Cl] | 5-[({2-[(1-benzofuran-2-ylsulfonyl)amino]-4-chlorophenyl}amino)sulfonyl]-2,4-dichlorobenzoic acid | Method B |
| 431 | 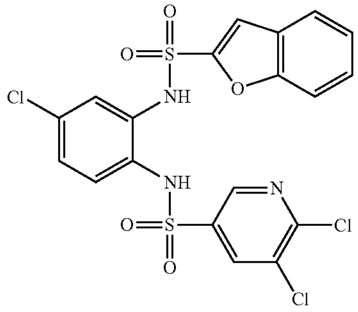 [SMILES: O=S(=O)(Nc1ccc(Cl)cc1NS(=O)(=O)c1cc2ccccc2o1)c1cnc(Cl)c(Cl)c1] | N-{2-[(1-benzofuran-2-ylsulfonyl)amino]-4-chlorophenyl}-5,6-dichloropyridine-3-sulfonamide | Method C |
| 432 | 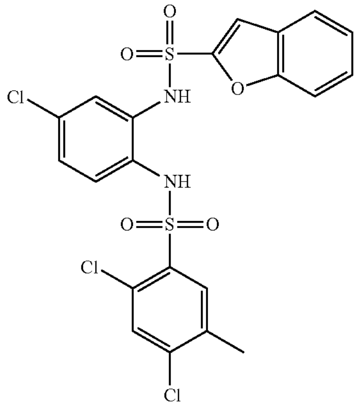 [SMILES: Cc1cc(S(=O)(=O)Nc2ccc(Cl)cc2NS(=O)(=O)c2cc3ccccc3o2)c(Cl)cc1Cl] | N-(5-chloro-2-{[(2,4-dichloro-5-methylphenyl)sulfonyl]amino}phenyl)-1-benzofuran-2-sulfonamide | Method A |

TABLE 1-continued

| Comp. No. | Structure | IUPAC compound name | Synthesis |
|---|---|---|---|
| 433 | 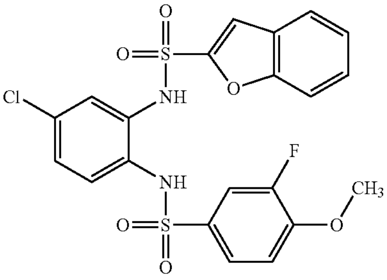 [SMILES: COc1ccc(S(=O)(=O)Nc2ccc(Cl)cc2NS(=O)(=O)c2cc3ccccc3o2)cc1F] | N-(5-chloro-2-{[(3-fluoro-4-methoxyphenyl)sulfonyl] amino}phenyl)-1-benzofuran-2-sulfonamide | Method A |
| 434 | 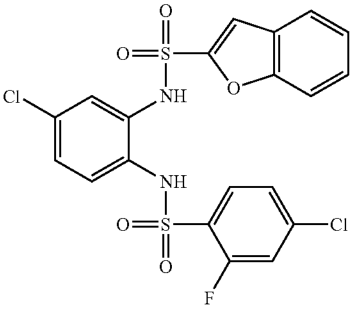 [SMILES: O=S(=O)(Nc1cc(Cl)ccc1NS(=O)(=O)c1ccc(Cl)cc1F)c1cc2ccccc2o1] | N-(5-chloro-2-{[(4-chloro-2-fluorophenyl)sulfonyl] amino}phenyl)-1-benzofuran-2-sulfonamide | Method A |
| 435 | 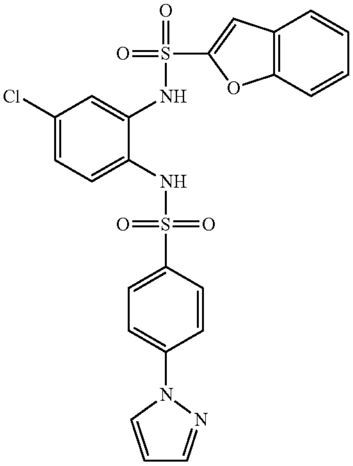 [SMILES: O=S(=O)(Nc1ccc(Cl)cc1NS(=O)(=O)c1cc2ccccc2o1)c1ccc(-n2cccn2)cc1] | N-[5-chloro-2-({[4-(1H-pyrazol-1-yl)phenyl]sulfonyl}amino) phenyl]-1-benzofuran-2-sulfonamide | Method A |
| 436 | 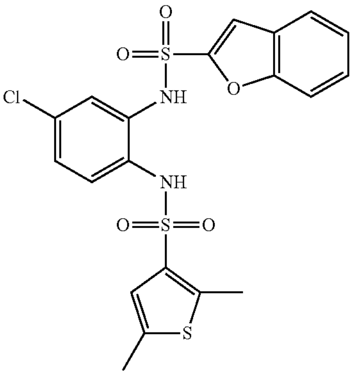 [SMILES: Cc1cc(S(=O)(=O)Nc2ccc(Cl)cc2NS(=O)(=O)c2cc3ccccc3o2)c(C)s1] | N-(5-chloro-2-{[(2,5-dimethyl-3-thienyl)sulfonyl]amino}phenyl)-1-benzofuran-2-sulfonamide | Method A |

TABLE 1-continued
| Comp. No. | Structure | IUPAC compound name | Synthesis |
|---|---|---|---|
| 437 | 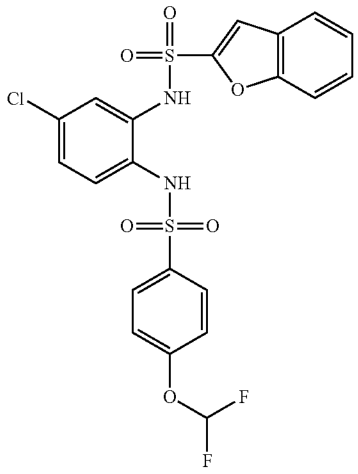 [SMILES: O=S(=O)(Nc1ccc(Cl)cc1NS(=O)(=O)c1cc2ccccc2o1)c1ccc(OC(F)F)cc1] | N-[5-chloro-2-({[4-(difluoromethoxy)phenyl] sulfonyl}amino)phenyl]-1-benzofuran-2-sulfonamide | Method A |
| 438 | 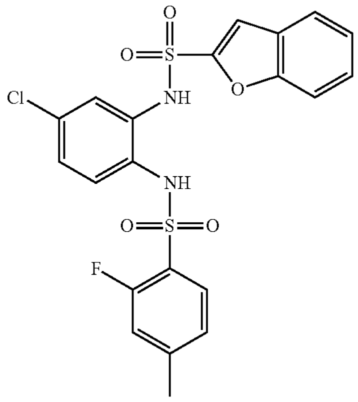 [SMILES: Cc1ccc(S(=O)(=O)Nc2ccc(Cl)cc2NS(=O)(=O)c2cc3ccccc3o2)c(F)c1] | N-(5-chloro-2-{[(2-fluoro-4-methylphenyl)sulfonyl] amino}phenyl)-1-benzofuran-2-sulfonamide | Method A |
| 439 | 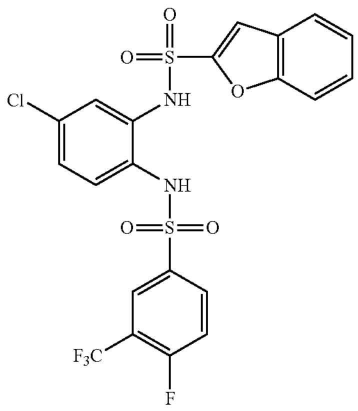 [SMILES: O=S(=O)(Nc1ccc(Cl)cc1NS(=O)(=O)c1cc2ccccc2o1)c1ccc(F)c(C(F)(F)F)c1] | N-[5-chloro-2-({[4-fluoro-3-(trifluoromethyl)phenyl] sulfonyl}amino)phenyl]-1-benzofuran-2-sulfonamide | Method A |

TABLE 1-continued
| Comp. No. | Structure | IUPAC compound name | Synthesis |
|---|---|---|---|
| 440 | 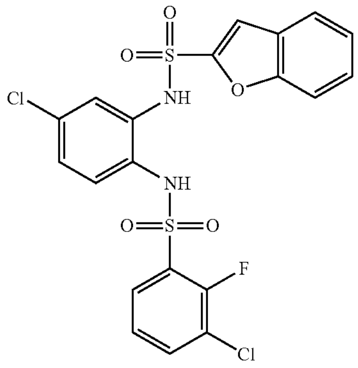 [SMILES: O=S(=O)(Nc1cc(Cl)ccc1NS(=O)(=O)c1cccc(Cl)c1F)c1cc2ccccc2o1] | N-(5-chloro-2-{[(3-chloro-2-fluorophenyl)sulfonyl] amino}phenyl)-1-benzofuran-2-sulfonamide | Method C |
| 441 | 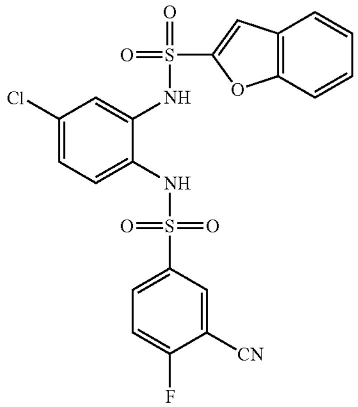 [SMILES: N#Cc1cc(S(=O)(=O)Nc2ccc(Cl)cc2NS(=O)(=O)c2cc3ccccc3o2)ccc1F] | N-(5-chloro-2-{[(3-cyano-4-fluorophenyl)sulfonyl] amino}phenyl)-1-benzofuran-2-sulfonamide | Method A |
| 442 | 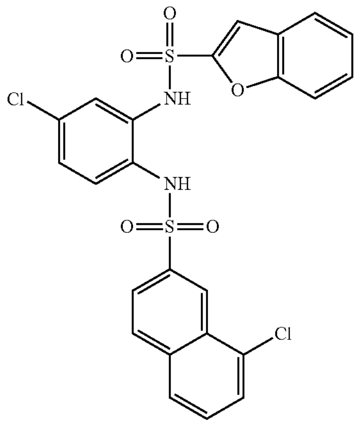 [SMILES: O=S(=O)(Nc1ccc(Cl)cc1NS(=O)(=O)c1cc2ccccc2o1)c1ccc2cccc(Cl)c2c1] | N-(5-chloro-2-{[(5-chloro-2-naphthyl)sulfonyl]amino} phenyl)-1-benzofuran-2-sulfonamide | Method A |

TABLE 1-continued

| Comp. No. | Structure | IUPAC compound name | Synthesis |
|---|---|---|---|
| 443 | 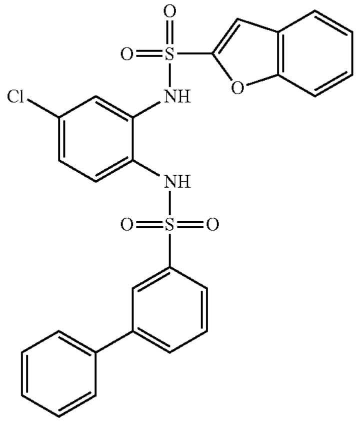 [SMILES: O=S(=O)(Nc1ccc(Cl)cc1NS(=O)(=O)c1cc2ccccc2o1)c1cccc(-c2ccccc2)c1] | N-{2-[(biphenyl-3-ylsulfonyl)amino]-5-chlorophenyl}-1-benzofuran-2-sulfonamide | Method A |
| 444 | 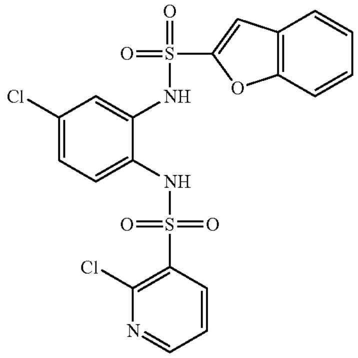 [SMILES: O=S(=O)(Nc1cc(Cl)ccc1NS(=O)(=O)c1cccnc1Cl)c1cc2ccccc2o1] | N-{2-[(1-benzofuran-2-ylsulfonyl)amino]-4-chlorophenyl}-2-chloropyridine-3-sulfonamide | Method A |
| 445 | 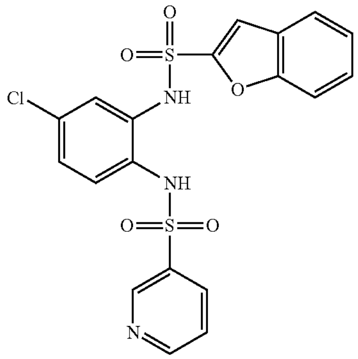 [SMILES: O=S(=O)(Nc1ccc(Cl)cc1NS(=O)(=O)c1cc2ccccc2o1)c1cccnc1] | N-{2-[(1-benzofuran-2-ylsulfonyl)amino]-4-chlorophenyl}pyridine-3-sulfonamide | Method A |
| 446 | 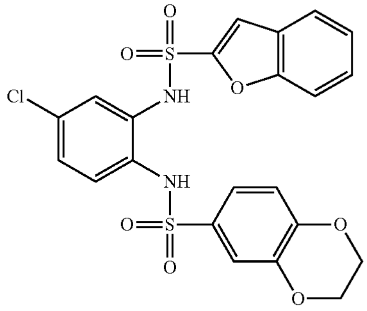 [SMILES: O=S(=O)(Nc1ccc(Cl)cc1NS(=O)(=O)c1cc2ccccc2o1)c1ccc2c(c1)OCCO2] | N-{2-[(1-benzofuran-2-ylsulfonyl)amino]-4-chlorophenyl}-2,3-dihydro-1,4-benzodioxine-6-sulfonamide | Method A |

TABLE 1-continued

| Comp. No. | Structure | IUPAC compound name | Synthesis |
|---|---|---|---|
| 447 | 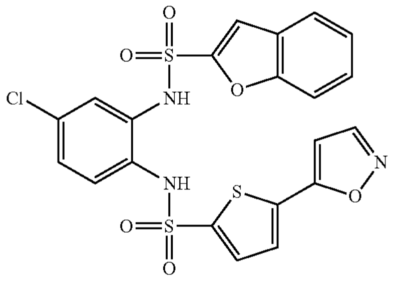 [SMILES: O=S(=O)(Nc1cc(Cl)ccc1NS(=O)(=O)c1ccc(-c2ccno2)s1)c1cc2ccccc2o1] | N-(5-chloro-2-{[(5-isoxazol-5-yl-2-thienyl)sulfonyl]amino}phenyl)-1-benzofuran-2-sulfonamide | Method A |
| 448 | 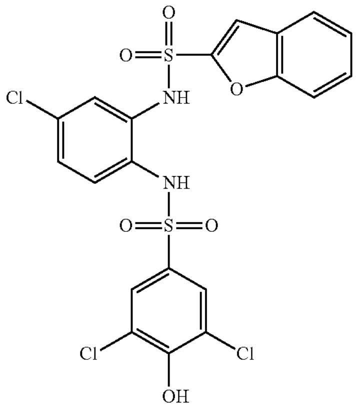 [SMILES: O=S(=O)(Nc1ccc(Cl)cc1NS(=O)(=O)c1cc2ccccc2o1)c1cc(Cl)c(O)c(Cl)c1] | N-(5-chloro-2-{[(3,5-dichloro-4-hydroxyphenyl)sulfonyl]amino}phenyl)-1-benzofuran-2-sulfonamide | Method A |
| 449 | 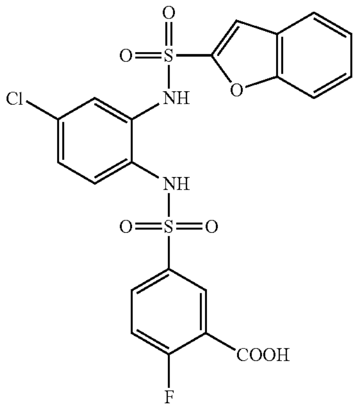 [SMILES: O=C(O)c1cc(S(=O)(=O)Nc2ccc(Cl)cc2NS(=O)(=O)c2cc3ccccc3o2)ccc1F] | 5-[({2-[(1-benzofuran-2-ylsulfonyl)amino]-4-chlorophenyl}amino)sulfonyl]-2-fluorobenzoic acid | Method B |
| 450 | 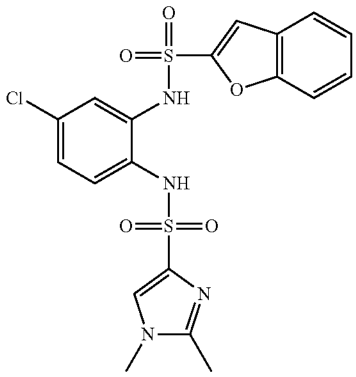 [SMILES: Cc1nc(S(=O)(=O)Nc2ccc(Cl)cc2NS(=O)(=O)c2cc3ccccc3o2)cn1C] | N-{2-[(1-benzofuran-2-ylsulfonyl)amino]-4-chlorophenyl}-1,2-dimethyl-1H-imidazole-4-sulfonamide | Method A |

TABLE 1-continued
| Comp. No. | Structure | IUPAC compound name | Synthesis |
|---|---|---|---|
| 451 | 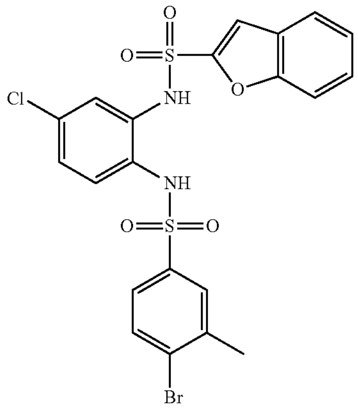 [SMILES: Cc1cc(S(=O)(=O)Nc2ccc(Cl)cc2NS(=O)(=O)c2cc3ccccc3o2)ccc1Br] | N-(2-{[(4-bromo-3-methylphenyl)sulfonyl]amino}-5-chlorophenyl)-1-benzofuran-2-sulfonamide | Method A |
| 452 | 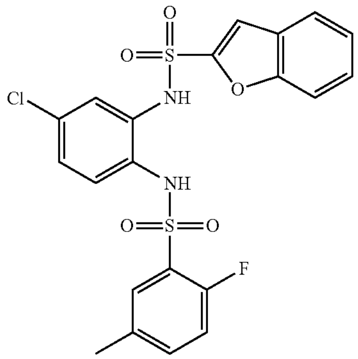 [SMILES: Cc1ccc(F)c(S(=O)(=O)Nc2ccc(Cl)cc2NS(=O)(=O)c2cc3ccccc3o2)c1] | N-(5-chloro-2-{[(2-fluoro-5-methylphenyl)sulfonyl]amino}phenyl)-1-benzofuran-2-sulfonamide | Method A |
| 453 | 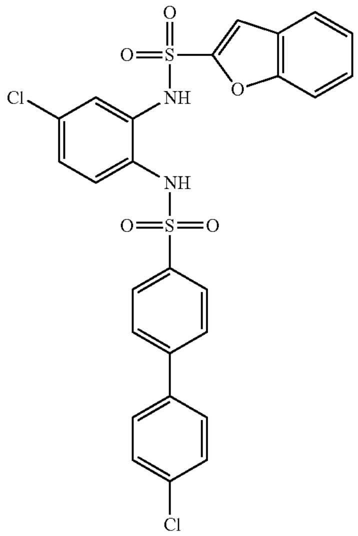 [SMILES: O=S(=O)(Nc1ccc(Cl)cc1NS(=O)(=O)c1cc2ccccc2o1)c1ccc(-c2ccc(Cl)cc2)cc1] | N-(5-chloro-2-{[(4'-chlorobiphenyl-4-yl)sulfonyl]amino}phenyl)-1-benzofuran-2-sulfonamide | Method A |

TABLE 1-continued
| Comp. No. | Structure | IUPAC compound name | Synthesis |
|---|---|---|---|
| 454 | 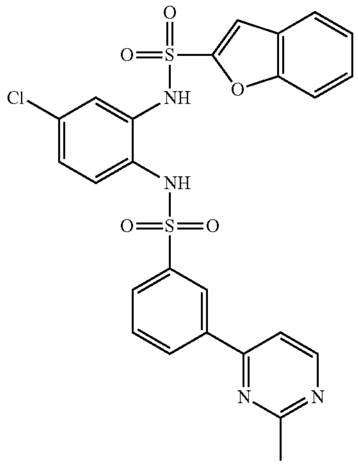 [SMILES: Cc1nccc(-c2cccc(S(=O)(=O)Nc3ccc(Cl)cc3NS(=O)(=O)c3cc4ccccc4o3)c2)n1] | N-[5-chloro-2-({[3-(2-methylpyrimidin-4-yl)phenyl]sulfonyl}amino)phenyl]-1-benzofuran-2-sulfonamide | Method A |
| 455 | 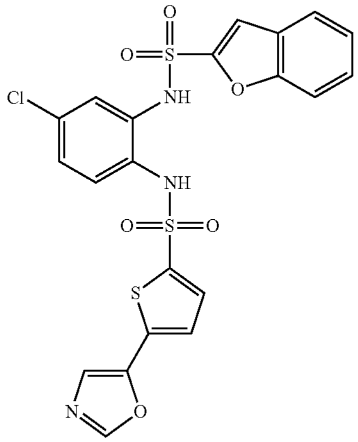 [SMILES: O=S(=O)(Nc1cc(Cl)ccc1NS(=O)(=O)c1ccc(-c2cnco2)s1)c1cc2ccccc2o1] | N-[5-chloro-2-({[5-(1,3-oxazol-5-yl)-2-thienyl]sulfonyl}amino)phenyl]-1-benzofuran-2-sulfonamide | Method A |
| 456 | 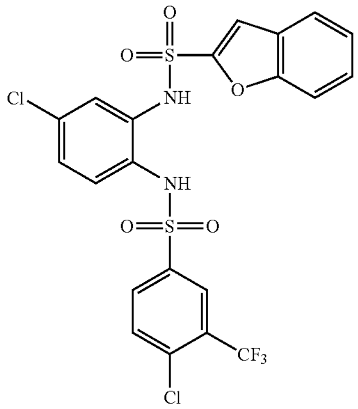 [SMILES: O=S(=O)(Nc1ccc(Cl)cc1NS(=O)(=O)c1cc2ccccc2o1)c1ccc(Cl)c(C(F)(F)F)c1] | N-[5-chloro-2-({[4-chloro-3-(trifluoromethyl)phenyl]sulfonyl}amino)phenyl]-1-benzofuran-2-sulfonamide | Method A |

TABLE 1-continued
| Comp. No. | Structure | IUPAC compound name | Synthesis |
|---|---|---|---|
| 457 | 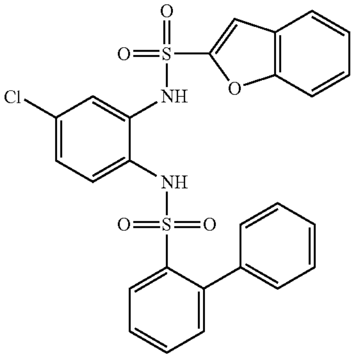 [SMILES: O=S(=O)(Nc1cc(Cl)ccc1NS(=O)(=O)c1ccccc1-c1ccccc1)c1cc2ccccc2o1] | N-{2-[(biphenyl-2-ylsulfonyl)amino]-5-chlorophenyl}-1-benzofuran-2-sulfonamide | Method A |
| 458 | 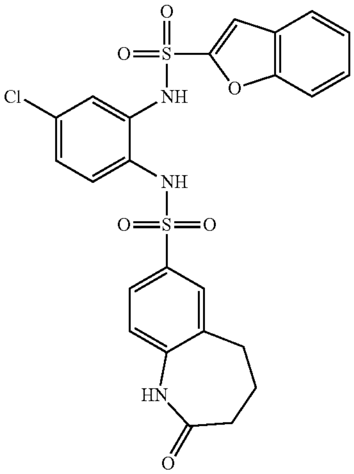 [SMILES: O=C1CCCc2cc(S(=O)(=O)Nc3ccc(Cl)cc3NS(=O)(=O)c3cc4ccccc4o3)ccc2N1] | N-{2-[(1-benzofuran-2-ylsulfonyl)amino]-4-chlorophenyl}-2-oxo-2,3,4,5-tetrahydro-1H-1-benzazepine-7-sulfonamide | Method A |
| 459 | 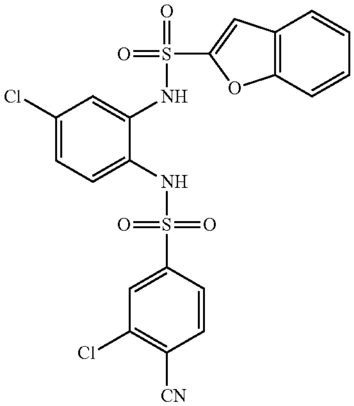 [SMILES: N#Cc1ccc(S(=O)(=O)Nc2ccc(Cl)cc2NS(=O)(=O)c2cc3ccccc3o2)cc1Cl] | N-(5-chloro-2-{[(3-chloro-4-cyanophenyl)ulfonyl] amino}phenyl)-1-benzofuran-2-sulfonamide | Method A |

TABLE 1-continued

| Comp. No. | Structure | IUPAC compound name | Synthesis |
|---|---|---|---|
| 460 | 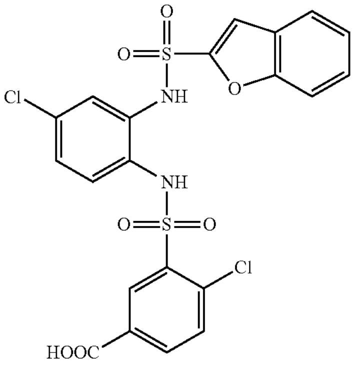 [SMILES: O=C(O)c1ccc(Cl)c(S(=O)(=O)Nc2ccc(Cl)cc2NS(=O)(=O)c2cc3ccccc3o2)c1] | 3-[({2-[(1-benzofuran-2-ylsulfonyl)amino]-4-chlorophenyl}amino)phenyl]-4-chlorobenzoic acid | Method B |
| 461 | 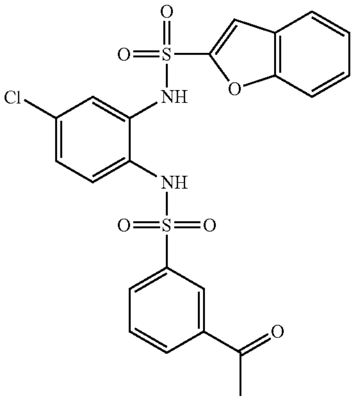 [SMILES: CC(=O)c1cccc(S(=O)(=O)Nc2ccc(Cl)cc2NS(=O)(=O)c2cc3ccccc3o2)c1] | N-(2-{[(3-acetylphenyl)sulfonyl]amino}-5-chlorophenyl)-1-benzofuran-2-sulfonamide | Method A |
| 462 | 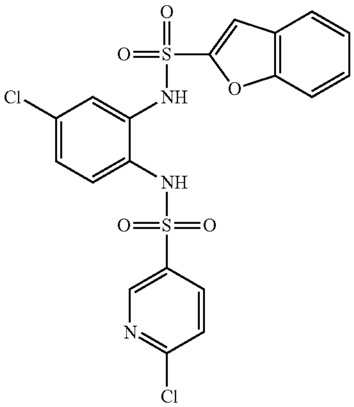 [SMILES: O=S(=O)(Nc1ccc(Cl)cc1NS(=O)(=O)c1cc2ccccc2o1)c1ccc(Cl)nc1] | N-{2-[(1-benzofuran-2-ylsulfonyl)amino]-4-chlorophenyl}-6-chloropyridine-3-sulfonamide | Method C |
| 463 | 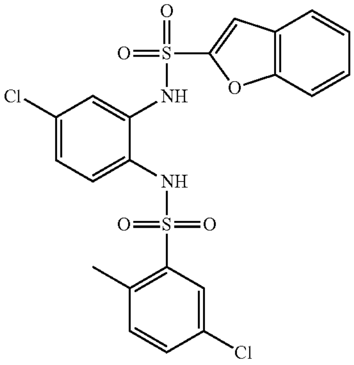 [SMILES: Cc1ccc(Cl)cc1S(=O)(=O)Nc1ccc(Cl)cc1NS(=O)(=O)c1cc2ccccc2o1] | N-(5-chloro-2-{[(5-chloro-2-methylphenyl)sulfonyl]amino}phenyl)-1-benzofuran-2-sulfonamide | Method A |

TABLE 1-continued
| Comp. No. | Structure | IUPAC compound name | Synthesis |
|---|---|---|---|
| 464 | 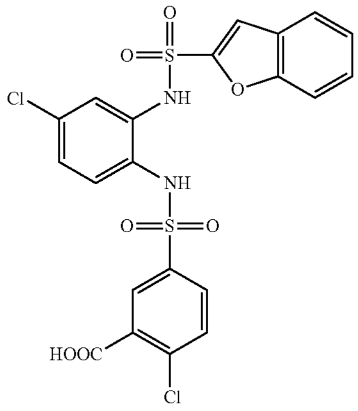 [SMILES: O=C(O)c1cc(S(=O)(=O)Nc2ccc(Cl)cc2NS(=O)(=O)c2cc3ccccc3o2)ccc1Cl] | 5-[({2-[(1-benzofuran-2-ylsulfonyl)amino]-4-chlorophenyl}amino)sulfonyl]-2-chlorobenzoic acid | Method B |
| 465 | 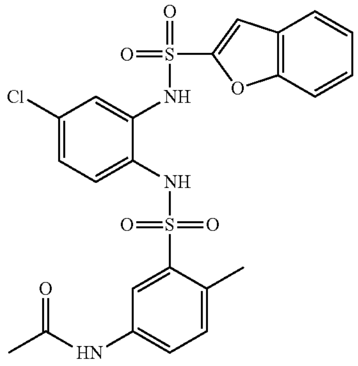 [SMILES: CC(=O)Nc1ccc(C)c(S(=O)(=O)Nc2ccc(Cl)cc2NS(=O)(=O)c2cc3ccccc3o2)c1] | N-{3-[({2-[(1-benzofuran-2-ylsulfonyl)amino]-4-chlorophenyl}amino) sulfonyl]-4-methylphenyl}acetamide | Method A |
| 466 | 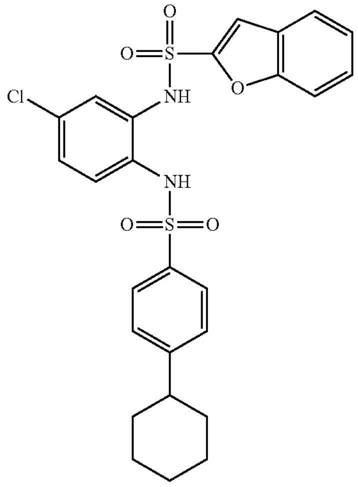 [SMILES: O=S(=O)(Nc1ccc(Cl)cc1NS(=O)(=O)c1cc2ccccc2o1)c1ccc(C2CCCCC2)cc1] | N-(5-chloro-2-{[(4-cyclohexylphenyl)sulfonyl] amino}phenyl)-1-benzofuran-2-sulfonamide | Method A |

TABLE 1-continued
| Comp. No. | Structure | IUPAC compound name | Synthesis |
|---|---|---|---|
| 467 | 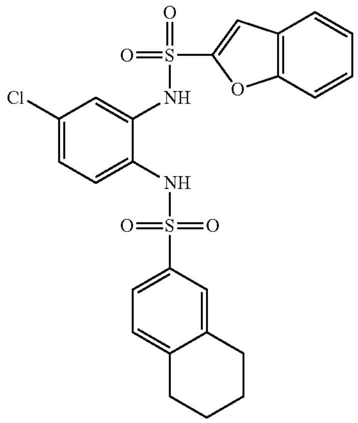 [SMILES: O=S(=O)(Nc1ccc(Cl)cc1NS(=O)(=O)c1cc2ccccc2o1)c1ccc2c(c1)CCCC2] | N-{5-chloro-2-[(5,6,7,8-tetrahydronaphthalen-2-ylsulfonyl)amino]phenyl}-1-benzofuran-2-sulfonamide | Method A |
| 468 | 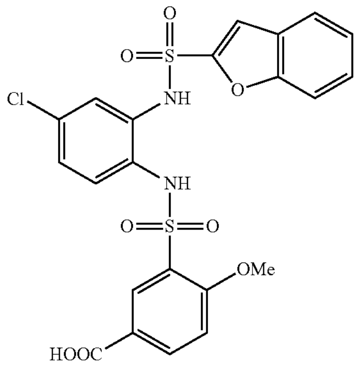 [SMILES: COc1ccc(C(=O)O)cc1S(=O)(=O)Nc1ccc(Cl)cc1NS(=O)(=O)c1cc2ccccc2o1] | 3-[({2-[(1-benzofuran-2-ylsulfonyl)amino]-4-chlorophenyl}amino)sulfonyl]-4-methoxybenzoic acid | Method B |
| 469 | 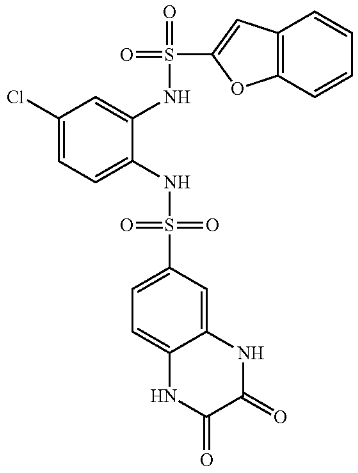 [SMILES: O=c1[nH]c2ccc(S(=O)(=O)Nc3ccc(Cl)cc3NS(=O)(=O)c3cc4ccccc4o3)cc2[nH]c1=O] | N-{2-[(1-benzofuran-2-ylsulfonyl)amino]-4-chlorophenyl}-2,3-dioxo-1,2,3,4-tetrahydroquinoxaline-6-sulfonamide | Method C |

TABLE 1-continued
| Comp. No. | Structure | IUPAC compound name | Synthesis |
|---|---|---|---|
| 470 | 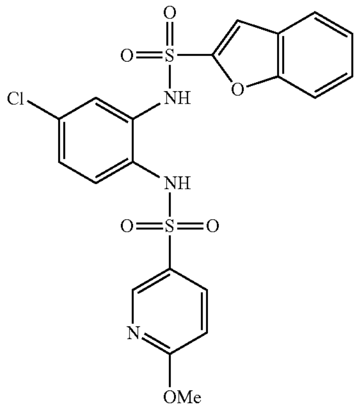 [SMILES: COc1ccc(S(=O)(=O)Nc2ccc(Cl)cc2NS(=O)(=O)c2cc3ccccc3o2)cn1] | N-{2-[(1-benzofuran-2-ylsulfonyl)amino]-4-chlorophenyl}-6-methoxypyridine-3-sulfonamide | Method A |
| 471 | 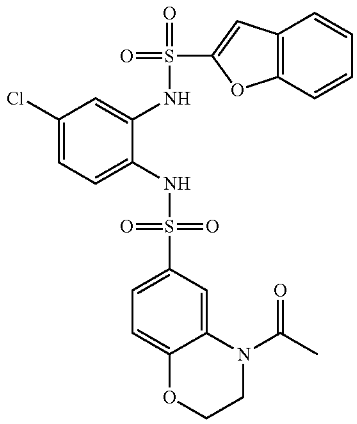 [SMILES: CC(=O)N1CCOc2ccc(S(=O)(=O)Nc3ccc(Cl)cc3NS(=O)(=O)c3cc4ccccc4o3)cc21] | 4-acetyl-N-{2-[(1-benzofuran-2-ylsulfonyl)amino]-4-chlorophenyl}-3,4-dihydro-2H-1,4-benzoxazine-6-sulfonamide | Method A |
| 472 | 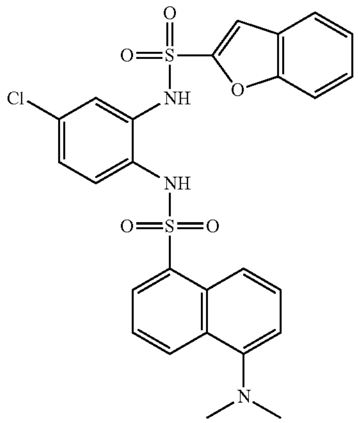 [SMILES: CN(C)c1cccc2c(S(=O)(=O)Nc3ccc(Cl)cc3NS(=O)(=O)c3cc4ccccc4o3)cccc12] | N-[5-chloro-2-({[5-(dimethylamino)-1-naphthyl]sulfonyl}amino)phenyl]-1-benzofuran-2-sulfonamide | Method A |

TABLE 1-continued
| Comp. No. | Structure | IUPAC compound name | Synthesis |
|---|---|---|---|
| 473 | 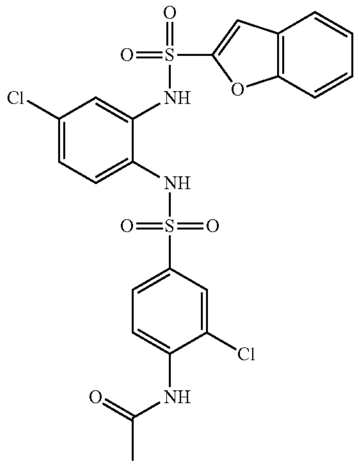 [SMILES: CC(=O)Nc1ccc(S(=O)(=O)Nc2ccc(Cl)cc2NS(=O)(=O)c2cc3ccccc3o2)cc1Cl] | N-{4-[({2-[(1-benzofuran-2-ylsulfonyl)amino]-4-chlorophenyl}amino)sulfonyl]-2-chlorophenyl}acetamide | Method A |
| 474 | 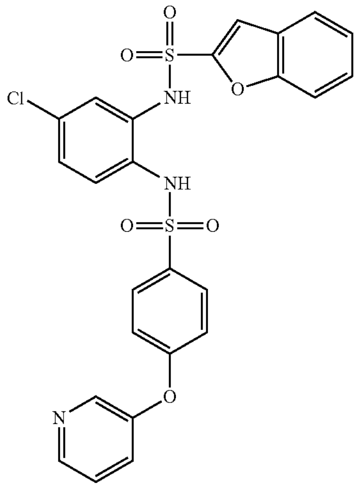 [SMILES: O=S(=O)(Nc1ccc(Cl)cc1NS(=O)(=O)c1cc2ccccc2o1)c1ccc(Oc2cccnc2)cc1] | N-[5-chloro-2-({[4-(pyridin-3-yloxy)phenyl]sulfonyl}amino)phenyl]-1-benzofuran-2-sulfonamide | Method C |
| 475 | 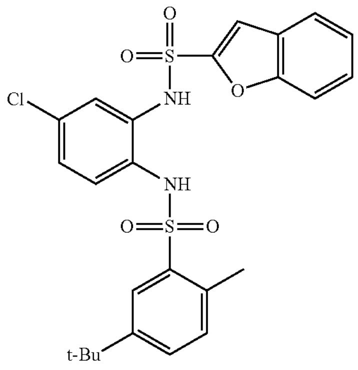 [SMILES: Cc1ccc(C(C)(C)C)cc1S(=O)(=O)Nc1ccc(Cl)cc1NS(=O)(=O)c1cc2ccccc2o1] | N-(2-{[(5-tert-butyl-2-methylphenyl)sulfonyl]amino}-5-chlorophenyl)-1-benzofuran-2-sulfonamide | Method A |

TABLE 1-continued
| Comp. No. | Structure | IUPAC compound name | Synthesis |
| --- | --- | --- | --- |
| 476 | 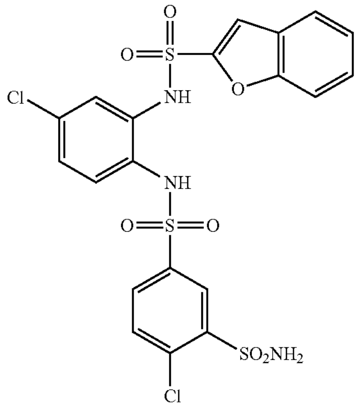 [SMILES: NS(=O)(=O)c1cc(S(=O)(=O)Nc2ccc(Cl)cc2NS(=O)(=O)c2cc3ccccc3o2)ccc1Cl] | N~1~-{2-[(1-benzofuran-2-ylsulfonyl)amino]-4-chlorophenyl}-4-chlorobenzene-1,3-disulfonamide | Method A |
| 477 | 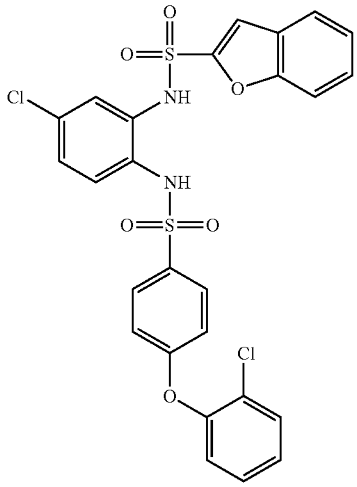 [SMILES: O=S(=O)(Nc1ccc(Cl)cc1NS(=O)(=O)c1cc2ccccc2o1)c1ccc(Oc2ccccc2Cl)cc1] | N-[5-chloro-2-({[4-(2-chlorophenoxy)phenyl] sulfonyl}amino)phenyl]-1-benzofuran-2-sulfonamide | Method A |
| 478 | 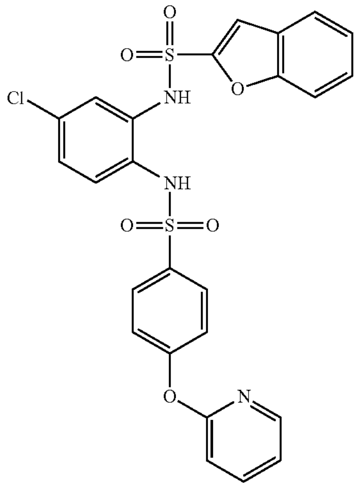 [SMILES: O=S(=O)(Nc1ccc(Cl)cc1NS(=O)(=O)c1cc2ccccc2o1)c1ccc(Oc2ccccn2)cc1] | N-[5-chloro-2-({[4-(pyridin-2-ylocu)phenyl]sulfonyl} amino)phenyl]-1-benzofuran-2-sulfonamide | Method C |

TABLE 1-continued
| Comp. No. | Structure | IUPAC compound name | Synthesis |
|---|---|---|---|
| 479 | 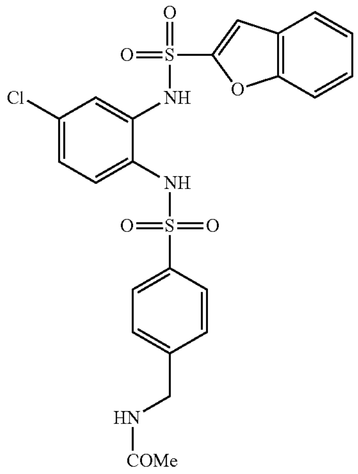 | N-{4-[({2-[(1-benzofuran-2-ylsulfonyl)amino]-4-chlorophenyl}amino)sulfonyl] benzyl}acetamide | Method C |
| 480 | 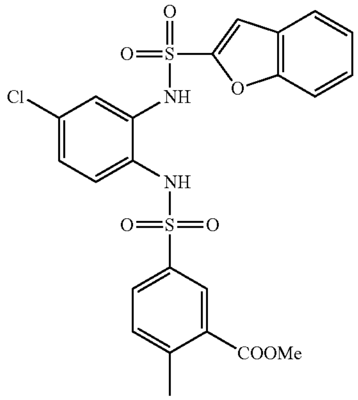 [SMILES: COC(=O)c1cc(S(=O)(=O)Nc2ccc(Cl)cc2NS(=O)(=O)c2cc3ccccc3o2)ccc1C] | methyl 5-[({2-[(1-benzofuran-2-ylsulfonyl)amino]-4-chlorophenyl}amino)phenyl]-2-methylbenzoate | Method A |
| 481 | 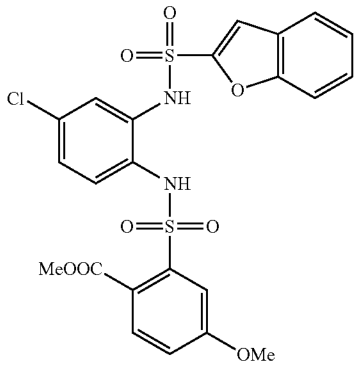 [SMILES: COC(=O)c1ccc(OC)cc1S(=O)(=O)Nc1ccc(Cl)cc1NS(=O)(=O)c1cc2ccccc2o1] | methyl 2-[({2-[(1-benzofuran-2-ylsulfonyl)amino]-4-chlorophenyl}amino)sulfonyl]-4-methoxybenzoate | Method C |

TABLE 1-continued
| Comp. No. | Structure | IUPAC compound name | Synthesis |
|---|---|---|---|
| 482 | 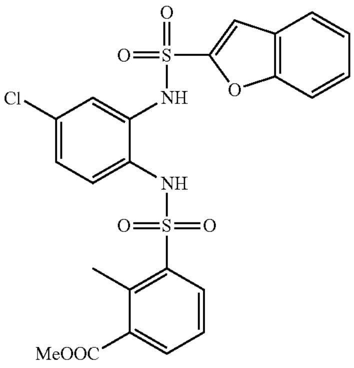 [SMILES: COC(=O)c1cccc(S(=O)(=O)Nc2ccc(Cl)cc2NS(=O)(=O)c2cc3ccccc3o2)c1C] | methyl 3-[({2-[(1-benzofuran-2-ylsulfonyl)amino]-4-chlorophenyl}amino)sulfonyl]-2-methylbenzoate | Method A |
| 483 | 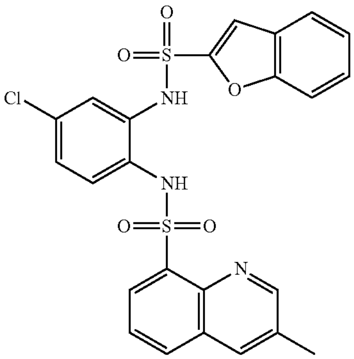 [SMILES: Cc1cnc2c(S(=O)(=O)Nc3ccc(Cl)cc3NS(=O)(=O)c3cc4ccccc4o3)cccc2c1] | N-{2-[(1-benzofuran-2-ylsulfonyl)amino]-4-chlorophenyl}-3-methylquinoline-8-sulfonamide | Method A |
| 484 | 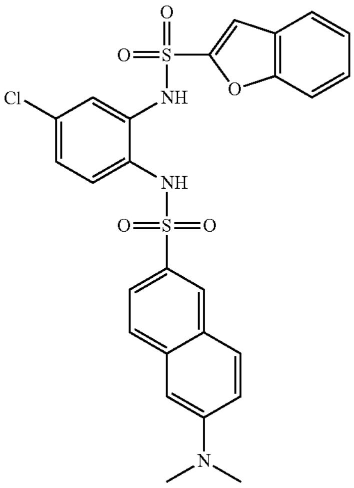 [SMILES: CN(C)c1ccc2cc(S(=O)(=O)Nc3ccc(Cl)cc3NS(=O)(=O)c3cc4ccccc4o3)ccc2c1] | N-[5-chloro-2-({[6-(dimethylamino)-2-naphthyl]sulfonyl}amino)phenyl]-1-benzofuran-2-sulfonamide | Method A |

TABLE 1-continued
| Comp. No. | Structure | IUPAC compound name | Synthesis |
|---|---|---|---|
| 485 | 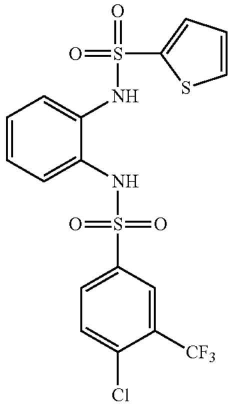 [SMILES: O=S(=O)(Nc1ccccc1NS(=O)(=O)c1cccs1)c1ccc(Cl)c(C(F)(F)F)c1] | N-[2-({[4-chloro-3-(trifluoromethyl)phenyl] sulfonyl}amino)phenyl]thiophene-2-sulfonamide | Method A |
| 486 | 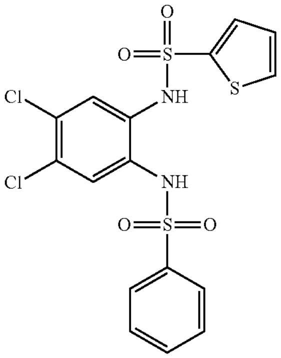 [SMILES: O=S(=O)(Nc1cc(Cl)c(Cl)cc1NS(=O)(=O)c1cccs1)c1ccccc1] | N-{4,5-dichloro-2-[(phenylsulfonyl)amino] phenyl}thiophene-2-sulfonamide | Method A |
| 487 | 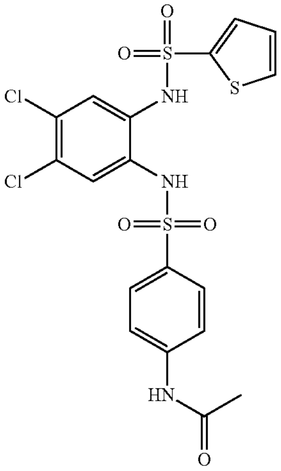 [SMILES: CC(=O)Nc1ccc(S(=O)(=O)Nc2cc(Cl)c(Cl)cc2NS(=O)(=O)c2cccs2)cc1] | N-{4-[({4,5-dichloro-2-[(2-thienylsulfonyl)amino] phenyl}amino)sulfonyl]phenyl} acetamide | Method A |

TABLE 1-continued

| Comp. No. | Structure | IUPAC compound name | Synthesis |
|---|---|---|---|
| 488 | 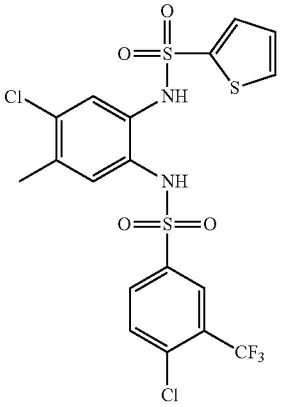 [SMILES: Cc1cc(NS(=O)(=O)c2ccc(Cl)c(C(F)(F)F)c2)c(NS(=O)(=O)c2cccs2)cc1Cl] | N-[5-chloro-2-({[4-chloro-3-(trifluoromethyl)phenyl] sulfonyl}amino)-4-methylphenyl]thiophene-2-sulfonamide | Method A |
| 489 | 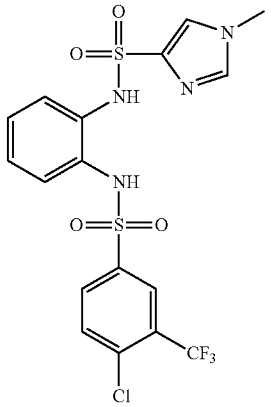 [SMILES: Cn1cnc(S(=O)(=O)Nc2ccccc2NS(=O)(=O)c2ccc(Cl)c(C(F)(F)F)c2)c1] | N-[2-({[4-chloro-3-(trifluoromethyl)phenyl] sulfonyl}amino)phenyl]-1-methyl-1H-imidazole-4-sulfonamide | Method A |
| 490 | 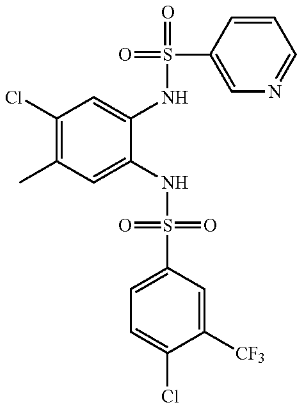 [SMILES: Cc1cc(NS(=O)(=O)c2ccc(Cl)c(C(F)(F)F)c2)c(NS(=O)(=O)c2cccnc2)cc1Cl] | N-[5-chloro-2-({[4-chloro-3-(trifluoromethyl)phenyl] sulfonyl}amino)-4-methylphenyl]pyridine-3-sulfonamide | Method A |

TABLE 1-continued

| Comp. No. | Structure | IUPAC compound name | Synthesis |
|---|---|---|---|
| 491 | 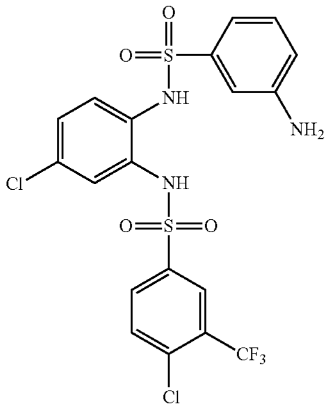 [SMILES: Nc1cccc(S(=O)(=O)Nc2ccc(Cl)cc2NS(=O)(=O)c2ccc(Cl)c(C(F)(F)F)c2)c1] | N-(2-{[(4-aminophenyl)sulfonyl]amino}-5-chlorophenyl)-4-chloro-3-(trifluoromethyl)benzene-sulfonamide | Method A |
| 492 | 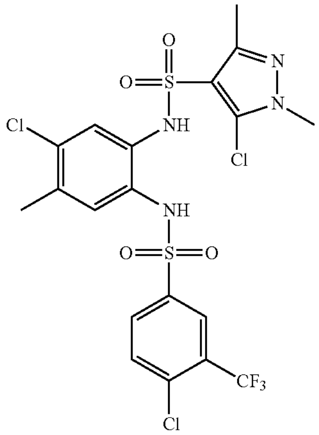 [SMILES: Cc1cc(NS(=O)(=O)c2ccc(Cl)c(C(F)(F)F)c2)c(NS(=O)(=O)c2c(C)nn(C)c2Cl)cc1Cl] | 5-chloro-N-[5-chloro-2-({[4-chloro-3-(trifluoromethyl)phenyl]sulfonyl}amino)-4-methylphenyl]-1,3-dimethyl-1H-pyrazole-4-sulfonamide | Method A |
| 493 | 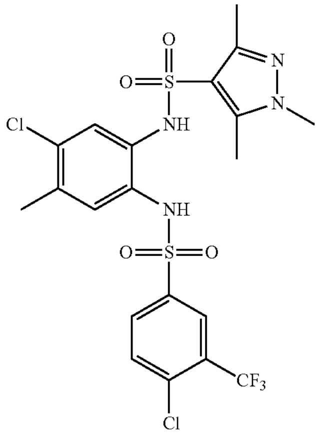 [SMILES: Cc1cc(NS(=O)(=O)c2ccc(Cl)c(C(F)(F)F)c2)c(NS(=O)(=O)c2c(C)nn(C)c2C)cc1Cl] | N-[5-chloro-2-({[4-chloro-3-(trifluoromethyl)phenyl]sulfonyl}amino)-4-methylphenyl]-1,3,5-trimethyl-1H-pyrazole-4-sulfonamide | Method A |

TABLE 1-continued

| Comp. No. | Structure | IUPAC compound name | Synthesis |
|---|---|---|---|
| 494 | 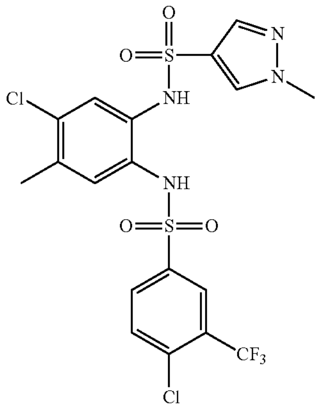 [SMILES: Cc1cc(NS(=O)(=O)c2ccc(Cl)c(C(F)(F)F)c2)c(NS(=O)(=O)c2cnn(C)c2)cc1Cl] | N-[5-chloro-2-({[4-chloro-3-(trifluoromethyl)phenyl] sulfonyl}amino)-4-methylphenyl]-1-methyl-1H-pyrazole-4-sulfonamide | Method A |
| 495 | 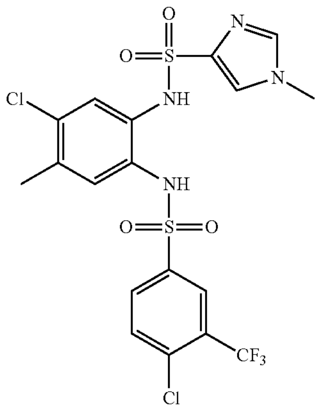 [SMILES: Cc1cc(NS(=O)(=O)c2ccc(Cl)c(C(F)(F)F)c2)c(NS(=O)(=O)c2cn(C)cn2)cc1Cl] | N-[5-chloro-2-({[4-chloro-3-(trifluoromethyl)phenyl] sulfonyl}amino)-4-methylphenyl]-1-methyl-1H-imidazole-4-sulfonamide | Method A |
| 496 | 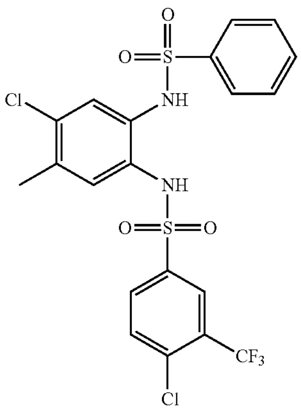 [SMILES: Cc1cc(NS(=O)(=O)c2ccc(Cl)c(C(F)(F)F)c2)c(NS(=O)(=O)c2ccccc2)cc1Cl] | 4-chloro-N-{4-chloro-5-methyl-2-[(phenylsulfonyl)amino] phenyl}-3-(trifluoromethyl)benzene-sulfonamide | Method A |

TABLE 1-continued
| Comp. No. | Structure | IUPAC compound name | Synthesis |
|---|---|---|---|
| 497 | 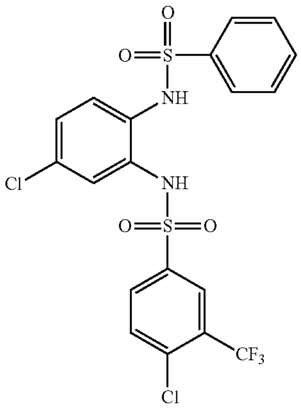 [SMILES: O=S(=O)(Nc1ccc(Cl)cc1NS(=O)(=O)c1ccc(Cl)c(C(F)(F)F)c1)c1ccccc1] | 4-chloro-N-{5-chloro-2-[(phenylsulfonyl)amino]phenyl}-3-(trifluoromethyl)benzene-sulfonamide | Method A |
| 498 | 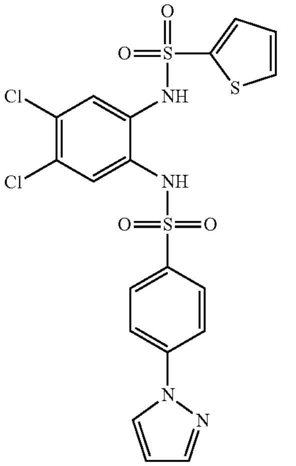 [SMILES: O=S(=O)(Nc1cc(Cl)c(Cl)cc1NS(=O)(=O)c1cccs1)c1ccc(-n2cccn2)cc1] | N-[4,5-dichloro-2-({[4-(1H-pyrazol-1-yl)phenyl]sulfonyl}amino)phenyl]thiophene-2-sulfonamide | Method A |
| 499 | 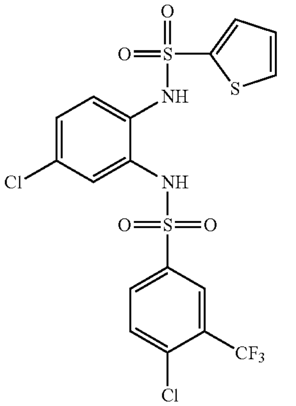 [SMILES: O=S(=O)(Nc1cc(Cl)ccc1NS(=O)(=O)c1cccs1)c1ccc(Cl)c(C(F)(F)F)c1] | N-[4-chloro-2-({[4-chloro-3-(trifluoromethyl)phenyl]sulfonyl}amino)phenyl]thio-phene-2-sulfonamide | Method A |

TABLE 1-continued
| Comp. No. | Structure | IUPAC compound name | Synthesis |
|---|---|---|---|
| 500 | 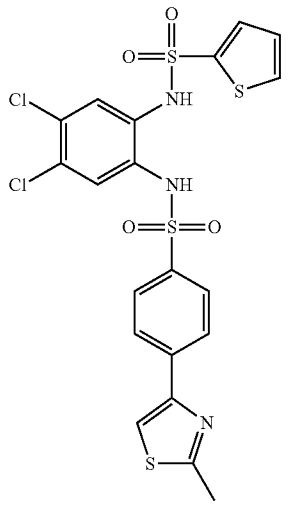 [SMILES: Cc1nc(-c2ccc(S(=O)(=O)Nc3cc(Cl)c(Cl)cc3NS(=O)(=O)c3cccs3)cc2)cs1] | N-[4,5-dichloro-2-({[4-(2-methyl-1,3-thiazol-4-yl)phenyl]sulfonyl}amino)phenyl]thiophene-2-sulfonamide | Method A |
| 501 | 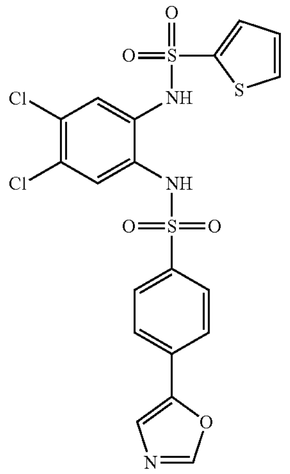 [SMILES: O=S(=O)(Nc1cc(Cl)c(Cl)cc1NS(=O)(=O)c1cccs1)c1ccc(-c2cnco2)cc1] | N-[4,5-dichloro-2-({[4-(1,3-oxazol-5-yl)phenyl]sulfonyl}amino)phenyl]thiophene-2-sulfonamide | Method A |
| 502 | 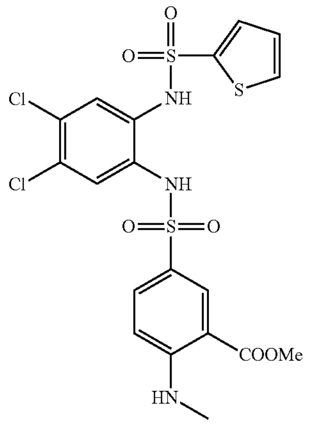 [SMILES: CNc1ccc(S(=O)(=O)Nc2cc(Cl)c(Cl)cc2NS(=O)(=O)c2cccs2)cc1C(=O)OC] | methyl 5-[({4,5-dichloro-2-[(2-thienylsulfonyl)amino]phenyl}amino)sulfonyl]-2-(methylamino)benzoate | Method A |

TABLE 1-continued
| Comp. No. | Structure | IUPAC compound name | Synthesis |
|---|---|---|---|
| 503 | 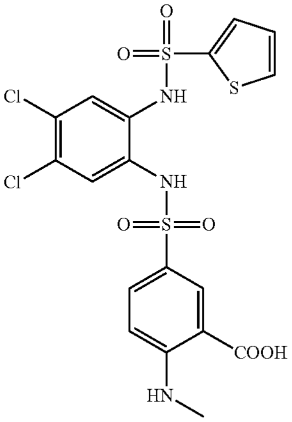 [SMILES: CNc1ccc(S(=O)(=O)Nc2cc(Cl)c(Cl)cc2NS(=O)(=O)c2cccs2)cc1C(=O)O] | 5-[({4,5-dichloro-2-[(2-thienylsulfonyl)amino]phenyl}amino)sulfonyl]-2-(methylamino)benzoic acid | Method A |
| 504 | 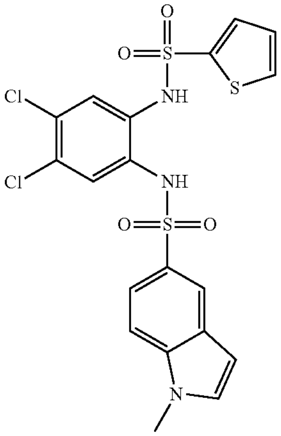 [SMILES: Cn1ccc2cc(S(=O)(=O)Nc3cc(Cl)c(Cl)cc3NS(=O)(=O)c3cccs3)ccc21] | N-{4,5-dichloro-2-[(2-thienylsulfonyl)amino]phenyl}-1-methyl-1H-indole-5-sulfonamide | Method A |
| 505 | 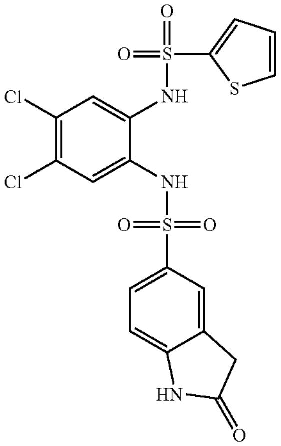 [SMILES: O=C1Cc2cc(S(=O)(=O)Nc3cc(Cl)c(Cl)cc3NS(=O)(=O)c3cccs3)ccc2N1] | N-{4,5-dichloro-2-[(2-thienylsulfonyl)amino]phenyl}-2-oxoindoline-5-sulfonamide | Method A |

TABLE 1-continued

| Comp. No. | Structure | IUPAC compound name | Synthesis |
|---|---|---|---|
| 506 | 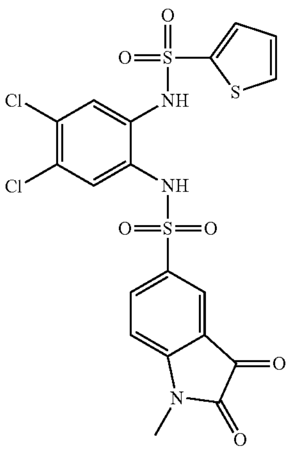 [SMILES: CN1C(=O)C(=O)c2cc(S(=O)(=O)Nc3cc(Cl)c(Cl)cc3NS(=O)(=O)c3cccs3)ccc21] | N-{4,5-dichloro-2-[(2-thienylsulfonyl)amino]phenyl}-1-methyl-2,3-dioxoindoline-5-sulfonamide | Method A |
| 507 | 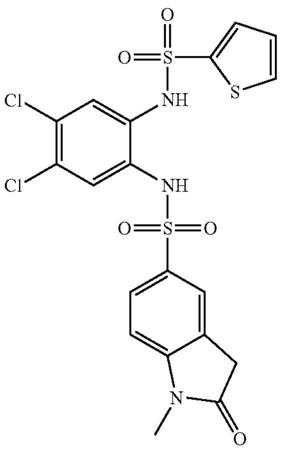 [SMILES: CN1C(=O)Cc2cc(S(=O)(=O)Nc3cc(Cl)c(Cl)cc3NS(=O)(=O)c3cccs3)ccc21] | N-{4,5-dichloro-2-[(2-thienylsulfonyl)amino]phenyl}-1-methyl-2-oxoindoline-5-sulfonamide | Method A |

Biological Data

HEK-Gqi5 cells stably expressing CCR2 were cultured in (DMEM high glucose, 10% FBS, 1% PSA, 400 μg/ml geneticin and 50 μg/ml hygromycin. Appropriate positive control chemokines (MCP-1, MIP1A or RANTES) was used as the positive control agonist for screening compound-induced calcium activity assayed on the FLIPR$^{Tetra}$. The drug plates were prepared in 384-well microplates using the EP3 and the MuItiPROBE robotic liquid handling systems. Compounds were synthesized and tested for $CCR^2$ activity.

Table 2 shows activity for $CCR^2$ receptor ($IC_{50}$) nM

TABLE 2

| Compound Name | CCR2 $IC_{50}$ (nM) | CCR2 % Antagonism |
|---|---|---|
| 5-chloro-N-{4,5-dichloro-2-[(2-thienylsulfonyl)amino]phenyl}thiophene-2-sulfonamide | 263 | 89 |
| 6-chloro-N-{4,5-dichloro-2-[(2-thienylsulfonyl)amino]phenyl}pyridine-3-sulfonamide | 281 | 100 |
| methyl 3-[({2-[(1-benzofuran-2-ylsulfonyl)amino]-4-chlorophenyl}amino)sulfonyl]thiophene-2-carboxylate | 246 | 96 |
| N-(2-{[(4-bromo-3-methylphenyl)sulfonyl]amino}-4,5-dichlorophenyl)thiophene-2-sulfonamide | 471 | 91 |
| N-(4,5-dichloro-2-{[(2,4-difluorophenyl)sulfonyf]amino}phenyl)thiophene-2-sulfonamide | 451 | 89 |
| N-(4,5-dichloro-2-{[(2-fluorophenyl)sulfonyl]amino}phenyl)thiophene-2-sulfonamide | 402 | 67 |
| N-(4,5-dichloro-2-{[(3,4-dichlorophenyl)sulfonyl]amino}phenyl)thiophene-2-sulfonamide | 394 | 79 |

TABLE 2-continued

| Compound Name | CCR2 $IC_{50}$ (nM) | CCR2 % Antagonism |
|---|---|---|
| N-(4,5-dichloro-2-{[(3,5-dichloro-2-hydroxyphenyl)sulfonyl]amino}phenyl)thiophene-2-sulfonamide | 482 | 82 |
| N-(4,5-dichloro-2-{[(3-chloro-2-fluorophenyl)sulfonyl]amino}phenyl)thiophene-2-sulfonamide | 217 | 96 |
| N-(4,5-dichloro-2-{[(3-chlorophenyl)sulfonyl]amino}phenyl)thiophene-2-sulfonamide | 391 | 90 |
| N-(4,5-dichloro-2-{[(4-chloro-2-fluorophenyl)sulfonyl]amino}phenyl)thiophene-2-sulfonamide | 361 | 94 |
| N-(4,5-dichloro-2-{[(4-fluorophenyl)sulfonyl]amino}phenyl)thiophene-2-sulfonamide | 441 | 91 |
| N-(5-chloro-2-{[(2,6-dichlorophenyl)sulfonyl]amino}phenyl)-1-benzofuran-2-sulfonamide | 478 | 89 |
| N-(5-chloro-2-{[(2,6-difluorophenyl)sulfonyl]amino}phenyl)-1-benzofuran-2-sulfonamide | 153 | 99 |
| N-(5-chloro-2-{[(5-methyl-2-thienyl)sulfonyl]amino}phenyl)-1-benzofuran-2-sulfonamide | 339 | 96 |
| N-[3-({[4-chloro-3-(trifluoromethyl)phenyl]sulfonyl}amino)pyridin-2-yl]thiophene-2-sulfonamide | 349 | 85 |
| N-[4,5-dichloro-2-({[3-(trifluoromethyl)phenyl]sulfonyl}amino)phenyl]thiophene-2-sulfonamide | 306 | 88 |
| N-[4,5-<dichloro-2-({[4-fluoro-3-(trifluoromethyl)phenyl]sulfonyl}amino)phenyl]thiophene-2-sulfonamide | 432 | 89 |
| N-{2-[(1-benzofuran-2-ylsulfonyl)amino]-4-chlorophenyl}-1-methyl-1H-pyrazole-3-sulfonamide | 185 | 96 |
| N-{2-[(1-benzofuran-2-ylsulfonyl)amino]-4-chlorophenyl}-1-methyl-1H-imidazole-4-sulfonamide | 423 | 110 |
| N-{2-[(1-benzofuran-2-ylsulfonyl)amino]-4-chlorophenyl}-3,5-dimethyl-1H-pyrazole-4-sulfonamide | 183 | 108 |
| N-{2-[(1-benzofuran-2-ylsulfonyl)amino]-4-chlorophenyl}-5-chloro-1,3-dimethyl-1H-pyrazole-4-sulfonamide | 294 | 80 |
| N-{4,5-dichloro-2-[(2-thienylsulfonyl)amino]phenyl}-1-benzofuran-2-sulfonamide | 96 | 100 |
| N-{4,5-dichloro-2-[(2-thienylsulfonyl)amino]phenyl}-1-benzothiophene-2-sulfonamide | 494 | 94 |
| N-{4,5-dichloro-2-[(2-thienylsulfonyl)amino]phenyl}-5-methylfuran-2-sulfonamide | 311 | 95 |
| N-{4-chloro-2-[(2-thienylsulfonyl)amino]phenyl}-1-benzofuran-2-sulfonamide | 145 | 90 |
| N-{5-chloro-2-[(2-thienylsulfonyi)amino]phenyl}-1-benzofuran-2-sulfonamide | 20 | 86 |

What is claimed is:

1. A compound having Formula I, its enantiomers, diastereoisomers, tautomers or a pharmaceutically acceptable salt thereof, Formula I

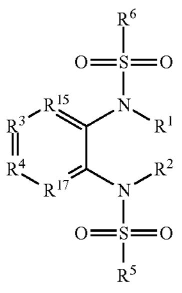

wherein:

$R^1$ is H or substituted or unsubstituted $C_{1-6}$ alkyl;

$R^2$ is H or substituted or unsubstituted $C_{1-6}$ alkyl;

$R^3$ is C-$R^7$;

$R^4$ is C-$R^8$;

$R^5$ is selected from 5-isoxazol-3-ylthiophene, 2-oxo-2,3-dihydro-1,3-benzoxazole, 1,3-benzothiazole, 1,3-benzodioxole, 4-methyl-1,3-thiazol-2-yl-acetamide, 1-(phenylsulfonyl)-1H-pyrrole, 2-oxo-2H-chromene, imidazo[2,1-b][1,3]thiazole, 6-morpholin-4-ylpyridine, 2-oxo-2,3,4,5-tetrahydro-1H-1-benzazepine, 5-isoxazol-5-ylthiophene, 6-chloroimidazo[2,1-b][1,3]thiazole, 4-methyl-3,4-dihydro-2H-1,4-benzoxazine, 3,4-dihydro-2H-1,5-benzodioxepine, 2,2-dimethylchromane, 5-pyridin-2-yl-2-thienyl, 4-methyl-3,4-dihydro-2H-pyrido[3,2b][1,4]oxazine, 3-oxo-3,4-dihydro-2H-1,4-benzoxazine, 2,3-dioxo-1,2,3,4-tetrahydroquinoxaline and 4-acetyl-3,4-dihydro-2H-1,4-benzoxazine;

$R^6$ is 2-benzofuran;

$R^{15}$ is C-$R^{16}$;

$R^{17}$ is C-$R^{18}$;

$R^7$ is H, substituted or unsubstituted $C_{1-6}$ alkyl or halogen;

$R^8$ is H, substituted or unsubstituted $C_{1-6}$ alkyl or halogen;

$R^{16}$ is H, substituted or unsubstituted $C_{1-6}$ alkyl or halogen; and $R^{18}$ is H, substituted or unsubstituted $C_{1-6}$ alkyl or halogen.

2. The compound according to claim 1, wherein:

$R^1$ is H; and $R^2$ is H.

3. The compound according to claim 1, wherein:

$R^7$ is H or halogen; and $R^8$ is H or halogen.

4. The compound according to claim 1, wherein:

$R^7$ is halogen; and $R^8$ is H.

5. The compound according to claim 1, wherein:

$R^7$ is H; and $R^8$ is halogen.

6. The compound according to claim 1, wherein:

$R^7$ is halogen; and $R^8$ is halogen.

7. The compound according to claim 1, wherein:

$R^{16}$ is H or halogen; and $R^{18}$ is H or halogen.

8. The compound according to claim 1, wherein:

$R^{16}$ is H; and $R^{18}$ is H.

9. The compound according to claim 1, selected from:

N-{2-[(1-benzofuran-2-ylsulfonyl)amino ]-4-chlorophenyl}-2-oxo-2H-chromene-6-sulfonamide;

N-{2-[(1-benzofuran-2-ylsulfonyl)amino ]-4-chlorophenyl}-6-chloroimidazo-b [2,1-b][1,3]thiazole-5-sulfonamide;

N-{2-[(1-benzofuran- 2-ylsulfonyl)amino ]-4-chlorophenyl}-6-morpholin-4-ylpyridine-3-sulfonamide;

N-{2-[(1-benzofuran-2-ylsulfonyl)amino ]-4-chlorophenyl}-3,4-dihydro- 2H-1,5-benzodioxepine-7-sulfonamide;

N-{2-[(1-benzofuran-2-ylsulfonyl)amino ]- 4-chlorophenyl}-4-methyl-3,4-dihydro-2H-1,4-benzoxazine-6-sulfonamide;

N-{2-[(1-benzofuran-2-ylsulfonyl)amino]-4-chlorophenyl}-3-oxo-3,4-dihydro-2H-1,4-benzoxazine-6-sulfonamide;

N-{2-[(1-benzofuran-2-ylsulfonyl)amino]-4-chlorophenyl}-2-oxo-2,3,4,5-tetrahydro-1H-1-benzazepine-7-sulfonamide;

N-{2-[(1-benzofuran-2-ylsulfonyl)amino]-4-chlorophenyl}-2,3-dioxo-1,2,3,4-tetrahydrocluinoxaline-6-sulfonamide; and 4-acetyl-N-{2-[1-benzofuran-2-ylsulfonyl)amino]4-chlorophenyl}-3,4-dihydro-2H-1,4-benzoxazine-6-sulfonamide.

10. A pharmaceutical composition comprising as active ingredient a therapeutically effective amount of a compound according to claim 1 and a pharmaceutically acceptable adjuvant, diluents or carrier.

11. The pharmaceutical composition according to claim 10 wherein the compound is selected from:

N-{2-[(1-benzofuran-2-ylsulfonyl)amino]-4-chlorophenyl}-2-oxo-2H-chromene-6-sulfonamide;

N-{2-[(1-benzofuran-2-ylsulfonyl)amino]-4-chlorophenyl}-6-chloroimidazo[2,1-b][1,3]thiazole-5-sulfonamide;

N-{2-[(1-benzofuran-2-ylsulfonyl)amino]-4-chlorophenyl}-6-morpholin-4-ylpyridine-3-sulfonamide;

N-{2-[(1-benzofuran-2-ylsulfonyl)amino]- 4-chlorophenyl}-3,4-dihydro-2H-1,5-benzodioxepine-7-sulfonamide;

N-{2-[(1-benzofuran-2-ylsulfonyl)amino]-4-chlorobhenyl}-4-methyl-3,4-dihydro-2H-1,4-benzoxazine-6-sulfonamide;

N-{2-[(1-benzofuran-2-ylsulfonyl)amino]-4-chlorophenyl}-4-methyl-3,4-dihydro-2H -pvrido[3,2-b ][1,4]oxazine-7-sulfonamide;

N-{2-[(1-benzofuran-2-ylsulfonyl)amino]-4-chlorobhenyl}-3-oxo-3,4-dihydro-2H-1,4-benzoxazine-6-sulfonamide;

N-{2-[(1-benzofuran-2-ylsulfonyl)amino]-4-chlorophenyl}-2-oxo-2,3,4,5-tetrahydro-1H-1-benzazepine-7-sulfonamide; N-{2-[(1-benzofuran-2-ylsulfonyl) amino]-4-chlorophenyl}-2,3-dioxo-1,2,3,4-tetrahydroquinoxaline-6-sulfonamide; and 4-acetyl-N-{2-[(1-benzofuran-2-ylsulfonyl)amino-]-4-chlorophenyl}-3,4-dihydro-2H-1,4-benzoxazine-6-sulfonamide.

* * * * *